US011191722B2

(12) United States Patent
Muhlen-Bartmer et al.

(10) Patent No.: US 11,191,722 B2
(45) Date of Patent: *Dec. 7, 2021

(54) TREATMENT OF DIABETES MELLITUS BY LONG-ACTING FORMULATIONS OF INSULINS

(71) Applicant: SANOFI, Paris (FR)

(72) Inventors: Isabel Muhlen-Bartmer, Frankfurt am Main (DE); Monika Ziemen, Frankfurt am Main (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/700,541

(22) Filed: Dec. 2, 2019

(65) Prior Publication Data
US 2020/0170945 A1    Jun. 4, 2020

Related U.S. Application Data

(63) Continuation of application No. 16/117,310, filed on Aug. 30, 2018, now abandoned, which is a continuation of application No. 14/781,857, filed as application No. PCT/EP2014/056498 on Apr. 1, 2014, now Pat. No. 10,092,513.

(30) Foreign Application Priority Data

Apr. 3, 2013   (EP) .................................... 13305432
Aug. 8, 2013   (EP) .................................... 13290188
Oct. 15, 2013  (EP) .................................... 13306412

(51) Int. Cl.

| A61K 9/08 | (2006.01) |
| A61K 38/28 | (2006.01) |
| A61K 9/00 | (2006.01) |
| A61P 3/10 | (2006.01) |
| A61K 31/155 | (2006.01) |
| A61K 38/26 | (2006.01) |
| A61K 47/02 | (2006.01) |
| A61K 47/10 | (2017.01) |
| A61K 47/26 | (2006.01) |

(52) U.S. Cl.
CPC .............. *A61K 9/08* (2013.01); *A61K 9/0019* (2013.01); *A61K 31/155* (2013.01); *A61K 38/26* (2013.01); *A61K 38/28* (2013.01); *A61K 47/02* (2013.01); *A61K 47/10* (2013.01); *A61K 47/26* (2013.01); *A61P 3/10* (2018.01)

(58) Field of Classification Search
None
See application file for complete search history.

(56) References Cited

U.S. PATENT DOCUMENTS

| 4,153,689 A | 5/1979 | Hirai et al. |
| 4,165,370 A | 8/1979 | Coval |
| 4,783,441 A | 11/1988 | Thurow |
| 4,960,702 A | 10/1990 | Rice et al. |
| 5,070,186 A | 12/1991 | Joergensen |
| 5,149,716 A | 9/1992 | Vertesy et al. |
| 5,370,629 A | 12/1994 | Michel et al. |
| 5,509,905 A | 4/1996 | Michel et al. |
| 5,656,722 A | 8/1997 | Dorschug |
| 5,935,566 A | 8/1999 | Yuen et al. |
| 5,952,297 A | 9/1999 | DeFilippis et al. |
| 6,034,054 A | 3/2000 | DeFilippis et al. |
| 6,100,376 A | 8/2000 | Dorschug |
| 6,268,335 B1 | 6/2001 | Brader |
| 6,335,316 B1 | 1/2002 | Hughes et al. |
| 6,410,511 B2 | 6/2002 | L'Ltalien et al. |
| 6,528,486 B1 | 4/2003 | Larsen et al. |
| 6,737,401 B2 | 5/2004 | Kim et al. |
| 6,852,694 B2 | 2/2005 | Van Antwerp et al. |
| 6,902,744 B1 | 6/2005 | Kolterman et al. |
| 7,022,674 B2 | 4/2006 | DeFelippis |
| 7,115,563 B2 | 10/2006 | Younis |
| 7,119,086 B2 | 10/2006 | Malta et al. |
| 7,192,919 B2 | 3/2007 | Tzannis et al. |
| 7,238,663 B2 | 7/2007 | DeFelippis et al. |
| 7,405,196 B2 | 7/2008 | Rosskamp et al. |
| 7,476,652 B2 | 1/2009 | Brunner-Schwarz et al. |
| 7,544,656 B2 | 6/2009 | Sabetsky |
| 7,713,930 B2 | 5/2010 | Brunner-Schwarz et al. |
| 7,803,763 B2 | 9/2010 | Thurow et al. |
| 7,807,242 B2 | 10/2010 | Soerensen et al. |
| 7,918,833 B2 | 4/2011 | Veasey et al. |

(Continued)

FOREIGN PATENT DOCUMENTS

| AU | 200072263 | 2/2001 |
| CA | 1 258 427 | 8/1989 |

(Continued)

OTHER PUBLICATIONS

Amiel et al. ("Hypoglycemia in Type 2 Diabetes," Diabet. Med. 25, 245-254 (2008)) (Year: 2008).*
Brunton et al. ("Nocturnal Hypoglycemia: Answering the Challenge With Long-acting Insulin Analogs," MedGenMed. 2007; 9(2): 38, pp. 1-11. Published online May 1, 2007) (Year: 2007).*
Raslova et al. ("Insulin detemirand insulin aspart: a promising basal-bolus regimen for type 2 diabetes," Diabetes Research and Clinical Practice 66 (2004) 193-201) (Year: 2004).*
U.S. Appl. No. 15/162,563, filed May 23, 2016, Becker et al.
U.S. Appl. No. 14/624,575, filed Feb. 17, 2015, Becker et al.
U.S. Appl. No. 14/220,562, filed Mar. 20, 2014, Becker et al.
U.S. Appl. No. 13/310,118, filed Dec. 2, 2011, Becker et al.
U.S. Appl. No. 13/110,568, filed May 18, 2011, Becker et al.
Hallas-Moller, "The Lente Insulins", Diabetes 5:7-14 (Jan.-Feb. 1956).

(Continued)

*Primary Examiner* — Christina Bradley
(74) *Attorney, Agent, or Firm* — McDonnell Boehnen Hulbert & Berghoff LLP

(57) ABSTRACT

The application relates to an aqueous pharmaceutical formulation for use in the treatment of Type I or Type II Diabetes Mellitus, wherein the treatment reduces the risk of nocturnal hypoglycemia, said formulation comprising 200-1000 U/mL [equimolar to 200-1000 IU human insulin] of insulin glargine, with the proviso that the concentration of said formulation is not 684 U/mL of insulin glargine.

20 Claims, 15 Drawing Sheets

(56) References Cited

U.S. PATENT DOCUMENTS

| | | | |
|---|---|---|---|
| 7,977,310 | B2 | 7/2011 | Rosskamp et al. |
| 8,048,854 | B2 | 11/2011 | Habermann et al. |
| 8,084,420 | B2 | 12/2011 | Steiner et al. |
| 2003/0026872 | A1 | 2/2003 | Dake et al. |
| 2004/0235710 | A1 | 1/2004 | DeFelippis et al. |
| 2004/0048783 | A1 | 3/2004 | Brunner-Schwarz et al. |
| 2005/0106147 | A1 | 5/2005 | Jordan et al. |
| 2005/0171009 | A1 | 8/2005 | Brunner-Schwarz et al. |
| 2007/0128193 | A1 | 6/2007 | O'Neil et al. |
| 2007/0135338 | A1 | 6/2007 | O'Neil et al. |
| 2007/0237827 | A1 | 10/2007 | Sung et al. |
| 2008/0248999 | A1 | 10/2008 | Steiner |
| 2009/0088369 | A1 | 4/2009 | Steiness |
| 2009/0099064 | A1 | 4/2009 | Lougheed |
| 2009/0175840 | A1 | 7/2009 | Kashyap et al. |
| 2009/0176692 | A1 | 7/2009 | Habermann et al. |
| 2009/0214657 | A1 | 8/2009 | Qazi |
| 2009/0312236 | A1 | 12/2009 | Beals et al. |
| 2010/0029558 | A1 | 2/2010 | Bristow |
| 2010/0055049 | A1 | 3/2010 | Kuo et al. |
| 2010/0057194 | A1 | 3/2010 | Ryan |
| 2010/0069292 | A1 | 3/2010 | Pohl et al. |
| 2010/0069293 | A1 | 3/2010 | Bolotin et al. |
| 2011/0020294 | A1 | 1/2011 | Hammerman |
| 2011/0021423 | A1 | 1/2011 | Olsen et al. |
| 2011/0118178 | A1 | 5/2011 | Silvestre et al. |
| 2011/0118180 | A1 | 5/2011 | Silvestre et al. |
| 2011/0152185 | A1 | 6/2011 | Plum et al. |
| 2011/0230402 | A1 | 9/2011 | Johansen et al. |
| 2011/0236925 | A1 | 9/2011 | Hazra et al. |
| 2011/0281790 | A1 | 11/2011 | Pohl et al. |
| 2011/0301081 | A1* | 12/2011 | Becker .................. A61K 38/26 514/6.5 |
| 2012/0021978 | A1 | 1/2012 | Werner et al. |
| 2012/0121611 | A1 | 5/2012 | Lodie et al. |
| 2012/0122774 | A1 | 5/2012 | Becker et al. |
| 2012/0183616 | A1 | 7/2012 | Sprogoe et al. |
| 2012/0283179 | A1 | 11/2012 | Brunner-Schwarz et al. |
| 2012/0295846 | A1 | 11/2012 | Hagendorf et al. |
| 2012/0316108 | A1 | 12/2012 | Chen et al. |
| 2013/0012433 | A1 | 1/2013 | Rosskamp et al. |
| 2013/0096059 | A1 | 4/2013 | Stechl et al. |
| 2013/0178415 | A1 | 7/2013 | Soula |
| 2014/0206611 | A1 | 7/2014 | Becker et al. |

FOREIGN PATENT DOCUMENTS

| | | |
|---|---|---|
| CN | 1662252 A | 8/2005 |
| CN | 101454019 A | 6/2009 |
| DE | 102008053048 | 4/2010 |
| EA | 006019 | 8/2005 |
| EP | 0 200 383 | 11/1986 |
| EP | 2 389 945 | 11/2011 |
| EP | 2 329 848 | 10/2012 |
| EP | 2 387 989 | 7/2014 |
| JP | 2005-508895 | 4/2005 |
| JP | 2005-532365 | 10/2005 |
| RU | 2008-116057 | 10/2009 |
| WO | WO 83/00288 | 2/1983 |
| WO | WO 95/24183 | 9/1995 |
| WO | WO 00/23098 | 4/2000 |
| WO | WO 00/72582 | 11/2000 |
| WO | WO 01/04156 | 1/2001 |
| WO | WO 02/24214 | 3/2002 |
| WO | WO 02/076495 | 10/2002 |
| WO | WO 03/105888 | 12/2003 |
| WO | WO 2004/064862 | 8/2004 |
| WO | WO 2004/078196 | 9/2004 |
| WO | WO 2004/078197 | 9/2004 |
| WO | WO 2004/078198 | 9/2004 |
| WO | WO 2005/061222 | 7/2005 |
| WO | WO 2007/050656 | 5/2007 |
| WO | WO 2008/013938 | 1/2008 |
| WO | WO 2008/124522 | 10/2008 |
| WO | WO 2009/063072 | 5/2009 |
| WO | WO 2009/089181 | 7/2009 |
| WO | WO 2009/134380 | 11/2009 |
| WO | WO 2009/143014 | 11/2009 |
| WO | WO 2010/092163 | 8/2010 |
| WO | WO 2011/012719 | 3/2011 |
| WO | WO 2011/058082 | 5/2011 |
| WO | WO 2011/058083 | 5/2011 |
| WO | WO 2011/103575 | 8/2011 |
| WO | WO 2011/122921 | 10/2011 |
| WO | WO 2011/128374 | 10/2011 |
| WO | WO 2011/144673 | 11/2011 |
| WO | WO 2011/144674 | 11/2011 |
| WO | WO 2011/147980 | 12/2011 |
| WO | WO 2011/157402 | 12/2011 |
| WO | WO 2011/160066 | 12/2011 |
| WO | WO 2012/028172 | 3/2012 |
| WO | WO 2012/055967 | 5/2012 |
| WO | WO 2012/065996 | 5/2012 |
| WO | WO 2012/066086 | 5/2012 |
| WO | WO 2012/104342 | 8/2012 |
| WO | WO 2012/125569 | 9/2012 |

OTHER PUBLICATIONS

Heile & Schneider, "The Evolution of Insulin Therapy in Diabetes Mellitus", J Fam Pract 61(5 Suppl.):S6-12 (May 2012).

HOE 901/2004 Study Investigators Group, "Safety and efficacy of insulin glargine (HOE 901) versus NPH insulin in combination with oral treatment in Type 2 diabetic patients," Diabetic Medicine (2003), vol. 20, pp. 545-551, XP002671079.

Humalog-HumaPen (100U/mL, 3.0 mL)—EMA Community Register, pp. 1-41 (1997).

Humalog Vials—EMA Community Register pp. 1-81 (1997).

Insuman Infusat entry in Rote Liste, one page (2001).

Insuman Infusat; FASS Entry for Insuman Infusat; pp. 1-6 (Jan. 2000). English translation of Jun. 5, 2017, pp. 1-8 also submitted.

Johnson et al., "When is a unit of insulin not a unit of insulin? Detemir dosing in type 2 diabetes" 2008. http://professional.diabetes.org/ContenUPosters/2008/p8-LB.pdf; see entire poster, esp. "Background" section.

Jones, "Insulin Glargine Aventis Pharma", IDrugs 3(9):1081-87 (Sep. 2000).

Jones et al. "Surfactant-Stabilized Protein Formulations: A Review of Protein-Surfactant interactions and Novel Analytical Methodologies," Therapeutic Protein & Peptide Delivery, ACS Symposium Series; Chapter 12, pp. 206-222 (1997).

Jorgensen, K. H., et al., "Five fold increase of insulin concentration delays the absorption of subcutaneously injected human insulin suspension in pigs", Diabetes Research and Clinical Practice, 50:161-167 (2000).

Katakam et al., "Effect of Surfactants on the Physical Stability of Recombinant Human Growth Hormone" J Pharm Sci 84(6):713-16 (Jun. 1995).

Kielgast et al., "Treatment of type 1 diabetic patients with glucagon-like peptide-1 (GLP-1) and GLP-1R agonists." Curr Diabetes Rev. 5(4):266-75 (Nov. 2009).

Knee et al., "A Novel Use of U-500 Iunsulin for Continuous Subcutaneous Insulin Infusion in Patients With Insulin Resistance: A Case Series", Endocrine Practice, vol. 9, No. 3 May/Jun. 2003, pp. 181-186.

Lando, "The New 'Designer' Insulins", Clinical Diabetes, vol. 18, No. 4, Fall 2000, (http://journal.diabetes.org/clinical diabelesN18N42000/pg154.htm; accessed Oct. 22, 2013, pp. 1-13).

LANTUS® entry in Physician's Desk Reference; pp. 1-6 (2001).

LANTUS®—FDA Drug Approval Letter for LANTUS® (NDA 02-1081) at https://www.accessdata.fda.gov/scripts/cder/daf/index.cfm?event=overview.process&ApplNo=021081 (accessed Jan. 25, 2018), pp. 1-5.

LANTUS®—FDA Drug Approval Label for LANTUS® (NDA 02-1081) (Apr. 20, 2000) at https://www.accessdata.fda.gov/scripts/cder/daf/index.cfm?event=overview.process&ApplNo=021081 (accessed Jan. 25, 2018), pp. 1-14.

(56) References Cited

OTHER PUBLICATIONS

Lantus® 100U/ml solution for injection (insuline glargine); published in vol. 24 No. 9 of Pract. Diab. Int. Nov./Dec. 2007, p. 472.
LANTUS, FDA Prescribing Information, LANTUS (insulin glargine [rDNA origin] injection) solution for subcutaneous injection Initial U.S Approval: 2000, updated Jun. 2009, pp. 1-24.
LANTUS®—Prescribing Information as of Apr. 2000, pp. 1-16 (accessed from web archive dated Jan. 10, 2001).
Lee et al., "Effect of Brij-78 on Systemic Delivery of Insulin from an Ocular Device" J Pharm Sci 86(4):430-33 (Apr. 1997).
Lee et al., "Review on the Systemic Delivery of Insulin via the Ocular Route" Int'l J Pharmaceutics 233(1-2):1-18 (Feb. 2002).
Lee et al. "Comparison of Safety and Efficacy of Insulin Glargine and Neutral Protamine Hagedorn Insulin in Older Adults with Type 2 Diabetes Mellitus: Results from a Pooled Analysis," Journal of American Geriatrics Society, 60(1):51-59 (Jan. 2012).
Lougheed et al., "Insulin Aggregation in Artificial Delivery Systems" Diabetologia 19(1):1-9 (Jul. 1980).
Lougheed et al., "Physical stability of insulin formulations," Diabetes 32(5):424-32 (May 1983).
Manning et al., "Stability of Protein Pharmaceuticals," Pharm Research, 6(11):903-18 (Nov. 1989).
McKeage & Goa, "Insulin Glargine: A Review of its Therapeutic Use as Long-Acting Agent for the Management of Type 1 and Type 2 Diabetes Mellitus," Drugs 61(11):1599-1624 (Sep. 2001).
Mikhail, "Is liraglutide a useful addition to diabetes therapy?" Endocr Practice 16(6):1028-37 (Nov.-Dec. 2010).
Morwessel for Net Wellness, "Ask an Expert: Missed dose of glargine insulin," dated Jan. 23, 2006, pp. 1-3, accessed and downloaded on Apr. 20, 2016 from www.netwellness.uc.edu/question.cfm/35963.htm.
NCT01195454, NIH Clinical Trials, "Euglycemic clamp dose-response study comparing insulin glargine U300 with Lantus U100" last updated Sep. 3, 2010, pp. 1-3.
NCT01195454, NIH Clinical Trials, "Euglycemic clamp dose-response study comparing insulin glargine U300 with Lantus U100" last updated Dec. 13, 2010, pp. 1-4.
Organization for Economic Co-Operation and Development; OECD Principles of Good Laboratory Practice and Compliance Monitoring (as revised in 1997); ENV/MC/CHEM (98) 17; Jan. 21. 1998; pp. 1-41.
Owens et al., "Pharmacokinetics of 125I-labeled insulin glargine (HOE 901) in healthy men: comparison with NPH insulin and the influence of different subcutaneous injection sites." Diabetes Care 23(6):813-19 (Jun. 2000).
Peyrot et al., "Insulin adherence behaviours and barriers in the multinational Global Attitudes of Patients and Physicians in Insulin Therapy study," Diabet. Med. 29, 682-89 (Jan. 2012).
Profile of Lantus® (insulin glargine injection) 100 units/ml vs. NPH in patients with type 1 diabetes; https://www.lantus.com/hcp/aboutlantus/vs-nph, pp. 1-4, last accessed Feb. 19, 2016.
Request for "Type C" Meeting letter sent by Michael Lutz addressed to Mary Parks, dated Apr. 21, 2006, pp. 1-10.
Rosenstock et al., "Reduced Hypoglycemia Risk with Insulin Glargine: A meta-analysis comparing insulin glargine with human NPH insulin in type 2 diabetes" Diabetes Care 28(4):950-55 (Apr. 2005).
Rubin, "Adherence to pharmacologic therapy in patients with type 2 diabetes mellitus", The American Journal of Medicine, 118(5A):27S-34S (May 2005).
Russell-Jones, "Current developments in the treatment of diabetes: the incretin therapies" Br J Diabetes Vasc Dis. 10:21-30 (Feb. 2010).
Sampson, H.A., et al. Second Symposium on the definition and management of anaphylaxis: Summary report—Second National Institute of Allergy and Infectious Disease/Food Allergy and Anaphylaxis network symposium; J. Allergy Clin Immunol; Feb. 2006; pp. 391-397.
Sanofi's Lantus Draft Prescribing Information/Package Insert: (around the lime of U.S. FDA approval): NDA 21-081 Draft package insert (Sponsor revision #5) Date of submission: Apr. 20, 2000; see http://www.drugbank.ca/system/fds_labels/DB00047.pdf 1265922812; see entire document; esp. p. 1.
SANOFI Press Release entitled "FDA Accepts Sanofi's New Drug Application for Basal Insulin Toujeo®," dated Jul. 8, 2014, pp. 1-2.
SANOFI Press Release entitled "Sanofi Receives FDA Approval of Once-Daily Basal Insulin Toujeo®," dated Feb. 26, 2015, pp. 1-4.
Schmolka, "Poloxamers in the Pharmaceutical Industry" in Polymers for Controlled Drug Delivery, Chapter 10, pp. 189-214 (CRC Press) (1991).
Schubert-Zsilavecz et al., "Better blood sugar control in diabetics. Insulin glargin—a long acting insulin analogue," Pharmazie in UnsererZeit 30(2):125-30 (2001) With English translation.
Secnik Boye, Kristina et al., "Patient-reported outcomes in a trial of exenatide and insulin glargine for the treatment of type 2 diabetes," Health and Quality of Life Outcomes, vol. 4, No. 80, pp. 1-8 (Oct. 2006).
Shao et al., "Differential Effects of Anionic, Cationic, Nonionic and Physiologic Surfactants on the Dissociation, alpha-Chymotryptic Degradation, and Enteral Absorption of Insulin Hexamers," Pharmaceutical Research, 10(2):243-251 (1993).
Shi, "The Newest Handbook of Clinical Drugs" Military Medical Science Press, p. 809, (Jan. 2008). English translation submitted.
Sluzky et al., "Kinetics of insulin aggregation in aqueous solution upon agitation in the presence of hydrophobic surfaces," Proc Natl Sci USA 88(21):9377-81 (Nov. 1991).
http://diabetes.emedtv.com/lantus/generic-lantus.html.
18th World Health Congress (Helsinki). WMA Declaration of Helsinki—Ethical Principles for Medical Research Involving Human Subjects; WMA; pp. 1-8, Jun. 1964.
ADA—American Diabetes Association; Report of the Expert Committee on the Diagnosis and Classifcation of Diabetes Mellitus; Diabetes Care. vol. 21. Supplement 1, Jan. 1998; pp. S5-S19.
ADA Workgroup Report, "Defining and Reporting Hypoglycemia in Diabetes, A report from the American Diabetes Associate Workgroup on Hypoglycemia" Diabetes Care 28(2):1245-49 (May 2005).
Adis R&D Profile "Insulin Glargine: Glargine, HOE 71GT15, HOE 71GT80, HOE 901", Drugs R&D 2(2):107-109 (Aug. 1999).
Arnolds et al., "Insulin Glargine (GLAR) plus Metformin (MET): An Efficacious and Safe Regimen That Can Be Combined with Exenatide (EXE) or Sitagliptin (SIT A)," Diabetes, American Diabetes Association, vol. 58 abstract A141 (2009).
Ashford & Landi, "Stabilizing Properties of Tween 80 in Dilute Protein Solutions" Bull Parenteral Drug Assoc. 20(3):74-84 (May-Jun. 1966).
Aventis SEC Form 20-F; pp. 1-303 (Apr. 8, 2002).
Bam et al., "Tween protects recombinant human growth hormone against agitation-induced damage via hydrophobic interactions" J. Ph. Sci. 87(12):1554-59 (Dec. 1998).
Bam et al., "Stability of Protein Formulations: Investigation of Surfactant Effects by a Novel EPR Spectroscopic Technique," Pharmaceutical Research, 12(1):2-11 (Jan. 1995).
Barnett et al., "Tolerability and efficacy of exenatide and titrated insulin glargine in adult patients with type 2 diabetes previously uncontrolled with metformin or a sulfonylurea: a multinational, randomized, open-label, two-period, crossover noninferiority trial." Clinical Therapeutics 29(11):2333-48 (Nov. 2007).
Bates et al., "Kinetics of hydrolysis of polyoxyethylene (20) sorbitan fatty acid ester surfactants," J. Pharmacy and Pharmacology 25(6):470-77 (Jun. 1973).
Berchtold & Hilgenfeld, "Binding of Phenol to R6 Insulin Hexamers" Biopolymers 51(2):165-72 (1999).
Bettley, "The Toxicity of Soaps and Detergents" Br. J. Derm., 80:635-642 (1968).
Brange et al., "Toward Understanding Insulin Fibrillation," J Pharm Sciences 86(5):517-25 (May 1997).
Brange & Langkær, "Insulin Structure and Stability", in Stability and Characterization of Protein and Peptide Drugs, Case Histories Chapter 11, 315-50 (vol. 5 of Pharmaceutical Biotechnology) (eds. Y.J. Wan Wang and R. Pearlman) (Plenum Press, New York) (1993).
Brod et al., "Adherence patterns in patients with type 2 diabetes on basal insulin analogues: missed, mistimed and reduced doses," Current Medical Research & Opinion 28(12): 1933-46 (Nov. 2012).

(56) References Cited

OTHER PUBLICATIONS

Buse et al., "Use of twice-daily exenatide in Basal insulin-treated patients with type 2 diabetes: a randomized, controlled trial." Annals of Internal Medicine 154(2):103-12 (Jan. 2011).
Chatterjee et al., "Insulin glargine and its place in the treatment of Types 1 and 2 diabetes mellitus." Expert Opin Pharmacother 7(10): 1357-71 (2006).
Chawla et al., "Aggregation of Insulin, Containing Surfactants, in Contact with Different Materials", Diabetes 34(5):420-24 (May 1985).
Christensen, "Lixisenatide, a Novel GLP-1 Receptor Agonist for the Treatment of Type 2 Diabetes Millitus," I Drugs, (Aug. 2009), vol. 12, No. 8, pp. 503-513.
Cochran & Gorden, "Use of U-500 insulin in the treatment of severe insulin resistance" Insulin, 3(4):211-218 (Oct. 2008).
Cochran et al., "The Use of U-500 in Patients with Extreme Insulin Resistance" Diabetes Care, 28(5):1240-44 (May 2005).
Coling et al., "Therapy with insulin glargine (Lantus) in toddlers, children and adolescents with type 1 diabetes," Diabetes Research and Clinical Practice (2005), vol. 70, pp. 1-7.
Cramer & Pugh, "The Influence of Insulin Use on Glycemic Control How well do adults follow prescriptions for insulin?" Diabetes Care, 28(1):78-83 (Jan. 2005).
Drasto et al., "Insulin U-500 in severe insulin resistance in type 2 diabetes mellitus" Post-Graduate Medical Journal 85(1002):219-222 (Apr. 2009).
Database, Adiscti, "A randomized, 4-sequence, cross-over, double bind, dose response study of 0.4, 0.6 and 0.09 U/kg insulin glargine U300 compared to 0.4 U/kg Lantus U100 in patients with diabetes mellitus type I using euglycemic clamp technique" last updated Dec. 16, 2010, pp. 1-4.
Davies et al., "Real-world factors affecting adherence to insulin therapy in patients with Type 1 or Type 2 diabetes mellitus: a systematic review", Diabetic Medicine, 30:512-524 (2013).
De Le Pena, "Pharmacokinetics and Pharmadynamics of High-Dose Human Regular U-500 Insulin Versus Human Regular U-1 00 Insulin in Healthy Obese Subjects" Diabetes Care, 34(12):2496-501 (2011).
Derewenda et al., "Phenol Stabilizes More Helix in a New Symmetrical Zinc Insulin Hexamer" Nature 338 (6216):594-96 (Apr. 1989).
Drug Facts and Comparison; J. B. Lippincot Company, St. Louis, MO; pp. 1781-1790 (1988).
EMEA Public Statement on Insuman Infusat (Feb. 14, 2000), at http://www.ema.europa.eu/ema/index.jsp?curl=pages/news_and_events/news/2010/08/news_detail_001094.jsp&mid=WC0b01ac058004d5c1 (accessed Jun. 1, 2017); pp. 1-2.
European Medicines Agency—Science Medicines Health, "Guideline on clinical investigation of medicinal products in the treatment of diabetes mellitus" Committee for Medicinal Products for Human Use, Jan. 20, 2010, pp. 1-19.
European Medicines Agency—Science Medicines Health, "Toujeo" EPAR Summary for the public, first published Nov. 5, 2009, pp. 1-3.
European Medicines Agency, "Toujeo (previously Optisulin) insulin glargine," <http://www.ema.europa.eu/ema/index.jsp?curl=pages/medicines/human/medicines/000309/human_med_000955.jsp&mid=WCOb01ac058001d124>, last updated Jan. 25, 2016, visited Feb. 3, 2016, pp. 1-6—screenshot of "About" tab of webpage and printouts of "About" tab of webpage with listed items collapsed and expanded.
European Public Assessment Report (EPAR) Optisulin EPAR summary for the public. Last updated Feb. 2009; pp. 1-3. (submitted as Exhibit A on Mar. 10, 2016).
Ex Parte Herrmann, Appeal No. 2009-001777 U.S. Appl. No. 10/616,457 (B. PAI. Nov. 13, 2009).
Excerpts from "Handbook of Pharmaceutical Excipients" 2nd Edition (eds. A. Wade and P.J. Weller) American Pharmaceutical Association, Washington, The Pharmaceutical Press, London; pp. 1-55 (1994).
Feinglos et al., "Effects of liraglutide (NN2211 ), a long-acting GLP-1 analogue, on glycaemic control and bodyweight in subjects with type 2 diabetes." Diabetic Medicine, 22(8): 1016-23 (Jul. 2005).
FDA, "Guidance of Industry—Bioequivalence studies with pharmacokinetic endpoints for drugs submitted under an ANDA" Draft Guidance by the U.S. Department of Health and Human Services, Food and Drug Administration, Center for Drug Evaluation and Research (CDER), Dec. 2013, pp. 1-24.
Fieller, E. C. Symposium on Interval Estimation; Some Problems with Interval Estimation; No. 2; 1954; pp. 175-185.
Garnero, "Adjusting Your Insulin Dose," JoslinEZstart Resource Manual, pp. 1-3 (2006).
Gatlin & Gatlin, "Formulation and Administration Techniques to Minimize Injection Pain and Tissue Damage Associated with Parenteral Products" in Injectable Drug Development, Chapter 17; pp. 401-421 (eds. P.K. Gupta and G.A. Brazeau) (CRC Press) (1999).
Garg, R., et al., "U-500 insulin: why, when and how to use in clinical practice", Diabetes/Meiabolism Research and Reviews, 23:265-268 (2007).
Gillies et al., "Insulin Glargine" Drugs 59(2):253-60 (Feb. 2000).
Glasgow Diabetes Managed Clinical Network, "Guidelines for Insulin Initiation and Adjustment in Primary Care in patients with Type 2 Diabetes: for the guidance of Diabetes Specialist Nurses" Guidelines revised and updated Jan. 2010, Review Jan. 2012, pp. 1-37.
Gough, K. et al.; Assessment of Dose Proportionality: Report from the Statisticians in the Pharmaceutical Industry/Pharmacokinetics UK Joint Working Party; Drug Information Journal, vol. 29, 1995, pp. 1039-1048.
Goykhman et al., "Insulin Glargine: a review 8 years after its introduction." Expert Opin. Pharmacother. 10(4):705-18 (2009).
Grau & Saudek, "Stable Insulin Preparation for Implanted Insulin Pumps", Diabetes 36(12):1453-59 (Dec. 1987).
Gualandi-Signorini & Giorgi, "Insulin formulations—a review" European Review for Medical and Pharmacological Sciences 5:73-83 (2001).
Soeborg et al., "Absorption kinetics of insulin after subcutaneous administration" European Journal of Pharmaceutical Sciences 36(1)178-90 (Jan. 2009; Epub Nov. 5, 2008).
Starkova, ed., "Clinical Endocrinology", Guide for physicians, Moscow, "Medicine", 1991, p. 192-262.
Strickley, "Review Article: Solubilizing Excipients in Oral and Injectable Formulations," Pharmaceutical Research 21(2):201-230 (Feb. 2004).
Tang, "Biotech Drugs—Introduction and Practice Handbook" Chemical Industry Press, pp. 635-636, (Jan. 2008). English translation submitted.
Tang, "Biotech Drugs—Introduction and Practice Handbook" Chemical Industry Press, pp. 635-642 (Jan. 2008). English translation of pp. 635-636 submitted.
Tews et al., "Enhanced Protection against Cytokine- and Fatty Acid-induced Apoptosis in Pancreatic Beta Cells by Combined Treatment with Glucagon-like Peptide-1 Receptor Agonists and Insulin Analogues," Hormone and Metabolic Research 40(3): 172-80 (2008).
Thurow & Geisen, "Stabilisation of dissolved proteins against denaturation at hydrophobic interfaces", Diabetologia 27(2):212-18 (Aug. 1984).
Tomizawa & Kondo, "Mechanism of hemolysis by anionic surface-active agents," Kolloid-Z. u. Z. Polymere 246:694-99 (1971).
Wafa et al., "Use of U-500 Regular Insulin in Type 2 Diabetes", Diabetes Care, 29(9):2175-2176 (2006).
Wang, "Instability, Stabilization and Formulation of Liquid Protein Pharmaceuticals," Int'l J Pharm, 185(2):129-88 (Aug. 1999).
Werner et al., "Pharmacological profile of lixisenatide: A new GLP-1 receptor agonist for the treatment of type 2 diabetes." Regulatory Peptides 164(2-3):58-64 (Epub Jun. 2, 2010).
Werner et al., "Insulin Glargine U-100 Has a Favourable Time-Action Profile Compared to U-40 or NPH Insulin in Healthy, Normoglycaemic Dogs", Poster-Abstract 37th Annual Meeting of Endocrine Society of India, Tirupati, A.P., India ESICON (2007) (2 pages including Abstract and Poster).

(56) References Cited

OTHER PUBLICATIONS

Yki-Jarvinen et al., "Insulin glargine or NPH combined with metformin in type 2 diabetes: the LANMET study," (2006), vol. 49, No. 3, pp. 442-451.
Final Rejection issued in U.S. Appl. No. 13/110,568; dated Feb. 21, 2013, pp. 1-20.
Non-Final Rejection issued in U.S. Appl. No. 13/110,568; dated Mar. 19, 2012, pp. 1-18.
Non-Final Rejection issued in U.S. Appl. No. 13/310,118, dated Mar. 25, 2015, pp. 1-15.
Non-Final Rejection issued in U.S. Appl. No. 13/310,118, dated Mar. 29, 2013, pp. 1-21.
Final Rejection issued in U.S. Appl. No. 13/310,118; dated Aug. 2, 2012, pp. 1-20.
Non-Final Rejection issued in U.S. Appl. No. 13/310,118; dated Mar. 19, 2012, pp. 1-19.
Non-Final Rejection issued in U.S. Appl. No. 14/220,562; dated Apr. 8, 2015, pp. 1-18.
Non-Final Rejection issued in U.S. Appl. No. 14/624,575; dated Mar. 26, 2015, pp. 1-14.
Non-Final Rejection issued in U.S. Appl. No. 15/162,563; dated Feb. 8, 2017, pp. 1-13.
Final Rejection issued in U.S. Appl. No. 15/162,563; dated Aug. 9, 2017, pp. 1-13.
Final Rejection issued in U.S. Appl. No. 15/162,563; dated Dec. 18, 2017, pp. 1-16.
Final Rejection issued in U.S. Appl. No. 15/162,563; dated Apr. 17, 2018, pp. 1-16.
Final Rejection issued in U.S. Appl. No. 15/162,563; dated Oct. 1, 2018, pp. 1-16.
European Search Report in European Application No. 11 16 6415, dated Mar. 12, 2012, pp. 1-12.
European Search Report in European Application No. 10 30 5780, dated Nov. 16, 2010, pp. 1-3.
Extended European Search Report in European Application No. 13 30 5432.0; dated Sep. 6, 2013, pp. 1-5.
European Search Report in European Application No. 13 29 0188.5; dated Jan. 7, 2014, pp. 1-3.
European Search Report in European Application No. 13 30 6412.1; dated Mar. 6, 2014, pp. 1-2.
Extended European Search Report in European Application No. 14 16 6877.2; dated Aug. 18, 2014, pp. 1-6.
Extended European Search Report from European Application No. EP 18 15 5758; dated Oct. 15, 2018, pp. 1-4.
International Search Report in International Application No. PCT/EP2011/058079, dated Mar. 22, 2012, pp. 1-6 (submitted as WO 2011/144673 A3).
Written Opinion of the International Searching Authority for International Application No. PCT/EP2011/058079, dated Mar. 22, 2012, pp. 1-8.
International Search Report and Written Opinion of the International Searching Authority in International Application No. PCT/EP2014/056498; dated Jun. 25, 2014, pp. 1-10.
English translation of Search Report for Chinese Patent Application No. 20140220537.9; dated Feb. 13, 2015, pp. 1-2.
Search Report in Chinese Patent Application No. 201410818149.0; dated Jan. 10, 2017, pp. 1-3. English translation submitted.
Chandran et al., "Have Insulin, Will Fly: Diabetes Maganement During Air Travel and Time Zone Adjustmetn Strategies" Clinical Diabetes 21(2):82-85 (2003).
Cogen, Fran, Traveling With Diabetes; pp. 1-6; Apr. 14, 2009; www.healthcentral.comjarticlejtraveling-with-diabetes.
Definition of the term "week" from Wikipedia—one page, last updated Mar. 2020.
Definition of the term "bioequivalence" from Wikipedia—5 pages, last updated Mar. 2020.
EMA—Summary of product characteristics for Toujeo 300 units/ml insulin glargine, annex I; 18 pages; 2020.
Jonassen et al. "Design of the Novel Protraction Mechanisms of Insulin Degludec, an Ultra-long-Acting Basal Insulin" Parm. Res. 29:2104-2114 (2012).
Joslin Clinic 2012 Guideline http://www.joslin.org/policies and procedures.HTML 3 pages; 2012.
LANTUS—Annex I—Summary of Product Characteristics—2 pages, 2012.
Mathieu et al., Efficacy and Safety of Insulin Degludec in a Flexible Dosing Regimen vs Insulin Glargine in patients with Type I Diabetes (BEGIN: Flex T1): A 26-week randomized, treat-to-target trial with a 26-week extension J. Clin. Endo. Metab. 98(3):1154-62 (Mar. 2013).
Meneghini et al., "The Efficacy and Safety on Insulin Degludec given in Variable once-daily dosing intervals campared with insuline glargine and insulin degludec dosed at the same time daily" Diabetes Care 36:858-64 (2013).
Metha et al., Contemporary Management of Patients with Type I Diabetes; in: Schatz et al.: Type I Diabetes, An Issue of Endocrinology and Metabolism Clinics of North America, vol. 39(3); Elsevier Inc., Sep. 2010, pp. 573-593.
Owens et al., "Beyond the Era of NPH Insulin—Long-Acting Insulin Analogs; Chemistry, Comparative Pharmacology, and Clinical Application," Diabetes Tech. & Ther., 10(5):333-349 (2008).
Rosenstock et al., "Basal Insulin Glargine (HOE 901) Versus NHP Insulin in Patients with Type I Diabetes on Multiple Daily Insulin Regimens" Diabetes Care 23(8):1137-42 (Aug. 2000).

* cited by examiner

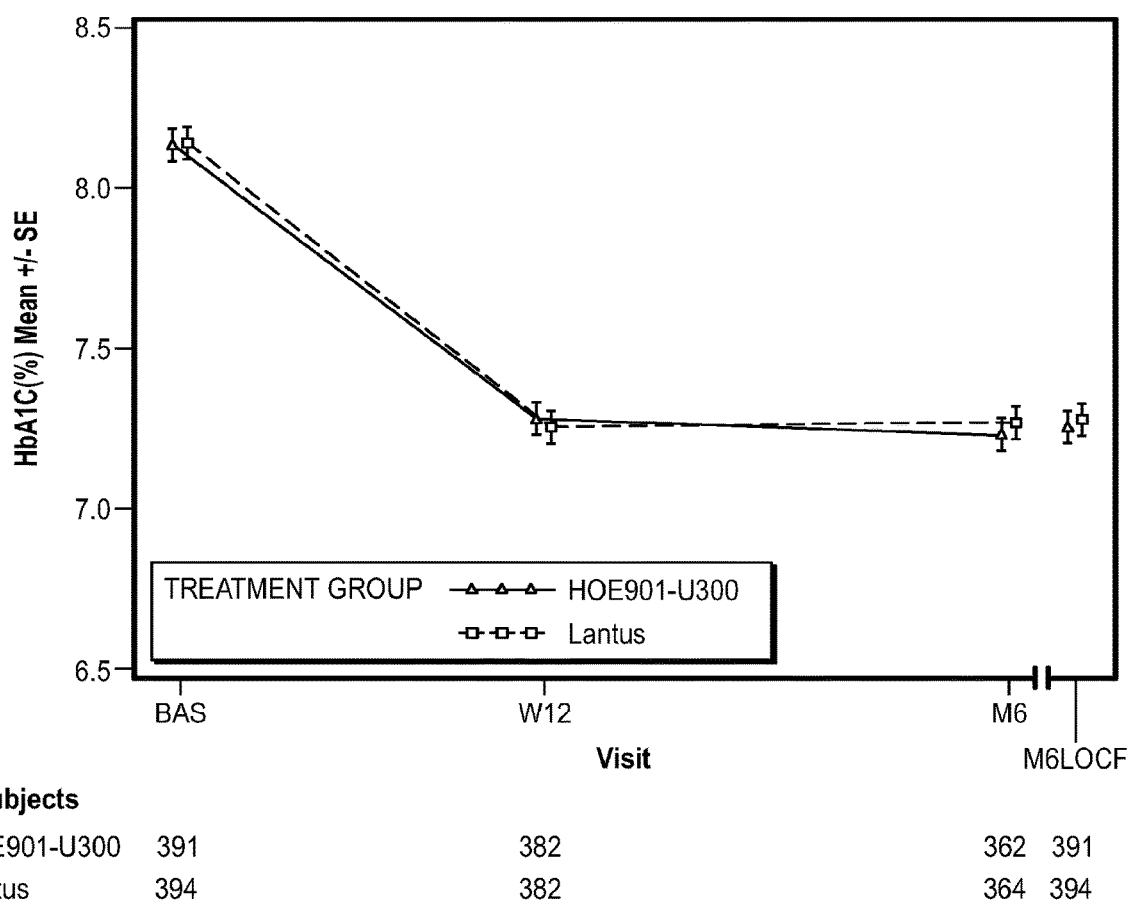
Figure 1 - Main efficacy analysis - Mean HbA1c (%) by visit during the main 6-month on-treatment period - mITT population

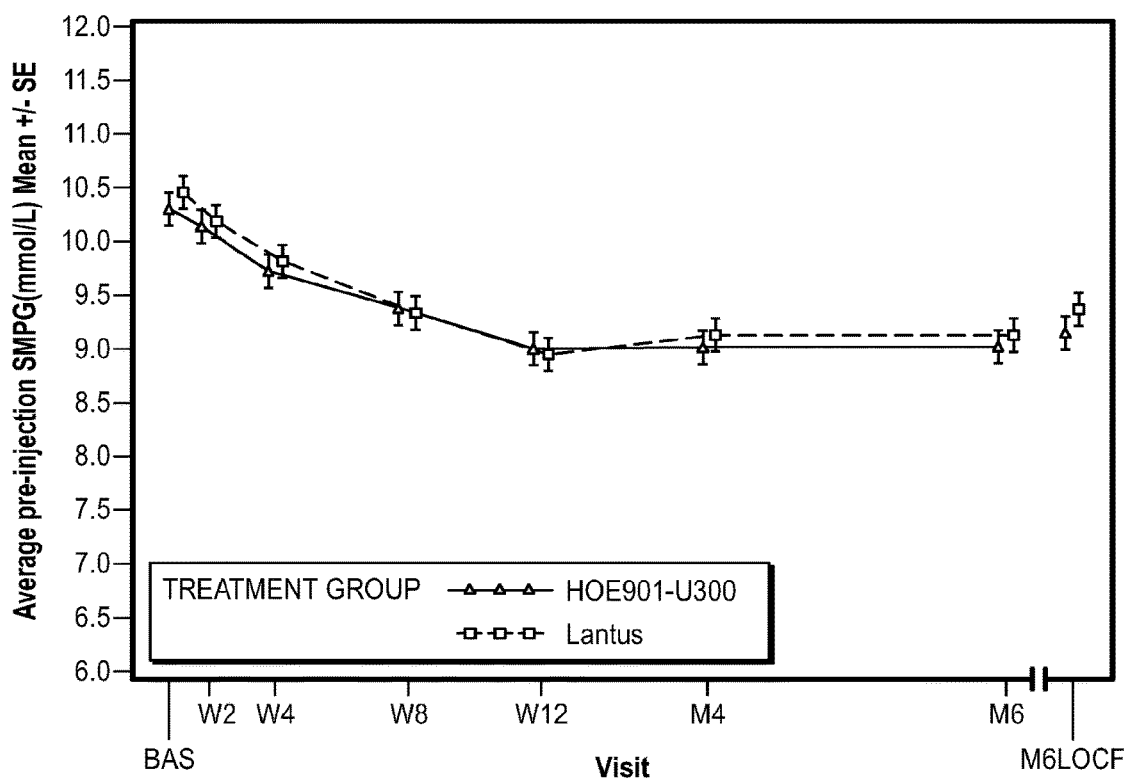
Figure 2 -Other secondary efficacy endpoints - Mean average pre-injection SMPG (mmol/L) by visit during the main 6-month on-treatment period -mITT population

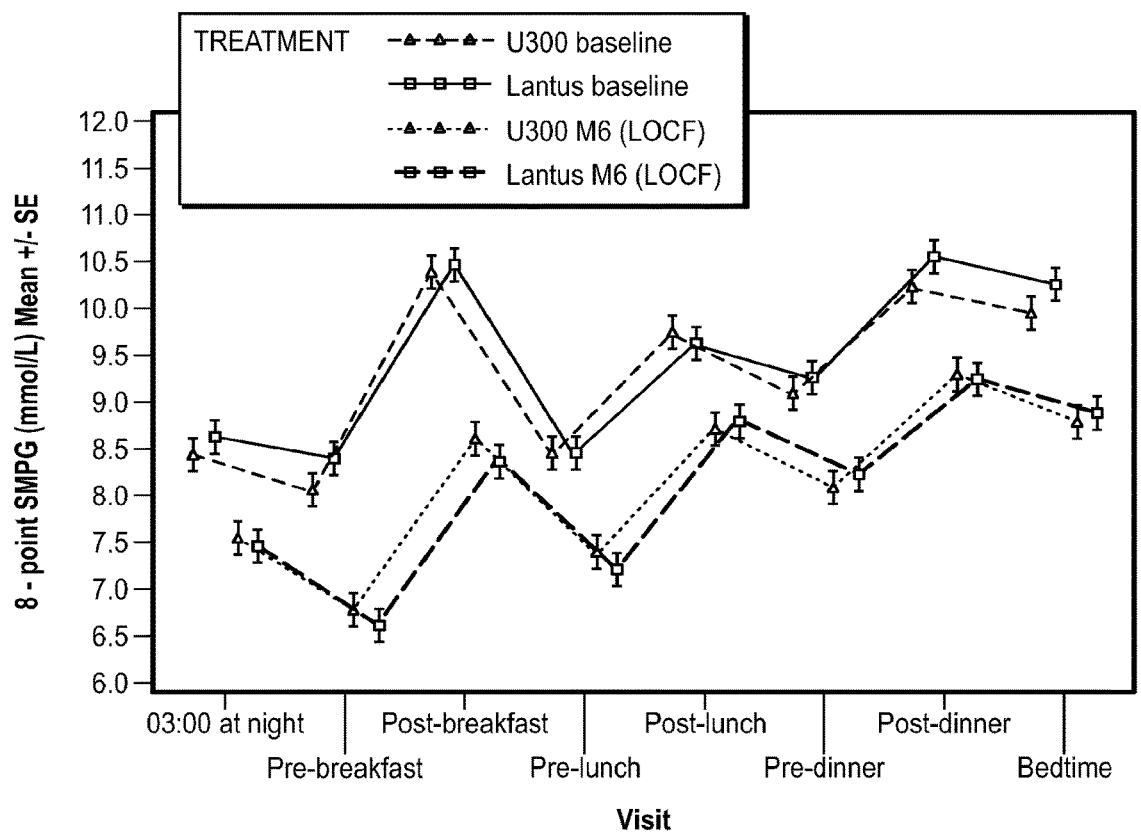
Figure 3 - Other secondary efficacy endpoints - Mean 8-point SMPG profile (mmol/L) at baseline and Month 6 endpoint - mITT population Figure 4 - Other secondary efficacy endpoints - Average daily basal insulin and mealtime insulin dose (U) by visit during the main 6-month on-treatment period- mITT population
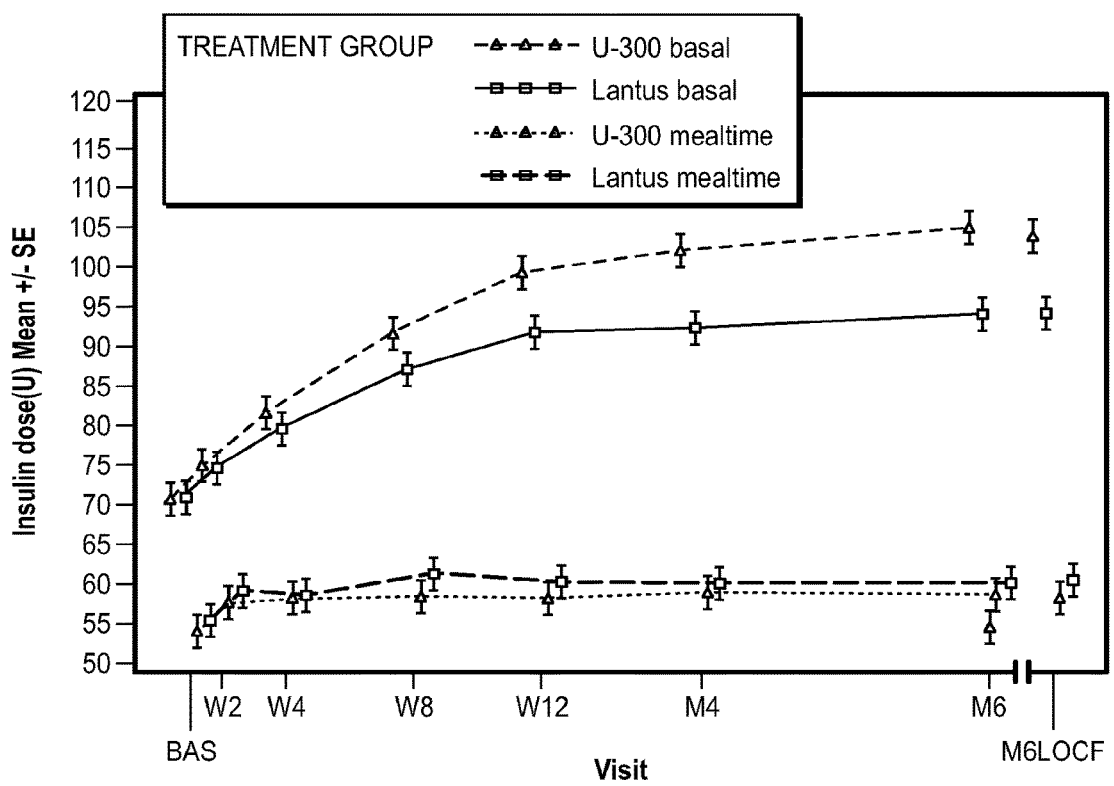

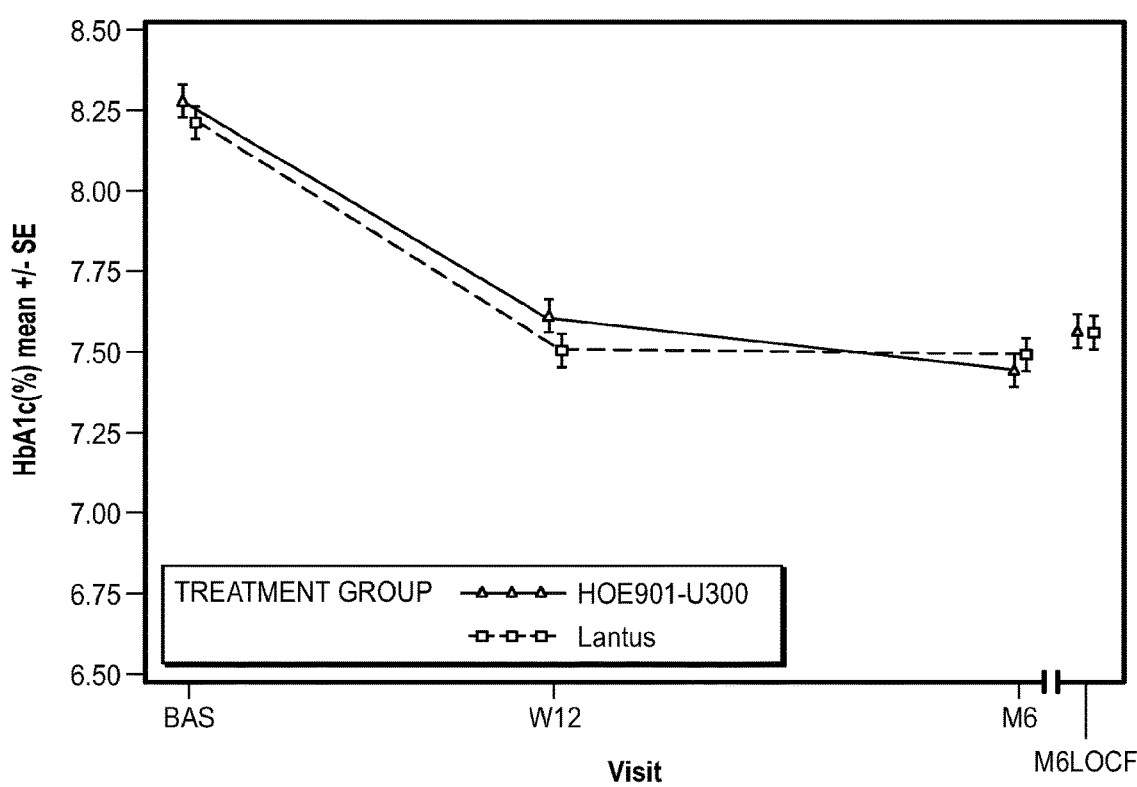
Figure 5 - Main efficacy analysis - Mean HbA1c (%) by visit during the main 6-month on-treatment period - mITT population

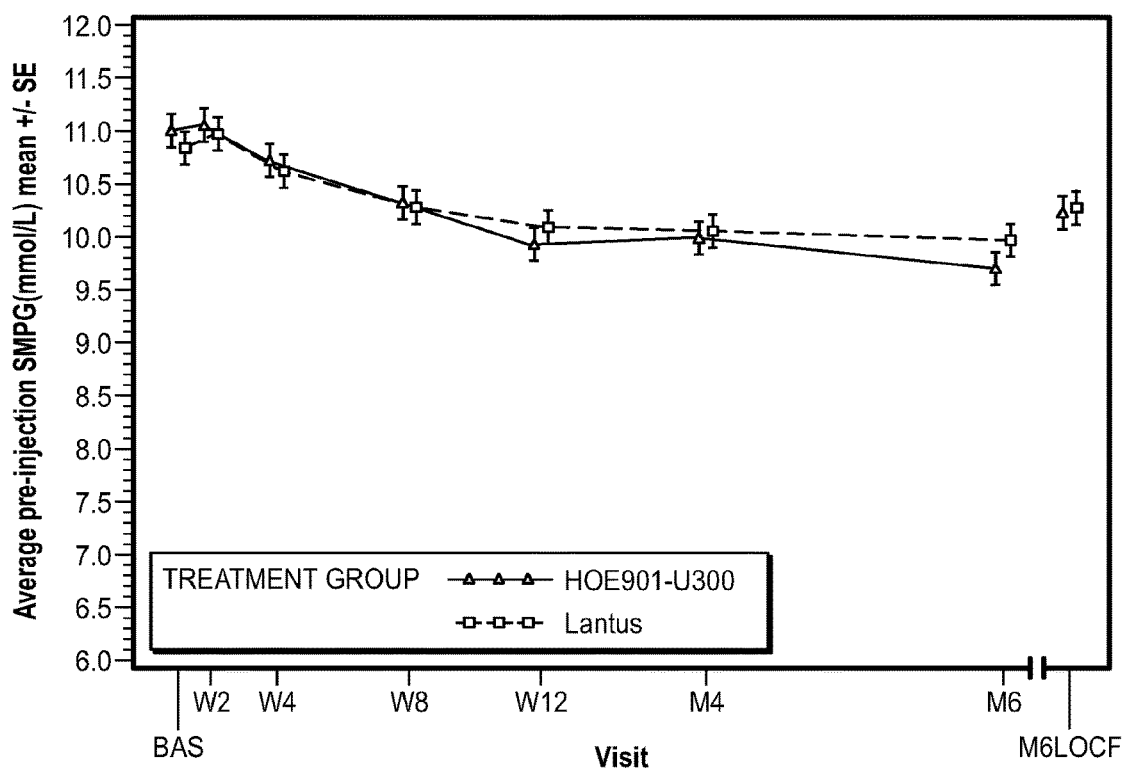
Figure 6 - Other secondary efficacy endpoints - Mean average pre-injection SMPG (mmol/L) by visit during the main 6-month on-treatment period - mITT population

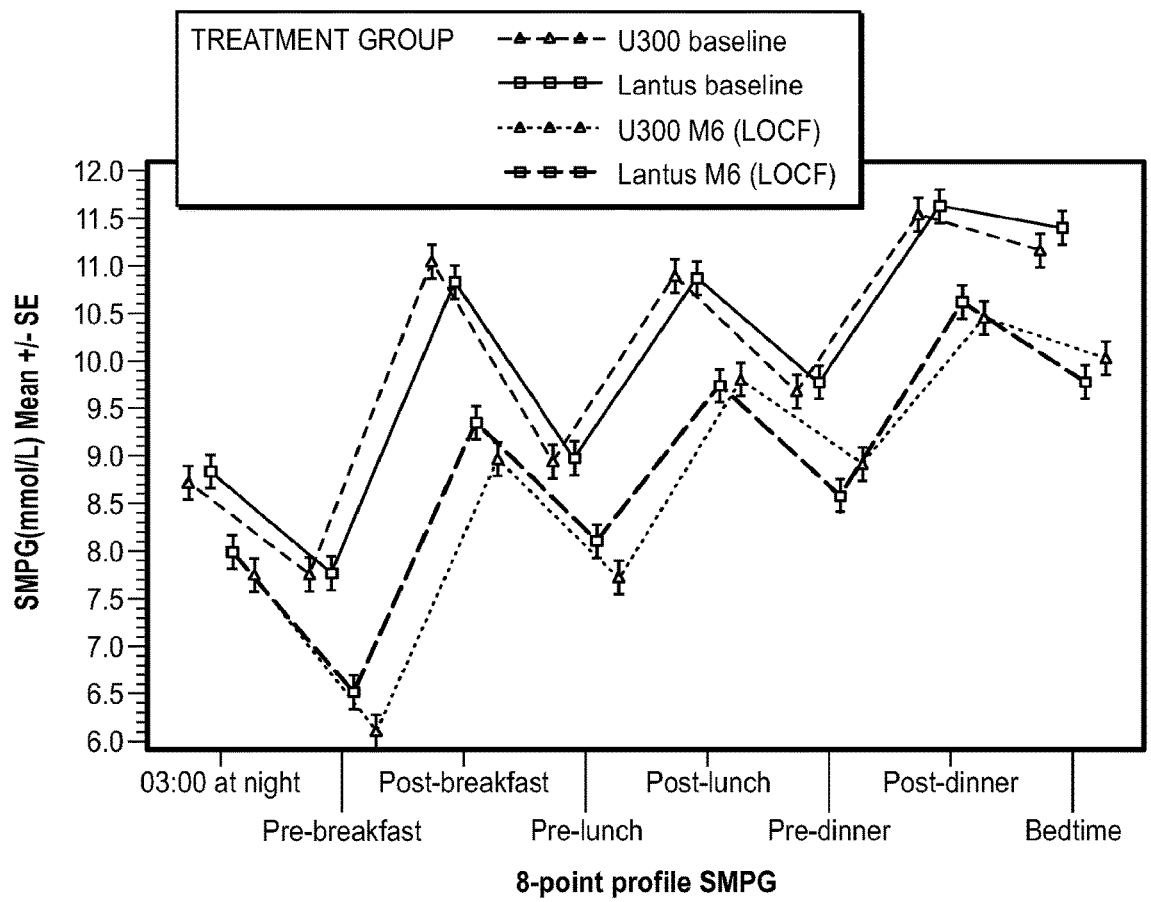
Figure 7 - Other secondary efficacy endpoints - Mean 8-point SMPG profile (mmol/l) at baseline and Month 6 endpoint - mITT population
| # subjects | | | | | | | | |
|---|---|---|---|---|---|---|---|---|
| U300baseline | 338 | 347 | 341 | 344 | 339 | 347 | 338 | 325 |
| Lantusbaseline | 328 | 338 | 328 | 332 | 328 | 336 | 327 | 303 |
| U300M6(LOCF) | 338 | 347 | 341 | 344 | 339 | 347 | 338 | 325 |
| LantusM6(LOCF) | 328 | 338 | 328 | 332 | 328 | 336 | 327 | 303 |

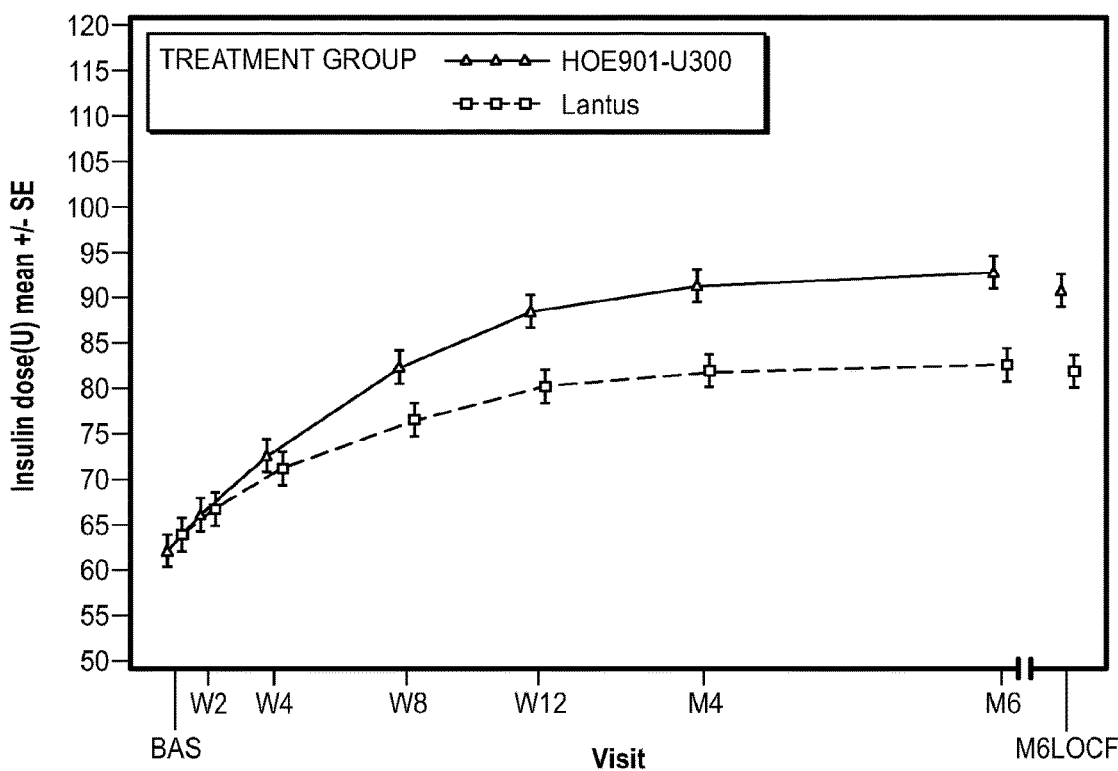
Figure 8 - Other secondary efficacy endpoints - Average daily basal insulin dose (U) by visit during the main 6-month on-treatment period - mITT population

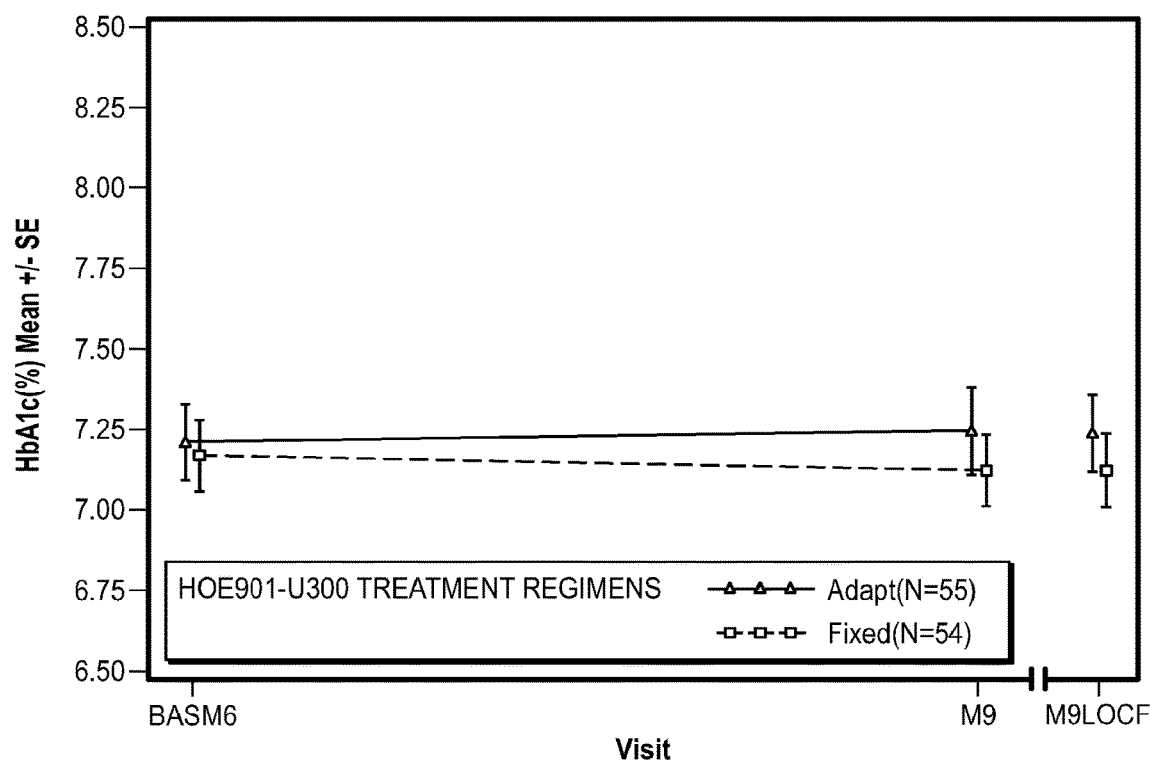
Figure 9 - Main efficacy analysis - Mean HbA1c (%) by visit during the 3-month comparative regimen period - mITT sub-study population

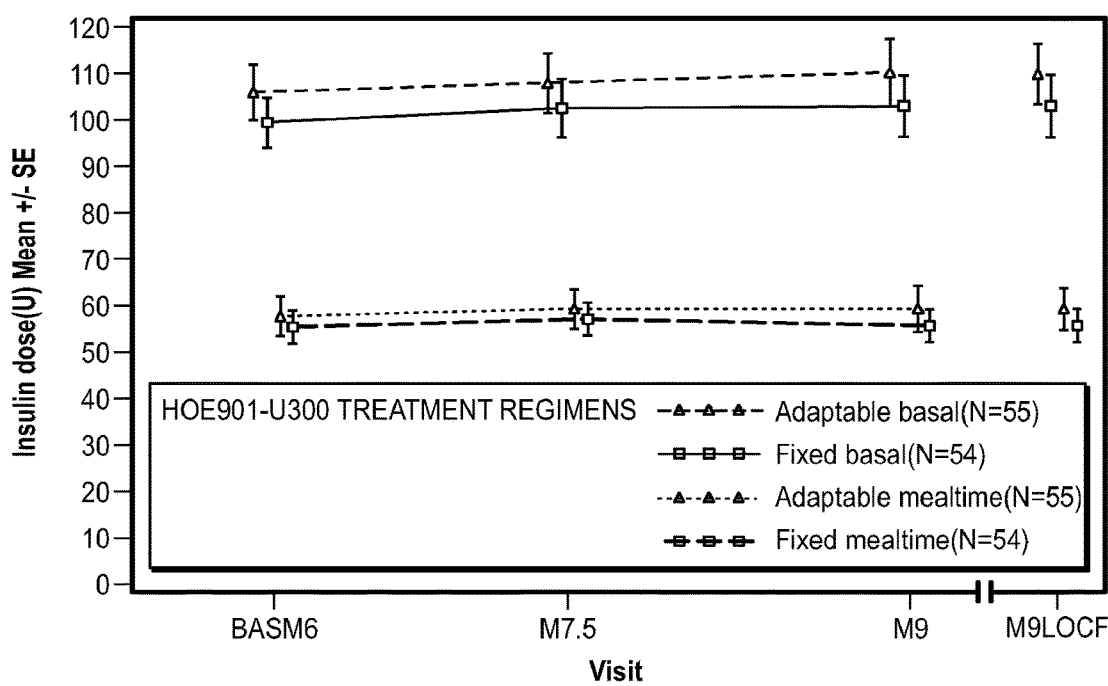
Figure 10 - Average daily basal (glargine) and mealtime insulin dose (U) by visit during the 3-month comparative regimen period - mITT sub-study population

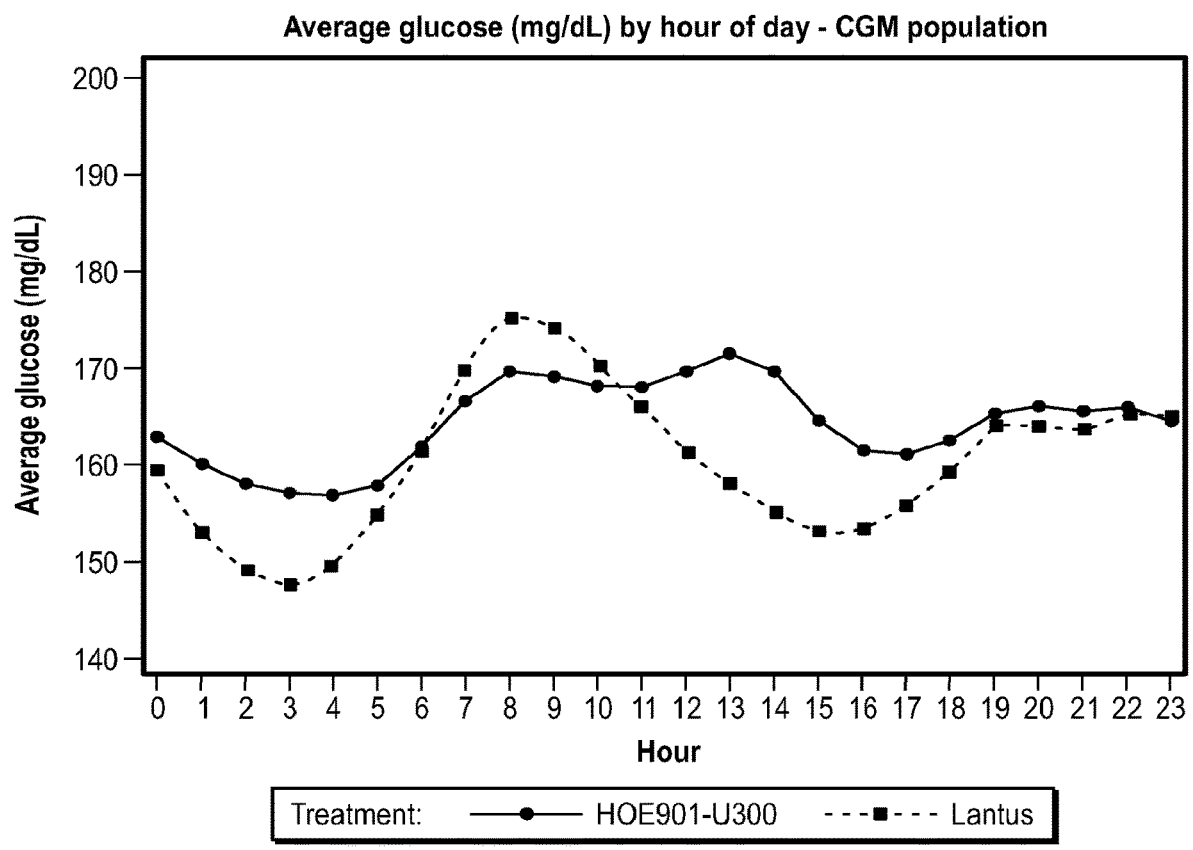
Figure 11 - Plot of average glucose (mg/dL) by hour of day during entire treatment period - CGM population

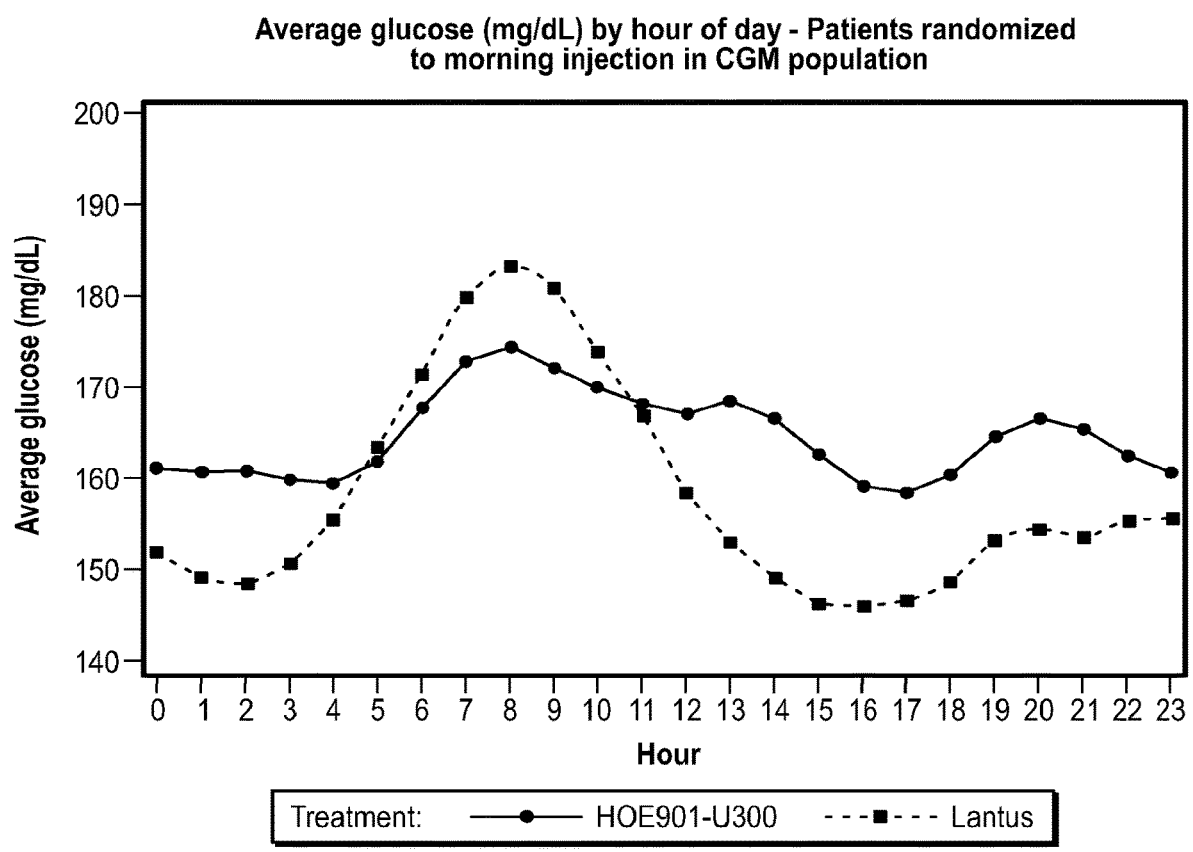
Figure 12 - Plot of average glucose (mg/dL) by hour of day during entire morning injection period - CGM population

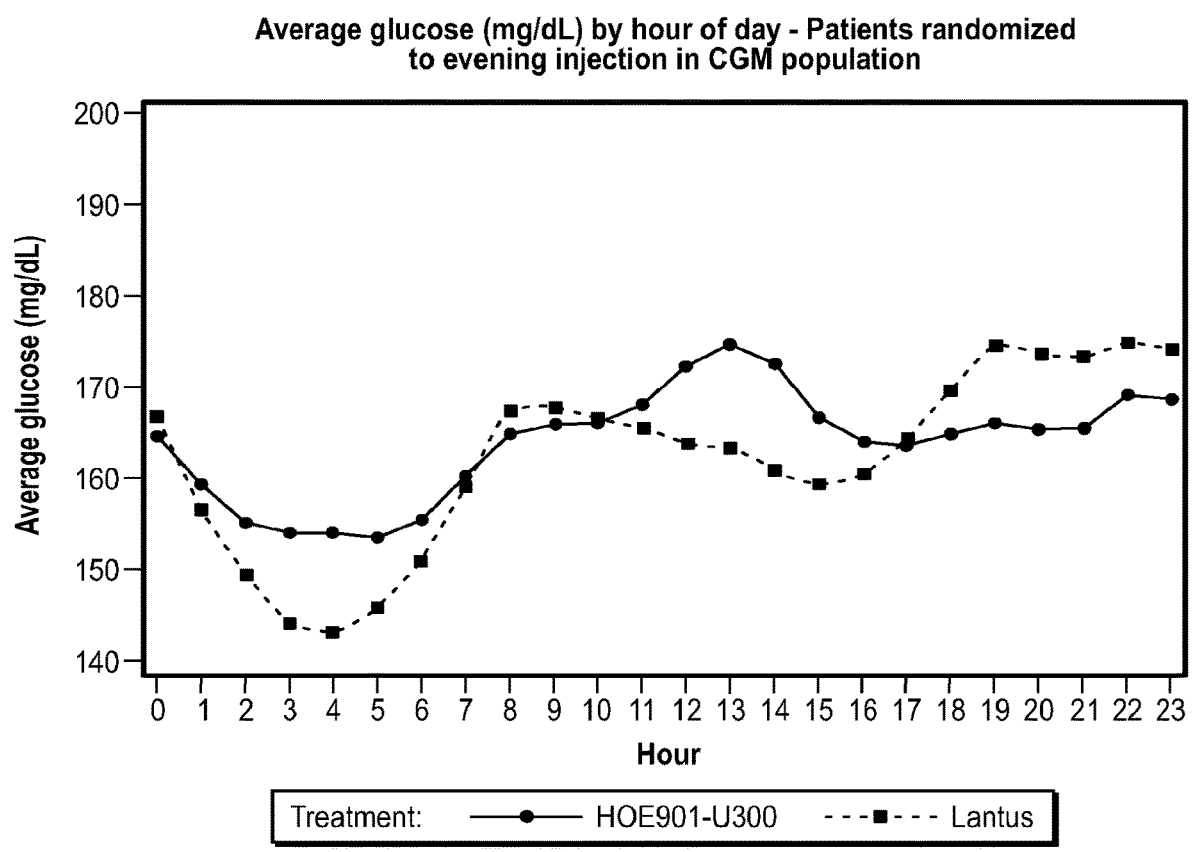
Figure 13 - Plot of average glucose (mg/dL) by hour of day during entire evening injection period - CGM population

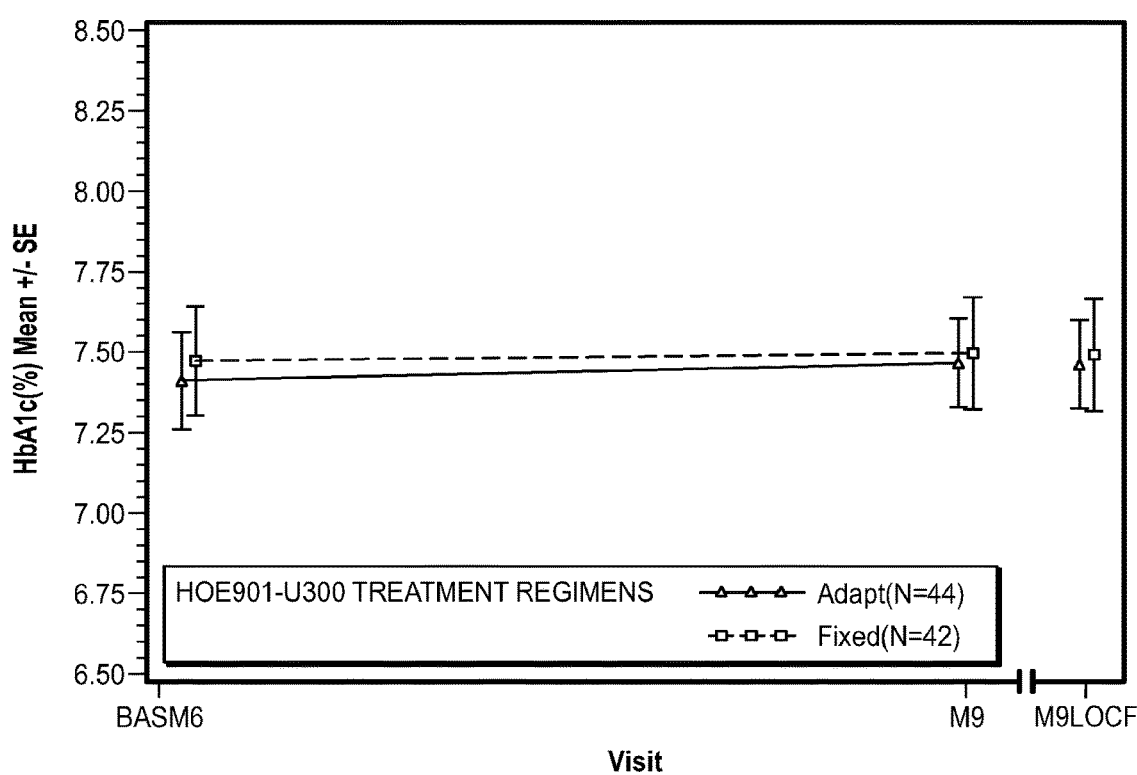
Figure 14 - Main efficacy analysis - Mean HbA1c (%) by visit during the 3-month comparative regimen period - mITT sub-study population

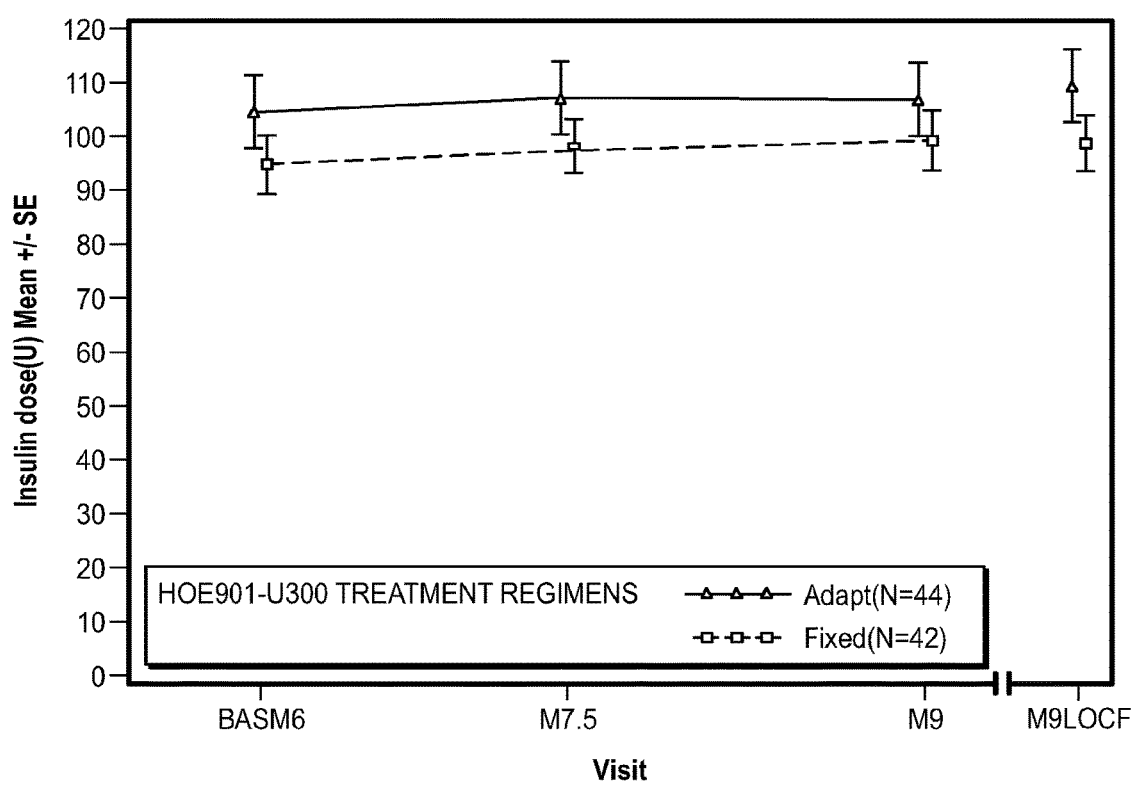
Figure 15 - Average daily basal (glargine) insulin (U) by visit during the 3-month comparative regimen period - mITT sub-study population

TREATMENT OF DIABETES MELLITUS BY LONG-ACTING FORMULATIONS OF INSULINS

This application is continuation of U.S. patent application Ser. No. 16/117,310, filed Aug. 30, 2018, which is continuation of U.S. patent application Ser. No. 14/781,857, filed Oct. 1, 2015, which is a national stage application under 35 U.S.C. § 371 of International Application No. PCT/EP2014/056498, filed Apr. 1, 2014, which claims the benefit of European Patent Application No. 13305432.0, filed Apr. 3, 2013, European Patent Application No. 13290188.5, filed Aug. 8, 2013, and European Patent Application No. 13306412.1, filed Oct. 15, 2013 the disclosures of each of which are explicitly incorporated by reference herein.

The application relates to an aqueous pharmaceutical formulation for use in the treatment of Type I or Type II Diabetes Mellitus, wherein the treatment reduces the risk of nocturnal hypoglycemia, said formulation comprising 200-1000 U/mL [equimolar to 200-1000 IU human insulin] of insulin glargine, with the proviso that the concentration of said formulation is not 684 U/mL of insulin glargine.

Insulin glargine is $31^B$-$32^B$-Di-Arg human insulin, an analogue of human insulin, with further substitution of asparagine in position A21 by glycine.

WO2008/013938 A2 discloses an aqueous pharmaceutical formulation comprising insulin glargine at a concentration of 684 U/mL.

Metformin is a biguanide hypoglycemic agent used in the treatment of non-insulin-dependent diabetes mellitus (diabetes mellitus type 2) not responding to dietary modification. Metformin improves glycemic control by improving insulin sensitivity and decreasing intestinal absorption of glucose. Metformin is usually administered orally.

Lantus® is an insulin product containing insulin glargine providing 24 hour basal insulin supply after single dose subcutaneous injection.

The glucodynamic effect of Lantus® is distinguished from other currently marketed insulin products by virtue of a delayed and predictable absorption of insulin glargine from the subcutaneous injection site resulting in a smooth, 24 hour time-concentration and action profile without a definite peak. Lantus® was developed to meet the medical need for a long-acting insulin product that can be administered as a single daily injection to yield normal or near-normal blood glucose control with a basal insulin profile that is as smooth as possible over a 24-hour period. Such a preparation provides good control of blood glucose all day, while minimizing the tendency to produce hypoglycemia seen with other insulin preparations with a more definite "peak" effect.

A considerable number of patients, in particular those with increased insulin resistance due to obesity, use large doses to control blood glucose. For example, a dose of 100 U requires injection of 1 mL Lantus® U100, which may confer some discomfort; each mL Lantus® U100 contains 100 U (3.6378 mg) insulin glargine. To reduce the volume of injection, a formulation containing 300 U insulin glargine per mL has been developed.

The purpose of the multicenter, randomized, open-label, parallel-group study as described in Example 1 was to compare the efficacy and safety of insulin glargine U300 with that of Lantus, both given once-daily subcutaneous (S.C.) as part of a basal-bolus insulin regimen in patients with type 2 diabetes. Patients with type 2 diabetes and glycated hemoglobin A1c (HbA1c) in the range of 7% to 10% injecting at least 42 U Lantus U100 or equivalents of neutral protamine Hagedorn (NPH) insulin in a basal plus mealtime insulin regimen were eligible for the study. These patients on relative high doses of basal insulin benefited from the lower injection volume of a U300 insulin formulation as compared with U100 formulations.

Each mL insulin glargine U300 contains 300 U (10.9134 mg) insulin glargine. This formulation would allow patients to inject the same number of units of insulin glargine at one third the volume of injection. This formulation is also termed herein as HOE901-U300.

In the study described in Example 1, patients were stratified by their HbA1c (<8.0%; 8.0%). The primary efficacy analysis tested non-inferiority of insulin glargine U300 compared to Lantus in terms of change of HbA1c from baseline to endpoint (scheduled at month 6; non-inferiority margin 0.4% HbA1c units). HbA1c reflects the average glycemia over several months and has strong predictive value for diabetes complications. The 6-months duration of study treatment is considered to be sufficient for achieving steady state conditions with insulin glargine U300 after changing over from Lantus or NPH insulin enabling an adequate assessment of time-dependent changes in HbA1c and the concomitant risk of hypoglycemia.

Main secondary endpoints included nocturnal hypoglycemia. Hypoglycemia is the critical limiting factor in the glycemic management of diabetes in both the short and long term. Despite steady improvements in the glycemic management of diabetes, population-based data indicate that hypoglycemia continues to be a major problem for people with both type 1 and type 2 diabetes (American diabetes association, workgroup on hypoglycemia: Defining and Reporting Hypoglycemia in Diabetes. Diabetes Care 28(5), 2005, 1245-1249).

In the study described in Example 1, it was surprisingly found that by treatment of diabetes type 2 patients with an insulin glargine U300 formulation, the risk of a nocturnal hypoglycemic event can be significantly reduced compared with the treatment with Lantus® U100. The incidence of patients with at least one nocturnal severe and/or confirmed hypoglycemia between start of Week 9 and Month 6 was lower in the U300 group [136/404 (33.7%)] than in the Lantus group [180/400 (45.0%)] (see Table 6). Superiority of U300 versus Lantus was shown with a relative risk of 0.75 (95% CI [0.63, 0.89]) (p=0.0010).

Example 2 describes a clinical trial comparing the efficacy and safety of an insulin glargine U300 (HOE901-U300) formulation and Lantus® U 100, both in combination with oral antihyperglycemic drug(s) in patients with type 2 Diabetes Mellitus.

In Example 2, non-inferiority of U300 versus Lantus was demonstrated with the least square mean difference in HbA1c versus Lantus of −0.01% (95% CI [−0.139; 0.119]) (Table 26). The least square mean change in pre-injection SMPG was similar in the U300 (−0.56 mmol/L) and Lantus groups (−0.51 mmol/L) (Table 28).

Example 2 confirmed that by treatment with an insulin glargine U300 formulation, the risk of a nocturnal hypoglycemic event can be significantly reduced compared with the treatment with Lantus® U100. In a different patient group, namely type 2 Diabetes Mellitus patients not adequate controlled with antihyperglycemic drug(s) alone, it was surprisingly found that the incidence of patients with at least one nocturnal severe and/or confirmed hypoglycemia between was lower in the U300 group [87/403 (21.6%)] than in the Lantus group [113/405 (27.9%)] (see Table 27). Superiority of U300 versus Lantus was shown with a relative risk of 0.77 (95% CI [0.61, 0.99]) (p=0.0380).

Example 3 compares adaptable dosing intervals with fixed dosing intervals of once-daily administration of an U300 insulin glargine formulation in combination with mealtime insulin. Example 3 is a substudy of the trial described in example 1. No negative effects were seen on HbA1c (Table 50) and on fasting plasma glucose (Table 51). The overall incidence of hypoglycemia was similar in both regimens regardless of the category of hypoglycemia (Table 53).

Example 6 compares adaptable dosing intervals with fixed dosing intervals of once-daily administration of an U300 insulin glargine formulation in combination with oral antihyperglycemic drugs(s). Example 6 is a substudy of the trial described in example 2. No negative effects were seen on HbA1c (Table 67) and on fasting plasma glucose (Table 68). The overall incidence of hypoglycemia was similar in both regimens regardless of the category of hypoglycemia (Table 70).

An aspect of the present invention relates to an aqueous pharmaceutical formulation for use in the treatment of Type I or Type II Diabetes Mellitus, wherein the treatment reduces the risk of nocturnal hypoglycemia, said formulation comprising 200-1000 U/mL [equimolar to 200-1000 IU human insulin] of insulin glargine, with the proviso that the concentration of said formulation is not 684 U/mL of insulin glargine. The present invention relates to an aqueous pharmaceutical formulation for use in the reduction of the risk of nocturnal hypoglycemia.

The formulation of the present invention can reduce the incidence of nocturnal hypoglycemia when administered to a Diabetes Mellitus patient, as described herein. "Reduction of the incidence of nocturnal hypoglycemia" includes reduction of the number of nocturnal hypoglycemic events, and/or the severity of nocturnal hypoglycemia events. The formulation as described herein is suitable for use in the reduction of the incidence of nocturnal hypoglycemia.

The formulation of the present invention can prevent nocturnal hypoglycemia when administered to a Diabetes Mellitus patient, as described herein. "Prevention of nocturnal hypoglycemia" includes reduction of the number of nocturnal hypoglycemic events and/or the severity of nocturnal hypoglycemia events. The formulation as described herein is suitable for use in the prevention of nocturnal hypoglycemia.

The formulation of the present invention is suitable for use in the reduction of the number of nocturnal hypoglycemic events and/or the severity of nocturnal hypoglycemia events.

In the present invention, hypoglycemia is a condition wherein a diabetes mellitus type 2 patient experiences a plasma glucose concentration of below 70 mg/dL (or below 3.9 mmol/L), below 60 mg/dL (or below 3.3 mmol/L), below 54 mg/dL (or below 3.0 mmol/L), below 50 mg/dL, below 40 mg/dL, or below 36 mg/dL.

In the present invention, "symptomatic hypoglycemia" or "symptomatic hypoglycemic event" is a condition associated with a clinical symptom that results from the hypoglycemia, wherein the plasma glucose concentration can be below 70 mg/dL (or below 3.9 mmol/L), below 60 mg/dL (or below 3.3 mmol/L), below 54 mg/dL (or below 3.0 mmol/L), below 50 mg/dL, or below 40 mg/dL. A clinical symptom can be, for example, sweating, palpitations, hunger, restlessness, anxiety, fatigue, irritability, headache, loss of concentration, somnolence, psychiatric disorders, visual disorders, transient sensory defects, transient motor defects, confusion, convulsions, and coma. In the method of the present invention, one or more clinical symptoms of symptomatic hypoglycemia, as indicated herein, can be selected. Symptomatic hypoglycemia may be associated with prompt recovery after oral carbohydrate administration.

In the present invention, "severe symptomatic hypoglycemia" or "severe symptomatic hypoglycemic event" is a condition with a clinical symptom, as indicated herein, that results from hypoglycemia, wherein the plasma glucose concentration can be below 70 mg/dL (or below 3.9 mmol/L), below 54 mg/dL (or below 3.0 mmol/L) or below 36 mg/dL (or below 2.0 mmol/L). Severe symptomatic hypoglycemia can be associated with acute neurological impairment resulting from the hypoglycemic event. In a severe symptomatic hypoglycemia, the patient may require the assistance of another person to actively administer carbohydrate, glucagon, or other resuscitative actions. These episodes may be associated with sufficient neuroglycopenia to induce seizure, unconsciousness or coma. Plasma glucose measurements may not be available during such an event, but neurological recovery attributable to the restoration of plasma glucose to normal is considered sufficient evidence that the event was induced by a low plasma glucose concentration.

The definition of severe symptomatic hypoglycemia may include all episodes in which neurological impairment is severe enough to prevent self-treatment and which were thus thought to place patients at risk for injury to themselves or others. The acute neurological impairment may be at least one selected from somnolence, psychiatric disorders, visual disorders, transient sensory defects, transient motor defects, confusion, convulsions, and coma. "Requires assistance" means that the patient could not help himself or herself. Assisting a patient out of kindness, when assistance is not required, should not be considered a "requires assistance" incident.

Severe symptomatic hypoglycemia may be associated with prompt recovery after oral carbohydrate, intravenous glucose, or/and glucagon administration.

In the present invention, "documented symptomatic hypoglycemia" or "documented symptomatic hypoglycemic event" is an event during which typical symptoms of hypoglycemia accompanied by a measured plasma glucose concentration of 70 mg/dL 3.9 mmol/L), or less than or equal to 54 mg/dL 3.0 mmol/L). Clinical symptoms that are considered to result from a hypoglycemic episode are, e.g., increased sweating, nervousness, asthenia/weakness, tremor, dizziness, increased appetite, palpitations, headache, sleep disorder, confusion, seizures, unconsciousness, coma.

In the present invention, "asymptomatic hypoglycemia" or "asymptomatic hypoglycemic event" is an event not accompanied by typical symptoms of hypoglycemia but with a measured plasma glucose concentration less than or equal to 70 mg/dL (3.9 mmol/L), or less than or equal to 54 mg/dL (3.0 mmol/L).

In the present invention, "probable symptomatic hypoglycemia" or "probable symptomatic hypoglycemic event" is an event during which symptoms of hypoglycemia are not accompanied by a plasma glucose determination, but was presumably caused by a plasma glucose concentration less than or equal to 70 mg/dL (or less than or equal to 3.9 mmol/L), or less than or equal to 54 mg/dL (or less than or equal to 3.0 mmol/L); symptoms treated with oral carbohydrate without a test of plasma glucose.

In the present invention, "relative hypoglycemia" or "relative hypoglycemic event" is an event during which the person with diabetes reports any of the typical symptoms of hypoglycemia, and interprets the symptoms as indicative of hypoglycemia, but with a measured plasma glucose concentration greater than 70 mg/dL (or greater than 3.9 mmol/L).

In the present invention, "nocturnal hypoglycemia" or "nocturnal hypoglycemic event" is any hypoglycemia of the hypoglycema categories as described above that occurs night-time. "Nocturnal hypoglycemia" can be defined by the clock time. In particular, nocturnal hypoglycemia is a hypoglycemia that occurs between 00:00 and 05:59 a.m. hours. The patient can be awake or can wake up because of the event. The patient can also sleep during the event.

In the present invention, "daytime hypoglycemia" or "daytime hypoglycemic event" is in particular any hypoglycemia of the hypoglycema categories as described above that occurs between 06:00 a.m. and 23:59.

In the present invention, the nocturnal hypoglycemia can be a symptomatic hypoglycemia, a severe symptomatic hypoglycemia, a documented symptomatic hypoglycemia, a probable symptomatic hypoglycemia, a relative symptomatic hypoglycemia, or an asymptomatic hypoglycemia. Preferred is a symptomatic hypoglycemia, more preferably a severe symptomatic hypoglycemia.

"Reducing the risk of hypoglycemia", as used herein, can include reducing the incidence of hypoglycemia. The incidence of hypoglycemia per patient year can be computed per patient as: 365.25×(number of episodes of hypoglycemia)/(number of days exposed) and summarized by type of event and treatment group. "Reducing the risk of hypoglycemia", as used herein, can further include prevention of hypoglycemia in a patient, when the formulation described herein is administered to a Diabetes Mellitus patient, as described herein. "Reducing the risk of hypoglycemia", as used herein, can further include reduction of the number of nocturnal hypoglycemic events, and/or the severity of nocturnal hypoglycemia events.

Example 3 and 6 demonstrate that occasional adaptation of injection intervals of insulin glargine U300 have no negative effects on HbA1c (Tables 50 and 67) and on fasting plasma glucose (Tables 51 and 69). The overall incidence of hypoglycemia was similar in administration by adaptable dosing intervals and in administration by a fixed dosing interval regardless of the category of hypoglycemia (Tables 53 and 70).

An aspect of the present invention relates to an aqueous pharmaceutical formulation to be administered in adaptable time intervals. This aspect relates to an aqueous pharmaceutical formulation for use in the treatment of Type I or Type II Diabetes Mellitus, wherein the formulation is administered once daily to a patient, and wherein the time interval from the previous administration is in the range of 24.5 h to 28 h or in the range of 20 h to 23.5 h on at least two days per week, and wherein the average time interval from the previous administration is about 24 h, said formulation comprising 200-1000 U/mL [equimolar to 200-1000 IU human insulin] of insulin glargine, with the proviso that the concentration of said formulation is not 684 U/mL of insulin glargine.

As used herein, the time interval from the previous administration is the time interval between two consecutive administrations, in particular injections.

It is preferred that the formulation comprises 300 U/ml insulin glargin.

In the treatment regimen, the formulation can be administered in a time range around a fixed time, for example around a fixed time in the evening or in the morning. The average time interval from the previous administration can about 24 h (see Table 46). An interval of "about 24 h" in particular refers to a range of 24 h+/−10 min, a range of 24 h+/−20 min, or range of 24 h+/−30 min. The average time interval can be calculated for example, on weekly basis, on monthly basis, or on the basis of two or three months, or can be calculated on a longer time basis.

Table 47 describes the dosing regimen compliance in the test group and control group patients in Example 3. The % of injections by patients in different dosing interval categories is described. In the control group (fixed dosing interval of 24 h), about 88% of U300 doses were injected in an interval of 23 to 25 h from previous injection. About 12% of doses were injected at an interval of less than 23 h or more than 25 h. Taking into account one injection per day, the patients dosed the U300 formulation at an interval of less than 23 h or more than 25 h at less than one day per week. In the test group (adaptable dosing interval), about 63% of U300 doses were injected in an interval of 23 to 25 h from previous injection. About 37% of doses were injected at an interval of less than 23 h or more than 25 h. Taking into account one injection per day, the patients dosed the U300 formulation at an interval of less than 23 h or more than 25 h at two or three days per week.

The aqueous formulation can be administered with the time interval specified herein on at least two days per week, on at least three days per week, on at least four days per week or on at least five days per week. The aqueous formulation can be administered with the time interval specified herein on at the maximum five days per week, on at the maximum four days per week or on at the maximum three days per week. More particular, the aqueous formulation is administered with the time interval specified herein on two or three days per week, or on two to three days per week.

"Occasional adaptation" in particular means that the aqueous formulation is administered on two or three days per week with the time interval specified herein.

"Days per week", as indicated herein, can be calculated for example, on weekly basis, on monthly basis, or on the basis of two or three months, or can be calculated on a longer time basis.

"Adaptable injection intervals" means that the time interval from the previous injection is variable within a predetermined time range. The time interval from the previous administration can be in the range of 24.5 h to 28 h or in the range of 20 h to 23.5 h. In particular, the time interval from the previous administration is in the range of 25 h to 28 h or in the range of 20 h to 23 h.

The time interval from the previous administration can also be in the range of 25 h to 27 h or in the range of 21 h to 23 h.

The time interval from the previous administration can also be in the range of 25 h to 26.5 h or in the range of 21.5 h to 23 h.

In this aspect, the excipients of the formulation can be excipients as described herein. The patient to be treated can be a patient as described herein.

The treatment regimen of adaptable time intervals, as described herein, can be combined with the reduction of the risk of nocturnal hypoglycemia, as described herein.

The formulation for use in the treatment of Diabetes Mellitus Type 1 or 2 administered in adaptable time intervals, as described herein, can be combined with the use in the treatment of Diabetes Mellitus Type 1 or 2 with reduction of the risk of nocturnal hypoglycemia, as described herein.

In the present invention, normoglycemia may relate to a blood plasma concentration of glucose of from 70 mg/dL to 140 mg/dL (corresponding to 3.9 mmol/L to 7.8 mmol/L).

The patient to be treated by the formulation as described herein may be a Type I or Type II Diabetes Mellitus patient. Preferable, the patient is a Type II Diabetes Mellitus patient.

The pharmaceutical formulation of the present invention may be administered in combination with at least one antihyperglycemic agent. In particular, the at least one antihyperglycemic is metformin or/and a pharmaceutically acceptable salt thereof. Metformin is the international non-proprietary name of 1,1-dimethylbiguanide (CAS Number 657-24-9). In the present invention, the term "metformin" includes any pharmaceutically acceptable salt thereof.

In the present invention, metformin may be administered orally. The skilled person knows formulations of metformin suitable for treatment of diabetes mellitus by oral administration. Metformin may be administered to a patient in need thereof, in an amount sufficient to induce a therapeutic effect. Metformin may be administered in a dose of at least 1.0 g/day or at least 1.5 g/day. For oral administration, metformin may be formulated in a solid dosage form, such as a tablet or pill. Metformin may be formulated with suitable pharmaceutically acceptable carriers, adjuvants, or/and auxiliary substances.

The formulation of the present invention and metformin may be administered by different administration routes. Metformin may be administered orally, and the formulation of the present invention may be administered parenterally.

The patient to be treated by the formulation of the present invention may be a patient suffering from Diabetes Mellitus type 2, wherein diabetes type 2 is not adequately controlled by treatment with at least one antihyperglycemic alone. The antihyperglycemic may be metformin, wherein administration does not adequately control Diabetes Mellitus type 2, for example after treatment for at least 2 or at least 3 months, for example with a dose of at least 1.0 g/day or at least 1.5 g/day of metformin.

In the present invention, a patient the diabetes type 2 is not adequately controlled if at least one physiological parameter describing blood glucose concentration (e.g. the HbA1c value, the pre-injection SMPG or/and the fasting plasma glucose concentration) exceeds normoglycemic values, as described herein. In particular, a patient the diabetes type 2 of which is not adequately controlled may have
(i) a HbA1c value in the range of 7% to 10% or even larger,
(ii) a pre-injection SMPG of at least 9 mmol/L, or/and
(iv) a fasting plasma glucose of at least 8.0 mmol/L.

The patient to be treated by the formulation as described herein may have a HbA1c value in the range of 7% to 10% at the onset of treatment. More particular, the patient to be treated may have a HbA1c value of at least 8%, or a HbA1c value in the range of 8% to 10% at the onset of treatment of the present invention.

The patient to be treated by the formulation as described herein may be an adult subject. The patient may have an age of at least 50 years, at least 57 years, at least 58 years, at least 59 years, at least 60 years, at least 65 years, at least 70 years, or at least 75 years at the onset of treatment of the present invention.

The patient to be treated by the formulation as described herein may be an obese subject at the onset of treatment of the present invention. In the present invention, an obese subject may have a body mass index (BMI) of at least 30 kg/m$^2$, at least 31 kg/m$^2$, at least 32 kg/m$^2$, at least 33 kg/m$^2$, at least 34 kg/m$^2$, at least 35 kg/m$^2$, at least 36 kg/m$^2$, at least 37 kg/m$^2$, at least 38 kg/m$^2$, at least 39 kg/m$^2$ or at least 40 kg/m$^2$ at the onset of treatment. It is preferred that the patient has a BMI of at least 34 kg/m$^2$ or of at least 36 kg/m$^2$ at the onset of treatment.

The patient to be treated by the formulation as described herein may have an increased risk of hypoglycemia, in particular a diabetes type 2 patient having experienced at least one hypoglycemic event.

The patient to be treated by the formulation as described herein may have received an insulin directly prior to the treatment as described herein. In particular, the patient may have received a basal insulin, for example in a dose of at least 32 U/day or at least 42 U/day. In the present invention, any pre-treatment with a basal insulin can be considered. In particular, the basal insulin can be selected from insulin Glargine, Detemir, NPH, Lente, Ultralente, Novolin, Humalog and mixtures thereof. The mixture may comprise two different basal insulins. For example, a mixture comprising Detemir and Glargine, or a mixture comprising NPH and Novolin, may be employed. Preferably, the basal insulin is insulin Glargin, or a mixture comprising insulin Glargine. In the present invention, "basal insulin" includes suitable pharmaceutically acceptable salts thereof.

The patient to be treated by the formulation as described herein may have received a mealtime short-acting insulin directly prior to the treatment as described herein. The mealtime short-acting insulin may be an insulin analogue, for example insulin glulisin, insulin lispro, or insulin aspart.

The formulation as described herein may be administered once or twice daily. In particular, the formulation as described herein may be administered once daily, for example in the evening. The formulation as described herein may be administered once daily in the evening at a predetermined time.

The patient may additionally receive a mealtime short-acting insulin. The mealtime short-acting insulin may be an insulin analogue, for example insulin glulisin, insulin lispro, or insulin aspart.

The patient to be treated by the formulation of the present invention may have a pre-injection self-monitored plasma glucose (SMPG) concentration of at least 9 mmol/L, at least 10 mmol/L, at least 10.5 mmol/L, or at least 11 mmol/L at the onset of treatment of the present invention. In the present invention, self-monitored plasma glucose can be a fasting SMPG or a pre-injection SMPG (for example, measured 30 minutes prior to injection of the formulation described herein).

The patient to be treated may have a fasting plasma glucose concentration of at least 7 mmol/L, at least 7.5 mmol/L, at least 8 mmol/L, at least 8.5 mmol/L or at least 9 mmol/L at the onset of treatment of the present invention.

Although the invention is not limited to a insulin glargine U 300 formulation but is effective with other higher concentrated formulations of insulin glargine as outlined in detail in the specification, the clinical study described herein were performed with a insulin glargine U 300 formulation.

1 mL of insulin glargine U 300 formulation contains 10.913 mg 21$^A$-Gly-30$^B$a-L-Arg-30$^B$b-L-Arg human insulin [equimolar to 300 IU human insulin], 90 µg zinc, 2.7 mg m-cresol, 20 mg glycerol 85%, HCl and NaOH ad pH 4.0; specific gravity 1.006 g/mL However, variations with regard to the kind of excipients and their concentrations are possible.

The pharmaceutical formulation contains 200-1000 U/mL of insulin glargine [equimolar to 200-1000 IU human insulin], wherein the concentration of said formulation is not 684 U/mL, preferably 250-500 U/mL of insulin glargine [equimolar to 250-500 IU human insulin], more preferred 270-330 U/mL of insulin glargine [equimolar to 270-330 IU human insulin], and even more preferred 300 U/mL of insulin glargine [equimolar to 300 IU human insulin].

Surfactants can be added to pharmaceutical formulation, for example, inter alia, non-ionic surfactants. In particular, pharmaceutically customary surfactants are preferred, such as, for example: partial and fatty acid esters and ethers of polyhydric alcohols such as of glycerol, sorbitol and the like (Span®, Tween®, in particular Tween® 20 and Tween® 80, Myrj®, Brij®), Cremophor® or poloxamers. The surfactants are present in the pharmaceutical composition in a concentration of 5-200 µg/ml, preferably of 5-120 µg/ml and particularly preferably of 20-75 µg/ml.

The formulation can additionally contain preservatives (e.g. phenol, m-cresol, p-cresol, parabens), isotonic agents (e.g. mannitol, sorbitol, lactose, dextrose, trehalose, sodium chloride, glycerol), buffer substances, salts, acids and alkalis and also further excipients. These substances can in each case be present individually or alternatively as mixtures.

Glycerol, dextrose, lactose, sorbitol and mannitol can be present in the pharmaceutical preparation in a concentration of 100-250 mM, NaCl in a concentration of up to 150 mM. Buffer substances, such as, for example, phosphate, acetate, citrate, arginine, glycylglycine or TRIS (i.e. 2-amino-2-hydroxymethyl-1,3-propanediol) buffer and corresponding salts, are present in a concentration of 5-250 mM, preferably 10-100 mM. Further excipients can be, inter alia, salts or arginine.

The zinc concentration of the formulation is in the range of the concentration which is reached by the presence of 0-1000 µg/mL, preferably 20-400 µg/mL zinc, most preferably 90 µg/mL. However, the zinc may be present in form of zinc chloride, but the salt is not limited to be zinc chloride.

In the pharmaceutical formulation glycerol and/or mannitol can be present in a concentration of 100-250 mmol/L, and/or NaCl is preferably present in a concentration of up to 150 mmol/L.

In the pharmaceutical formulation a buffer substance can be present in a concentration of 5-250 mmol/L.

A further subject of the invention is a pharmaceutical insulin formulation for use as described herein which contains further additives such as, for example, salts which delay the release of insulin. Mixtures of such delayed-release insulins with formulations described above are included therein.

A further subject of the invention is directed to a method for the production of such pharmaceutical formulations for use as described herein. For producing the formulations the ingredients are dissolved in water and the pH is adjusted by using HCl and/or NaOH. Likewise, a further subject of the invention is directed to the use of such formulations for the treatment of diabetes mellitus.

A further subject of the invention is directed to the use or the addition of surfactants as stabilizer during the process for the production of insulin, insulin analogs or insulin derivatives or their preparations.

The invention further relates to a formulation as described above which additionally comprises also a glucagon-like peptide-1 (GLP1) or an analogue or derivative thereof, or exendin-3 or -4 or an analogue or derivative thereof, preferably exendin-4.

The invention further relates to a formulation as described above in which an analogue of exendin-4 is selected from a group comprising
H-desPro$^{36}$-exendin-4-Lys$_6$-NH$_2$ (Lixisenatide, AVE0010),
H-des(Pro$^{36,37}$)-exendin-4-Lys$_4$-NH$_2$ and
H-des(Pro$^{36,37}$)-exendin-4-Lys$_6$-NH$_2$,
or a pharmacologically tolerable salt thereof.

The invention further relates to a formulation as described above in which an analogue of exendin-4 is selected from a group comprising
desPro$^{36}$ [Asp$^{28}$]exendin-4 (1-39),
desPro$^{36}$ [IsoAsp$^{28}$]exendin-4 (1-39),
desPro$^{36}$ [Met(O)$^{14}$, Asp$^{28}$]exendin-4 (1-39),
desPro$^{36}$ [Met(O)$^{14}$, IsoAsp$^{28}$]exendin-4 (1-39),
desPro$^{36}$ [Trp(O$_2$)$^{25}$, Asp$^{28}$]exendin-2 (1-39),
desPro$^{36}$ [Trp(O$_2$)$^{25}$, IsoAsp$^{28}$]exendin-2 (1-39),
desPro$^{36}$ [Met(O)$^{14}$Trp(O$_2$)$^{25}$, Asp$^{28}$]exendin-4 (1-39) and
desPro$^{36}$ [Met(O)$^{14}$Trp(O$_2$)$^{25}$, IsoAsp$^{28}$]exendin-4 (1-39),
or a pharmacologically tolerable salt thereof.

The invention further relates to a formulation as described in the preceding paragraph, in which the peptide -Lys$_6$-NH$_2$ is attached to the C termini of the analogues of exendin-4.

The invention further relates to a formulation as described above in which an analogue of exendin-4 is selected from a group comprising
H-(Lys)$_6$-des Pro$^{36}$ [Asp$^{28}$]exendin-4(1-39)-Lys$_6$-NH$_2$
des Asp$^{28}$Pro$^{36}$, Pro$^{37}$, Pro$_{38}$ exendin-4(1-39)-NH$_2$,
H-(Lys)$_6$-des Pro$^{36}$, Pro$^{37}$, Pro$^{38}$ [Asp$^{28}$]exendin-4(1-39)-NH$_2$,
H-Asn-(Glu)$_5$ des Pro$^{36}$, Pro$^{37}$, Pro$^{38}$ [Asp$^{28}$]exendin-4(1-39)-NH$_2$,
des Pro$^{36}$, Pro$^{37}$, Pro$^{38}$ [Asp$^{28}$]exendin-4(1-39)-(Lys)$_6$-NH$_2$,
H-(Lys)$_6$-des Pro$^{36}$, Pro$^{37}$, Pro$^{38}$ [Asp$^{28}$]exendin-4(1-39)-(Lys)$_6$-NH$_2$,
H-Asn-(Glu)$_5$-des Pro$^{36}$, Pro$^{37}$, Pro$^{38}$ [Asp$^{28}$]exendin-4(1-39)-(Lys)$_6$-NH$_2$,
H-(Lys)$_6$-des Pro$^{36}$ [Trp(O$_2$)$^{25}$, Asp$^{28}$]exendin-4(1-39)-Lys$_6$-NH$_2$,
H-des Asp$^{28}$ Pro$^{36}$, Pro$^{37}$, Pro$^{38}$ [Trp(O$_2$)$^{25}$]exendin-4(1-39)-NH$_2$,
H-(Lys)$_6$-des Pro$^{36}$, Pro$^{37}$, Pro$^{38}$ [Trp(O$_2$)$^{25}$, Asp$^{28}$]exendin-4(1-39)-NH$_2$,
H-Asn-(Glu)$_5$-des Pro$^{36}$, Pro$^{37}$, Pro$^{38}$ [Trp(O$_2$)$^{25}$, Asp$^{28}$]exendin-4(1-39)-NH$_2$,
des Pro$^{36}$, Pro$^{37}$, Pro$^{38}$ [Trp(O$_2$)$^{25}$, Asp$^{28}$]exendin-4(1-39)-(Lys)$_6$-NH$_2$,
H-(Lys)$_6$-des Pro$^{36}$, Pro$^{37}$, Pro$^{38}$ [Trp(O$_2$)$^{25}$, Asp$^{28}$]exendin-4(1-39)-(Lys)$_6$-NH$_2$,
H-Asn-(Glu)$_5$-des Pro$^{36}$, Pro$^{37}$, Pro$^{38}$ [Trp(O$_2$)$^{25}$, Asp$^{28}$]exendin-4(1-39)-(Lys)$_6$-NH$_2$,
H-(Lys)$_6$-des Pro$^{36}$ [Met(O)$^{14}$, Asp$^{28}$]exendin-4(1-39)-Lys$_6$-NH$_2$,
des Met(O)$^{14}$ Asp$^{28}$ Pro$^{36}$, Pro$^{37}$, Pro$^{38}$ exendin-4(1-39)-NH$_2$,
H-(Lys)$_6$-des Pro$^{36}$, Pro$^{37}$, Pro$^{38}$ [Met(O)$^{14}$, Asp$^{28}$]exendin-4(1-39)-NH$_2$,
H-Asn-(Glu)$_5$-des Pro$^{36}$, Pro$^{37}$, Pro$^{38}$ [Met(O)$^{14}$, Asp$^{28}$]exendin-4(1-39)-NH$_2$,
des Pro$^{36}$, Pro$^{37}$, Pro$^{38}$ [Met(O)$^{14}$, Asp$^{28}$]exendin-4(1-39)-(Lys)$_6$-NH$_2$,
H-(Lys)$_6$-des Pro$^{36}$, Pro$^{37}$, Pro$^{38}$ [Met(O)$^{14}$, Asp$^{28}$]exendin-4(1-39)-Lys$_6$-NH$_2$,
H-Asn-(Glu)$_5$ des Pro$^{36}$, Pro$^{37}$, Pro$^{38}$ [Met(O)$^{14}$, Asp$^{28}$]exendin-4(1-39)-(Lys)$_6$-NH$_2$,
H-(Lys)$_6$-des Pro$^{36}$ [Met(O)$^{14}$, Trp(O$_2$)$^{25}$, Asp$^{28}$]exendin-4(1-39)-Lys$_6$-NH$_2$,
des Asp$^{28}$ Pro$^{36}$, Pro$^{37}$, Pro$^{38}$ [Met(O)$^{14}$, Trp(O$_2$)$^{25}$]exendin-4(1-39)-NH$_2$,
H-(Lys)$_6$-des Pro$^{36}$, Pro$^{37}$, Pro$^{38}$ [Met(O)$^{14}$, Trp(O$_2$)$^{25}$, Asp$^{28}$]exendin-4(1-39)-NH$_2$,
H-Asn-(Glu)$_5$-des Pro$^{36}$, Pro$^{37}$, Pro$^{38}$ [Met(O)$^{14}$, Asp$^{28}$] exendin-4(1-39)-NH$_2$,
des Pro$^{36}$, Pro$^{37}$, Pro$^{38}$ [Met(O)$^{14}$, Trp(O$_2$)$^{25}$, Asp$^{28}$]exendin-4(1-39)-(Lys)$_6$-NH$_2$, H-(Lys)$_6$-des Pro$^{36}$, Pro$^{37}$, Pro$^{38}$ [Met(O)$^{14}$, Trp(O$_2$)$^{25}$, Asp$^{28}$]exendin-4(1-39)-(Lys)$_6$-NH$_2$,
H-Asn-(Glu)$_5$-des Pro$^{36}$, Pro$^{37}$, Pro$^{38}$ [Met(O)$^{14}$, Trp(O$_2$)$^{25}$, Asp$^{28}$] exendin-4(1-39)-(Lys)$_6$-NH$_2$,
or a pharmacologically tolerable salt thereof.

The invention further relates to a formulation as described above which additionally comprises Arg$^{34}$, Lys$^{26}$ (N$^{\epsilon}$(γ-glutamyl(N$^{\alpha}$-hexadecanoyl))) GLP-1 (7-37) [liraglutide] or a pharmacologically tolerable salt thereof.

In one embodiment, the present invention is directed to an aqueous pharmaceutical formulation for use as described herein comprising insulin glargine in the range of 200-1000 U/mL [equimolar to 200-1000 IU human insulin], preferably 200 U/ml to 650 U/mL, still preferably 700 U/mL to 1000 U/ml, more preferably 270-330 U/mL and most preferably in a concentration of 300 U/mL, with the proviso that the concentration of said formulation is not 684 U/mL of insulin glargine.

Additionally, the formulation can also comprise an analogue of exendin-4, such, for example, lixisentatide, exenatide and liraglutide. These exendin-4 analogues are present in the formulation in the range of 0.1 µg to 10 µg per U insulin glargine, preferably 0.2 to 1 µg per U insulin glargine, and more preferably 0.25 µg to 0.7 µg per U insulin glargine. Lixisenatide is preferred.

Additionally, the aqueous pharmaceutical formulation can comprise one or more excipients selected from a group comprising zinc, m-cresol, glycerol, polysorbate 20 and sodium. Specifically, the aqueous pharmaceutical formulation can comprise 90 µg/mL zinc, 2.7 mg/mL m-cresol and 20 mg/ml glycerol 85%. Optionally, the aqueous pharmaceutical formulation can comprise 20 µg/mL polysorbate 20.

The pH of the aqueous pharmaceutical formulation as described herein can be 4.6 or lower, preferably 4.5 or lower.

The pH of the aqueous pharmaceutical formulation as described herein can also be in the range from 3.4 to 4.6, preferably in the range from 4 to 4.5.

Another aspect of the present invention is directed to a method for treating a disease or condition as described herein, in particular a method for treating Type I or Type II Diabetes Mellitus comprising administering to said patient the aqueous pharmaceutical composition of the present invention to a diabetic patient, wherein treatment reduces the risk of nocturnal hypoglycemia. The method preferably refers to treatment of Type II Diabetes Mellitus. Preferred among the various disclosed concentration ranges is a concentration of 300 U/mL. Further the aqueous pharmaceutical formulation also can comprise zinc, m-cresol, glycerol, polysorbate 20 and sodium and mixtures thereof in the ranges disclosed herein in relation to the aqueous pharmaceutical formulation of the present invention. In a preferred embodiment the aqueous pharmaceutical formulation also comprises 0.1 µg to 10 µg lixisenatide per U insulin glargine. The nocturnal hypoglycemia can be any nocturnal hypoglycemia, as defined herein. The patient can be any patient as defined herein.

The insulin is administered preferably once daily but can be administered twice daily as needed. Dosage requirements are a function of the needs of the individual patient determined by the achievement of normal or acceptable blood glucose levels.

The method can also be a method of treating Type I or Type II Diabetes Mellitus in a patient comprising administering to said patient an aqueous pharmaceutical composition as described herein, wherein the formulation is administered once daily, and wherein the time interval from the previous administration is in the range of 24.5 h to 28 h or in the range of 20 h to 23.5 h on at least two days per week, and wherein the average time interval from the previous administration is about 24 h. The time interval can be a time interval as defined herein. The aqueous formulation can be administered on at least three days per week, on at least four days per week or on at least five days per week with the time interval specified herein. The method preferably refers to treatment of Type II Diabetes Mellitus. Preferred among the various disclosed concentration ranges is a concentration of 300 U/mL. Further the aqueous pharmaceutical formulation also can comprise zinc, m-cresol, glycerol, polysorbate 20 and sodium and mixtures thereof in the ranges disclosed herein in relation to the aqueous pharmaceutical formulation of the present invention. In a preferred embodiment the aqueous pharmaceutical formulation also comprises 0.1 µg to 10 µg lixisenatide per U insulin glargine. The patient can be any patient as defined herein.

The treatment method of Diabetes Mellitus Type 1 or 2 administered in adaptable time intervals, as described herein, can be combined with the method of treatment of Diabetes Mellitus Type 1 or 2 with reduction of the risk of nocturnal hypoglycemia, as described herein.

Yet another aspect of the present invention is directed to the use of an aqueous formulation as described herein for the manufacture of a medicament for the treatment of a disease or condition as described herein, in particular for the treatment of Type I or Type II Diabetes Mellitus, wherein the treatment reduces the risk of nocturnal hypoglycemia. The use preferably refers to treatment of Type II Diabetes Mellitus. Preferred among the various disclosed concentration ranges is a concentration of 300 U/mL. Further the aqueous pharmaceutical formulation also can comprise zinc, m-cresol, glycerol, polysorbate 20 and sodium and mixtures thereof in the ranges disclosed herein in relation to the aqueous pharmaceutical formulation of the present invention. In a preferred embodiment the aqueous pharmaceutical formulation also comprises 0.1 µg to 10 µg lixisenatide per U insulin glargine. The nocturnal hypoglycemia can be any nocturnal hypoglycemia, as defined herein. The patient can be any patient as defined herein.

The insulin is administered preferably once daily but can be administered twice daily as needed. Dosage requirements are a function of the needs of the individual patient determined by the achievement of normal or acceptable blood glucose levels.

Another aspect refers to the use of an aqueous formulation as described herein for the manufacture of a medicament for treating Type I or Type II Diabetes Mellitus in a patient comprising administering to said patient an aqueous pharmaceutical composition as described herein, wherein the formulation is administered once daily, and wherein the time interval from the previous administration is in the range of 24.5 h to 28 h or in the range of 20 h to 23.5 h on at least two days per week, and wherein the average time interval from the previous administration is about 24 h. The time interval can be a time interval as defined herein. The aqueous formulation can be administered on at least three days per week, on at least four days per week or on at least five days per week with the time interval specified herein. The method preferably refers to treatment of Type II Diabetes Mellitus. Preferred among the various disclosed concentration ranges is a concentration of 300 U/mL. Further the aqueous pharmaceutical formulation also can comprise zinc, m-cresol, glycerol, polysorbate 20 and sodium and mixtures thereof in the ranges disclosed herein in relation to the aqueous pharmaceutical formulation of the present invention. In a preferred embodiment the aqueous pharmaceutical formulation also comprises 0.1 µg to 10 µg lixisenatide per U insulin glargine. The patient can be any patient as defined herein.

The use for the manufacture of a medicament for the treatment of Diabetes Mellitus Type 1 or 2 administered in adaptable time intervals, as described herein, can be combined with the use for the manufacture of a medicament for the treatment of Diabetes Mellitus Type 1 or 2 with reduction of the risk of nocturnal hypoglycemia, as described herein.

The invention relates, inter alia, to the following items:
1. An aqueous pharmaceutical formulation for use in the treatment of Type I or Type II Diabetes Mellitus, wherein the treatment reduces the risk of nocturnal hypoglycemia, said formulation comprising 200-1000 U/mL [equimolar to 200-1000 IU human insulin] of insulin glargine, with the proviso that the concentration of said formulation is not 684 U/mL of insulin glargine.
2. The aqueous formulation for use of item 1 comprising 200 U/ml to 650 U/mL of insulin glargine.
3. The aqueous formulation for use of item 1 comprising 700 U/ml to 1000 U/mL of insulin glargine.
4. The aqueous formulation for use of item 2 comprising 270-330 U/mL of insulin glargine [equimolar to 270-330 IU human insulin].
5. The aqueous formulation for use of item 4 comprising 300 U/mL of insulin glargine [equimolar to 300 IU human insulin].
6. The aqueous pharmaceutical formulation for use of any of the foregoing items, wherein the nocturnal hypoglycemia is selected from symptomatic hypoglycemia, severe symptomatic hypoglycemia, documented symptomatic hypoglycemia, probable symptomatic hypoglycemia, relative symptomatic hypoglycemia, and asymptomatic hypoglycemia.
7. The aqueous pharmaceutical formulation for use of any of the foregoing items, wherein the patient to be treated has a HbA1c value of at least 8% at the onset of treatment.
8. The aqueous pharmaceutical formulation for use of any of the foregoing items, wherein the patient to be treated has an age of at least 60 years at the onset of treatment.
9. The aqueous pharmaceutical formulation for use of any of the foregoing items, wherein the patient to be treated has a BMI of at least 30 kg/m$^2$ at the onset of treatment.
10. The aqueous pharmaceutical formulation for use of any of the foregoing items, wherein the patient to be treated received a basal insulin directly prior to the treatment.
11. The aqueous pharmaceutical formulation for use of any of the foregoing items, wherein the patient to be treated received a mealtime short-acting insulin directly prior to the treatment.
12. The aqueous pharmaceutical formulation for use of item 10 or 11, wherein the patient to be treated has a pre-injection SMPG of at least 9 mmol/L at the onset of treatment.
13. The aqueous pharmaceutical formulation for use of item 10 or 11, wherein the patient to be treated has a fasting plasma glucose concentration of at least 8 mmol/L at the onset of treatment.
14. The aqueous pharmaceutical formulation for use of any of the foregoing items, wherein the formulation is administered once daily in the evening at a predetermined time.
15. The aqueous pharmaceutical formulation for use of any of the foregoing items, wherein the patient additionally receives a mealtime short-acting insulin.
16. The aqueous pharmaceutical formulation for use of any of the foregoing items comprising an analogue of exendin-4.
17. The aqueous formulation for use of item 16, wherein the analogue of exendin-4 is selected from a group comprising lixisentatide, exenatide and liraglutide.
18. The aqueous formulation for use of item 17 comprising 0.1 µg to 10 µg lixisenatide per U insulin glargine.
19. The aqueous formulation for use of item 18 comprising 0.2 to 1 µg lixisenatide per U insulin glargine.
20. The aqueous formulation for use of item 19 comprising 0.25 µg to 0.7 µg lixisenatide per U insulin glargine.
21. The aqueous formulation for use of any of the foregoing items comprising one or more excipients selected from a group comprising zinc, m-cresol, glycerol, polysorbate 20 and sodium.
22. The aqueous formulation for use of item 21 comprising 90 µg/mL zinc, 2.7 mg/mL m-cresol and 20 mg/ml glycerol 85%.
23. The aqueous formulation for use of item 21 comprising 90 µg/mL zinc, 2.7 mg/mL m-cresol, 20 µg/mL polysorbate 20 and 20 mg/mL glycerol 85%.
24. The aqueous formulation for use of any of the foregoing items, wherein the pH is between 3.4 and 4.6.
25. The aqueous formulation for use of item 24, wherein the pH is 4.
26. The aqueous formulation for use of item 24, wherein the pH is 4.5.
27. The pharmaceutical formulation for use of any one of the items 1 to 26, wherein the Diabetes Mellitus is Type II Diabetes Mellitus.
28. The pharmaceutical formulation for use of item 27, wherein the Diabetes Mellitus Type II is not adequately controlled with at least one oral antihyperglycemic alone.
29. The pharmaceutical formulation for use of item 28, wherein the at least one oral antihyperglycemic is metformin.
30. The pharmaceutical formulation for use of item 29, wherein a treatment with at least 1.5 g/day of metformin does not adequately control the Diabetes Mellitus.
31. The aqueous pharmaceutical formulation for use of any of the items 27 to 30, administered in combination with at least one oral antihyperglycemic agent.
32. The aqueous pharmaceutical formulation for use of item 31, wherein the at least one antihyperglycemic agent is metformin.
33. The aqueous pharmaceutical formulation for use of any one of the preceding items, wherein the formulation is administered once daily, and wherein the time interval from the previous administration is in the range of 24.5 h to 28 h or in the range of 20 h to 23.5 h on at least two days per week, and wherein the average time interval from the previous administration is about 24 h.
34. A method of treating Type I or Type II Diabetes Mellitus in a patient comprising administering to said patient an aqueous pharmaceutical composition comprising insulin glargine in a concentration of 300 U/mL, wherein the treatment reduces the risk of nocturnal hypoglycemia.
35. The method of item 34 wherein said pharmaceutical composition further comprises excipients selected from the group consisting of zinc, m-cresol, glycerol, polysorbate 20 and sodium.

36. The method of item 34 wherein said pharmaceutical composition further comprises 0.1 μg to 10 μg lixisenatide per U insulin glargine.
37. Use of an aqueous formulation according to any of the foregoing items for the manufacture of a medicament for the treatment of Type 1 Diabetes Mellitus and Type 2 Diabetes Mellitus, wherein the treatment reduces the risk of nocturnal hypoglycemia.
38. An aqueous pharmaceutical formulation for use in the treatment of Type I or Type II Diabetes Mellitus, wherein the formulation is administered once daily to a patient, and wherein the time interval from the previous administration is in the range of 24.5 h to 28 h or in the range of 20 h to 23.5 h on at least two days per week, and wherein the average time interval from the previous administration is about 24 h, said formulation comprising 200-1000 U/mL [equimolar to 200-1000 IU human insulin] of insulin glargine, with the proviso that the concentration of said formulation is not 684 U/mL of insulin glargine.
39. The aqueous formulation of item 38 administered on at least three days per week with the time interval specified in item 38.
40. The aqueous formulation of item 38 administered on at least four days per week with the time interval specified in item 38.
41. The aqueous formulation of any one of the items 38 to 40, wherein the time interval from the previous administration is in the range of 25 h to 28 h or in the range of 20 h to 23 h.
42. The aqueous formulation of any one of the items 38 to 41, wherein the time interval from the previous administration is in the range of 25 h to 27 h or in the range of 21 h to 23 h.
43. The aqueous formulation of any one of the items 38 to 42, wherein the time interval from the previous administration is in the range of 25 h to 26.5 h or in the range of 21.5 h to 23 h.
44. The aqueous formulation for use of any one of the items 38 to 43, comprising insulin glargine in an amount as defined in any one of the items 2 to 5.
45. The aqueous formulation for use of any one of the items 38 to 44, wherein the patient is defined as in any one of the items 7 to 15.
46. The aqueous formulation for use of any one of the items 38 to 45, further comprising an analogue of exendin-4, as defined in any one of the items 16 to 20.
47. The aqueous formulation for use of any one of the items 38 to 46, further comprising one or more excipients as defined in any one of the items 21 to 23.
48. The aqueous formulation for use of any one of the items 38 to 47, having a pH as defined in any one of the items 24 to 26.
49. The aqueous formulation for use of any one of the items 38 to 48, wherein the treatment reduces the risk of nocturnal hypoglycaemia.
50. The aqueous formulation for use of item 49, wherein the nocturnal hypoglycemia is selected from symptomatic hypoglycemia, severe symptomatic hypoglycemia, documented symptomatic hypoglycemia, probable symptomatic hypoglycemia, relative symptomatic hypoglycemia, and asymptomatic hypoglycemia.
51. The aqueous formulation for use of any one of the items 38 to 50, wherein the Diabetes Mellitus is Type II Diabetes Mellitus.
52. The aqueous formulation for use of item 51, wherein the Diabetes Mellitus type II is not adequately controlled with a least one oral antihyperglycemic agent alone, as defined in any one of the items 28 to 32.
53. A method of treating Type I or Type II Diabetes Mellitus in a patient comprising administering to said patient an aqueous pharmaceutical composition comprising insulin glargine in a concentration of 300 U/mL, wherein the formulation is administered once daily, and wherein the time interval from the previous administration is in the range of 24.5 h to 28 h or in the range of 20 h to 23.5 h on at least two days per week, and wherein the average time interval from the previous administration is about 24 h.
54. The method of item 53 wherein said pharmaceutical composition further comprises excipients selected from the group consisting of zinc, m-cresol, glycerol, polysorbate 20 and sodium.
55. The method of item 53 wherein said pharmaceutical composition further comprises 0.1 μg to 10 μg lixisenatide per U insulin glargine.
56. Use of an aqueous formulation according to any of the foregoing items for the manufacture of a medicament for the treatment of Type 1 Diabetes Mellitus and Type 2 Diabetes Mellitus, wherein the formulation is administered once daily, and wherein the time interval from the previous administration is in the range of 24.5 h to 28 h or in the range of 20 h to 23.5 h on at least two days per week, and wherein the average time interval from the previous administration is about 24 h.
57. An article of manufacture comprising a packaging material, an aqueous formulation according to any of the foregoing items, and a label or packaging material indicating that the formulation is administered once daily, and wherein the time interval from the previous administration is between 21 h and 27 h, and wherein the average time interval from the previous administration is about 24 h.
58. An article of manufacture comprising a packaging material, an aqueous formulation according to any of the foregoing items, and a label or packaging material indicating that the formulation can be given together with other anti-hyperglyaemic medicinal products.
59. An article of manufacture comprising a packaging material, an aqueous formulation according to any of the foregoing items, and a label or packaging material indicating that changing from a once-daily administration of a basal insulin products to a once daily administration of the formulation can be done unit-to-unit based on the previous basal insulin dose; and changing from twice daily administration of a basal insulin product to once-daily administration of the formulation, the recommended initial dose of the formulation is 80% of the total daily dose of basal insulin that is being discontinued.
60. An article of manufacture comprising a packaging material, an aqueous formulation according to any of the foregoing items, and a label or packaging material indicating that in case the formulation is given together with a substance that may enhance the blood-glucose-lowering effect of the formulation selected from a group comprising anti-hyperglycaemic medicinal products, angiotensin converting enzyme (ACE) inhibitors, disopyramide, fibrates, fluoxetine, monoamine oxidase (MAO) inhibitors, pentoxifylline, propoxyphene, salicylates and sulfonamide antibiotics, a dose adjustment of the formulation may be needed.
61. An article of manufacture comprising a packaging material, an aqueous formulation according to any of the foregoing items, and a label or packaging material indicating that in case the formulation is given together with a substance that may reduce the blood-glucose-lowering effect of the formulation selected from a group comprising corticosteroids, danazol, diazoxide, diuretics, glucagon, isoniazid, oestrogens and progestogens, phenothiazine derivatives, somatropin, sympathomimetic medicinal products (e.g. epinephrine [adrenaline], salbutamol, terbutaline), thyroid hormones, atypical antipsychotic medicinal products (e.g. clozapine and olanzapine) and protease inhibitors a dose adjustment of the formulation may be needed.

The application is described below with the aid of the following figures and examples, which are in no way intended to act restrictively.

LEGENDS

FIG. 1—Main efficacy analysis—Mean HbA1c (%) by visit during the main 6-month on-treatment period—mITT population (Example 1). BAS=Baseline, M6LOCF=last value during main 6-month on-treatment (LOCF). LOCF=Last observation carried forward.

FIG. 2—Other secondary efficacy endpoints—Mean average pre-injection SMPG (mmol/L) by visit during the main 6-month on-treatment period—mITT population (Example 1). BAS=Baseline, M6LOCF=last value during main 6-month on-treatment (LOCF). LOCF=Last observation carried forward.

FIG. 3—Other secondary efficacy endpoints—Mean 8-point SMPG profile (mmol/l) at baseline and Month 6 endpoint—mITT population (Example 1). LOCF=Last observation carried forward.

FIG. 4—Other secondary efficacy endpoints—Average daily basal insulin and mealtime insulin dose (U) by visit during the main 6-month on-treatment period—mITT population (Example 1). BAS=Baseline, M6LOCF=last value during main 6-month on-treatment (LOCF). LOCF=Last observation carried forward.

FIG. 5—Main efficacy analysis—Mean HbA1c (%) by visit during the main 6-month on-treatment period—mITT population (Example 2). BAS=Baseline, M6LOCF=Month-6 endpoint (LOCF), LOCF=Last observation carried forward. Note: For all patients rescued during the 6-month period, the last postbaseline HbA1c measurement before rescue and during the 6-month on-treatment period will be used as the HbA1c endpoint.

FIG. 6—Other secondary efficacy endpoints—Mean average pre-injection SMPG (mmol/L) by visit during the main 6-month on-treatment period—mITT population (Example 2). BAS=Baseline, M6LOCF=Month 6 endpoint (LOCF). SMPG=Self Monitoring Plasma Glucose. LOCF=Last observation carried forward. Note: For all patients rescued during the 6-month period, the last postbaseline average pre-injection SMPG measurement before rescue and during the 6-month on-treatment period will be used as the average pre-injection SMPG endpoint.

FIG. 7—Other secondary efficacy endpoints—Mean 8-point SMPG profile (mmol/l) at baseline and Month 6 endpoint—mITT population (Example 2). LOCF=Last observation carried forward. SMPG=Self Monitoring Plasma Glucose. M6 (LOCF)=Month 6 endpoint LOCF. Note: For all patients rescued during the 6-month period, the last postbaseline 8-point profile SMPG measurement before rescue and during the 6-month on-treatment period will be used as the 8-point profile SMPG endpoint.

FIG. 8—Other secondary efficacy endpoints—Average daily basal insulin dose (U) by visit during the main 6-month on-treatment period—mITT population (Example 2). BAS=Baseline, M6LOCF=last value during main 6-month on-treatment (LOCF). LOCF=Last observation carried forward. Note: For all patients rescued during the 6-month period, the last postbaseline insulin dose measurement before rescue and during the 6-month on-treatment period will be used as the insulin dose endpoint.

FIG. 9—Main efficacy analysis—Mean HbA1c (%) by visit during the 3-month comparative regimen period—mITT sub-study population. BASM6=Baseline (month 6), M9LOCF=last value during the 3-month comparative regimen period (LOCF). LOCF=Last observation carried forward.

FIG. 10—Average daily basal (glargine) and mealtime insulin dose (U) by visit during the 3-month comparative regimen period—mITT sub-study population. BASM6=Baseline (month 6), M9LOCF=last value during the 3-month comparative regimen period (LOCF). LOCF=Last observation carried forward.

FIG. 11—Plot of average glucose (mg/dL) by hour of day during entire treatment period—CGM population FIG. 12—Plot of average glucose (mg/dL) by hour of day during entire morning injection period—CGM population FIG. 13—Plot of average glucose (mg/dL) by hour of day during entire evening injection period—CGM population FIG. 14—Main efficacy analysis—Mean HbA1c (%) by visit during the 3-month comparative regimen period—mITT sub-study population. BASM6=Baseline (month 6), M9LOCF=last value during the 3-month comparative regimen period (LOCF). LOCF=Last observation carried forward. Note: For all patients rescued during the 3-month comparative regimen period, the last postbaseline HbA1c measurement before rescue and during sub-study 3-month on-treatment period will be used as the HbA1c endpoint.

FIG. 15—Average daily basal (glargine) insulin dose (U) by visit during the 3-month comparative regimen period—mITT sub-study population. BASM6=Baseline (month 6), M9LOCF=last value during the 3-month comparative regimen period (LOCF). LOCF=Last observation carried forward. Note: For all patients rescued during the 3-month comparative regimen period, the last postbaseline insulin dose measurement before rescue and during sub-study 3-month on-treatment period will be used as the insulin dose endpoint.

EXAMPLE 1: 6-MONTH, MULTICENTER, RANDOMIZED, OPEN-LABEL, PARALLEL-GROUP STUDY COMPARING THE EFFICACY AND SAFETY OF A NEW FORMULATION OF INSULIN GLARGINE AND LANTUS® BOTH PLUS MEALTIME INSULIN IN PATIENTS WITH TYPE 2 DIABETES MELLITUS WITH A 6-MONTH SAFETY EXTENSION PERIOD

Synopsis

Phase of Development:

Phase 3

Objectives:

Primary Objective:

To assess the effects on glycemic control of HOE901-U300 in comparison to Lantus when given as basal insulin in a regimen with mealtime insulin in terms of $HbA_{1c}$ change over a period of 6 months in patients with type 2 diabetes mellitus.

Main Secondary Objectives:

To compare HOE901-U300 and Lantus in terms of occurrence of nocturnal hypoglycemia, change in preinjection plasma glucose, and change in variability of preinjection plasma glucose.

Further Secondary Objectives:

To compare HOE901-U300 and Lantus in terms of reaching target $HbA_{1c}$ values and controlled plasma glucose;

To compare HOE901-U300 and Lantus in terms of treatment satisfaction of patients using the Diabetes Treatment Satisfaction Questionnaire (status) (DTSQs) (not presented in KRM);

To assess the safety and tolerability of HOE901-U300.

Methodology:

The randomization was 1:1 (HOE901-U300 versus Lantus) and was stratified according to $HbA_{1c}$ values at screening (<8.0%; ≥8.0%). The sample size (400 with HOE901-U300 and 400 with Lantus) was chosen to ensure sufficient power for the primary endpoint (change in $HbA_{1c}$ from baseline to endpoint [Month 6]) as well as to allow conclusions on the first main secondary endpoint (occurrence of nocturnal hypoglycemia).

| | | |
|---|---|---|
| Number of patients: | Planned: 800 (400 per treatment arm) Treated: 806 | Randomized: 807 |
| Evaluated: | efficacy: 804 | Safety: 806 |

Diagnosis and Criteria for Inclusion:

Inclusion criteria: Patients with type 2 diabetes mellitus as defined by WHO; signed written informed consent. Key exclusion criteria: Age<18 years; $HbA_{1c}$<7.0% or >10% at screening; diabetes other than type 2 diabetes mellitus; less than 1 year on basal plus mealtime insulin and self-monitoring of blood glucose; total daily dose insulin glargine <42 U or equivalent dose of NPH in the last 4 weeks prior to the study (if NPH was used as basal insulin prior to the study).

Study Treatments

Investigational Medicinal Products:

Tested drug: HOE901-U300; Control drug: Lantus

Formulations:

HOE901-U300 (insulin glargine 300 U/mL solution) is a sterile, non-pyrogenic, clear, colorless solution in a glass cartridge that has been assembled in a pen-injector (prefilled ie, disposable pen). Lantus (insulin glargine 100 U/mL solution) is a sterile, non-pyrogenic, clear, colorless solution supplied in the marketed Solostar® (prefilled ie, disposable pen).

Route of Administration:

subcutaneous injection

Dose Regimen:

Once daily injection in the evening. The injection time was fixed at the time of randomization and was to be maintained for the duration of the study.

HOE901-U300 or Lantus will be injected once daily subcutaneously in the evening, ie, anytime immediately prior to the evening meal until bedtime. The injection time will be always at the same time within this time window and will be fixed at randomization at the discretion of the patient/investigator. Patients will continue with their mealtime insulin analogue.

Starting Dose:

Patients on Lantus or NPH once daily prior to the baseline visit: the daily dose (U) of HOE901-U300 or Lantus was equal to the median of the total daily basal insulin doses in the last 3 days prior to the baseline visit.

Patients on NPH More than Once Daily Prior to the Baseline Visit:

the daily dose of for HOE901-U300 or Lantus (U) was to be approximately 20% less than the median of the total daily NPH insulin doses in the last 3 days prior to the baseline visit.

The basal insulin dose was adjusted once weekly to achieve fasting SMPG in the target range of 80 to 100 mg/dL (4.4 to 5.6 mmol/L):

by +3 U, if the median fasting SMPG of last 3 days was in the range of >100 mg/dL and <140 mg/dL (>5.6 and <7.8 mmol/L)

by +6 U, if the median fasting SMPG of last 3 days was 140 mg/dL (≥7.8 mmol/L)

by −3 U, if the median fasting SMPG of last 3 days was in the range of ≥60 mg/dL and <80 mg/dL (≥3.3 and <4.4 mmol/L).

Mealtime insulin doses were to be adjusted to optimize glycemic control after basal insulin doses have been optimized. Bolus insulin doses could be reduced as basal insulin doses were increased.

Noninvestigational Medicinal Products:

Patients in both treatment groups were to continue with their mealtime insulin analogue during the study. Patients on concomitant metformin treatment were to continue during the study on a stable dose as received prior to the study, unless safety concerns necessitated a dose reduction or discontinuation of metformin.

Duration of Treatment:

Up to 12 months

Duration of Observation:

up to 54 weeks (up to 2-week screening period+6-month efficacy and safety period+6-month safety extension period+2-day safety follow-up).

The analysis period for efficacy and safety is the main 6-month on-treatment period. Results presented in the present KRM refer to this period.

Criteria for Evaluation:

Efficacy:

Primary Efficacy Endpoint:

change in $HbA_{1c}$ from baseline to endpoint (Month 6).

Main Secondary Endpoints:

incidence of patients (%) with at least one nocturnal hypoglycemia between start of Week 9 and endpoint (month 6), indicated as severe and/or confirmed by plasma glucose ≤70 mg/dL (3.9 mmol/L); change in preinjection SMPG from baseline to endpoint (Month 6) and change in variability of preinjection SMPG from baseline to endpoint (Month 6).

Safety:

Hypoglycemia, occurrence of adverse events particularly treatment-emergent adverse events (TEAEs) and serious adverse events (SAEs), injection site reactions and hypersensitivity reactions. Following information not presented in KRM: physical examination, other safety information including clinical laboratory data, vital signs (including body weight), 12-lead ECG and anti-insulin antibodies.

Statistical Methods:

The primary efficacy endpoint (change in $HbA_{1c}$ from baseline to endpoint [Month 6]) was analyzed using an analysis of covariance (ANCOVA) model with treatment, strata of screening $HbA_{1c}$ (<8.0 and ≥8.0%), and country as fixed effects and using the $HbA_{1c}$ baseline value as a covariate. Differences between HOE901-U300 and Lantus and two-sided 95% confidence intervals were estimated within the framework of ANCOVA.

A stepwise closed testing approach was used for the primary efficacy endpoint to assess non-inferiority and superiority sequentially. Step 1 assessed non inferiority of HOE901-U300 versus Lantus. To assess non-inferiority, the upper bound of the two sided 95% CI for the difference in the mean change in HbA1c from baseline to endpoint between HOE901-U300 and Lantus was compared with a predefined non inferiority margin of 0.4% for HbA1c. Non-inferiority would be demonstrated if the upper bound of the two-sided 95% CI of the difference between HOE901-U300 and Lantus on mITT population is <0.4%. Step 2 assessed superiority of HOE901-U300 versus Lantus only if non inferiority was demonstrated. The superiority of HOE901-U300 over Lantus was demonstrated if the upper bound of the two-sided 95% CI of the difference between HOE901-U300 and Lantus on mITT population was <0.

Only if non-inferiority of HOE901-U300 versus Lantus had been demonstrated for the primary endpoint, would testing for superiority of HOE901-U300 over Lantus on the main secondary endpoints occur within the frame of a hierarchical testing procedure. Safety analyses were descriptive, based on the safety population.

Summary:

Population Characteristics:

A total of 807 patients with type 2 diabetes were randomized to HOE901-U300 (n=404) or to Lantus (n=403); 806 patients were exposed to IMP (safety population). The mITT population (efficacy population) included 804 patients.

Overall, a comparable number of patients in each treatment group discontinued the study prematurely (HOE901-U300: 30/404, 7.4%; Lantus 31/403, 7.7%).

Demographics and baseline characteristics were well-balanced between the treatment groups. The mean age of the study population was 60 years, 246/807 (30.4%) were 65 years. The mean BMI at baseline was 36.6 kg/m². The mean duration of diabetes prior to study start was 15.8 years, the mean duration of prior treatment with basal insulin was 6.6 years and the median total daily insulin dose was 1.1 U/kg body weight. In both treatment groups, mean HbA1c at baseline was 8.14%.

Efficacy Results:

Primary endpoint: The LS mean change in HbA1c from baseline to endpoint (Month 6) was similar in both treatment groups (HOE901-U300: −0.83% (95% CI [−0.946; −0.709]); Lantus: −0.83% (95% CI [−0.944; −0.706]). Non-inferiority of HOE901-U300 versus Lantus was demonstrated with the LS mean difference in HbA1c versus Lantus of −0.00% (95% CI [−0.112; 0.107]) with the upper bound lower than the predefined non-inferiority margin of 0.4%. Superiority of HOE901-U300 versus Lantus was not demonstrated.

1st Main Secondary Endpoint:

The incidence of patients with at least one nocturnal severe and/or confirmed hypoglycemia between start of Week 9 and Month 6 was lower in the HOE901-U300 group [136/404 (33.7%)] than in the Lantus group [180/400 (45.0%)]. Superiority of HOE901-U300 versus Lantus was shown with a relative risk of 0.75 (95% CI [0.63, 0.89]) (p=0.0010).

2nd Main Secondary Endpoint:

The LS mean change in pre-injection SMPG from baseline to endpoint (Month 6) was similar in the HOE901-U300 (−0.90 mmol/L) and Lantus groups (−0.84 mmol/L). The difference between the treatment groups was not statistically significant (LS mean difference −0.06 (95% CI [−0.383, 0.255], p=0.6921).

3rd Main Secondary Endpoint:

As the superiority of HOE901-U300 versus Lantus was not demonstrated for the second main secondary endpoint, no further test was performed for the third main secondary endpoint (decrease in variability of pre-injection SMPG at Month 6, which was similar for both treatment groups).

Other Secondary Efficacy Endpoints (Month 6):

Both the proportion of patients having reached HbA1c<7% and the mean change in FPG were similar between treatment groups. Graphical presentation of the 8-point SMPG profiles of HOE901-U300- and Lantus-treated patients showed a marked decrease in plasma glucose at endpoint (Month 6) compared with baseline. The profiles of the 2 treatment groups are almost superimposable at both baseline and endpoint.

The increase of basal insulin dose in the HOE901-U300 group resulted in a mean daily dose of 103 U at Month 6 compared to Lantus group with a mean daily dose of 94 U (the mean basal insulin dose at baseline was 70 U in both treatment groups). The increase of the daily mealtime insulin dose was comparable between treatment groups with a small increase in the first two weeks. Thereafter, mealtime insulin doses remained stable.

Safety Results:

Overall, hypoglycemia was reported by a consistently lower percentage of patients in the HOE901-U300 group than in the Lantus group. This difference was even more pronounced during the first 2 months of study treatment as well as for events of nocturnal hypoglycemia. During the main 6-month on-treatment period severe hypoglycemia was reported in 21/404 (5.2%) of HOE901-U300 treated patients and 23/402 (5.7%) of Lantus treated patients.

The percentages of patients with any TEAEs (HOE901-U300, 222/404 [55.0%]; Lantus: 215/402 [53.5%]) or with serious TEAEs (HOE901-U300, 25 [6.2%]; Lantus, 21 [5.2%]) were similar between both groups. A similar proportion of patients experienced serious cardiac TEAEs (SOC—cardiac disorders) in both treatment groups (HOE901-U300: n=5, 1.2%; Lantus: n=7; 1.7%).

Six patients died during the study, 3 (0.7%) in each treatment group. Of these, 4 patients died during the first 6 months, 2 (0.5%) in each treatment group. The events with fatal outcome in the three patients in the HOE901-U300 group included the following conditions: infected thrombosis and embolism in the heart, bronchogenic carcinoma with metastasis and—for the third patient—pulmonary emboli. The leading cause of the fatal events in the three patients in the Lantus group included: chronic depression and intoxication with medication, one patient had multitude of conditions including worsening of chronic heart failure (NYHA IV), chronic kidney failure stage 4 with acute decompensation, decompensated diabetes and diabetic nephropathy contributing to the fatal outcome and the last patient suffered acute cardiopulmonary arrest of unknown etiology. None of the deaths were considered related to study drug. A similar number of patients in both treatment groups experienced TEAEs leading to permanent treatment discontinuation (HOE901-U300: n=6, 1.5%; Lantus: n=7, 1.7%).

Hypersensitivity reactions during the main 6-month on-treatment period were reported at a similar rate in both treatment groups (HOE901-U300: n=3, 0.7%; Lantus: n=2, 0.5%).

Overall injection site reactions during the main 6-month on-treatment period showed similar rate in both treatment groups (HOE901-U300: n=9, 2.2%; Lantus: n=6, 1.5%).

Conclusions:

In this study in 807 patients with T2DM on basal insulin in combination with mealtime insulin, the baseline characteristics and demographic characteristics were well balanced across treatment groups. Non-inferiority of HOE901-U300 versus Lantus was shown for the primary efficacy endpoint (change in HbA1c from baseline to endpoint [Month 6]). The incidence of patients (%) reporting nocturnal hypoglycemia (severe and/or confirmed by SMPG ≤70 mg/dL [3.9 mmol/L]) between start of Week 9 and Month 6 was significantly lower in the HOE901-U300 group than in the Lantus group (33.7% and 45% respectively, RR of 0.75, p-value 0.0010; $1^{st}$ main secondary efficacy endpoint). Comparable results between the treatment groups were found for other secondary endpoints such as pre-injection plasma glucose, variability of pre-injection plasma glucose, number of patients reaching target HbA1c, mean change of FPG and 8-point profiles of plasma glucose.

Overall incidence of hypoglycemia (% of patients with at least one event) during the main 6-month on-treatment period was lower in the HOE901-U300 group than in the Lantus group regardless of the category of hypoglycemia.

HOE901-U300 was well tolerated during the main 6-month on-treatment period of the study and no specific safety concerns were observed.

Summary of the efficacy and safety results of the twelve month EDITION 1 extension study
- HbA1c: during the safety extension period (from the main study endpoint [Month 6] to the End of Treatment [Month 12]) HbA1c remained stable and was comparable in both treatment groups
- hypoglycemia: overall, similarly as during the main 6-month treatment period, during the whole study on-treatment period hypoglycemia occurred in a similar or lower percentage of patients in the HOE901-U300 group than in the Lantus group
- safety: HOE901-U300 was well tolerated during the study and no specific safety concerns were observed; during the whole treatment period, the percentages of patients with any TEAEs were similar in both groups (289/404 [71.5%] in the HOE901-U300 and 278/402 [69.2%] in the Lantus treatment group), with no specific SOC contributing. Serious TEAEs were reported by a similar number of patients: (53 [13.1%]) in the HOE901-U300 and 62 [15.4%] in the Lantus treatment group). Two (0.5%) patients in the HOE901-U300 and 4 (1.0%) patient in the Lantus treatment group had TEAE leading to death during the whole study on-treatment period
- body weight: in both treatment groups, during the whole study on-treatment period there was small increase in body weight (1.17 kg for HOE901-U300 and 1.40 kg for Lantus).

1 RESULTS

1.1 STUDY PATIENTS

1.1.1 Study Disposition

TABLE 1

Patient disposition—Randomized population

|  | HOE901-U300 (N = 404) | Lantus (N = 403) |
|---|---|---|
| Randomized and treated | 404 (100%) | 402 (99.8%) |
| Completed main 6-month treatment period | 374 (92.6%) | 371 (92.1%) |
| Permanently discontinued the treatment during the main 6-month period | 30 (7.4%) | 31 (7.7%) |
| Subject's request for treatment discontinuation | 21 (5.2%) | 20 (5.0%) |
| Randomized and treated | 404 (100%) | 402 (99.8%) |
| Reason for treatment discontinuation during the main 6-month period |  |  |
| Adverse event | 9 (2.2%) | 8 (2.0%) |
| Lack of efficacy | 1 (0.2%) | 1 (0.2%) |
| Poor compliance to protocol | 2 (0.5%) | 5 (1.2%) |
| Other reasons | 18 (4.5%) | 17 (4.2%) |
| Status at last study contact of patients who permanently discontinued the treatment during the main 6-month period |  |  |
| Alive | 27 (6.7%) | 28 (6.9%) |
| Dead | 3 (0.7%) | 2 (0.5%) |

Note:

percentages are calculated using the number of patients randomized as denominator

TABLE 2

Analysis populations

|  | HOE901-U300 | Lantus | All |
|---|---|---|---|
| Randomized population | 404 (100%) | 403 (100%) | 807 (100%) |
| Efficacy populations |  |  |  |
| Modified Intent-to-Treat (mITT) | 404 (100%) | 400 (99.3%) | 804 (99.6%) |
| Month 6 completers | 374 (92.6%) | 371 (92.1%) | 745 (92.3%) |
| Safety population | 404 | 402 | 806 |

Note:
For the safety population, patients are tabulated according to treatment actually received (as treated)
For the other populations, patients are tabulated according to their randomized treatment

1.1.2 Demographics and Baseline Characteristics

TABLE 3

Demographics and patient characteristics at baseline—Randomized population

|  | HOE901-U300 (N = 404) | Lantus (N = 403) | All (N = 807) |
|---|---|---|---|
| Age (years) |  |  |  |
| Number | 404 | 403 | 807 |
| Mean (SD) | 60.1 (8.5) | 59.8 (8.7) | 60.0 (8.6) |
| Median | 61.0 | 60.0 | 61.0 |
| Min:Max | 28:83 | 32:86 | 28:86 |
| Age Group (years) [n (%)] |  |  |  |
| Number | 404 | 403 | 807 |
| <65 | 277 (68.6%) | 284 (70.5%) | 561 (69.5%) |

TABLE 3-continued

| Demographics and patient characteristics at baseline—Randomized population | | | |
|---|---|---|---|
| | HOE901-U300 (N = 404) | Lantus (N = 403) | All (N = 807) |
| [65-75[ | 114 (28.2%) | 105 (26.1%) | 219 (27.1%) |
| ≥75 | 13 (3.2%) | 14 (3.5%) | 27 (3.3%) |
| Gender [n (%)] | | | |
| Number | 404 | 403 | 807 |
| Male | 217 (53.7%) | 210 (52.1%) | 427 (52.9%) |
| Female | 187 (46.3%) | 193 (47.9%) | 380 (47.1%) |
| Race [n (%)] | | | |
| Number | 404 | 403 | 807 |
| Caucasian/White | 371 (91.8%) | 374 (92.8%) | 745 (92.3%) |
| Black | 26 (6.4%) | 21 (5.2%) | 47 (5.8%) |
| Asian/Oriental | 6 (1.5%) | 5 (1.2%) | 11 (1.4%) |
| Other | 1 (0.2%) | 3 (0.7%) | 4 (0.5%) |
| Ethnicity [n (%)] | | | |
| Number | 404 | 403 | 807 |
| Hispanic | 26 (6.4%) | 25 (6.2%) | 51 (6.3%) |
| Not Hispanic | 378 (93.6%) | 378 (93.8%) | 756 (93.7%) |
| World region [n (%)] | | | |
| Number | 404 | 403 | 807 |
| Northern America | 206 (51.0%) | 207 (51.4%) | 413 (51.2%) |
| Western Europe | 33 (8.2%) | 33 (8.2%) | 66 (8.2%) |
| Eastern Europe | 147 (36.4%) | 141 (35.0%) | 288 (35.7%) |
| Rest of the world | 18 (4.5%) | 22 (5.5%) | 40 (5.0%) |
| Baseline weight (kg) | | | |
| Number | 404 | 403 | 807 |
| Mean (SD) | 106.2 (21.5) | 106.4 (20.0) | 106.3 (20.8) |
| Median | 104.3 | 104.1 | 104.1 |
| Min:Max | 60:197 | 62:164 | 60:197 |
| Baseline BMI (kg/m$^2$) | | | |
| Number | 404 | 403 | 807 |
| Mean (SD) | 36.6 (6.8) | 36.6 (6.1) | 36.6 (6.4) |
| Median | 35.8 | 36.0 | 35.9 |
| Min:Max | 23:62 | 24:62 | 23:62 |
| Baseline BMI categories (kg/m$^2$) [n (%)] | | | |
| Number | 404 | 403 | 807 |
| <25 | 5 (1.2%) | 2 (0.5%) | 7 (0.9%) |
| [25-30[ | 54 (13.4%) | 47 (11.7%) | 101 (12.5%) |
| [30-40[ | 241 (59.7%) | 244 (60.5%) | 485 (60.1%) |
| ≥40 | 104 (25.7%) | 110 (27.3%) | 214 (26.5%) |
| Baseline estimated GFR (mL/min/1.73 m$^2$) | | | |
| Number | 404 | 403 | 807 |
| Mean (SD) | 73.67 (19.32) | 74.77 (21.38) | 74.22 (20.37) |
| Median | 73.62 | 75.63 | 74.41 |
| Min:Max | 19.9:144.2 | 15.0:141.5 | 15.0:144.2 |
| Baseline estimated GFR categories (mL/min/1.73 m$^2$) [n (%)] | | | |
| Number | 404 | 403 | 807 |
| ≥90 | 75 (18.6%) | 89 (22.1%) | 164 (20.3%) |
| [60-90[ | 235 (58.2%) | 221 (54.8%) | 456 (56.5%) |
| [30-60[ | 92 (22.8%) | 83 (20.6%) | 175 (21.7%) |
| <30 | 2 (0.5%) | 10 (2.5%) | 12 (1.5%) |
| Randomization strata of screening HbA1c (%) [n (%)] | | | |
| Number | 404 | 403 | 807 |
| <8 | 144 (35.6%) | 144 (35.7%) | 288 (35.7%) |
| ≥8 | 260 (64.4%) | 259 (64.3%) | 519 (64.3%) |

BMI = Body Mass Index
GFR = Glomerular filtration rate
GFR is derived from MDRD formula

TABLE 4

Summary of disease characteristics at baseline—Randomized population

| | HOE901-U300 (N = 404) | Lantus (N = 403) | All (N = 807) |
|---|---|---|---|
| Duration of T2D (years) | | | |
| Number | 404 | 403 | 807 |
| Mean (SD) | 15.6 (7.2) | 16.1 (7.8) | 15.8 (7.5) |
| Median | 15.2 | 15.2 | 15.2 |
| Min:Max | 2:43 | 2:44 | 2:44 |
| Category of duration of T2D (years) | | | |
| Number | 404 | 403 | 807 |
| <10 | 90 (22.3%) | 84 (20.8%) | 174 (21.6%) |
| ≥10 | 314 (77.7%) | 319 (79.2%) | 633 (78.4%) |
| Age at onset of T2D (years) | | | |
| Number | 404 | 403 | 807 |
| Mean (SD) | 45.0 (8.8) | 44.2 (9.5) | 44.6 (9.2) |
| Median | 44.9 | 44.4 | 44.7 |
| Min:Max | 18:78 | 15:73 | 15:78 |
| Duration of basal insulin treatment (years) | | | |
| Number | 404 | 403 | 807 |
| Mean (SD) | 6.71 (4.74) | 6.48 (4.78) | 6.59 (4.76) |
| Median | 5.50 | 5.20 | 5.40 |
| Min:Max | 0.3:32.8 | 1.0:33.2 | 0.3:33.2 |
| Previous basal insulin type [n (%)] | | | |
| Number | 402 | 399 | 801 |
| Insulin glargine | 372 (92.5%) | 365 (91.5%) | 737 (92.0%) |
| NPH | 30 (7.5%) | 34 (8.5%) | 64 (8.0%) |
| Previous basal insulin daily injection number[a] [n (%)] | | | |
| Number | 403 | 399 | 802 |
| Once daily | 333 (82.6%) | 334 (83.7%) | 667 (83.2%) |
| Twice daily | 70 (17.4%) | 65 (16.3%) | 135 (16.8%) |
| More than twice daily | 0 | 0 | 0 |
| Previous basal insulin daily dose[b] (U) | | | |
| Number | 371 | 363 | 734 |
| Mean (SD) | 69.93 (30.42) | 70.17 (28.31) | 70.05 (29.38) |
| Median | 60.00 | 60.00 | 60.00 |
| Q1:Q3 | 49.00:81.00 | 50.00:80.00 | 50.00:80.00 |
| Min:Max | 42.0:200.0 | 42.0:200.0 | 42.0:200.0 |
| Previous basal insulin daily dose[b] (U/kg) | | | |
| Number | 371 | 363 | 734 |
| Mean (SD) | 0.668 (0.264) | 0.667 (0.240) | 0.667 (0.252) |
| Median | 0.598 | 0.609 | 0.601 |
| Duration of T2D (years) | | | |
| Q1:Q3 | 0.487:0.769 | 0.493:0.770 | 0.490:0.769 |
| Min:Max | 0.30:2.12 | 0.31:1.76 | 0.30:2.12 |
| Previous mealtime insulin daily dose[b] (U) | | | |
| Number | 396 | 397 | 793 |
| Mean (SD) | 57.11 (36.45) | 58.42 (37.89) | 57.77 (37.16) |
| Median | 49.30 | 52.00 | 50.00 |
| Q1:Q3 | 32.00:72.80 | 31.70:75.00 | 32.00:73.70 |
| Min:Max | 5.0:350.0 | 3.6:280.0 | 3.6:350.0 |
| Previous mealtime insulin daily dose[b] (U/kg) | | | |
| Number | 396 | 397 | 793 |
| Mean (SD) | 0.537 (0.336) | 0.540 (0.315) | 0.538 (0.325) |
| Median | 0.474 | 0.488 | 0.480 |
| Q1:Q3 | 0.332:0.670 | 0.329:0.687 | 0.330:0.685 |
| Min:Max | 0.06:3.08 | 0.03:2.30 | 0.03:3.08 |
| Previous total insulin daily dose[b] (U) | | | |
| Number | 366 | 361 | 727 |
| Mean (SD) | 126.00 (56.57) | 127.78 (55.97) | 126.88 (56.24) |
| Median | 112.00 | 114.00 | 113.00 |
| Q1:Q3 | 88.00:149.10 | 87.00:154.90 | 87.90:152.00 |
| Min:Max | 47.0:530.0 | 52.4:384.0 | 47.0:530.0 |

TABLE 4-continued

Summary of disease characteristics at baseline—Randomized population

|  | HOE901-U300 (N = 404) | Lantus (N = 403) | All (N = 807) |
|---|---|---|---|
| Previous total insulin daily dose[b] (U/kg) | | | |
| Number | 366 | 361 | 727 |
| Mean (SD) | 1.193 (0.484) | 1.199 (0.447) | 1.196 (0.465) |
| Median | 1.085 | 1.101 | 1.096 |
| Q1:Q3 | 0.875:1.401 | 0.871:1.388 | 0.871:1.398 |
| Min:Max | 0.50:4.66 | 0.51:3.13 | 0.50:4.66 |
| Prior use of Lantus[c] | | | |
| Number | 404 | 403 | 807 |
| Yes | 373 (92.3%) | 369 (91.6%) | 742 (91.9%) |
| No | 31 (7.7%) | 34 (8.4%) | 65 (8.1%) |
| Prior use of Metformin[c] | | | |
| Number | 404 | 403 | 807 |
| Yes | 227 (56.2%) | 234 (58.1%) | 461 (57.1%) |
| No | 177 (43.8%) | 169 (41.9%) | 346 (42.9%) |

T2D = Type 2 diabetes
[a]Maximal injection number of the patient.
[b]Mean of the patient from the basal/mealtime/total daily doses during the last 7 days prior to randomization
[c]Taken within 3 months before screening

1.2 Efficacy Evaluation
1.2.1 Primary Efficacy Endpoint

TABLE 5

Main efficacy analysis—Mean change in HbA1c (%) from baseline to Month 6 endpoint using LOCF procedure—mITT population (FIG. 1)

| HbA1c (%) | HOE901-U300 (N = 404) | Lantus (N = 400) |
|---|---|---|
| Baseline | | |
| Number | 391 | 394 |
| Mean (SD) | 8.14 (0.78) | 8.14 (0.76) |
| Median | 8.10 | 8.10 |
| Min:Max | 6.5:10.6 | 6.4:10.3 |
| Month 6 endpoint (LOCF) | | |
| Number | 391 | 394 |
| Mean (SD) | 7.25 (0.85) | 7.28 (0.92) |
| Median | 7.10 | 7.20 |
| Min:Max | 5.3:10.6 | 5.2:13.8 |
| Change from baseline to Month 6 endpoint (LOCF) | | |
| Number | 391 | 394 |
| Mean (SD) | −0.88 (0.81) | −0.86 (0.92) |
| Median | −0.90 | −0.90 |
| Min:Max | −3.4:1.8 | −3.1:4.6 |
| LS Mean (SE)[a] | −0.83 (0.060) | −0.83 (0.061) |
| 95% CI | (−0.946 to −0.709) | (−0.944 to −0.706) |
| LS Mean difference (SE) vs. Lantus[a] | −0.00 (0.056) | |
| 95% CI | (−0.112 to 0.107) | |

LOCF = Last observation carried forward.
[a]Analysis of covariance (ANCOVA) model with treatment groups (HOE901-U300 and LANTUS), randomization strata of screening HbA1c (<8.0, ≥8.0%), and country as fixed effects and baseline HbA1c value as a covariate.

1.2.2 Main Secondary Endpoints
1.2.2.1 Nocturnal Hypoglycemia

TABLE 6

First main secondary efficacy endpoint—Number (%) of patients with at least one nocturnal hypoglycemia [00:00 to 05:59] occurring between start of Week 9 and Month 6 endpoint (using LOCF procedure), indicated as severe and/or confirmed by plasma glucose ≤3.9 mmol/L (70 mg/dL)—mITT population

|  | HOE901-U300 (N = 404) | Lantus (N = 400) |
|---|---|---|
| Severe and/or confirmed nocturnal hypoglycemia [00:00 to 05:59] | | |
| n (%) | 136 (33.7%) | 180 (45.0%) |
| RR (95% CI) vs. Lantus[a] | 0.75 (0.63 to 0.89) | — |
| p-value (CMH) | 0.0010 | — | n (%) = number and percentage of patients with at least one nocturnal hypoglycemia event, indicated as severe and/or confirmed by plasma glucose 3.9 mmol/L (70 mg/dL)
[a]Based on RR stratified by randomization strata of screening HbA1c (<8.0 or ≥8.0%), using a CMH methodology

1.2.2.2 Pre-Injection Plasma Glucose—Month 6 Endpoint

TABLE 7

Second main secondary efficacy endpoint—Mean change in average pre-injection SMPG (mmol/L) from baseline to Month 6 endpoint using LOCF procedure—mITT population (FIG. 2)

| Average pre-injection SMPG (mmol/L) | HOE901-U300 (N = 404) | Lantus (N = 400) |
|---|---|---|
| Baseline | | |
| Number | 365 | 360 |
| Mean (SD) | 10.31 (2.58) | 10.44 (2.65) |
| Median | 10.02 | 9.98 |
| Min:Max | 4.4:20.6 | 5.6:20.8 |
| Month 6 endpoint (LOCF) | | |
| Number | 365 | 360 |
| Mean (SD) | 9.11 (2.42) | 9.28 (2.45) |

TABLE 7-continued

Second main secondary efficacy endpoint—Mean change in average pre-injection SMPG (mmol/L) from baseline to Month 6 endpoint using LOCF procedure—mITT population (FIG. 2)

| Average pre-injection SMPG (mmol/L) | HOE901-U300 (N = 404) | Lantus (N = 400) |
|---|---|---|
| Median | 8.77 | 8.69 |
| Min:Max | 3.8:20.3 | 4.8:19.1 |
| Change from baseline to Month 6 endpoint (LOCF) | | |
| Number | 365 | 360 |
| Mean (SD) | −1.20 (2.84) | −1.16 (2.70) |
| Median | −1.19 | −1.24 |
| Min:Max | −13.2:8.9 | −11.3:7.5 |
| LS Mean (SE)[b] | −0.90 (0.183) | −0.84 (0.183) |
| 95% CI | (−1.260 to −0.543) | (−1.196 to −0.478) |
| LS Mean difference (SE) vs. Lantus[b] | −0.06 (0.162) | |
| 95% CI | (−0.383 to 0.255) | |
| p-value(ANCOVA) | 0.6921 | |

LOCF = Last observation carried forward.
SMPG = Self Monioring Plasma Glucose
[a] Average is assessed by the mean of at least 3 SMPG calculated over the 7 days preceding the given visit.
[b] Analysis of covariance (ANCOVA) model with treatment groups (HOE901-U300 and LANTUS), randomization strata of screening HbA1c (<8.0, ≥8.0%), and country as fixed effects and baseline average pre-injection SMPG value as a covariate.

At V1 (week-2), the investigator or a member of the investigational staff will provide patients with a blood glucometer and the corresponding supplies (needles, control solutions, test strips etc.) and with diaries in order to perform self-measurement of plasma glucose and its recording. Patients will be shown how to accurately measure plasma glucose values with the blood glucometer. The investigator or a member of the investigational staff will explain the need to measure glucose at the times requested for profiles and to correctly record the values in the patient diaries. Training is repeated as often as necessary at the study visits and the investigational staff reviews the patient's diary at each visit. Blood glucose values will be measured by the patient using the sponsor-provided blood glucose meter. Patients will document their SMPG data in the diary.

The patients will be instructed to bring the blood glucometers provided by the sponsor with them to each office visit. The blood glucometers should be calibrated according to instructions given in the package leaflet and the investigational site should also check regularly the glucometers using the provided control solutions for data validity.

Starting with V1 (screening visit), the diary includes sections for recording by patients of Study treatment and mealtime insulin: time and dose of HOE901-U300 or Lantus injections (Lantus or NPH injections during screening period) and mealtime/bolus insulin analogue injections;

SMPG: time and value of SMPG;
1. Fasting SMPG in the morning (prebreakfast)
2. SMPG within 30 minutes prior to injection of basal insulin during 7 days before each visit
3. 4-point profile and 8-point profile SMPG
4. SMPG related to hypoglycemic events
5. Any other SMPG (whatever the reason of measurement)

SMPG measurements are scheduled as follows:
Fasting plasma glucose (SMPG): The fasting (prebreakfast) SMPG will be measured daily throughout the study. During the week before visit 3 (Day 1, Baseline) compliance to the fasting SMPG measurement schedule will be used to assess eligibility for entry in the randomized treatment period. During the study, when uptitration has been completed and fasting (prebreakfast) SMPG is stable in the target range, at least of 3 measurements per week should be performed.

Plasma glucose within 30 minutes prior to injection of study drug (preinjection SMPG): Preinjection SMPG will be done within 30 min prior to the injection of the IMP (HOE901-U300 or Lantus) on at least 7 days before baseline and before each on site visit throughout the study. At days when 4-point or 8-point profiles are done: if time of preinjection SMPG is the same as a time point of the 4-point or 8-point profile, the SMPG value has to be assigned by the patient in the diary to both (eg, preinjection PG; bedtime).

4-point SMPG profiles (prebreakfast, prelunch, predinner, bedtime): During the week before baseline visit and during the first 12 weeks of treatment with IMP, patients will perform 4-point SMPG profiles at least on 3 days per week. Once the titration goal is reached, the number of 4-point SMPG profiles can be reduced according to the investigator's judgment but 4-point SMPG profiles at least on 3 days in the week before each visit are mandatory. It is, however, recommended to perform 4-point SMPG profiles daily throughout the study for optimal adjustment of the insulin regimen;

8-point blood glucose profiles (starting with a measurement at 03:00 am at night; before and 2 hours after breakfast; before and 2 hours after lunch; before and 2 hours after dinner; at bedtime): Patients will perform 8-point SMPG profiles at least one day in the 5 days before each on-site visit. It is, however, recommended to perform 8-point SMPG profiles at least once weekly up to week 8, and once every second week thereafter. Special attention should be paid that the 3.00 a.m. SMPG value is recorded.

SMPG during episodes of symptomatic hypoglycemia: Whenever the patients feel hypoglycemic symptoms, plasma glucose should be measured by the patient (or others, if applicable), if possible. Patients should be instructed to measure plasma glucose levels prior to the administration of glucose or carbohydrate intake whenever symptomatic hypoglycemia is suspected, unless safety considerations necessitate immediate glucose/carbohydrate rescue prior to confirmation.

The following SMPG values have to be copied into the eCRF:

During the week prior to baseline visit and during the first 12 weeks until Visit 8 (week 12):
Fasting (prebreakfast) SMPG: daily
Preinjection SMPG (within 30 minutes prior to injection of the basal insulin): at 7 days prior to each on-site visit
4-point profile SMPG: at 3 different days in each week until visit 8 (week 12)
8-point profile SMPG: 1 profile within 5 days before each on-site visit
SMPG related to hypoglycemic event: whenever documented Note: following phone call visits the following data at the minimum will be entered into the e-CRF: fasting (prebreakfast) SMPG over last 3 days, SMPG related to hypoglycemic event: whenever documented. The remaining SMPG data of the week prior to the phone call visits will be entered into the e-CRF at a subsequent on-site visit. After Visit 8 (week 12):
Fasting (prebreakfast) SMPG: during 7 days before each on-site visit
Preinjection SMPG (within 30 minutes prior to injection of the basal insulin): at 7 days prior to each on-site visit 4-point profile SMPG: at 3 different days within 7 days before each on-site visit 8-point profile SMPG: at one day within 5 days before each on-site visit SMPG related to hypoglycemic event: whenever documented All glucose values will be used by the investigator to monitor glycemia.

1.2.2.3 Variability of Preinjection SMPG—Month 6 Endpoint

TABLE 8

Third main secondary efficacy endpoint—Mean change in variability of pre-injection SMPG from baseline to Month 6 endpoint using LOCF procedure—mITT population

| Variability of pre-injection SMPG | HOE901-U300 (N = 404) | Lantus (N = 400) |
|---|---|---|
| Baseline | | |
| Number | 365 | 360 |
| Mean (SD) | 25.55 (12.41) | 24.97 (11.82) |
| Median | 23.92 | 24.34 |
| Min:Max | 0.0:82.8 | 1.7:74.3 |
| Month 6 endpoint (LOCF) | | |
| Number | 365 | 360 |
| Mean (SD) | 22.23 (11.76) | 21.57 (11.47) |
| Median | 21.79 | 20.42 |
| Min:Max | 0.0:60.3 | 0.9:64.1 |
| Change from baseline to Month 6 endpoint (LOCF) | | |
| Number | 365 | 360 |
| Mean (SD) | −3.32 (14.59) | −3.40 (14.54) |
| Median | −2.88 | −3.17 |
| Min:Max | −62.5:48.1 | −54.7:41.7 |
| LS Mean (SE)[a] | −1.09 (1.222) | −1.11 (1.222) |
| 95% CI | (−3.486 to 1.310) | (−3.508 to 1.292) |
| LS Mean difference (SE) vs. Lantus[a] | 0.02 (1.087) | |
| 95% CI | (−2.114 to 2.154) | |

LOCF = Last observation carried forward.
SMPG = Self Monioring Plasma Glucose
Variability is assessed by the mean of coefficient of variation calculated over at least 3 SMPG measured during the 7 days preceding the given visit
[a]Analysis of variance (ANOVA) model with treatment groups (HOE901-U300 and LANTUS), randomization strata of screening HbA1c (<8.0, ≥8.0%), and country as fixed effects

1.2.3 Other Secondary Efficacy Endpoints

1.2.3.1 Percentage of Patients with HbA1c <7% at Month 6

TABLE 9

Other secondary efficacy endpoint—Number (%) of patients with HbA1c <7% at Month 6 endpoint (using LOCF procedure) and Number (%) of patients with HbA1c <7% at Month 6 endpoint (using LOCF procedure) having experienced no hypoglycemia indicated as severe and/or confirmed by plasma glucose <3 mmol/L (54 mg/dL) during the last 3 months of the main 6-month treatment period—mITT population

| | HOE901-U300 (N = 404) | Lantus (N = 400) |
|---|---|---|
| HbA1c <7% | | |
| Number | 391 | 394 |
| n (%) | 155 (39.6%) | 161 (40.9%) |
| RR (95% CI) vs. Lantus[a] | 0.97 (0.83 to 1.14) | — |

TABLE 9-continued

Other secondary efficacy endpoint—Number (%) of patients with HbA1c <7% at Month 6 endpoint (using LOCF procedure) and Number (%) of patients with HbA1c <7% at Month 6 endpoint (using LOCF procedure) having experienced no hypoglycemia indicated as severe and/or confirmed by plasma glucose <3 mmol/L (54 mg/dL) during the last 3 months of the main 6-month treatment period—mITT population

| | HOE901-U300 (N = 404) | Lantus (N = 400) |
|---|---|---|
| HbA1c <7% and no severe and/or confirmed (<3.0 mmol/L;<54 mg/dL) hypoglycemia | | |
| Number | 393 | 394 |
| n (%) | 99 (25.2%) | 95 (24.1%) |
| RR (95% CI) vs. Lantus[a] | 1.05 (0.82 to 1.33) | — |

[a]Based on RR stratified by randomization strata of screening HbA1c (<8.0 or ≥8.0%), using a CMH methodology
LOCF = Last observation carried forward.
RR = relative risk

1.2.3.2 Change in FPG from Baseline to Month 6 Endpoint

TABLE 10

Other secondary efficacy endpoint - Mean change in FPG (mmol/L) from baseline to Month 6 endpoint using LOCF procedure - mITT population

| FPG(mmol/L) | HOE901-U300 (N = 404) | Lantus (N = 400) |
|---|---|---|
| Baseline | | |
| Number | 378 | 385 |
| Mean (SD) | 8.72 (2.83) | 8.90 (2.94) |
| Median | 8.40 | 8.60 |
| Min:Max | 2.3:19.2 | 2.4:20.8 |
| Month 6 endpoint (LOCF) | | |
| Number | 378 | 385 |
| Mean (SD) | 7.25 (2.56) | 7.21 (2.40) |
| Median | 6.80 | 6.90 |
| Min:Max | 2.4:18.2 | 2.7:17.6 |
| Change from baseline to Month 6 endpoint (LOCF) | | |
| Number | 378 | 385 |
| Mean (SD) | −1.47 (3.10) | −1.69 (3.21) |
| Median | −1.40 | −1.70 |
| Min:Max | −13.7:11.3 | −12.5:9.0 |
| LS Mean (SE)[a] | −1.29 (0.191) | −1.39 (0.191) |
| 95% CI | (−1.661 to −0.910) | (−1.763 to −1.012) |
| LS Mean difference (SE) vs. Lantus[a] | 0.10 (0.171) | |
| 95% CI | (−0.234 to 0.437) | |

FPG = Fasting Plasma Glucose
LOCF = Last observation carried forward.
[a]Analysis of covariance (ANCOVA) model with treatment groups (HOE901-U300 and LANTUS), randomization strata of screening HbA1c (<8.0, ≥8.0%), and country as fixed effects and baseline FPG value as a covariate.

1.2.3.3 Eight-Point SMPG Profile

FIG. 3 Describes the Mean 8-Point SMPG Profile (Mmol/l) at Baseline and Month 6 Endpoint—mITT Population

1.2.3.4 Basal and Mealtime Insulin Dose

FIG. 4 Describes the Average Daily Basal Insulin and Mealtime Insulin Dose (U) by Visit During the Main 6-Month On-Treatment Period—mITT Population

1.3 SAFETY EVALUATION

1.3.1 Extent of Exposure

TABLE 11

Exposure to investigational product for the main 6-month on-treatment period - Safety population

|  | HOE901-U300 (N = 404) | Lantus (N = 402) |
|---|---|---|
| Cumulative exposure to main 6-month treatment |  |  |
| (patient years) | 194.7 | 193.3 |
| Duration of main 6-month study treatment (days) |  |  |
| Number | 404 | 401 |
| Mean (SD) | 176.0 (29.8) | 176.0 (30.0) |
| Median | 183.0 | 183.0 |
| Min:Max | 6:199 | 5:216 |

TABLE 11-continued

Exposure to investigational product for the main 6-month on-treatment period - Safety population

|  | HOE901-U300 (N = 404) | Lantus (N = 402) |
|---|---|---|
| Duration of main 6-month study treatment by category [n(%)] |  |  |
| up to 2 weeks | 2 (0.5%) | 5 (1.2%) |
| >2 to 4 weeks | 3 (0.7%) | 3 (0.7%) |
| >4 to 8 weeks | 8 (2.0%) | 2 (0.5%) |
| >8 to 12 weeks | 5 (1.2%) | 6 (1.5%) |
| >12 to 17 weeks | 2 (0.5%) | 3 (0.7%) |
| >17 to 26 weeks | 129 (31.9%) | 122 (30.4%) |
| >26 weeks | 255 (63.1%) | 260 (64.8%) |
| Cumulative duration of main 6-month study treatment by category [n(%)] |  |  |
| ≥1 days | 404 (100%) | 401 (100%) |
| >2 weeks | 402 (99.5%) | 396 (98.8%) |
| >4 weeks | 399 (98.8%) | 393 (98.0%) |
| >8 weeks | 391 (96.8%) | 391 (97.5%) |
| >12 weeks | 386 (95.5%) | 385 (96.0%) |
| >17 weeks | 384 (95.0%) | 382 (95.3%) |
| >26 weeks | 255 (63.1%) | 260 (64.8%) |

Note:
Patients are considered in the treatment group they actually received at randomization

1.3.2 Hypoglycemia

TABLE 12

Number (%) of patients with at least one emergent hypoglycemia event during the main 6-month on-treatment period - Safety population

| Type of hypoglycemia event n(%) | All hypoglycemia | | Nocturnal hypoglycemia (00:00-05:59) | |
|---|---|---|---|---|
|  | HOE901-U300 (N = 404) | Lantus (N = 402) | HOE901-U300 (N = 404) | Lantus (N = 402) |
| Any hypoglycemia event | 336 (83.2%) | 356 (88.6%) | 183 (45.3%) | 238 (59.2%) |
| Severe hypoglycemia | 21 (5.2%) | 23 (5.7%) | 8 (2.0%) | 10 (2.5%) |
| Documented symptomatic hypoglycemia |  |  |  |  |
| ≤3.9 mmol/L (70 mg/dL) | 282 (69.8%) | 312 (77.6%) | 145 (35.9%) | 193 (48.0%) |
| <3.0 mmol/L (54 mg/dL) | 157 (38.9%) | 171 (42.5%) | 55 (13.6%) | 73 (18.2%) |
| Asymptomatic hypoglycemia |  |  |  |  |
| ≤3.9 mmol/L (70 mg/dL) | 255 (63.1%) | 271 (67.4%) | 84 (20.8%) | 100 (24.9%) |
| <3.0 mmol/L (54 mg/dL) | 70 (17.3%) | 73 (18.2%) | 9 (2.2%) | 15 (3.7%) |
| Probable symptomatic hypoglycemia | 18 (4.5%) | 28 (7.0%) | 6 (1.5%) | 9 (2.2%) |
| Relative hypoglycemia |  |  |  |  |
| >3.9 mmol/L (70 mg/dL) | 56 (13.9%) | 76 (18.9%) | 15 (3.7%) | 33 (8.2%) |
| Severe and/or confirmed[a] hypoglycemia |  |  |  |  |
| ≤3.9 mmol/L (70 mg/dL) | 329 (81.4%) | 352 (87.6%) | 180 (44.6%) | 229 (57.0%) |
| <3.0 mmol/L (54 mg/dL) | 185 (45.8%) | 202 (50.2%) | 65 (16.1%) | 84 (20.9%) | n (%) = number and percentage of patients with at least one hypoglycemia event
[a]Confirmed hypoglycemia = documented symptomatic hypoglycemia or asymptomatic hypoglycemia Hypoglycemia events are categorized as follows (American Diabetes Association Workgroup on Hypoglycemia. Defining and Reporting Hypoglycemia in Diabetes. Diabetes Care 2005; 28:1245-49):

Severe Hypoglycemia

Severe hypoglycemia is an event requiring assistance of another person to actively administer carbohydrate, glucagon, or other resuscitative actions.

These episodes may be associated with sufficient neuroglycopenia to induce seizure, unconsciousness or coma. Plasma glucose measurements may not be available during such an event, but neurological recovery attributable to the restoration of plasma glucose to normal is considered sufficient evidence that the event was induced by a low plasma glucose concentration.

The definition of severe symptomatic hypoglycemia includes all episodes in which neurological impairment was severe enough to prevent self-treatment and which were thus thought to place patients at risk for injury to themselves or others.

Note that "requires assistance" means that the patient could not help himself or herself. Assisting a patient out of kindness, when assistance is not required, should not be considered a "requires assistance" incident.

Severe symptomatic hypoglycemia will be qualified as an SAE only if it fulfills SAE criteria. All events of seizure, unconsciousness or coma must be reported as SAEs.

Documented Symptomatic Hypoglycemia

Documented symptomatic hypoglycemia is an event during which typical symptoms of hypoglycemia accompanied by a measured plasma glucose concentration of ≤70 mg/dL (3.9 mmol/L) (American Diabetes Association Workgroup on Hypoglycemia. Defining and Reporting Hypoglycemia in Diabetes. Diabetes Care 2005; 28:1245-49).

Clinical symptoms that are considered to result from a hypoglycemic episode are, eg, increased sweating, nervousness, asthenia/weakness, tremor, dizziness, increased appetite, palpitations, headache, sleep disorder, confusion, seizures, unconsciousness, coma.

Asymptomatic Hypoglycemia

Asymptomatic hypoglycemia is an event not accompanied by typical symptoms of hypoglycemia but with a measured plasma glucose concentration less than or equal to 70 mg/dL (3.9 mmol/L);

Probable Symptomatic Hypoglycemia

Probable symptomatic hypoglycemia is an event during which symptoms of hypoglycemia are not accompanied by a plasma glucose determination, but was presumably caused by a plasma glucose concentration less than or equal to 70 mg/dL (3.9 mmol/L); symptoms treated with oral carbohydrate without a test of plasma glucose.

Relative Hypoglycemia

Relative hypoglycemia is an event during which the person with diabetes reports any of the typical symptoms of hypoglycemia, and interprets the symptoms as indicative of hypoglycemia, but with a measured plasma glucose concentration greater than 70 mg/dL (3.9 mmol/L).

Nocturnal Hypoglycemia

Nocturnal hypoglycemia is any hypoglycemia of the above categories that occurs between 00:00 and 05:59 hours. Note: Relative nocturnal hypoglycemia will not be included in the analysis of the main secondary endpoint (patients with at least one nocturnal hypoglycemia).

In addition of the threshold of less than or equal to 70 mg/dL (3.9 mmol/L), hypoglycemia episodes with a plasma glucose of <54 mg/dL (3.0 mmol/L) will be analyzed separately (Guideline on clinical investigation of medicinal products in the treatment of diabetes mellitus. Draft. EMA, 20 Jan. 2010).

The classification of hypoglycemia will be done on basis of the clock time: Hypoglycemia episodes will be analyzed by their diurnal distribution (0:00-24:00) and in addition by time of the day:

nocturnal hypoglycemia defined by time of the day: any hypoglycemia of the above categories that occurs between 00:00 and 05:59 a.m. hours, regardless whether patient was awake or woke up because of the event);

daytime hypoglycemia: any hypoglycemia of the above categories that occurs between 6:00 a.m. and 23:59.

Patients will be instructed to measure finger stick plasma glucose levels prior to the administration of carbohydrates whenever symptomatic hypoglycemia is suspected, unless safety considerations necessitate immediate glucose rescue prior to confirmation, and then a glucose measurement should be performed as soon as safe, with appropriate diary documentation.

Details on hypoglycemia episodes will be captured in the patient diaries, and patients will contact the sites as soon as possible following severe events to review the details and decide on any necessary measures to be taken.

All hypoglycemia episodes will be documented on the "hypoglycemia specific form" in the e-CRF. This includes all symptomatic hypoglycemia events and asymptomatic hypoglycemia. Hypoglycemia events fulfilling the criteria of a SAE will be documented on the SAE form in the e-CRF.

Incidences of hypoglycemia per patient year will be computed per patient as: 365.25×(number of episodes of hypoglycemia)/(number of days exposed) and summarized by type of event and treatment group.

TABLE 13

Number (%) of patients with at least one emergent hypoglycemia event during the main 6-month on-treatment period by study period - Safety population

| | All hypoglycemia | | Nocturnal hypoglycemia (00:00-05:59) | |
|---|---|---|---|---|
| Type of hypoglycemia event n(%) | HOE901-U300 (N = 404) | Lantus (N = 402) | HOE901-U300 (N = 404) | Lantus (N = 402) |
| Any hypoglycemia event | | | | |
| Overall | 336 (83.2%) | 356 (88.6%) | 183 (45.3%) | 238 (59.2%) |
| Treatment Start to Week 8 | 275 (68.1%) | 310 (77.1%) | 112 (27.7%) | 153 (38.1%) |
| After Week 8 to Month 6 | 298 (73.8%) | 304 (75.6%) | 140 (34.7%) | 181 (45.0%) |

TABLE 13-continued

Number (%) of patients with at least one emergent hypoglycemia event during the main 6-month on-treatment period by study period - Safety population

| Type of hypoglycemia event n(%) | All hypoglycemia | | Nocturnal hypoglycemia (00:00-05:59) | |
|---|---|---|---|---|
| | HOE901-U300 (N = 404) | Lantus (N = 402) | HOE901-U300 (N = 404) | Lantus (N = 402) |
| Severe hypoglycemia | | | | |
| Overall | 21 (5.2%) | 23 (5.7%) | 8 (2.0%) | 10 (2.5%) |
| Treatment Start to Week 8 | 7 (1.7%) | 12 (3.0%) | 3 (0.7%) | 3 (0.7%) |
| After Week 8 to Month 6 | 19 (4.7%) | 13 (3.2%) | 5 (1.2%) | 7 (1.7%) |
| Documented symptomatic hypoglycemia ≤3.9 mmol/L (70 mg/dL) | | | | |
| Overall | 282 (69.8%) | 312 (77.6%) | 145 (35.9%) | 193 (48.0%) |
| Treatment Start to Week 8 | 210 (52.0%) | 250 (62.2%) | 79 (19.6%) | 109 (27.1%) |
| After Week 8 to Month 6 | 242 (59.9%) | 242 (60.2%) | 108 (26.7%) | 146 (36.3%) |
| <3.0 mmol/L (54 mg/dL) | | | | |
| Overall | 157 (38.9%) | 171 (42.5%) | 55 (13.6%) | 73 (18.2%) |
| Treatment Start to Week 8 | 96 (23.8%) | 113 (28.1%) | 31 (7.7%) | 39 (9.7%) |
| After Week 8 to Month 6 | 119 (29.5%) | 115 (28.6%) | 40 (9.9%) | 47 (11.7%) |
| Asymptomatic hypoglycemia ≤3.9 mmol/L (70 mg/dL) | | | | |
| Overall | 255 (63.1%) | 271 (67.4%) | 84 (20.8%) | 100 (24.9%) |
| Treatment Start to Week 8 | 187 (46.3%) | 210 (52.2%) | 44 (10.9%) | 60 (14.9%) |
| After Week 8 to Month 6 | 203 (50.2%) | 206 (51.2%) | 57 (14.1%) | 64 (15.9%) |
| <3.0 mmol/L (54 mg/dL) | | | | |
| Overall | 70 (17.3%) | 73 (18.2%) | 9 (2.2%) | 15 (3.7%) |
| Treatment Start to Week 8 | 34 (8.4%) | 39 (9.7%) | 6 (1.5%) | 10 (2.5%) |
| After Week 8 to Month 6 | 52 (12.9%) | 46 (11.4%) | 4 (1.0%) | 6 (1.5%) |
| Severe and/or confirmed[a] hypoglycemia ≤3.9 mmol/L (70 mg/dL) | | | | |
| Overall | 329 (81.4%) | 352 (87.6%) | 180 (44.6%) | 229 (57.0%) |
| Treatment Start to Week 8 | 269 (66.6%) | 299 (74.4%) | 107 (26.5%) | 139 (34.6%) |
| After Week 8 to Month 6 | 295 (73.0%) | 303 (75.4%) | 135 (33.4%) | 180 (44.8%) |
| <3.0 mmol/L (54 mg/dL) | | | | |
| Overall | 185 (45.8%) | 202 (50.2%) | 65 (16.1%) | 84 (20.9%) |
| Treatment Start to Week 8 | 117 (29.0%) | 131 (32.6%) | 38 (9.4%) | 48 (11.9%) |
| After Week 8 to Month 6 | 148 (36.6%) | 146 (36.3%) | 44 (10.9%) | 51 (12.7%) | n (%) = number and percentage of patients with at least one hypoglycemia event
[a]Confirmed hypoglycemia = documented symptomatic hypoglycemia or asymptomatic hypoglycemia

1.3.3 Treatment-Emergent Adverse Events

TABLE 14

Treatment emergent adverse events during the main 6-month on-treatment period - Safety population

| n (%) | HOE901-U300 (N = 404) | Lantus (N = 402) |
|---|---|---|
| Patients with any TEAE | 222 (55.0%) | 215 (53.5%) |
| Patients with any treatment emergent SAE | 25 (6.2%) | 21 (5.2%) |
| Patients with any TEAE leading to death | 1 (0.2%) | 2 (0.5%) |
| Patients with any TEAE leading to permanent treatment discontinuation | 6 (1.5%) | 7 (1.7%) |

TEAE: Treatment emergent adverse event, SAE: Serious Adverse Event
n (%) = number and percentage of patients with at least one TEAE

TABLE 15

Number (%) of patients with TEAE(s) that occurred with HLT ≥ 2% in any treatment group by Primary SOC, HLT and PT for the main 6-month on-treatment period - Safety population

| PRIMARY SYSTEM ORGAN CLASS HLT: High Level Term Preferred Term n(%) | HOE901-U300 (N = 404) | Lantus (N = 402) |
|---|---|---|
| Any class | 222 (55.0%) | 215 (53.5%) |
| INFECTIONS AND INFESTATIONS | 115 (28.5%) | 121 (30.1%) |
| HLT: Abdominal and gastrointestinal infections | 6 (1.5%) | 12 (3.0%) |
| Abdominal wall abscess | 1 (0.2%) | 0 |
| Diverticulitis | 0 | 3 (0.7%) |
| Enteritis infectious | 1 (0.2%) | 0 |
| Gastroenteritis | 4 (1.0%) | 9 (2.2%) |
| HLT: Ear infections | 3 (0.7%) | 9 (2.2%) |
| Ear infection | 2 (0.5%) | 6 (1.5%) |
| Otitis externa | 1 (0.2%) | 1 (0.2%) |
| Otitis media | 0 | 2 (0.5%) |

TABLE 15-continued

Number (%) of patients with TEAE(s) that occurred with HLT ≥ 2% in any treatment group by Primary SOC, HLT and PT for the main 6-month on-treatment period - Safety population

| PRIMARY SYSTEM ORGAN CLASS<br>HLT: High Level Term<br>Preferred Term n(%) | HOE901-U300<br>(N = 404) | Lantus<br>(N = 402) |
|---|---|---|
| HLT: Influenza viral infections | 8 (2.0%) | 9 (2.2%) |
| Influenza | 8 (2.0%) | 9 (2.2%) |
| HLT: Lower respiratory tract and lung infections | 18 (4.5%) | 24 (6.0%) |
| Bronchitis | 14 (3.5%) | 19 (4.7%) |
| Bronchopneumonia | 1 (0.2%) | 1 (0.2%) |
| Lower respiratory tract infection | 1 (0.2%) | 0 |
| Pneumonia | 2 (0.5%) | 4 (1.0%) |
| HLT: Upper respiratory tract infections | 56 (13.9%) | 51 (12.7%) |
| Acute sinusitis | 0 | 3 (0.7%) |
| Acute tonsillitis | 0 | 1 (0.2%) |
| Chronic tonsillitis | 1 (0.2%) | 0 |
| Laryngitis | 0 | 2 (0.5%) |
| Nasopharyngitis | 19 (4.7%) | 17 (4.2%) |
| Pharyngitis | 3 (0.7%) | 2 (0.5%) |
| Rhinitis | 1 (0.2%) | 0 |
| Sinusitis | 11 (2.7%) | 10 (2.5%) |
| Upper respiratory tract infection | 23 (5.7%) | 19 (4.7%) |
| HLT: Urinary tract infections | 10 (2.5%) | 12 (3.0%) |
| Cystitis | 2 (0.5%) | 3 (0.7%) |
| Kidney infection | 0 | 1 (0.2%) |
| Pyelonephritis | 0 | 1 (0.2%) |
| Pyelonephritis acute | 0 | 1 (0.2%) |
| Urinary tract infection | 8 (2.0%) | 6 (1.5%) |
| HLT: Viral infections NEC | 13 (3.2%) | 12 (3.0%) |
| Bronchitis viral | 1 (0.2%) | 0 |
| Gastroenteritis viral | 7 (1.7%) | 5 (1.2%) |
| Pneumonia viral | 0 | 1 (0.2%) |
| Respiratory tract infection viral | 1 (0.2%) | 2 (0.5%) |
| Viral infection | 3 (0.7%) | 2 (0.5%) |
| Viral rhinitis | 0 | 2 (0.5%) |
| Viral upper respiratory tract infection | 3 (0.7%) | 1 (0.2%) |
| NERVOUS SYSTEM DISORDERS | 42 (10.4%) | 40 (10.0%) |
| HLT: Headaches NEC | 13 (3.2%) | 11 (2.7%) |
| Headache | 12 (3.0%) | 10 (2.5%) |
| Sinus headache | 1 (0.2%) | 2 (0.5%) |
| VASCULAR DISORDERS | 12 (3.0%) | 13 (3.2%) |
| HLT: Vascular hypertensive disorders NEC | 8 (2.0%) | 10 (2.5%) |
| Hypertension | 8 (2.0%) | 10 (2.5%) |
| RESPIRATORY, THORACIC AND MEDIASTINAL DISORDERS | 32 (7.9%) | 32 (8.0%) |
| HLT: Breathing abnormalities | 10 (2.5%) | 4 (1.0%) |
| Dyspnoea | 6 (1.5%) | 2 (0.5%) |
| Dyspnoea exertional | 3 (0.7%) | 2 (0.5%) |
| Hyperventilation | 1 (0.2%) | 0 |
| HLT: Upper respiratory tract signs and symptoms | 10 (2.5%) | 7 (1.7%) |
| Dysphonia | 1 (0.2%) | 0 |
| Nasal discomfort | 0 | 1 (0.2%) |
| Oropharyngeal pain | 5 (1.2%) | 5 (1.2%) |
| Rhinorrhoea | 2 (0.5%) | 1 (0.2%) |
| Throat irritation | 1 (0.2%) | 0 |
| Upper respiratory tract congestion | 1 (0.2%) | 0 |
| GASTROINTESTINAL DISORDERS | 54 (13.4%) | 48 (11.9%) |
| HLT: Diarrhoea (excl infective) | 15 (3.7%) | 15 (3.7%) |
| Diarrhoea | 15 (3.7%) | 15 (3.7%) |
| HLT: Nausea and vomiting symptoms | 18 (4.5%) | 18 (4.5%) |
| Nausea | 15 (3.7%) | 11 (2.7%) |
| Vomiting | 5 (1.2%) | 10 (2.5%) |
| MUSCULOSKELETAL AND CONNECTIVE TISSUE DISORDERS | 54 (13.4%) | 61 (15.2%) |
| HLT: Joint related signs and symptoms | 11 (2.7%) | 16 (4.0%) |
| Arthralgia | 8 (2.0%) | 14 (3.5%) |
| Joint range of motion decreased | 0 | 2 (0.5%) |
| Joint swelling | 3 (0.7%) | 0 |
| HLT: Musculoskeletal and connective tissue pain and discomfort | 22 (5.4%) | 27 (6.7%) |
| Back pain | 9 (2.2%) | 14 (3.5%) |
| Flank pain | 1 (0.2%) | 0 |
| Musculoskeletal chest pain | 1 (0.2%) | 2 (0.5%) |
| Musculoskeletal pain | 5 (1.2%) | 4 (1.0%) |
| Pain in extremity | 7 (1.7%) | 10 (2.5%) |
| GENERAL DISORDERS AND ADMINISTRATION SITE CONDITIONS | 42 (10.4%) | 34 (8.5%) |
| HLT: Asthenic conditions | 12 (3.0%) | 8 (2.0%) |
| Asthenia | 1 (0.2%) | 1 (0.2%) |
| Fatigue | 10 (2.5%) | 6 (1.5%) |
| Malaise | 1 (0.2%) | 1 (0.2%) |
| HLT: Injection site reactions | 9 (2.2%) | 6 (1.5%) |
| Injection site discomfort | 1 (0.2%) | 0 |
| Injection site erythema | 0 | 1 (0.2%) |
| Injection site haematoma | 4 (1.0%) | 3 (0.7%) |
| Injection site haemorrhage | 0 | 2 (0.5%) |
| Injection site induration | 0 | 1 (0.2%) |
| Injection site pain | 4 (1.0%) | 0 |
| Injection site pruritus | 1 (0.2%) | 0 |
| HLT: Oedema NEC | 15 (3.7%) | 14 (3.5%) |
| Generalised oedema | 1 (0.2%) | 0 |
| Oedema peripheral | 14 (3.5%) | 14 (3.5%) |

TEAE: Treatment emergent adverse event, SOC: System organ class, HLT: High level term, PT: Preferred term MedDRA 15.1
n (%) = number and percentage of patients with at least one TEAE
Note:
Table sorted by SOC internationally agreed order and HLT, PT by alphabetic order
Only HLT with at least one <HLT ≥ 2%> in at least one group are presented

1.3.4 Deaths, Serious Treatment-Emergent Adverse Events

1.3.4.1 Death

TABLE 16

Number (%) of patients who died by study period (on study, on-treatment, post-study)- Safety population

| | HOE901-U300<br>(N = 404) | Lantus<br>(N = 402) |
|---|---|---|
| Death on-study[a] | 3 (0.7%) | 3 (0.7%) |
| Death on-study during first 6 months | 2 (0.5%) | 2 (0.5%) |
| Death on-treatment[b] | 0 | 2 (0.5%) |
| Death post-study[c] | 0 | 0 |

TEAE: Treatment emergent adverse event, SAE: Serious adverse event
[a]Includes all deaths that occurred after the start of treatment up to end of study (defined as last protocol planned visit or the resolution/stabilization of all treatment emergent SAE and adverse event of pre-specified monitoring)
[b]On-treatment is main 6-month on-treatment period
[c]Includes deaths that occurred after the end of the study (as defined in footnote a) and reported in the database

1.3.4.2 Serious Adverse Events

TABLE 17

Number (%) of patients with treatment emergent SAEs by Primary SOC, HLGT, HLT and PT for the main 6-month on-treatment period - Safety population

| PRIMARY SYSTEM ORGAN CLASS<br>HLGT: High Level Group Term<br>HLT: High Level Term<br>Preferred Term n(%) | HOE901-U300<br>(N = 404) | Lantus<br>(N = 402) |
|---|---|---|
| Any class | 25 (6.2%) | 21 (5.2%) |
| INFECTIONS AND INFESTATIONS | 7 (1.7%) | 5 (1.2%) |
| HLGT: Bacterial infectious disorders | 1 (0.2%) | 1 (0.2%) |
| HLT: Bacterial infections NEC | 0 | 1 (0.2%) |
| Cellulitis | 0 | 1 (0.2%) |
| HLT: Streptococcal infections | 1 (0.2%) | 0 |
| Erysipelas | 1 (0.2%) | 0 |
| HLGT: Infections - pathogen unspecified | 6 (1.5%) | 5 (1.2%) |

TABLE 17-continued

Number (%) of patients with treatment emergent SAEs by Primary SOC, HLGT, HLT and PT for the main 6-month on-treatment period - Safety population

| PRIMARY SYSTEM ORGAN CLASS<br>HLGT: High Level Group Term<br>HLT: High Level Term<br>Preferred Term n(%) | HOE901-U300<br>(N = 404) | Lantus<br>(N = 402) |
|---|---|---|
| HLT: Abdominal and gastrointestinal infections | 0 | 1 (0.2%) |
| Diverticulitis | 0 | 1 (0.2%) |
| HLT: Bone and joint infections | 2 (0.5%) | 1 (0.2%) |
| Osteomyelitis | 2 (0.5%) | 1 (0.2%) |
| HLT: Cardiac infections | 1 (0.2%) | 0 |
| Endocarditis | 1 (0.2%) | 0 |
| HLT: Infections NEC | 1 (0.2%) | 0 |
| Groin abscess | 1 (0.2%) | 0 |
| HLT: Lower respiratory tract and lung infections | 2 (0.5%) | 2 (0.5%) |
| Bronchitis | 1 (0.2%) | 0 |
| Bronchopneumonia | 1 (0.2%) | 0 |
| Pneumonia | 0 | 2 (0.5%) |
| HLT: Sepsis, bacteraemia, viraemia and fungaemia NEC | 1 (0.2%) | 1 (0.2%) |
| Sepsis | 1 (0.2%) | 1 (0.2%) |
| Septic embolus | 1 (0.2%) | 0 |
| HLT: Urinary tract infections | 0 | 1 (0.2%) |
| Pyelonephritis acute | 0 | 1 (0.2%) |
| NEOPLASMS BENIGN, MALIGNANT AND UNSPECIFIED (INCL CYSTS AND POLYPS) | 3 (0.7%) | 1 (0.2%) |
| HLGT: Breast neoplasms malignant and unspecified (incl nipple) | 1 (0.2%) | 0 |
| HLGT: Breast and nipple neoplasms malignant | 1 (0.2%) | 0 |
| Breast cancer | 1 (0.2%) | 0 |
| HLGT: Leukaemias | 0 | 1 (0.2%) |
| HLT: Leukaemias chronic myeloid | 0 | 1 (0.2%) |
| Chronic myeloid leukaemia | 0 | 1 (0.2%) |
| HLGT: Reproductive neoplasms male malignant and unspecified | 1 (0.2%) | 0 |
| HLT: Prostatic neoplasms malignant | 1 (0.2%) | 0 |
| Prostate cancer | 1 (0.2%) | 0 |
| HLGT: Respiratory and mediastinal neoplasms malignant and unspecified | 1 (0.2%) | 0 |
| HLT: Respiratory tract and pleural neoplasms malignant cell type unspecified NEC | 1 (0.2%) | 0 |
| Metastatic bronchial carcinoma | 1 (0.2%) | 0 |
| METABOLISM AND NUTRITION DISORDERS | 1 (0.2%) | 3 (0.7%) |
| HLGT: Electrolyte and fluid balance conditions | 0 | 1 (0.2%) |
| HLT: Potassium imbalance | 0 | 1 (0.2%) |
| Hyperkalaemia | 0 | 1 (0.2%) |
| HLGT: Glucose metabolism disorders (incl diabetes mellitus) | 1 (0.2%) | 2 (0.5%) |
| HLT: Diabetes mellitus (incl subtypes) | 0 | 1 (0.2%) |
| Diabetes mellitus inadequate control | 0 | 1 (0.2%) |
| HLT: Hypoglycaemic conditions NEC | 1 (0.2%) | 1 (0.2%) |
| Hypoglycaemia | 1 (0.2%) | 1 (0.2%) |
| PSYCHIATRIC DISORDERS | 0 | 1 (0.2%) |
| HLGT: Depressed mood disorders and disturbances | 0 | 1 (0.2%) |
| HLT: Depressive disorders | 0 | 1 (0.2%) |
| Depression | 0 | 1 (0.2%) |
| NERVOUS SYSTEM DISORDERS | 3 (0.7%) | 2 (0.5%) |
| HLGT: Central nervous system vascular disorders | 1 (0.2%) | 0 |
| HLT: Transient cerebrovascular events | 1 (0.2%) | 0 |
| Transient ischaemic attack | 1 (0.2%) | 0 |
| HLGT: Neurological disorders NEC | 2 (0.5%) | 1 (0.2%) |
| HLT: Disturbances in consciousness NEC | 2 (0.5%) | 1 (0.2%) |
| Hypoglycaemic unconsciousness | 2 (0.5%) | 0 |
| Syncope | 0 | 1 (0.2%) |
| HLGT: Peripheral neuropathies | 0 | 1 (0.2%) |
| HLT: Acute polyneuropathies | 0 | 1 (0.2%) |
| Guillain-Barre syndrome | 0 | 1 (0.2%) |
| CARDIAC DISORDERS | 5 (1.2%) | 7 (1.7%) |
| HLGT: Cardiac arrhythmias | 1 (0.2%) | 2 (0.5%) |
| HLT: Cardiac conduction disorders | 0 | 1 (0.2%) |
| Bundle branch block left | 0 | 1 (0.2%) |
| HLT: Supraventricular arrhythmias | 0 | 1 (0.2%) |
| Atrial fibrillation | 0 | 1 (0.2%) |
| HLT: Ventricular arrhythmias and cardiac arrest | 1 (0.2%) | 0 |
| Ventricular tachycardia | 1 (0.2%) | 0 |
| HLGT: Cardiac valve disorders | 0 | 1 (0.2%) |
| HLT: Aortic valvular disorders | 0 | 1 (0.2%) |
| Aortic valve stenosis | 0 | 1 (0.2%) |
| HLGT: Coronary artery disorders | 4 (1.0%) | 3 (0.7%) |
| HLT: Coronary artery disorders NEC | 2 (0.5%) | 1 (0.2%) |
| Coronary artery disease | 2 (0.5%) | 1 (0.2%) |
| HLT: Ischaemic coronary artery disorders | 2 (0.5%) | 2 (0.5%) |
| Acute coronary syndrome | 1 (0.2%) | 0 |
| Angina pectoris | 0 | 1 (0.2%) |
| Myocardial ischaemia | 1 (0.2%) | 1 (0.2%) |
| HLGT: Heart failures | 0 | 2 (0.5%) |
| HLT: Heart failures NEC | 0 | 2 (0.5%) |
| Cardiac failure | 0 | 1 (0.2%) |
| Cardiac failure chronic | 0 | 1 (0.2%) |
| VASCULAR DISORDERS | 0 | 1 (0.2%) |
| HLGT: Arteriosclerosis, stenosis, vascular insufficiency and necrosis | 0 | 1 (0.2%) |
| HLT: Aortic necrosis and vascular insufficiency | 0 | 1 (0.2%) |
| Aortic stenosis | 0 | 1 (0.2%) |
| RESPIRATORY, THORACIC AND MEDIASTINAL DISORDERS | 1 (0.2%) | 0 |
| HLGT: Respiratory disorders NEC | 1 (0.2%) | 0 |
| HLT: Breathing abnormalities | 1 (0.2%) | 0 |
| Dyspnoea exertional | 1 (0.2%) | 0 |
| GASTROINTESTINAL DISORDERS | 1 (0.2%) | 0 |
| HLGT: Gastrointestinal stenosis and obstruction | 1 (0.2%) | 0 |
| HLT: Gastrointestinal stenosis and obstruction NEC | 1 (0.2%) | 0 |
| Ileus | 1 (0.2%) | 0 |
| HEPATOBILIARY DISORDERS | 0 | 1 (0.2%) |
| HLGT: Gallbladder disorders | 0 | 1 (0.2%) |
| HLT: Cholecystitis and cholelithiasis | 0 | 1 (0.2%) |
| Cholelithiasis | 0 | 1 (0.2%) |
| SKIN AND SUBCUTANEOUS TISSUE DISORDERS | 1 (0.2%) | 0 |
| HLGT: Skin and subcutaneous tissue disorders NEC | 1 (0.2%) | 0 |
| HLT: Skin and subcutaneous tissue ulcerations | 1 (0.2%) | 0 |
| Diabetic foot | 1 (0.2%) | 0 |
| MUSCULOSKELETAL AND CONNECTIVE TISSUE DISORDERS | 2 (0.5%) | 2 (0.5%) |
| HLGT: Joint disorders | 1 (0.2%) | 1 (0.2%) |
| HLT: Osteoarthropathies | 1 (0.2%) | 0 |
| Osteoarthritis | 1 (0.2%) | 0 |
| HLT: Spondyloarthropathies | 0 | 1 (0.2%) |
| Spondylitis | 0 | 1 (0.2%) |
| HLGT: Muscle disorders | 1 (0.2%) | 0 |
| HLT: Myopathies | 1 (0.2%) | 0 |
| Rhabdomyolysis | 1 (0.2%) | 0 |
| HLGT: Musculoskeletal and connective tissue disorders NEC | 0 | 1 (0.2%) |
| HLT: Musculoskeletal and connective tissue pain and discomfort | 0 | 1 (0.2%) |
| Musculoskeletal chest pain | 0 | 1 (0.2%) |
| RENAL AND URINARY DISORDERS | 2 (0.5%) | 3 (0.7%) |
| HLGT: Bladder and bladder neck disorders (excl calculi) | 1 (0.2%) | 0 |
| HLT: Bladder neoplasms | 1 (0.2%) | 0 |
| Urinary bladder polyp | 1 (0.2%) | 0 |
| HLGT: Nephropathies | 0 | 1 (0.2%) |
| HLT: Nephropathies and tubular disorders NEC | 0 | 1 (0.2%) |

TABLE 17-continued

Number (%) of patients with treatment emergent SAEs by Primary SOC, HLGT, HLT and PT for the main 6-month on-treatment period - Safety population

| PRIMARY SYSTEM ORGAN CLASS<br>HLGT: High Level Group Term<br>HLT: High Level Term<br>Preferred Term n(%) | HOE901-U300<br>(N = 404) | Lantus<br>(N = 402) |
|---|---|---|
| Diabetic nephropathy | 0 | 1 (0.2%) |
| HLGT: Renal disorders (excl nephropathies) | 1 (0.2%) | 2 (0.5%) |
| HLT: Renal failure and impairment | 1 (0.2%) | 2 (0.5%) |
| Renal failure acute | 1 (0.2%) | 0 |
| Renal failure chronic | 0 | 2 (0.5%) |
| HLGT: Urolithiases | 0 | 1 (0.2%) |
| HLT: Renal lithiasis | 0 | 1 (0.2%) |
| Nephrolithiasis | 0 | 1 (0.2%) |
| REPRODUCTIVE SYSTEM AND BREAST DISORDERS | 1 (0.2%) | 0 |
| HLGT: Menstrual cycle and uterine bleeding disorders | 1 (0.2%) | 0 |
| HLT: Menstruation and uterine bleeding NEC | 1 (0.2%) | 0 |
| Metrorrhagia | 1 (0.2%) | 0 |
| GENERAL DISORDERS AND ADMINISTRATION SITE CONDITIONS | 1 (0.2%) | 1 (0.2%) |
| HLGT: General system disorders NEC | 1 (0.2%) | 1 (0.2%) |
| HLT: Pain and discomfort NEC | 1 (0.2%) | 1 (0.2%) |
| Non-cardiac chest pain | 1 (0.2%) | 1 (0.2%) |
| INJURY, POISONING AND PROCEDURAL COMPLICATIONS | 2 (0.5%) | 4 (1.0%) |
| HLGT: Bone and joint injuries | 1 (0.2%) | 0 |
| HLT: Limb injuries NEC (incl traumatic amputation) | 1 (0.2%) | 0 |
| Meniscus lesion | 1 (0.2%) | 0 |
| HLGT: Exposures, chemical injuries and poisoning | 0 | 1 (0.2%) |
| HLT: Poisoning and toxicity | 0 | 1 (0.2%) |
| Toxicity to various agents | 0 | 1 (0.2%) |
| HLGT: Injuries NEC | 1 (0.2%) | 2 (0.5%) |
| HLT: Cerebral injuries NEC | 0 | 1 (0.2%) |
| Subdural haematoma | 0 | 1 (0.2%) |
| HLT: Non-site specific injuries NEC | 1 (0.2%) | 1 (0.2%) |
| Fall | 1 (0.2%) | 1 (0.2%) |
| HLT: Site specific injuries NEC | 0 | 1 (0.2%) |
| Head injury | 0 | 1 (0.2%) |
| HLGT: Procedural related injuries and complications NEC | 0 | 1 (0.2%) |
| HLT: Anaesthetic complications | 0 | 1 (0.2%) |
| Airway complication of anaesthesia | 0 | 1 (0.2%) |

SAE: Serious adverse event, SOC: System organ class, HLGT: High level group term, HLT: High level term, PT: Preferred term
MedDRA 15.1
n (%) = number and percentage of patients with at least one treatment emergent SAE
Note:
Table sorted by SOC internationally agreed order and HLGT, HLT, PT by alphabetic order

1.3.5 Adverse Events Leading to Withdrawal

TABLE 18

Number (%) of patients with TEAE(s) leading to permanent treatment discontinuation by Primary SOC, HLGT, HLT and PT for the main 6-month on-treatment period - Safety population

| PRIMARY SYSTEM ORGAN CLASS<br>HLGT: High Level Group Term<br>HLT: High Level Term<br>Preferred Term n(%) | HOE901-U300<br>(N = 404) | Lantus<br>(N = 402) |
|---|---|---|
| Any class | 6 (1.5%) | 7 (1.7%) |
| INFECTIONS AND INFESTATIONS | 0 | 2 (0.5%) |
| HLGT: Infections - pathogen unspecified | 0 | 2 (0.5%) |
| HLT: Infections NEC | 0 | 1 (0.2%) |
| Wound infection | 0 | 1 (0.2%) |
| HLT: Upper respiratory tract infections | 0 | 1 (0.2%) |
| Acute sinusitis | 0 | 1 (0.2%) |
| NEOPLASMS BENIGN, MALIGNANT AND UNSPECIFIED (INCL CYSTS AND POLYPS) | 1 (0.2%) | 1 (0.2%) |
| HLGT: Leukaemias | 0 | 1 (0.2%) |
| HLT: Leukaemias chronic myeloid | 0 | 1 (0.2%) |
| Chronic myeloid leukaemia | 0 | 1 (0.2%) |
| HLGT: Respiratory and mediastinal neoplasms malignant and unspecified | 1 (0.2%) | 0 |
| HLT: Respiratory tract and pleural neoplasms malignant cell type unspecified NEC | 1 (0.2%) | 0 |
| Metastatic bronchial carcinoma | 1 (0.2%) | 0 |
| METABOLISM AND NUTRITION DISORDERS | 0 | 1 (0.2%) |
| HLGT: Glucose metabolism disorders (incl diabetes mellitus) | 0 | 1 (0.2%) |
| HLT: Diabetes mellitus (incl subtypes) | 0 | 1 (0.2%) |
| Diabetes mellitus inadequate control | 0 | 1 (0.2%) |
| PSYCHIATRIC DISORDERS | 1 (0.2%) | 1 (0.2%) |
| HLGT: Anxiety disorders and symptoms | 1 (0.2%) | 1 (0.2%) |
| HLT: Anxiety symptoms | 1 (0.2%) | 0 |
| Anxiety | 1 (0.2%) | 0 |
| HLT: Stress disorders | 0 | 1 (0.2%) |
| Burnout syndrome | 0 | 1 (0.2%) |
| NERVOUS SYSTEM DISORDERS | 0 | 1 (0.2%) |
| HLGT: Central nervous system vascular disorders | 0 | 1 (0.2%) |
| HLT: Central nervous system haemorrhages and cerebrovascular accidents | 0 | 1 (0.2%) |
| Cerebral ischaemia | 0 | 1 (0.2%) |
| HLGT: Peripheral neuropathies | 0 | 1 (0.2%) |

TABLE 18-continued

Number (%) of patients with TEAE(s) leading to permanent treatment discontinuation by Primary SOC, HLGT, HLT and PT for the main 6-month on-treatment period - Safety population

| PRIMARY SYSTEM ORGAN CLASS<br>HLGT: High Level Group Term<br>HLT: High Level Term<br>Preferred Term n(%) | HOE901-U300<br>(N = 404) | Lantus<br>(N = 402) |
|---|---|---|
| HLT: Chronic polyneuropathies | 0 | 1 (0.2%) |
| Diabetic neuropathy | 0 | 1 (0.2%) |
| CARDIAC DISORDERS | 1 (0.2%) | 2 (0.5%) |
| HLGT: Cardiac arrhythmias | 1 (0.2%) | 0 |
| HLT: Ventricular arrhythmias and cardiac arrest | 1 (0.2%) | 0 |
| Ventricular tachycardia | 1 (0.2%) | 0 |
| HLGT: Coronary artery disorders | 0 | 1 (0.2%) |
| HLT: Ischaemic coronary artery disorders | 0 | 1 (0.2%) |
| Myocardial ischaemia | 0 | 1 (0.2%) |
| HLGT: Heart failures | 0 | 1 (0.2%) |
| HLT: Heart failures NEC | 0 | 1 (0.2%) |
| Cardiac failure chronic | 0 | 1 (0.2%) |
| RESPIRATORY, THORACIC AND MEDIASTINAL DISORDERS | 0 | 1 (0.2%) |
| HLGT: Pulmonary vascular disorders | 0 | 1 (0.2%) |
| HLT: Pulmonary thrombotic and embolic conditions | 0 | 1 (0.2%) |
| Pulmonary embolism | 0 | 1 (0.2%) |
| MUSCULOSKELETAL AND CONNECTIVE TISSUE DISORDERS | 1 (0.2%) | 1 (0.2%) |
| HLGT: Joint disorders | 1 (0.2%) | 1 (0.2%) |
| HLT: Osteoarthropathies | 1 (0.2%) | 0 |
| Osteoarthritis | 1 (0.2%) | 0 |
| HLT: Spondyloarthropathies | 0 | 1 (0.2%) |
| Spondylitis | 0 | 1 (0.2%) |
| RENAL AND URINARY DISORDERS | 0 | 1 (0.2%) |
| HLGT: Nephropathies | 0 | 1 (0.2%) |
| HLT: Nephropathies and tubular disorders NEC | 0 | 1 (0.2%) |
| Diabetic nephropathy | 0 | 1 (0.2%) |
| HLGT: Renal disorders (excl nephropathies) | 0 | 1 (0.2%) |
| HLT: Renal failure and impairment | 0 | 1 (0.2%) |
| Renal failure chronic | 0 | 1 (0.2%) |
| GENERAL DISORDERS AND ADMINISTRATION SITE CONDITIONS | 0 | 1 (0.2%) |
| HLGT: General system disorders NEC | 0 | 1 (0.2%) |
| HLT: Pain and discomfort NEC | 0 | 1 (0.2%) |
| Non-cardiac chest pain | 0 | 1 (0.2%) |
| INVESTIGATIONS | 2 (0.5%) | 0 |
| HLGT: Metabolic, nutritional and blood gas investigations | 1 (0.2%) | 0 |
| HLT: Carbohydrate tolerance analyses (incl diabetes) | 1 (0.2%) | 0 |
| Blood glucose decreased | 1 (0.2%) | 0 |
| HLGT: Physical examination and organ system status topics | 1 (0.2%) | 0 |
| HLT: Physical examination procedures and organ system status | 1 (0.2%) | 0 |
| Weight increased | 1 (0.2%) | 0 |
| INJURY, POISONING AND PROCEDURAL COMPLICATIONS | 0 | 2 (0.5%) |
| HLGT: Exposures, chemical injuries and poisoning | 0 | 1 (0.2%) |
| HLT: Poisoning and toxicity | 0 | 1 (0.2%) |
| Toxicity to various agents | 0 | 1 (0.2%) |
| HLGT: Procedural related injuries and complications NEC | 0 | 1 (0.2%) |
| HLT: Anaesthetic complications | 0 | 1 (0.2%) |
| Airway complication of anaesthesia | 0 | 1 (0.2%) |

TEAE: Treatment emergent adverse event, SOC: System organ class, HLGT: High level group term, HLT: High level term, PT: Preferred term
MedDRA 15.1 n (%) = number and percentage of patients with at least one TEAE leading to permanent treatment discontinuation Note:
Table sorted by SOC internationally agreed order and HLGT, HLT, PT by alphabetic order 1.3.6 Other Significant Adverse Events
1.3.6.1 Hypersensitivity Reaction

TABLE 19

Number (%) of patients experiencing at least one TEAE by relevant Standardized MedDRA Queries and Preferred Term - Hypersensitivity reactions during the main 6-month on-treatment period - Safety population

| Preferred Term | HOE901-U300 (N = 404) | Lantus (N = 402) |
|---|---|---|
| Any hypersensitivity reactions | 3 (0.7%) | 2 (0.5%) |
| Blister | 2 (0.5%) | 2 (0.5%) |
| Skin exfoliation | 1 (0.2%) | 0 |
| Drug eruption | 0 | 1 (0.2%) |

MedDRA 15.1
TEAE: Treatment emergent adverse event
n (%) = number and percentage of patients with at least one hypersensitivity reaction event 1.3.6.2 Injection Site Reactions

TABLE 20

Number (%) of patients experiencing at least one TEAE by relevant Standardized MedDRA Queries and Preferred Term - Injection site reactions during the main 6-month on-treatment period - Safety population

| Preferred Term | HOE901-U300 (N = 404) | Lantus (N = 402) |
|---|---|---|
| Any injection site reaction | 9 (2.2%) | 6 (1.5%) |
| Injection site haematoma | 4 (1.0%) | 3 (0.7%) |
| Injection site pain | 4 (1.0%) | 0 |
| Injection site discomfort | 1 (0.2%) | 0 |
| Injection site pruritus | 1 (0.2%) | 0 |
| Injection site erythema | 0 | 1 (0.2%) |
| Injection site haemorrhage | 0 | 2 (0.5%) |
| Injection site induration | 0 | 1 (0.2%) |

MedDRA 15.1
TEAE: Treatment emergent adverse event
n (%) = number and percentage of patients with at least one local tolerability at injection site event EXAMPLE 2: 6-MONTH, MULTICENTER, RANDOMIZED, OPEN-LABEL, PARALLEL-GROUP STUDY COMPARING THE EFFICACY AND SAFETY OF A NEW FORMULATION OF INSULIN GLARGINE AND LANTUS® BOTH IN COMBINATION WITH ORAL ANTIHYPERGLYCEMIC DRUG(S) IN PATIENTS WITH TYPE 2 DIABETES MELLITUS WITH A 6-MONTH SAFETY EXTENSION PERIOD)

Synopsis
Study Center(s):
Multicenter
Phase of Development:
3
Objectives:
Primary Objective: To assess the effects on glycemic control of HOE901-U300 in comparison to Lantus when given as basal insulin in a regimen with oral antihyperglycemic drug(s) in terms of HbA1c change over a period of 6 months in patients with type 2 diabetes mellitus.
Main secondary Objectives: To compare HOE901-U300 and Lantus in terms of occurrence of nocturnal hypoglycemia, change in preinjection plasma glucose, and change in variability of preinjection plasma glucose.

Further secondary objectives:
To compare HOE901-U300 and Lantus in terms of reaching target $HbA_{1c}$ values and controlled plasma glucose;
To compare HOE901-U300 and Lantus in terms of treatment satisfaction of patients using the Diabetes Treatment Satisfaction Questionnaire (status) (DTSQs) (not presented in KRM);
To assess the safety and tolerability of HOE901-U300.
Methodology:
The randomization was 1:1 (HOE901-U300 versus Lantus) and was stratified according to $HbA_{1c}$ values at screening (<8.0%; 8.0%). The sample size (400 with HOE901-U300 and 400 with Lantus) was chosen to ensure sufficient power for the primary endpoint (change in $HbA_{1c}$ from baseline to endpoint [Month 6]) as well as to allow conclusions on the first main secondary endpoint (occurrence of nocturnal hypoglycemia).
Number of Patients:

| Planned: 800 (400 per treatment arm) | Randomized: 811 | Treated: 809 |
|---|---|---|
| Evaluated: | Efficacy: 808 | Safety: 809 |

Diagnosis and Criteria for Inclusion:
Inclusion criteria: Patients with type 2 diabetes mellitus as defined by WHO diagnosed for at least 1 year at the time of the screening visit; signed written informed consent. Key exclusion criteria: Age <18 years; $HbA_{1c}$<7.0% or >10% at screening; diabetes other than type 2 diabetes mellitus; Less than 6 months on basal insulin treatment together with oral antihyperglycemic drugs and self-monitoring of blood glucose; total daily dose insulin glargine <42 U or equivalent dose of NPH in the last 4 weeks prior to the study (if NPH was used as basal insulin prior to the study).
Study Treatments
Investigational Medicinal Products:
Tested drug: HOE901-U300; Control drug: Lantus
Formulations:
HOE901-U300 (insulin glargine 300 U/mL solution) is a sterile, non-pyrogenic, clear, colorless solution in a glass cartridge that has been assembled in a pen-injector (prefilled ie, disposable pen). Lantus (insulin glargine 100 U/mL solution) is a sterile, non-pyrogenic, clear, colorless solution supplied in the marketed Solostar® (prefilled ie, disposable pen).
Route of Administration:
subcutaneous injection
Dose Regimen:
Once daily injection in the evening. The injection time was fixed at the time of randomization and was to be maintained for the duration of the study.
Starting Dose:
Patients on Lantus or NPH once daily prior to the baseline visit: the daily dose (U) of HOE901-U300 or Lantus was equal to the median of the total daily basal insulin doses in the last 3 days prior to the baseline visit.
Patients on NPH more than once daily prior to the baseline visit: the daily dose of for HOE901-U300 or Lantus (U) was to be approximately 20% less than the median of the total daily NPH insulin doses in the last 3 days prior to the baseline visit.
The basal insulin dose was adjusted once weekly to achieve fasting SMPG in the target range of 80 to 100 mg/dL (4.4 to 5.6 mmol/L):

by +3 U, if the median fasting SMPG of last 3 days was in the range of >100 mg/dL and <140 mg/dL (>5.6 and <7.8 mmol/L)

by +6 U, if the median fasting SMPG of last 3 days was 140 mg/dL 7.8 mmol/L)

by −3 U, if the median fasting SMPG of last 3 days was in the range of 60 mg/dL and <80 mg/dL 3.3 and <4.4 mmol/L).

Rescue Treatment:

If the basal insulin adjustment failed to decrease FPG/HbA1c under the threshold values of 11.1 mmol/L (200 mg/dL) for FPG and 8% for HbA1c at week 12 or later and no apparent reason for insufficient control was identified, intensification of the treatment was to be considered. The choice of the anti-diabetic treatment to be added to the basal insulin and oral antihyperglycemic background therapy was based on Investigator's decision and local labeling documents.

Noninvestigational Medicinal Products:

Patients in both treatment groups were to continue with their oral antihyperglycemic background therapy at a stable dose during the study, except sulfonylurea which were prohibited within 2 months before the screening visit and during the study. Rescue therapy was also considered as non investigational medicinal product.

Duration of Treatment:

Up to 12 months

Duration of Observation:

up to 58 weeks (up to 2-week screening period+6-month efficacy and safety period+6-month safety extension period+a 4-week post-treatment follow up period)

The analysis period for efficacy and safety is the main 6-month on-treatment period. Results presented in the present KRM refer to this period.

For all patients requiring rescue therapy during the 6-month treatment period, the last post-baseline efficacy measurement before the start of rescue therapy was used as the efficacy endpoint. These patients were excluded from efficacy analyses after initiation of rescue treatment. For safety endpoints; the analysis period is the main 6-month on-treatment period regardless of the use of rescue therapy.

Criteria for Evaluation:

Efficacy:

Primary Efficacy Endpoint:

change in $HbA_{1c}$ from baseline to endpoint (Month 6).

Main Secondary Endpoints:

incidence of patients (%) with at least one nocturnal hypoglycemia between start of Week 9 and endpoint (month 6), indicated as severe and/or confirmed by plasma glucose ≤70 mg/dL (3.9 mmol/L); change in preinjection SMPG from baseline to endpoint (Month 6) and change in variability of preinjection SMPG from baseline to endpoint (Month 6).

Safety:

Hypoglycemia, occurrence of adverse events particularly treatment-emergent adverse events (TEAEs) and serious adverse events (SAEs), TEAEs leading to withdrawal and TEAEs leading to death, injection site reactions and hypersensitivity reactions. Following information not presented in this KRM: physical examination, other safety information including clinical laboratory data, vital signs, 12-lead ECG and anti-insulin antibodies.

Following information not presented in this KRM: physical examination, other safety information including clinical laboratory data, vital signs, 12-lead ECG and anti-insulin antibodies.

Statistical Methods:

The primary efficacy endpoint (change in $HbA_{1c}$ from baseline to endpoint [Month 6]) was analyzed using an analysis of covariance (ANCOVA) model with treatment, strata of screening $HbA_{1c}$ (<8.0 and ≥8.0%), and country as fixed effects and using the $HbA_{1c}$ baseline value as a covariate. Differences between HOE901-U300 and Lantus and two-sided 95% confidence intervals were estimated within the framework of ANCOVA.

A stepwise closed testing approach was used for the primary efficacy endpoint to assess non-inferiority and superiority sequentially. Step 1 assessed non inferiority of HOE901-U300 versus Lantus. To assess non-inferiority, the upper bound of the two sided 95% CI for the difference in the mean change in HbA1c from baseline to endpoint between HOE901-U300 and Lantus was compared with a predefined non inferiority margin of 0.4% for HbA1c. Non-inferiority would be demonstrated if the upper bound of the two-sided 95% CI of the difference between HOE901-U300 and Lantus on mITT population is <0.4%. Step 2 assessed superiority of HOE901-U300 versus Lantus only if non inferiority was demonstrated. The superiority of HOE901-U300 over Lantus was demonstrated if the upper bound of the two-sided 95% CI of the difference between HOE901-U300 and Lantus on mITT population was <0.

Only if non-inferiority of HOE901-U300 versus Lantus had been demonstrated for the primary endpoint, would testing for superiority of HOE901-U300 over Lantus on the main secondary endpoints occur within the frame of a hierarchical testing procedure. Safety analyses were descriptive, based on the safety population.

Summary:

Population Characteristics:

A total of 811 patients with type 2 diabetes mellitus were randomized to HOE901-U300 (n=404) or to Lantus (n=407); 809 patients were exposed to IMP (safety population). The mITT population (efficacy population) included 808 patients.

Overall, a comparable number of patients in each treatment group discontinued the study treatment prematurely (HOE901-U300: 36/404, 8.9%; Lantus 38/407, 9.3%). A total of 344 (85.1%) patients in the HOE901-U300 arm and 349 (85.7%) in the Lantus arm completed the main 6-month treatment period (patients who received rescue medication were excluded from the completers population).

Demographics and baseline characteristics were well-balanced between the treatment groups. The mean age of the study population was 58.2 years, 190/811 (23.4%) were 65 years. The mean BMI at baseline was 34.8 $kg/m^2$. There were slightly more patients with a BMI above 40 $kg/m^2$ in the HOE901-U300 group (21.5%) than in the Lantus group (16.7%). The mean duration of diabetes prior to study start was 12.6 years; the mean duration of prior treatment with basal insulin was 3.8 years. The majority of patients took insulin glargine (78.8% vs. NPH 21.2%) on the 7 days before start of study treatment; more patients from the Lantus group were on insulin glargine (82.8%) compared to the HOE901-U300 group (74.9%). The median daily basal insulin dose at baseline was 0.614 U/kg body weight.

Mean HbA1c at baseline was similar in both treatment groups (HOE901-U300: 8.28% and Lantus: 8.22%; for evaluable patients, i.e. who had a baseline and at least one post-baseline HbA1c assessment).

Efficacy Results:

Primary Endpoint:

The LS mean change in HbA1c from baseline to endpoint (Month 6) was similar in both treatment groups (HOE901-U300: −0.57% (95% CI [−0.756; −0.387]); Lantus: −0.56%

(95% CI [−0.744; −0.379]). Non-inferiority of HOE901-U300 versus Lantus was demonstrated with the LS mean difference in HbA1c versus Lantus of −0.01% (95% CI [−0.139; 0.119]) with the upper bound lower than the predefined non-inferiority margin of 0.4%. Non-inferiority was also the case with the non-inferiority margin of 0.3%. Superiority of HOE901-U300 versus Lantus was not demonstrated.

1st Main Secondary Endpoint:

The incidence of patients with at least one nocturnal severe and/or confirmed hypoglycemia between start of Week 9 and Month 6 was lower in the HOE901-U300 group [87/403 (21.6%)] than in the Lantus group [113/405 (27.9%)]. Superiority of HOE901-U300 versus Lantus was shown with a relative risk of 0.77 (95% CI [0.61, 0.99]) (p=0.0380).

2nd Main Secondary Endpoint:

The LS mean change in pre-injection SMPG from baseline to endpoint (Month 6) was similar in the HOE901-U300 (−0.56 mmol/L) and Lantus groups (−0.51 mmol/L). The difference between the treatment groups was not statistically significant (LS mean difference −0.04 (95% CI [−0.438, 0.350], p=0.8279).

3rd Main Secondary Endpoint:

As the superiority of HOE901-U300 versus Lantus was not demonstrated for the second main secondary endpoint, no further test was performed for the third main secondary endpoint (decrease in variability of pre-injection SMPG at Month 6, which was numerically larger in the HOE901-U300 group (−2.34) compared to the Lantus group (−0.53).

Other Secondary Efficacy Endpoints (Month 6):

The proportion of patients having reached HbA1c<7% was similar between treatment groups (30.6% in the HOE901-U300; 30.4% in the Lantus). For the mean change in FPG, a similar decrease was shown for the two treatment groups. Graphical presentation of the 8-point SMPG profiles showed in both treatment groups a comparable, marked decrease in plasma glucose at endpoint (Month 6) compared with baseline.

At month 6, the mean daily insulin dose in the HOE901-U300 group was 91 U (0.92 U/kg) and 82 U (0.84 U/kg) in the Lantus group.

A similar number of patients in both treatment groups received a rescue therapy during the main 6-month treatment period (5.7% for HOE901-U300, 4.9% for Lantus.

Safety Results:

Overall, hypoglycemia was reported by a consistently lower percentage of patients in the HOE901-U300 group than in the Lantus group. This difference was even more pronounced during the first 2 months of study treatment as well as for events of nocturnal hypoglycemia. During the main 6-month on-treatment period severe hypoglycemia was reported in 4/403 (1%) of HOE901-U300 treated patients and 6/406 (1.5%) of Lantus treated patients.

The percentages of patients with any TEAEs (HOE901-U300, 236/403 [58.6%]; Lantus: 206/406 [50.7%]) was higher for the patients in the HOE901-U300 treatment group than in the Lantus group, with no specific SOC contributing. Serious TEAEs were reported by a similar number of patients in both treatment groups (HOE901-U300, 15 [3.7%]; Lantus, 15 [3.7%]).

Two (0.5%) patients in the HOE901-U300 and 1 (0.2%) patient in the Lantus treatment group died during the 6-months on-treatment period.

The events with fatal outcome in the two patients in the HOE901-U300 group included myocardial infarction and sudden cardiac death due to advanced coronary artery disease. Both patients suffered from pre-existing significant cardiovascular pathology and had multiple risk factors contributing to the fatal outcome. The patient in the Lantus group experienced exacerbation of chronic pyelonephritis with fatal outcome. None of the deaths occurred during the 6 months treatment period were considered related to study drug.

A similar number of patients in both treatment groups experienced TEAEs leading to permanent treatment discontinuation (HOE901-U300: n=6, 1.5%; Lantus: n=4, 1.0%).

Hypersensitivity reactions during the main 6-month on-treatment period were reported at a similar rate in both treatment groups (HOE901-U300: n=13, 3.2%; Lantus: n=16, 3.9%).

Overall injection site reactions during the main 6-month on-treatment period showed higher rate of reporting in the Lantus treatment group than in the HOE901-U300 group (Lantus: n=12, 3.0%; HOE901-U300: n=4, 1.0%).

In both treatment groups, there was no apparent change in body weight (0.08 kg for HOE901-U300 and 0.66 kg for Lantus).

Conclusions:

In this study in 811 patients with T2DM on basal insulin in combination with oral antidiabetic drug(s), the baseline characteristics and demographic characteristics were well balanced across treatment groups. Non-inferiority of HOE901-U300 versus Lantus was shown for the primary efficacy endpoint (change in HbA1c from baseline to endpoint [Month 6]). The incidence of patients (%) reporting nocturnal hypoglycemia (severe and/or confirmed by SMPG ≤70 mg/dL [3.9 mmol/L]) between start of Week 9 and Month 6 was significantly lower in the HOE901-U300 group than in the Lantus group (21.6% and 27.9% respectively, RR of 0.77, p-value 0.0380; 1st main secondary efficacy endpoint). Comparable results between the treatment groups were found for the other secondary endpoints of pre-injection plasma glucose, variability of pre-injection plasma glucose, number of patients reaching target HbA1c and mean change of FPG, change of 8-point SMPG profile and variability of 24-hour average plasma glucose.

Overall incidence of hypoglycemia (% of patients with at least one event) during the main 6-month on-treatment period was consistently lower in the HOE901-U300 group than in the Lantus group regardless of the category of hypoglycemia. This difference in favor of HOE901-U300 was even more pronounced for nocturnal hypoglycemia of all categories.

HOE901-U300 was well tolerated during the main 6-month on-treatment period of the study and no specific safety concerns were observed.

Summary of the efficacy and safety results of the twelve month EDITION 2 extension study HbA1c: during the safety extension period (from the main study endpoint [Month 6] to the End of Treatment [Month 12]) HbA1c remained stable and was comparable in both treatment groups rescue: during the whole treatment period, the percentages of patients requiring a rescue therapy was similar in both treatment groups (8.2% for HOE901-U300, 10.1% for Lantus). During the 6-month safety extension period rescue therapy was started in lower percentage of patients in the HOE901-U300 treatment group than in the Lantus group (2.5% for HOE901-U300, 5.4% for Lantus)

hypoglycemia: overall, similarly as during the main 6-month treatment period, during the whole study on-treatment period hypoglycemia occurred in a lower percentage of patients in the HOE901-U300 group than in the Lantus, regardless of category of hypoglycemia safety: HOE901-U300 was well tolerated during the study and no specific safety concerns were observed; during the whole treatment period, the percentages of patients with any TEAEs was higher for the patients in the HOE901-U300 treatment group than in the Lantus group (278/403 [69.0%] and 244/406 [60.1%], respectively), with no specific SOC contributing. Serious TEAEs were reported by a similar number of patients (30 [7.4%]) in both treatment groups. Four (1.0%) patients in the HOE901-U300 and 2 (0.5%) patient in the Lantus treatment group had TEAE leading to death during the whole study on-treatment period body weight: in both treatment groups, during the whole study on-treatment period there was small increase in body weight (0.41 kg for HOE901-U300 and 1.15 kg for Lantus).

2 Results 2.1 Study Patients 2.1.1 Study Disposition

TABLE 21

Patient disposition—Randomized population

|  | HOE901-U300 (N = 404) | Lantus (N = 407) |
|---|---|---|
| Randomized and treated | 403 (99.8%) | 406 (99.8%) |
| Completed main 6-month treatment period | 344 (85.1%) | 349 (85.7%) |
| Permanently discontinued the treatment during the main 6-month period [a] | 36 (8.9%) | 38 (9.3%) |
| Rescue intake during the main 6-month period | 23 (5.7%) | 20 (4.9%) |
| Subject's request for treatment discontinuation | 24 (5.9%) | 23 (5.7%) |
| Reason for treatment discontinuation during the main 6-month period |  |  |
| Adverse event | 6 (1.5%) | 4 (1.0%) |
| Lack of efficacy | 2 (0.5%) | 0 |
| Poor compliance to protocol | 4 (1.0%) | 4 (1.0%) |
| Other reasons | 24 (5.9%) | 30 (7.4%) |
| Status at last study contact of patients who permanently discontinued the treatment during the main 6-month period |  |  |
| Alive | 34 (8.4%) | 35 (8.6%) |
| Dead | 2 (0.5%) | 1 (0.2%) |

Note:
percentages are calculated using the number of patients randomized as denominator
Patients who completed the main 6-month treatment period are patients who did not permanently discontinue study treatment and who did not take any rescue medication
[a] Two subjects in the Lantus arm had their study status after the cut-off date

TABLE 22

| Analysis populations | | | |
|---|---|---|---|
|  | HOE901-U300 | Lantus | All |
| Randomized population | 404 (100%) | 407 (100%) | 811 (100%) |
| Efficacy populations |  |  |  |
| Modified Intent-to-Treat (mITT) | 403 (99.8%) | 405 (99.5%) | 808 (99.6%) |

TABLE 22-continued

| Analysis populations | | | |
|---|---|---|---|
|  | HOE901-U300 | Lantus | All |
| Month 6 completers | 344 (85.1%) | 349 (85.7%) | 693 (85.5%) |
| Safety population | 403 | 406 | 809 |

Note:
For the safety population, patients are tabulated according to treatment actually received (as treated)
For the other populations, patients are tabulated according to their randomized treatment

TABLE 23

Number (%) of patients requiring rescue therapy during the main 6-month on-treatment period-mITT population

|  | HOE901-U300 (N = 403) | Lantus (N = 405) |
|---|---|---|
| Rescue medication |  |  |
| Number | 403 | 405 |
| n (%) | 23 (5.7%) | 20 (4.9%) |
| RR (95% CI) vs. Lantus [a] | 1.16 (0.65 to 2.07) | — |

RR = relative risk
[a] Based on RR stratified by randomization strata of screening HbA1c (<8.0 or ≥8.0%)., using a CHM methodology 2.1.2 Demographics and Baseline Characteristics

TABLE 24

Demographics and patient characteristics at baseline—Randomized population

|  | HOE901-U300 (N = 404) | Lantus (N = 407) | All (N = 811) |
|---|---|---|---|
| Age (years) |  |  |  |
| Number | 404 | 407 | 811 |
| Mean (SD) | 57.9 (9.1) | 58.5 (9.2) | 58.2 (9.2) |
| Median | 59.0 | 59.0 | 59.0 |
| Min:Max | 24:84 | 27:80 | 24:84 |
| Age Group (years) [n(%)] |  |  |  |
| Number | 404 | 407 | 811 |
| <65 | 317 (78.5%) | 304 (74.7%) | 621 (76.6%) |
| [65-75[ | 80 (19.8%) | 88 (21.6%) | 168 (20.7%) |
| ≥75 | 7 (1.7%) | 15 (3.7%) | 22 (2.7%) |
| Gender [n (%)] |  |  |  |
| Number | 404 | 407 | 811 |
| Male | 187 (46.3%) | 185 (45.5%) | 372 (45.9%) |
| Female | 217 (53.7%) | 222 (54.5%) | 439 (54.1%) |
| Race [n (%)] |  |  |  |
| Number | 404 | 407 | 811 |
| Caucasian/White | 378 (93.6%) | 383 (94.1%) | 761 (93.8%) |
| Black | 20 (5.0%) | 16 (3.9%) | 36 (4.4%) |
| Asian/Oriental | 3 (0.7%) | 7 (1.7%) | 10 (1.2%) |
| Other | 3 (0.7%) | 1 (0.2%) | 4 (0.5%) |
| Ethnicity [n (%)] |  |  |  |
| Number | 404 | 407 | 811 |
| Hispanic | 102 (25.2%) | 91 (22.4%) | 193 (23.8%) |
| Not Hispanic | 302 (74.8%) | 316 (77.6%) | 618 (76.2%) |
| World region [n (%)] |  |  |  |
| Number | 404 | 407 | 811 |
| North America | 175 (43.3%) | 194 (47.7%) | 369 (45.5%) |
| Western Europe | 40 (9.9%) | 43 (10.6%) | 83 (10.2%) |

TABLE 24-continued

Demographics and patient characteristics at baseline—Randomized population

| | HOE901-U300 (N = 404) | Lantus (N = 407) | All (N = 811) |
|---|---|---|---|
| Eastern Europe | 122 (30.2%) | 103 (25.3%) | 225 (27.7%) |
| Rest of the world | 67 (16.6%) | 67 (16.5%) | 134 (16.5%) |
| Baseline weight (kg) | | | |
| Number | 404 | 407 | 811 |
| Mean (SD) | 98.7 (22.3) | 98.0 (20.8) | 98.3 (21.6) |
| Median | 94.4 | 95.0 | 95.0 |
| Min:Max | 48:209 | 48:188 | 48:209 |
| Baseline BMI (kg/m$^2$) | | | |
| Number | 404 | 407 | 811 |
| Mean (SD) | 34.8 (6.6) | 34.8 (6.1) | 34.8 (6.4) |
| Median | 33.6 | 34.0 | 33.8 |
| Min:Max | 20:63 | 21:59 | 20:63 |
| Baseline BMI categories (kg/m$^2$) [n(%)] | | | |
| Number | 404 | 407 | 811 |
| <25 | 11 (2.7%) | 5 (1.2%) | 16 (2.0%) |
| [25-30[ | 91 (22.5%) | 90 (22.1%) | 181 (22.3%) |
| [30-40[ | 215 (53.2%) | 244 (60.0%) | 459 (56.6%) |
| ≥40 | 87 (21.5%) | 68 (16.7%) | 155 (19.1%) |
| Baseline estimated GFR (mL/min/1.73 m$^2$) | | | |
| Number | 404 | 407 | 811 |
| Mean (SD) | 82.01 (21.73) | 80.47 (20.89) | 81.23 (21.31) |
| Median | 81.11 | 78.69 | 79.84 |
| Min:Max | 22.7:155.3 | 25.1:158.8 | 22.7:158.8 |
| Baseline estimated GFR categories (mL/min/1.73 m$^2$) [n(%)] | | | |
| Number | 404 | 407 | 811 |
| ≥90 | 134 (33.2%) | 132 (32.4%) | 266 (32.8%) |
| [60-90[ | 213 (52.7%) | 218 (53.6%) | 431 (53.1%) |
| [30-60[ | 55 (13.6%) | 55 (13.5%) | 110 (13.6%) |
| <30 | 2 (0.5%) | 2 (0.5%) | 4 (0.5%) |
| Randomization strata of screening HbA1c (%) [n(%)] | | | |
| Number | 404 | 407 | 811 |
| <8 | 144 (35.6%) | 146 (35.9%) | 290 (35.8%) |
| ≥8 | 260 (64.4%) | 261 (64.1%) | 521 (64.2%) |

BMI = Body Mass Index
GFR = Glomerular filtration rate
GFR is derived from MDRD formula

TABLE 25

Summary of disease characteristics at baseline—Randomized population

| | HOE901-U300 (N = 404) | Lantus (N = 407) | All (N = 811) |
|---|---|---|---|
| Duration of T2D (years) | | | |
| Number | 403 | 407 | 810 |
| Mean (SD) | 12.7 (7.1) | 12.5 (7.0) | 12.6 (7.0) |
| Median | 11.6 | 11.7 | 11.7 |
| Min:Max | 1:54 | 1:51 | 1:54 |
| Category of duration of T2D (years) | | | |
| Number | 403 | 407 | 810 |
| <10 | 149 (37.0%) | 160 (39.3%) | 309 (38.1%) |
| ≥10 | 254 (63.0%) | 247 (60.7%) | 501 (61.9%) |

TABLE 25-continued

Summary of disease characteristics at baseline—Randomized population

| | HOE901-U300 (N = 404) | Lantus (N = 407) | All (N = 811) |
|---|---|---|---|
| Age at onset of T2D (years) | | | |
| Number | 403 | 407 | 810 |
| Mean (SD) | 45.7 (9.8) | 46.5 (9.7) | 46.1 (9.7) |
| Median | 45.7 | 46.2 | 45.9 |
| Min:Max | 13:69 | 18:73 | 13:73 |
| Duration of basal insulin treatment (years) | | | |
| Number | 404 | 407 | 811 |
| Mean (SD) | 3.78 (3.73) | 3.83 (3.34) | 3.80 (3.54) |
| Median | 2.60 | 2.70 | 2.70 |
| Min:Max | 0.5:30.6 | 0.4:24.5 | 0.4:30.6 |
| Previous basal insulin type$^a$ [n(%)] | | | |
| Number | 402 | 401 | 803 |
| Insulin glargine | 301 (74.9%) | 332 (82.8%) | 633 (78.8%) |
| NPH | 101 (25.1%) | 69 (17.2%) | 170 (21.2%) |
| Previous basal insulin daily injection number$^a$ [n(%)] | | | |
| Number | 402 | 402 | 804 |
| Once daily | 315 (78.4%) | 322 (80.1%) | 637 (79.2%) |
| Twice daily | 83 (20.6%) | 76 (18.9%) | 159 (19.8%) |
| More than twice daily | 4 (1.0%) | 4 (1.0%) | 8 (1.0%) |
| Previous basal insulin daily closer$^b$ (U) | | | |
| Number | 378 | 382 | 760 |
| Mean (SD) | 64.08 (25.60) | 65.69 (26.14) | 64.89 (25.87) |
| Median | 58.00 | 56.00 | 57.55 |
| Q1:Q3 | 47.00:70.00 | 47.10:77.30 | 47.10:74.00 |
| Min:Max | 32.0:218.6 | 41.9:200.0 | 32.0:218.6 |
| Previous basal insulin daily dose$^b$ (U/kg) | | | |
| Number | 378 | 382 | 760 |
| Mean (SD) | 0.660 (0.221) | 0.681 (0.253) | 0.671 (0.238) |
| Median | 0.617 | 0.609 | 0.614 |
| Q1:Q3 | 0.505:0.767 | 0.504:0.796 | 0.504:0.777 |
| Min:Max | 0.31:1.83 | 0.30:2.02 | 0.30:2.02 |
| Prior use of Lantus$^c$ | | | |
| Number | 404 | 407 | 811 |
| Yes | 304 (75.2%) | 337 (82.8%) | 641 (79.0%) |
| No | 100 (24.8%) | 70 (17.2%) | 170 (21.0%) |

T2D = Type 2 diabetes
$^a$Previous basal insulin type and maximal injection number of the patient during the last 7 days prior to randomization.
$^b$Mean of the patient from the basal daily doses during the last 7 days prior to randomization
$^c$Taken within 3 months before screening

2.2 Efficacy Evaluation
2.2.1 Primary Efficacy Endpoint

TABLE 26

Main efficacy analysis—Mean change in HbA1c (%) from baseline to Month 6 endpoint using LOCF procedure-mITT population

| HbA1c (%) | HOE901-U300 (N = 403) | Lantus (N = 405) |
|---|---|---|
| Baseline | | |
| Number | 386 | 392 |
| Mean (SD) | 8.28 (0.87) | 8.22 (0.77) |
| Median | 8.20 | 8.10 |
| Min:Max | 6.0:12.6 | 6.7:10.4 |

TABLE 26-continued

Main efficacy analysis—Mean change in HbA1c (%) from baseline to Month 6 endpoint using LOCF procedure-mITT population

| HbA1c (%) | HOE901-U300 (N = 403) | Lantus (N = 405) |
|---|---|---|
| Month 6 endpoint (LOCF) | | |
| Number | 386 | 392 |
| Mean (SD) | 7.57 (1.02) | 7.56 (1.04) |
| Median | 7.40 | 7.50 |
| Min:Max | 5.4:14.2 | 5.3:12.0 |
| Change from baseline to Month 6 endpoint (LOCF) | | |
| Number | 386 | 392 |
| Mean (SD) | −0.71 (1.05) | −0.66 (0.90) |
| Median | −0.70 | −0.70 |
| Min:Max | −3.9:5.3 | −3.4:3.1 |
| LS Mean (SE) [a] | −0.57 (0.094) | −0.56 (0.093) |
| 95% CI | (−0.756 to −0.387) | (−0.744 to −0.379) |
| LS Mean difference (SE) vs. Lantus [a] | −0.01 (0.066) | |
| 95% CI | (−0.139 to 0.119) | |

LOCF = Last observation carried forward.
[a] Analysis of covariance (ANCOVA) model with treatment groups (HOE901-U300 and LANTUS), randomization strata of screening HbA1c (<8.0, ≥8.0%) and country as fixed effects and baseline HbA1c value as covariate.
Note:
For all patients rescued during the 6-month period, the last postbaseline HbA1c measurement before rescue and during the 6-month on-treatment period will be used as the HbA1c endpoint.

The data of Table 26 are summarized in FIG. 5.

2.2.2 Main Secondary Endpoints

2.2.2.1 Nocturnal Hypoglycemia

TABLE 27

First main secondary efficacy endpoint-Number (%) of patients with at least one nocturnal hypoglycemia [00:00 to 05:59] occuring between start of Week 9 and Month 6 endpoint (using LOCF procedure), indicated as severe and/or confirmed by plasma glucose ≤3.9 mmol/L (70 mg/dL)-mITT population

| | HOE901-U300 (N = 403) | Lantus (N = 405) |
|---|---|---|
| Severe and/or confirmed nocturnal hypoglycemia [00:00 to 05:59] | | |
| n (%) | 87 (21.6%) | 113 (27.9%) |
| RR (95% CI) vs. Lantus [a] | 0.77 (0.61 to 0.99) | — |
| p-value (CMH) | 0.0380 | — | n(%) = number and percentage of patients with at least one nocturnal hypoglycemia event, indicated as severe and/or confirmed by plasma glucose ≤3.9 mmol/L (70 mg/dL)
[a] Based on RR stratified by randomization strata of screening HbA1c (<8.0 or ≥8.0%), using a CMH methodology

2.2.2.2 Pre-Injection Plasma Glucose—Month 6 Endpoint

TABLE 28

Second main secondary efficacy endpoint—Mean change in average pre-injection SMPG (mmol/L) from baseline to Month 6 endpoint using LOCF procedure-mITT population

| Average pre-injection SMPG (mmol/L) | HOE901-U300 (N = 403) | Lantus (N = 405) |
|---|---|---|
| Baseline | | |
| Number | 353 | 350 |
| Mean (SD) | 11.01 (2.92) | 10.84 (2.79) |
| Median | 10.55 | 10.48 |
| Min:Max | 5.0:21.8 | 4.8:18.8 |
| Month 6 endpoint (LOCF) | | |
| Number | 353 | 350 |
| Mean (SD) | 10.23 (3.03) | 10.28 (3.05) |
| Median | 9.77 | 9.52 |
| Min:Max | 5.1:25.1 | 5.1:20.4 |
| Change from baseline to Month 6 endpoint (LOCF) | | |
| Number | 353 | 350 |
| Mean (SD) | −0.78 (3.10) | −0.57 (3.01) |
| Median | −0.82 | −0.72 |
| Min:Max | −9.6:9.9 | −8.8:10.9 |
| LS Mean (SE) [b] | −0.56 (0.278) | −0.51 (0.275) |
| 95% CI | (−1.101 to −0.010) | (−1.052 to 0.028) |
| LS Mean difference (SE) vs. Lantus [b] | −0.04 (0.201) | |
| 95% CI | (−0.438 to 0.350) | |
| p-value(ANCOVA) | 0.8279 | |

LOCF = Last observation carried forward.
SMPG = Self Monitoring Plasma Glucose
[a] Average is assessed by the mean of at least 3 SMPG calculated over the 7 days preceding the given visit.
[b] Analysis of covariance (ANCOVA) model with treatment groups (HOE901-U300 and LANTUS), randomization strata of screening HbA1c (<8.0, ≥8.0%) and country as fixed effects and baseline average pre-injection SMPG value as covariate.
Note:
For all patients rescued during the 6-month period, the last postbaseline average pre-injection SMPG measurement before rescue and during the 6-month on-treatment period will be used as the average pre-injection SMPG endpoint.

The data of Table 28 are summarized in FIG. 6.

2.2.2.3 Variability of Preinjection SMPG—Month 6 Endpoint

TABLE 29

Third main secondary efficacy endpoint—Mean change in variability of pre-injection SMPG from baseline to Month 6 endpoint using LOCF procedure-mITT population

| Variability of pre-injection SMPG | HOE901-U300 (N = 403) | Lantus (N = 405) |
|---|---|---|
| Baseline | | |
| Number | 353 | 350 |
| Mean (SD) | 22.44 (11.73) | 20.89 (10.46) |
| Median | 21.77 | 20.04 |
| Min:Max | 0.0:86.6 | 0.0:57.0 |
| Month 6 endpoint (LOCF) | | |
| Number | 353 | 350 |
| Mean (SD) | 19.84 (10.40) | 20.37 (11.65) |
| Median | 18.95 | 18.89 |
| Min:Max | 2.3:58.0 | 1.2:73.5 |
| Change from baseline to Month 6 endpoint (LOCF) | | |
| Number | 353 | 350 |
| Mean (SD) | −2.60 (14.00) | −0.52 (13.32) |
| Median | −1.69 | −0.54 |
| Min:Max | −66.6:46.4 | −37.8:67.1 |

TABLE 29-continued

Third main secondary efficacy endpoint—Mean change in
variability of pre-injection SMPG from baseline to
Month 6 endpoint using LOCF procedure-mITT population

| Variability of pre-injection SMPG | HOE901-U300 (N = 403) | Lantus (N = 405) |
|---|---|---|
| LS Mean (SE) [a] | −2.34 (1.425) | −0.53 (1.408) |
| 95% CI | (−5.142 to 0.452) | (−3.297 to 2.231) |
| LS Mean difference (SE) vs. Lantus [a] | −1.81 (1.029) | |
| 95% CI | (−3.833 to 0.210) | |

LOCF = Last observation carried forward.
SMPG = Self Monitoring Plasma Glucose
Variability is assessed by the mean of coefficient of variation calculated over at least 3 SMPG measured during the 7 days preceding the given visit
[a] Analysis of variance (ANOVA) model with treatment groups (HOE901-U300 and LANTUS), randomization strata of screening HbA1c (<8.0, ≥8.0%) and country as fixed effects
Note:
For all patients rescued during the 6-month period, the last postbaseline variability of pre-injection SMPG measurement before rescue and during the 6-month on-treatment period will be used as the variability of pre-injection SMPG endpoint.

2.2.3 Other Secondary Efficacy Endpoints 2.2.3.1 Percentage of Patients with HbA1c<7% at Month 6

TABLE 30

Other secondary efficacy endpoint—Number (%) of patients with
HbA1c <7% at Month 6 endpoint (using LOCF procedure) and
Number (%) of patients with HbA1c <7% at Month 6
endpoint (using LOCF procedure) having experienced
no hypoglycemia indicated as severe
and/or confirmed by plasma glucose <3 mmol/L
(54 mg/dL) during the last 3 months of the main
6-month treatment period-mITT population

| | HOE901-U300 (N = 403) | Lantus (N = 405) |
|---|---|---|
| HbA1c <7% | | |
| Number | 386 | 392 |
| n (%) | 118 (30.6%) | 119 (30.4%) |
| RR (95% CI) vs. Lantus [a] | 1.02 (0.83 to 1.25) | — |
| HbA1c <7% and no emergent severe or confirmed (<3.0 mmol/L; <54 mg/dL) hypoglycemia | | |
| Number | 387 | 396 |
| n (%) | 93 (24.0%) | 94 (23.7%) |
| RR (95% CI) vs. Lantus [a] | 1.02 (0.80 to 1.31) | — |
| HbA1c <7% and no nocturnal [00:00-05:59] emergent severe or confirmed (<3.0 mmol/L; <54 mg/dL) hypoglycemia | | |
| Number | 386 | 394 |
| n (%) | 107 (27.7%) | 113 (28.7%) |
| RR (95% CI) vs. Lantus [a] | 0.98 (0.78 to 1.22) | — |

LOCF = Last observation carried forward.
RR = relative risk
[a] Based on RR stratified by randomization strata of screening HbA1c (<8.0 or ≥8.0 %), using a CMH methodology
Note:
For all patients rescued during the 6-month period, the last postbaseline HbA1c measurement before rescue and during the 6-month on-treatment period will be used as the HbA1c endpoint.

2.2.3.2 Change in FPG from Baseline to Month 6 Endpoint

TABLE 31

Other secondary efficacy endpoint—Mean change
in FPG (mmol/L) from baseline to
Month 6 endpoint using LOCF procedure-mITT population

| FPG (mmol/L) | HOE901-U300 (N = 403) | Lantus (N = 405) |
|---|---|---|
| Baseline | | |
| Number | 375 | 379 |
| Mean (SD) | 8.24 (2.97) | 7.89 (2.67) |
| Median | 7.80 | 7.40 |
| Min:Max | 2.7:20.1 | 2.9:16.6 |
| Month 6 endpoint (LOCF) | | |
| Number | 375 | 379 |
| Mean (SD) | 7.09 (2.47) | 6.83 (2.37) |
| Median | 6.70 | 6.30 |
| Min:Max | 2.9:24.4 | 2.8:17.9 |
| Change from baseline to Month 6 endpoint (LOCF) | | |
| Number | 375 | 379 |
| Mean (SD) | −1.14 (3.42) | −1.06 (3.02) |
| Median | −0.90 | −0.90 |
| Min:Max | −13.1:11.0 | −11.2:10.5 |
| LS Mean (SE) [a] | −1.03 (0.242) | −1.21 (0.241) |
| 95% CI | (−1.501 to −0.551) | (−1.687 to −0.741) |
| LS Mean difference (SE) vs. Lantus [a] | 0.19 (0.171) | |
| 95% CI | (−0.148 to 0.524) | |

FPG = Fasting Plasma Glucose
LOCF = Last observation carried forward.
[a] Analysis of covariance (ANCOVA) model with treatment groups (HOE901-U300 and LANTUS), randomization strata of screening HbA1c (<8.0, ≥8.0%) and country as fixed effects and baseline FPG value as covariate.
Note:
For all patients rescued during the 6-month period, the last postbaseline FPG measurement before rescue and during the 6-month on-treatment period will be used as the FPG endpoint.

2.2.3.3 Eight-Point SMPG Profile

The mean 8-point SMPG profile (mmol/l) at baseline and Month 6 endpoint (mITT population) is described in FIG. 7.

2.2.3.4 Basal Insulin Dose

The average daily basal insulin dose (U) by visit during the main 6-month on-treatment period (mITT population) is described in FIG. 8.

2.3 Safety Evaluation 2.3.1 Extent of Exposure

TABLE 32

Exposure to investigational product for the main 6-month
on-treatment period—Safety population

| | HOE901-U300 (N = 403) | Lantus (N = 406) |
|---|---|---|
| Cumulative exposure to main 6-month treatment (patient years) | 191.1 | 193.6 |
| Duration of main 6-month study treatment (days) | | |
| Number | 402 | 406 |
| Mean (SD) | 1737 (357) | 174.2 (33.0) |
| Median | 183.0 | 183.0 |
| Min:Max | 1:208 | 4:228 |
| Duration of main 6-month study treatment by category [n(%)] | | |
| up to 2 weeks | 6 (1.5%) | 2 (0.5%) |
| >2 to 4 weeks | 4 (1.0%) | 6 (1.5%) |

TABLE 32-continued

Exposure to investigational product for the main 6-month on-treatment period—Safety population

| | HOE901-U300 (N = 403) | Lantus (N = 406) |
|---|---|---|
| >4 to 8 weeks | 7 (1.7%) | 6 (1.5%) |
| >8 to 12 weeks | 6 (1.5%) | 7 (1.7%) |
| >12 to 17 weeks | 2 (0.5%) | 5 (1.2%) |
| >17 to 26 weeks | 117 (29.1%) | 110 (27.1%) |
| >26 weeks | 260 (64.7%) | 270 (66.5%) |
| Cumulative duration of main 6-month study treatment by category [n(%)] | | |
| ≥1 days | 402 (100%) | 406 (100%) |
| >2 weeks | 396 (98.5%) | 404 (99.5%) |
| >4 weeks | 392 (97.5%) | 398 (98.0%) |
| >8 weeks | 385 (95.8%) | 392 (96.6%) |
| >12 weeks | 379 (94.3%) | 385 (94.8%) |
| >17 weeks | 377 (93.8%) | 380 (93.6%) |
| >26 weeks | 260 (64.7%) | 270 (66.5%) |

Note:
Patients are considered in the treatment group they actually received at randomization 2.3.2 Hypoglycemia

TABLE 33

Number (%) of patients with at least one emergent hypoglycemia event during the main 6-month on-treatment period—Safety population

| Type of hypoglycemia event n(%) | All hypoglycemia | | Nocturnal hypoglycemia (00:00-05:59) | |
|---|---|---|---|---|
| | HOE901-U300 (N = 403) | Lantus (N = 406) | HOE901-U300 (N = 403) | Lantus (N = 406) |
| Any hypoglycemia event | 288 (71.5%) | 322 (79.3%) | 123 (30.5%) | 169 (41.6%) |
| Severe hypoglycemia | 4 (1.0%) | 6 (1.5%) | 0 | 2 (0.5%) |
| Documented symptomatic hypoglycemia | | | | |
| ≤3.9 mmol/L (70 mg/dL) | 200 (49.6%) | 233 (57.4%) | 91 (22.6%) | 126 (31.0%) |
| <3.0 mmol/L (54 mg/dL) | 83 (20.6%) | 109 (26.8%) | 33 (8.2%) | 47 (11.6%) |
| Asymptomatic hypoglycemia | | | | |
| ≤3.9 mmol/L (70 mg/dL) | 200 (49.6%) | 238 (58.6%) | 43 (10.7%) | 77 (19.0%) |
| <3.0 mmol/L (54 mg/dL) | 43 (10.7%) | 59 (14.5%) | 10 (2.5%) | 9 (2.2%) |
| Probable symptomatic hypoglycemia | 6 (1.5%) | 10 (2.5%) | 3 (0.7%) | 3 (0.7%) |
| Relative hypoglycemia | | | | |
| >3.9 mmol/L (70 mg/dL) | 23 (5.7%) | 45 (11.1%) | 9 (2.2%) | 23 (5.7%) |
| Nocturnal hypoglycemia | | | | |
| Severe and/or confirmed[a] hypoglycemia | | | | |
| ≤3.9 mmol/L (70 mg/dL) | 282 (70.0%) | 314 (77.3%) | 114 (28.3%) | 162 (39.9%) |
| <3.0 mmol/L (54 mg/dL) | 110 (27.3%) | 143 (35.2%) | 40 (9.9%) | 54 (13.3%) | n (%) = number and percentage of patients with at least one hypoglycemia event
[a]Severe and/or confirmed hypoglycemia = severe and/or confirmed by plasma glucose ≤3.9 mmol/L (70 mg/dL) (resp. ≤3.0 mmol/L (54 mg/dL))

TABLE 34

Number (%) of patients with at least one emergent hypoglycemia event during the main 6-month on-treatment period by study period—Safety population

| Type of hypoglycemia event n(%) | All hypoglycemia | | Nocturnal hypoglycemia (00:00-05:59) | |
|---|---|---|---|---|
| | HOE901-U300 (N = 403) | Lantus (N = 406) | HOE901-U300 (N = 403) | Lantus (N = 406) |
| Any hypoglycemia event | | | | |
| Overall | 288 (71.5%) | 322 (79.3%) | 123 (30.5%) | 169 (41.6%) |
| Treatment Start to Week 8 | 198 (49.1%) | 258 (63.5%) | 58 (14.4%) | 109 (26.8%) |
| From start of week 9 to Month 6 | 241 (59.8%) | 267 (65.8%) | 94 (23.3%) | 119 (29.3%) |
| Severe hypoglycemia | | | | |
| Overall | 4 (1.0%) | 6 (1.5%) | 0 | 2 (0.5%) |
| Treatment Start to Week 8 | 1 (0.2%) | 2 (0.5%) | 0 | 0 |

TABLE 34-continued

Number (%) of patients with at least one emergent hypoglycemia event during the main 6-month on-treatment period by study period—Safety population

| Type of hypoglycemia event n(%) | All hypoglycemia | | Nocturnal hypoglycemia (00:00-05:59) | |
|---|---|---|---|---|
| | HOE901-U300 (N = 403) | Lantus (N = 406) | HOE901-U300 (N = 403) | Lantus (N = 406) |
| From start of week 9 to Month 6 | 3 (0.7%) | 5 (1.2%) | 0 | 2 (0.5%) |
| Documented symptomatic hypoglycemia | | | | |
| ≤3.9 mmol/L (70 mg/dL) Overall | 200 (49.6%) | 233 (57.4%) | 91 (22.6%) | 126 (31.0%) |
| Treatment Start to Week 8 | 119 (29.5%) | 158 (38.9%) | 34 (8.4%) | 79 (19.5%) |
| From start of week 9 to Month 6 | 163 (40.4%) | 180 (44.3%) | 77 (19.1%) | 90 (22.2%) |
| <3.0 mmol/L (54 mmg/dL) Overall | 83 (20.6%) | 109 (26.8%) | 33 (8.2%) | 47 (11.6%) |
| Treatment Start to Week 8 | 35 (8.7%) | 55 (13.5%) | 10 (2.5%) | 26 (6.4%) |
| From start of week 9 to Month 6 | 64 (15.9%) | 81 (20.0%) | 27 (6.7%) | 35 (8.6%) |
| Asymptomatic hypoglycemia | | | | |
| ≤3.9 mmol/L (70 mg/dL) Overall | 200 (49.6%) | 238 (58.6%) | 43 (10.7%) | 77 (19.0%) |
| Treatment Start to Week 8 | 131 (32.5%) | 171 (42.1%) | 22 (5.5%) | 46 (11.3%) |
| From start of week 9 to Month 6 | 163 (40.4%) | 195 (48.0%) | 25 (6.2%) | 50 (12.3%) |
| <3.0 mmol/L (54 mg/dL) Overall | 43 (10.7%) | 59 (14.5%) | 10 (2.5%) | 9 (2.2%) |
| Treatment Start to Week 8 | 22 (5.5%) | 30 (7.4%) | 7 (1.7%) | 5 (1.2%) |
| From start of week 9 to Month 6 | 26 (6.5%) | 40 (9.9%) | 4 (1.0%) | 5 (1.2%) |
| Severe and/or confirmed$^a$ hypoglycemia | | | | |
| ≤3.9 mmol/L (70 mg/dL) Overall | 282 (70.0%) | 314 (77.3%) | 114 (28.3%) | 162 (39.9%) |
| Treatment Start to Week 8 | 190 (47.1%) | 244 (60.1%) | 53 (13.2%) | 100 (24.6%) |
| From start of week 9 to Month 6 | 239 (59.3%) | 264 (65.0%) | 89 (22.1%) | 117 (28.8%) |
| <3.0 mmol/L (54 mg/dL) Overall | 110 (27.3%) | 143 (35.2%) | 40 (9.9%) | 54 (13.3%) |
| Treatment Start to Week 8 | 52 (12.9%) | 79 (19.5%) | 16 (4.0%) | 29 (7.1%) |
| From start of week 9 to Month 6 | 82 (20.3%) | 107 (26.4%) | 29 (7.2%) | 39 (9.6%) | n (%) = number and percentage of patients with at least one hypoglycemia event
$^a$Severe and/or confirmed hypoglycemia = severe and/or confirmed by plasma glucose ≤3.9 mmol/L (70 mg/dL) (resp. ≤3.0 mmol/L (54 mg/dL))

2.3.3 Treatment-Emergent Adverse Events

TABLE 35

Treatment emergent adverse events during the main 6-month on-treatment period-Safety population

| n (%) | HOE901-U300 (N = 403) | Lantus (N = 406) |
|---|---|---|
| Patients with any TEAE | 236 (58.6%) | 206 (50.7%) |
| Patients with any treatment emergent SAE | 15 (3.7%) | 15 (3.7%) |
| Patients with any TEAE leading to death | 2 (0.5%) | 1 (0.2%) |
| Patients with any TEAE leading to permanent treatment discontinuation | 6 (1.5%) | 4 (1.0%) |

TEAE: Treatment emergent adverse event, SAE:Serious Adverse Event
n (%) = number and percentage of patients with at least one TEAE

TABLE 36

Number (%) of patients with TEAE(s) that occurred with HLT ≥ 2% in any treatment group by Primary SOC, HLT and PT for the main 6-month on-treatment period—Safety population

| PRIMARY SYSTEM ORGAN CLASS<br>HLT: High Level Term<br>Preferred Term n (%) | HOE901-U300<br>(N = 403) | Lantus<br>(N = 406) |
|---|---|---|
| Any class | 236 (58.6%) | 206 (50.7%) |
| INFECTIONS AND INFESTATIONS | 133 (33.0%) | 129 (31.8%) |
| HLT: Influenza viral infections | 11 (2.7%) | 11 (2.7%) |
| Influenza | 11 (2.7%) | 11 (2.7%) |
| HLT: Lower respiratory tract and lung infections | 20 (5.0%) | 18 (4.4%) |
| Bronchitis | 19 (4.7%) | 14 (3.4%) |
| Lower respiratory tract infection | 0 | 1 (0.2%) |
| Pneumonia | 1 (0.2%) | 3 (0.7%) |
| HLT: Upper respiratory tract infections | 72 (17.9%) | 72 (17.7%) |
| Acute sinusitis | 2 (0.5%) | 2 (0.5%) |
| Acute tonsillitis | 1 (0.2%) | 0 |
| Chronic sinusitis | 1 (0.2%) | 0 |
| Laryngitis | 1 (0.2%) | 0 |
| Nasopharyngitis | 39 (9.7%) | 27 (6.7%) |
| Pharyngitis | 4 (1.0%) | 10 (2.5%) |
| Pharyngotonsillitis | 0 | 2 (0.5%) |
| Sinusitis | 7 (1.7%) | 9 (2.2%) |
| Tonsillitis | 2 (0.5%) | 0 |
| Tracheitis | 1 (0.2%) | 0 |
| Upper respiratory tract infection | 17 (4.2%) | 28 (6.9%) |
| HLT: Urinary tract infections | 13 (3.2%) | 11 (2.7%) |
| Pyelonephritis acute | 1 (0.2%) | 0 |
| Pyelonephritis chronic | 0 | 1 (0.2%) |
| Urinary tract infection | 12 (3.0%) | 10 (2.5%) |
| HLT: Viral infections NEC | 13 (3.2%) | 10 (2.5%) |
| Conjunctivitis viral | 1 (0.2%) | 0 |
| Gastroenteritis viral | 5 (1.2%) | 3 (0.7%) |
| Gastrointestinal viral infection | 0 | 1 (0.2%) |
| Respiratory tract infection viral | 0 | 3 (0.7%) |
| Viral infection | 1 (0.2%) | 0 |
| Viral pharyngitis | 1 (0.2%) | 0 |
| Viral upper respiratory tract infection | 5 (1.2%) | 3 (0.7%) |
| NERVOUS SYSTEM DISORDERS | 47 (11.7%) | 38 (9.4%) |
| HLT: Headaches NEC | 20 (5.0%) | 16 (3.9%) |
| Headache | 19 (4.7%) | 16 (3.9%) |
| Sinus headache | 1 (0.2%) | 0 |
| Tension headache | 1 (0.2%) | 0 |
| VASCULAR DISORDERS | 14 (3.5%) | 15 (3.7%) |
| HLT: Vascular hypertensive disorders NEC | 11 (2.7%) | 6 (1.5%) |
| Hypertension | 11 (2.7%) | 6 (1.5%) |
| GASTROINTESTINAL DISORDERS | 44 (10.9%) | 34 (8.4%) |
| HLT: Diarrhoea (excl infective) | 15 (3.7%) | 9 (2.2%) |
| Diarrhoea | 15 (3.7%) | 9 (2.2%) |
| HLT: Nausea and vomiting symptoms | 14 (3.5%) | 9 (2.2%) |
| Nausea | 9 (2.2%) | 4 (1.0%) |
| Vomiting | 5 (1.2%) | 5 (1.2%) |
| MUSCULOSKELETAL AND CONNECTIVE TISSUE DISORDERS | 44 (10.9%) | 41 (10.1%) |
| HLT: Musculoskeletal and connective tissue pain and discomfort | 20 (5.0%) | 22 (5.4%) |
| Back pain | 9 (2.2%) | 12 (3.0%) |
| Flank pain | 1 (0.2%) | 0 |
| Musculoskeletal chest pain | 0 | 1 (0.2%) |
| Musculoskeletal discomfort | 0 | 1 (0.2%) |
| Musculoskeletal pain | 4 (1.0%) | 2 (0.5%) |
| Neck pain | 3 (0.7%) | 3 (0.7%) |
| Pain in extremity | 5 (1.2%) | 3 (0.7%) |
| GENERAL DISORDERS AND ADMINISTRATION SITE CONDITIONS | 28 (6.9%) | 29 (7.1%) |
| HLT: Injection site reactions | 4 (1.0%) | 12 (3.0%) |
| Injection site atrophy | 0 | 1 (0.2%) |
| Injection site bruising | 0 | 2 (0.5%) |
| Injection site erythema | 0 | 2 (0.5%) |
| Injection site haemorrhage | 2 (0.5%) | 5 (1.2%) |
| Injection site induration | 0 | 3 (0.7%) |
| Injection site inflammation | 1 (0.2%) | 0 |
| Injection site irritation | 0 | 1 (0.2%) |
| Injection site pain | 1 (0.2%) | 4 (1.0%) |
| Injection site reaction | 1 (0.2%) | 1 (0.2%) |
| Injection site swelling | 0 | 1 (0.2%) |

TABLE 36-continued

Number (%) of patients with TEAE(s) that occurred with HLT ≥ 2% in any treatment group by Primary SOC, HLT and PT for the main 6-month on-treatment period—Safety population

| PRIMARY SYSTEM ORGAN CLASS<br>HLT: High Level Term<br>Preferred Term n (%) | HOE901-U300<br>(N = 403) | Lantus<br>(N = 406) |
|---|---|---|
| HLT: Oedema NEC | 6 (1.5%) | 12 (3.0%) |
| Oedema peripheral | 6 (1.5%) | 12 (3.0%) |
| INJURY, POISONING AND PROCEDURAL COMPLICATIONS | 34 (8.4%) | 21 (5.2%) |
| HLT: Muscle, tendon and ligament injuries | 11 (2.7%) | 3 (0.7%) |
| Epicondylitis | 0 | 1 (0.2%) |
| Ligament rupture | 1 (0.2%) | 0 |
| Ligament sprain | 7 (1.7%) | 0 |
| Muscle strain | 2 (0.5%) | 1 (0.2%) |
| Post-traumatic neck syndrome | 1 (0.2%) | 1 (0.2%) |

TEAE: Treatment emergent adverse event,
SOC: System organ class,
HLT: High level term,
PT: Preferred term
MedDRA 16.0
n (%) = number and percentage of patients with at least one TEAE
Note:
Table sorted by SOC internationally agreed order and HLT, PT by alphabetic order
Only HLT with at least one HLT ≥ 2% in at least one group are presented

2.3.4 Deaths, Serious Treatment-Emergent Adverse Events

2.3.4.1 Death

TABLE 37

Number (%) of patients who died by study period (on study, on-treatment, post-study)—Safety population

|  | HOE901-U300<br>(N = 403) | Lantus<br>(N = 406) |
|---|---|---|
| Death on-study[a] | 3 (0.7%) | 2 (0.5%) |
| Death on-study during first 6 months | 2 (0.5%) | 1 (0.2%) |
| Death on-treatment[b] | 2 (0.5%) | 1 (0.2%) |
| Death post-study[c] | 0 | 0 |

TEAE: Treatment emergent adverse event,
SAE: Serious adverse event
[a]Includes all deaths that occurred after the start of treatment up to end of study (defined as last protocol planned visit or the resolution/stabilization of all treatment emergent SAE and adverse event of pre-specified monitoring)
[b]On-treatment is main 6-month on-treatment period
[c]Includes deaths that occurred after the end of the study (as defined in footnote a) and reported in the database

2.3.4.2 Serious Adverse Events

TABLE 38

Number (%) of patients with treatment emergent SAEs by Primary SOC, HLGT, HLT and PT for the main 6-month on-treatment period—Safety population

| PRIMARY SYSTEM ORGAN CLASS<br>HLGT: High Level Group Term<br>HLT: High Level Term<br>Preferred Term n (%) | HOE901-U300<br>(N = 403) | Lantus<br>(N = 406) |
|---|---|---|
| Any class | 15 (3.7%) | 15 (3.7%) |
| INFECTIONS AND INFESTATIONS | 2 (0.5%) | 7 (1.7%) |
| HLGT: Infections-pathogen unspecified | 2 (0.5%) | 7 (1.7%) |
| HLT: Infections NEC | 1 (0.2%) | 2 (0.5%) |
| Infected bites | 0 | 1 (0.2%) |
| Localised infection | 0 | 1 (0.2%) |
| Wound infection | 1 (0.2%) | 0 |
| HLT: Lower respiratory tract and lung infections | 0 | 1 (0.2%) |
| Pneumonia | 0 | 1 (0.2%) |
| HLT: Upper respiratory tract infections | 1 (0.2%) | 1 (0.2%) |
| Chronic sinusitis | 1 (0.2%) | 0 |
| Upper respiratory tract infection | 0 | 1 (0.2%) |
| HLT: Urinary tract infections | 0 | 3 (0.7%) |
| Pyelonephritis chronic | 0 | 1 (0.2%) |
| Urinary tract infection | 0 | 2 (0.5%) |
| NEOPLASMS BENIGN, MALIGNANT AND UNSPECIFIED (INCL CYSTS AND POLYPS) | 1 (0.2%) | 1 (0.2%) |

TABLE 38-continued

Number (%) of patients with treatment emergent SAEs by Primary SOC, HLGT, HLT and PT for the main 6-month on-treatment period—Safety population

| PRIMARY SYSTEM ORGAN CLASS<br>HLGT: High Level Group Term<br>HLT: High Level Term<br>Preferred Term n (%) | HOE901-U300<br>(N = 403) | Lantus<br>(N = 406) |
|---|---|---|
| HLGT: Leukaemias | 1 (0.2%) | 0 |
| HLT: Myelodysplastic syndromes | 1 (0.2%) | 0 |
| Myelodysplastic syndrome | 1 (0.2%) | 0 |
| HLGT: Skin neoplasms malignant and unspecified | 0 | 1 (0.2%) |
| HLT: Skin melanomas (excl ocular) | 0 | 1 (0.2%) |
| Malignant melanoma | 0 | 1 (0.2%) |
| METABOLISM AND NUTRITION DISORDERS | 0 | 1 (0.2%) |
| HLGT: Glucose metabolism disorders (incl diabetes mellitus) | 0 | 1 (0.2%) |
| HLT: Hypoglycaemic conditions NEC | 0 | 1 (0.2%) |
| Hypoglycaemia | 0 | 1 (0.2%) |
| NERVOUS SYSTEM DISORDERS | 1 (0.2%) | 3 (0.7%) |
| HLGT: Central nervous system vascular disorders | 0 | 2 (0.5%) |
| HLT: Central nervous system haemorrhages and cerebrovascular accidents | 0 | 2 (0.5%) |
| Ischaemic stroke | 0 | 2 (0.5%) |
| HLGT: Neurological disorders NEC | 1 (0.2%) | 1 (0.2%) |
| HLT: Neurological signs and symptoms NEC | 1 (0.2%) | 0 |
| Cerebrospinal fluid leakage | 1 (0.2%) | 0 |
| HLT: Sensory abnormalities NEC | 0 | 1 (0.2%) |
| Hypoaesthesia | 0 | 1 (0.2%) |
| CARDIAC DISORDERS | 6 (1.5%) | 1 (0.2%) |
| HLGT: Cardiac arrhythmias | 0 | 1 (0.2%) |
| HLT: Rate and rhythm disorders NEC | 0 | 1 (0.2%) |
| Nodal rhythm | 0 | 1 (0.2%) |
| HLGT: Cardiac disorder signs and symptoms | 2 (0.5%) | 0 |
| HLT: Cardiac disorders NEC | 2 (0.5%) | 0 |
| Cardiac disorder | 1 (0.2%) | 0 |
| Cardiovascular disorder | 1 (0.2%) | 0 |
| HLGT: Coronary artery disorders | 2 (0.5%) | 0 |
| HLT: Ischaemic coronary artery disorders | 2 (0.5%) | 0 |
| Acute myocardial infarction | 1 (0.2%) | 0 |
| Myocardial infarction | 1 (0.2%) | 0 |
| HLGT: Heart failures | 2 (0.5%) | 0 |
| HLT: Heart failures NEC | 2 (0.5%) | 0 |
| Cardiac failure | 1 (0.2%) | 0 |
| Cardiac failure congestive | 1 (0.2%) | 0 |
| VASCULAR DISORDERS | 0 | 1 (0.2%) |
| HLGT: Decreased and nonspecific blood pressure disorders and shock | 0 | 1 (0.2%) |
| HLT: Vascular hypotensive disorders | 0 | 1 (0.2%) |
| Hypotension | 0 | 1 (0.2%) |
| RESPIRATORY, THORACIC AND MEDIASTINAL DISORDERS | 1 (0.2%) | 0 |
| HLGT: Bronchial disorders (excl neoplasms) | 1 (0.2%) | 0 |
| HLT: Bronchospasm and obstruction | 1 (0.2%) | 0 |
| Asthma | 1 (0.2%) | 0 |
| GASTROINTESTINAL DISORDERS | 1 (0.2%) | 0 |
| HLGT: Gastrointestinal haemorrhages NEC | 1 (0.2%) | 0 |
| HLT: Non-site specific gastrointestinal haemorrhages | 1 (0.2%) | 0 |
| Lower gastrointestinal haemorrhage | 1 (0.2%) | 0 |
| SKIN AND SUBCUTANEOUS TISSUE DISORDERS | 1 (0.2%) | 1 (0.2%) |
| HLGT: Angioedema and urticaria | 1 (0.2%) | 0 |
| HLT: Urticarias | 1 (0.2%) | 0 |
| Urticaria | 1 (0.2%) | 0 |
| HLGT: Skin and subcutaneous tissue disorders NEC | 0 | 1 (0.2%) |
| HLT: Skin and subcutaneous tissue ulcerations | 0 | 1 (0.2%) |
| Skin ulcer | 0 | 1 (0.2%) |
| MUSCULOSKELETAL AND CONNECTIVE TISSUE DISORDERS | 0 | 1 (0.2%) |
| HLGT: Joint disorders | 0 | 1 (0.2%) |
| HLT: Osteoarthropathies | 0 | 1 (0.2%) |
| Osteoarthritis | 0 | 1 (0.2%) |
| RENAL AND URINARY DISORDERS | 0 | 1 (0.2%) |
| HLGT: Urolithiases | 0 | 1 (0.2%) |
| HLT: Urinary tract lithiasis (excl renal) | 0 | 1 (0.2%) |

TABLE 38-continued

Number (%) of patients with treatment emergent SAEs by Primary SOC, HLGT, HLT and PT for the main 6-month on-treatment period—Safety population

| PRIMARY SYSTEM ORGAN CLASS<br>HLGT: High Level Group Term<br>HLT: High Level Term<br>Preferred Term n (%) | HOE901-U300<br>(N = 403) | Lantus<br>(N = 406) |
|---|---|---|
| Calculus urinary | 0 | 1 (0.2%) |
| GENERAL DISORDERS AND ADMINISTRATION SITE CONDITIONS | 1 (0.2%) | 0 |
| HLGT: Fatal outcomes | 1 (0.2%) | 0 |
| HLT: Death and sudden death | 1 (0.2%) | 0 |
| Sudden cardiac death | 1 (0.2%) | 0 |
| INJURY, POISONING AND PROCEDURAL COMPLICATIONS | 1 (0.2%) | 0 |
| HLGT: Injuries NEC | 1 (0.2%) | 0 |
| HLT: Skin injuries NEC | 1 (0.2%) | 0 |
| Contusion | 1 (0.2%) | 0 |

SAE: Serious adverse event,
SOC: System organ class,
HLGT: High level group term,
HLT: High level term,
PT: Preferred term
MedDRA 16.0
n (%) = number and percentage of patients with at least one treatment emergent SAE
Note:
Table sorted by SOC internationally agreed order and HLGT, HLT, PT by alphabetic order

2.3.5 Adverse Events Leading to Withdrawal

TABLE 39

Number (%) of patients with TEAE(s) leading to permanent treatment discontinuation by Primary SOC, HLGT, HLT and PT for the main 6-month on-treatment period—Safety population

| PRIMARY SYSTEM ORGAN CLASS<br>HLGT: High Level Group Term<br>HLT: High Level Term<br>Preferred Term n (%) | HOE901-U300<br>(N = 403) | Lantus<br>(N = 406) |
|---|---|---|
| Any class | 6 (1.5%) | 4 (1.0%) |
| INFECTIONS AND INFESTATIONS | 0 | 1 (0.2%) |
| HLGT: Infections-pathogen unspecified | 0 | 1 (0.2%) |
| HLT: Urinary tract infections | 0 | 1 (0.2%) |
| Pyelonephritis chronic | 0 | 1 (0.2%) |
| NEOPLASMS BENIGN, MALIGNANT AND UNSPECIFIED (INCL CYSTS AND POLYPS) | 1 (0.2%) | 0 |
| HLGT: Leukaemias | 1 (0.2%) | 0 |
| HLT: Myelodysplastic syndromes | 1 (0.2%) | 0 |
| Myelodysplastic syndrome | 1 (0.2%) | 0 |
| BLOOD AND LYMPHATIC SYSTEM DISORDERS | 1 (0.2%) | 0 |
| HLGT: White blood cell disorders | 1 (0.2%) | 0 |
| HLT: Neutropenias | 1 (0.2%) | 0 |
| Neutropenia | 1 (0.2%) | 0 |
| METABOLISM AND NUTRITION DISORDERS | 0 | 1 (0.2%) |
| HLGT: Glucose metabolism disorders (incl diabetes mellitus) | 0 | 1 (0.2%) |
| HLT: Hypoglycaemic conditions NEC | 0 | 1 (0.2%) |
| Hypoglycaemia | 0 | 1 (0.2%) |
| PSYCHIATRIC DISORDERS | 0 | 2 (0.5%) |
| HLGT: Manic and bipolar mood disorders and disturbances | 0 | 1 (0.2%) |
| HLT: Bipolar disorders | 0 | 1 (0.2%) |
| Bipolar disorder | 0 | 1 (0.2%) |
| HLGT: Sleep disorders and disturbances | 0 | 1 (0.2%) |
| HLT: Disturbances in initiating and maintaining sleep | 0 | 1 (0.2%) |
| Insomnia | 0 | 1 (0.2%) |
| NERVOUS SYSTEM DISORDERS | 1 (0.2%) | 0 |
| HLGT: Cranial nerve disorders (excl neoplasms) | 1 (0.2%) | 0 |
| HLT: Eye movement disorders | 1 (0.2%) | 0 |
| IIIrd nerve paralysis | 1 (0.2%) | 0 |
| CARDIAC DISORDERS | 1 (0.2%) | 0 |
| HLGT: Coronary artery disorders | 1 (0.2%) | 0 |
| HLT: Ischaemic coronary artery disorders | 1 (0.2%) | 0 |
| Myocardial infarction | 1 (0.2%) | 0 |
| RENAL AND URINARY DISORDERS | 1 (0.2%) | 0 |

TABLE 39-continued

Number (%) of patients with TEAE(s) leading to permanent treatment discontinuation by Primary SOC, HLGT, HLT and PT for the main 6-month on-treatment period—Safety population PRIMARY SYSTEM ORGAN CLASS
HLGT: High Level Group Term
HLT: High Level Term
Preferred Term n (%)

| | HOE901-U300 (N = 403) | Lantus (N = 406) |
|---|---|---|
| HLGT: Nephropathies | 1 (0.2%) | 0 |
| HLT: Nephropathies and tubular disorders NEC | 1 (0.2%) | 0 |
| Diabetic nephropathy | 1 (0.2%) | 0 |
| GENERAL DISORDERS AND ADMINISTRATION SITE CONDITIONS | 1 (0.2%) | 0 |
| HLGT: Fatal outcomes | 1 (0.2%) | 0 |
| HLT: Death and sudden death | 1 (0.2%) | 0 |
| Sudden cardiac death | 1 (0.2%) | 0 |

TEAE: Treatment emergent adverse event,
SOC: System organ class,
HLGT: High level group term,
HLT: High level term,
PT: Preferred term
MedDRA 16.0
n (%) = number and percentage of patients with at least one TEAE leading to permanent treatment discontinuation
Note:
Table sorted by SOC internationally agreed order and HLGT, HLT, PT by alphabetic order

2.3.6 Other Significant Adverse Events
2.3.6.1 Hypersensitivity Reaction

TABLE 40

Number (%) of patients experiencing at least one TEAE by relevant Standardized MedDRA Queries and Preferred Term—Hypersensitivity reactions during the main 6-month on-treatment period—Safety population

| Preferred Term | HOE901-U300 (N = 403) | Lantus (N = 406) |
|---|---|---|
| Any hypersensitivity reactions | 13 (3.2%) | 16 (3.9%) |
| Asthma | 2 (0.5%) | 3 (0.7%) |
| Allergic cough | 1 (0.2%) | 0 |
| Allergy to chemicals | 1 (0.2%) | 0 |
| Bronchial hyperreactivity | 1 (0.2%) | 0 |
| Dermatitis infected | 1 (0.2%) | 0 |
| Drug hypersensitivity | 1 (0.2%) | 1 (0.2%) |
| Eczema | 1 (0.2%) | 0 |
| Rash | 1 (0.2%) | 3 (0.7%) |
| Rhinitis allergic | 1 (0.2%) | 2 (0.5%) |
| Seasonal allergy | 1 (0.2%) | 1 (0.2%) |
| Sneezing | 1 (0.2%) | 0 |
| Urticaria | 1 (0.2%) | 0 |
| Asthmatic crisis | 0 | 1 (0.2%) |
| Blister | 0 | 1 (0.2%) |
| Erythema | 0 | 3 (0.7%) |
| Neurodermatitis | 0 | 1 (0.2%) |

MedDRA 16.0
TEAE: Treatment emergent adverse event
n (%) = number and percentage of patients with at least one hypersensitivity reaction event

2.3.6.2 Injection Site Reactions

TABLE 41

Number (%) of patients experiencing at least one TEAE by relevant Standardized MedDRA Queries and Preferred Term—Injection site reactions during the main 6-month on-treatment period—Safety population

| Preferred Term | HOE901-U300 (N = 403) | Lantus (N = 406) |
|---|---|---|
| Any injection site reaction | 4 (1.0%) | 12 (3.0%) |
| Injection site haemorrhage | 2 (0.5%) | 5 (1.2%) |
| Injection site inflammation | 1 (0.2%) | 0 |
| Injection site pain | 1 (0.2%) | 4 (1.0%) |

TABLE 41-continued

Number (%) of patients experiencing at least one TEAE by relevant Standardized MedDRA Queries and Preferred Term—Injection site reactions during the main 6-month on-treatment period—Safety population

| Preferred Term | HOE901-U300 (N = 403) | Lantus (N = 406) |
|---|---|---|
| Injection site reaction | 1 (0.2%) | 1 (0.2%) |
| Injection site atrophy | 0 | 1 (0.2%) |
| Injection site bruising | 0 | 2 (0.5%) |
| Injection site erythema | 0 | 2 (0.5%) |
| Injection site induration | 0 | 3 (0.7%) |
| Injection site irritation | 0 | 1 (0.2%) |
| Injection site swelling | 0 | 1 (0.2%) |

MedDRA 16.0
TEAE: Treatment emergent adverse event
n (%) = number and percentage of patients with at least one local tolerability at injection site event

2.3.7 Body Weight

TABLE 42

Vital signs—Descriptive statistics—Mean change in Weight (kg) from baseline to Month 6 endpoint using LOCF procedure during the main 6-month on-treatment period—Safety population

| Weight (kg) | HOE901-U300 (N = 403) | Lantus (N = 406) |
|---|---|---|
| Baseline | | |
| Number | 400 | 403 |
| Mean (SD) | 98.78 (22.37) | 98.17 (20.73) |
| Median | 94.50 | 95.10 |
| Min:Max | 48.0:208.6 | 55.0:187.7 |
| Month 6 endpoint (LOCF) | | |
| Number | 400 | 403 |
| Mean (SD) | 98.86 (22.09) | 98.84 (20.63) |
| Median | 94.70 | 96.00 |
| Min:Max | 46.5:213.2 | 57.9:189.1 |
| Change from baseline to Month 6 endpoint (LOCF) | | |
| Number | 400 | 403 |
| Mean (SD) | 0.08 (3.44) | 0.66 (3.01) |

TABLE 42-continued

Vital signs—Descriptive statistics—Mean change in Weight (kg) from baseline to Month 6 endpoint using LOCF procedure during the main 6-month on-treatment period—Safety population

| Weight (kg) | HOE901-U300 (N = 403) | Lantus (N = 406) |
|---|---|---|
| Median | 0.00 | 0.64 |
| Min:Max | −22.1:12.4 | −23.3:9.9 |

LOCF = Last observation carried forward.

EXAMPLE 3: 6-MONTH, MULTICENTER, RANDOMIZED, OPEN-LABEL, PARALLEL-GROUP STUDY COMPARING THE EFFICACY AND SAFETY OF A NEW FORMULATION OF INSULIN GLARGINE AND LANTUS® BOTH PLUS MEALTIME INSULIN IN PATIENTS WITH TYPE 2 DIABETES MELLITUS WITH A 6-MONTH SAFETY EXTENSION PERIOD—ADMINISTRATION SUB-STUDY COMPARING ADAPTABLE DOSING INTERVALS WITH FIXED DOSING INTERVALS

1 Synopsis
Phase of development:
3
Objectives:

Primary Objective: To compare the efficacy of HOE901-U300 injected once daily every 24 hours and HOE901-U300 injected once daily at intervals of 24±3 hours in terms of change of HbA1c from month 6 of the main study (=baseline of sub-study) to month 9 of the main study (=endpoint of sub-study) in patients with type 2 diabetes mellitus.

Main secondary Objectives: To compare the safety of the two injection regimens for HOE901-U300 in terms of occurrence of hypoglycemia.

Methodology:

Patients randomized on HOE901-U300 and having received HOE901-U300 in the 6-month main study period are randomized 1:1 to administer HOE901-U300 once daily either every 24 hours (fixed dosing intervals) or every 24±3 hours (adaptable dosing intervals).

Patients on HOE901-U300 completing the 6 months main study period (see Example 1) and meeting the eligibility criteria for the sub-study were eligible for the sub-study. No specific sample size was requested for the primary analysis that is descriptive.

| Number of patients: | Planned: up to 300 (150 pre-treatment arm) Randomized: 110 Treated: 110 | |
|---|---|---|
| Evaluated: | Efficacy: 109 | Safety: 110 |

Diagnosis and Criteria for Inclusion:

Inclusion criteria: Completion of the 6-month study period in main study described in Example 1 (Visit 10), Randomized and treated with HOE901-U300 during the 6-month treatment period (Baseline—month 6), Signed written informed consent for sub-study obtained.

Key Exclusion Criteria:

Patient not willing to use the adaptable injection intervals of 24±3 hours on at least two days per week; In the investigator's opinion, not able to comply with an adaptable dosing schedule; Health condition which precludes further participation of the patient in the study.

Study Treatments
Investigational Medicinal Product:
Tested drug: HOE901-U300
Formulation: HOE901-U300 (insulin glargine 300 U/mL solution) is a sterile, non-pyrogenic, clear, colorless solution in a glass cartridge assembled in a pen-injector (prefilled, disposable pen).
Route of administration: subcutaneous injection
Tested Regimen:
Adaptable dosing intervals: HOE901-U300 administered once daily every 24±3 hours.

The injection time may have been adapted according to individual needs by up to 3 hours earlier or later than the daily injection time in the evening fixed at the start of the main study. The maximum intervals, ie, 3 hours earlier or 3 hours later than the fixed daily injection time was to be used on at least 2 days of the week at the patients' choice. The injection time fixed at start of the main study was to be maintained as reference time for the variation.

Control Regimen:
Fixed dosing intervals: HOE901-U300, once daily injection every 24 hours.

Patients continued to inject HOE901-U300 once daily every 24 hours at the injection time fixed at start of the main study.

Dose:
The dose of HOE901-U300 was to be titrated as needed to achieve or maintain fasting plasma glucose in the target range of 80 to 100 mg/dL (4.4 mmol/L to 5.6 mmol/L) without hypoglycemia. Changes in the insulin dose were based on fasting self-monitored capillary plasma glucose (SMPG) measurements.

Non-Investigational Medicinal Products
Patients in both treatment groups were to continue with their mealtime insulin analogue during the sub-study.
Patients on concomitant metformin treatment were to continue during the sub-study on a stable dose, unless safety concerns necessitated a dose reduction or discontinuation of metformin Duration of Treatment:
The sub-study consisted of a 3 month comparative efficacy and safety treatment period starting at completion of the 6-month main study period and ending at completion of Month 9 of the main study.

After completion, patients on the adaptable dosing arm may have continued this regimen up to the end of the main study (Month 12). Patients injecting HOE901-U300 every 24 hours continued with their treatment regimen up to the end of the study.

Duration of Observation:
The analysis period for efficacy and safety is the 3-month study period starting at Month 6 of the main study and ending at Month 9 of the main study. Results presented in the present KRM refer to this period.

Criteria for Evaluation:
Efficacy:
Primary Efficacy Endpoint:
change in $HbA_{1c}$ from baseline (Month 6) to endpoint (Month 9).
Secondary Endpoints:
FPG (central laboratory) change from baseline (Month 6) to endpoint (Month 9), daily dose of basal insulin and mealtime insulin.

Safety:

Hypoglycemia, occurrence of adverse events particularly treatment-emergent adverse events (TEAEs) and serious adverse events (SAEs), injection site reactions and hypersensitivity reactions. Following information not presented in KRM: other safety information including vital signs and overdose.

Statistical Methods: For this 3-month sub-study, Baseline is defined as Month 6 of the main study period; the Endpoint is month 9 of the Main study.

The primary efficacy endpoint (change in $HbA_{1c}$ from baseline [Month 6] to endpoint [Month 9]) was analyzed using an analysis of covariance (ANCOVA) model with treatment regimen and country as fixed effects and using the $HbA_{1c}$ baseline value as a covariate. Differences between HOE901-U300 adaptable dosing regimen and HOE901-U300 fixed dosing regimen and two-sided 95% confidence intervals were estimated within the framework of ANCOVA.

All continuous secondary efficacy variables (except for change in variability of pre-injection SMPG) were analyzed using an ANCOVA model with treatment regimen and country as fixed effects and using the corresponding baseline value as a covariate.

Change in variability of pre-injection SMPG from baseline (month 6) to endpoint (month 9) is analyzed using an analysis of variance (ANOVA) model with treatment regimen and country as fixed effects.

Safety analyses were descriptive, based on the safety population.

Summary:

Population Characteristics:

A total of 110 patients with type 2 diabetes were randomized to the sub-study: 56 patients to the HOE901-U300 adaptable dosing interval regimen and 54 patients the to HOE901-U300 fixed dosing interval regimen; 110 patients were exposed to IMP (safety population). The mITT sub-study population (efficacy population) included 109 patients.

One patient (1/56, 1.8%) randomized to HOE901-U300 adaptable dosing intervals discontinued the sub-study prematurely and also discontinued the extension period of the main study (HOE901-U300 fixed dosing intervals: 0/54, 0%).

Demographics and patient characteristics at baseline (Month 6) were well-balanced between both regimen groups. The mean age of the sub-study population was 60 years; 35 of 110 (31.8%) patients were 65 years.

During the sub-study, on average 23.0% of the injections in patients in the adaptable dosing interval group were taken at the extreme intervals of <21.5 hours or >26.5 hours from previous injection versus 3.9% of injections in patients in the fixed dosing interval group. On average 13.5% of the injections in patients in the adaptable dosing interval group were taken in the intermediate interval (between 21.5-23 hours or between 25-26.5 hours after the previous injection) versus 8.2% of injections in patients in the fixed dosing interval group. Fewer injections by patients in the adaptable dosing interval group (63.4%) were taken within 23-25 hours after previous injection, compared with the fixed dosing interval group (88.0%).

A total of 34.5% of patients in the adaptable dosing group took less than 20% of their injections outside the 23-25 hours interval after previous injection and therefore around 65% of patients were considered to be compliant with the adaptable dosing interval regimen. In the fixed dosing interval group, 78.8% of patients took more than 80% of injections within 23-25 hours from the previous injection and therefore can be considered to be compliant with the fixed dosing interval regimen.

The compliance with either regimen was similar when intervals were calculated from the reference injection time as scheduled at the main study baseline.

Efficacy Results:

Primary Endpoint:

The LS mean change in $HbA_{1c}$ from baseline (Month 6) to endpoint (Month 9) was similar in the groups of adaptable dosing intervals (0.22% [95% CI: −0.006 to 0.436]) and fixed dosing intervals (0.14% [95% CI: −0.099 to 0.380]) with the LS mean difference of 0.07% [95% CI: −0.169 to 0.318].

Secondary Efficacy Endpoints (Month 9):

FPG (adaptable dosing interval 1.40 mmol/L [95% CI: 0.624 to 2.177]; fixed dosing interval (1.18 mmol/L [95% CI: 0.350 to 2.015]; LS mean difference 0.22 mmol/L [95% CI: −0.634 to 1.070]).

Pre-injection SMPG, variability of pre-injection SMPG:

Adaptation of the injection intervals for HOE901-U300 resulting in shorter and longer intervals than the regular 24-hour interval may have an impact on the secondary efficacy endpoints pre-injection SMPG and variability of pre-injection SMPG. Therefore in addition to the overall analysis per dosing interval regimen showing the mean of the average by patient over up to 7 days prior to the visit, a breakdown of the SMPG data by injection intervals will be presented in the CSR.

In both dosing interval regimen groups, the average basal and mealtime insulin daily doses remained stable during the 3-month comparative regimen period.

Safety:

During the 3-month comparative regimen period, hypoglycemia events, both overall and for each category of hypoglycemia, were reported by a similar percentage of patients in the HOE901-U300 adaptable dosing interval and HOE901-U300 fixed dosing interval regimens.

The percentages of patients with any TEAE (adaptable dosing intervals 15/56 [26.8%]; fixed dosing intervals 15/54 [27.8%]) or with a serious TEAE (adaptable dosing intervals 4/56 [7.1%]; fixed dosing intervals 5/56 [9.3%]) were comparable between the regimens.

No TEAEs leading to treatment discontinuation, leading to death, or linked to injection site reactions were observed in either dosing interval regimen during the 3-month sub-study period. One patient [1.9%] in the fixed dosing interval regimen had a TEAE linked to hypersensitivity reaction.

Conclusions:

The majority of patients in both dosing interval regimen groups followed the injection schedule as randomized and used either adaptable dosing intervals (HOE901-U300 once daily every 24 hours±3 hours on at least 2 days a week) or fixed dosing intervals (HOE901-U300 once daily every 24 hours). This allows a comparison of the two dosing interval regimens for efficacy and safety analyses.

The efficacy analyses in terms of HbA1c and FPG showed comparable results for the two dosing interval regimens.

Overall incidence of hypoglycemia (% of patients with at least one event) during the 3-month substudy period was similar in both regimens regardless of the category of hypoglycemia HOE901-U300 adaptable dosing intervals and HOE901-U300 fixed dosing intervals were well tolerated during the 3-month comparative substudy period; no specific safety concerns were observed.

Taken together, according to the substudy results, no negative effects on main efficacy and safety endpoints were seen with occasional adaptations of injection intervals.

2 Results
2.1 Study Patients
2.1.1 Study disposition

TABLE 43

Patient disposition—Randomized sub-study population

| | HOE901-U300 Adaptable Dosing Intervals (N = 56) | HOE901-U300 Fixed Dosing Intervals (N = 54) |
|---|---|---|
| Randomized and treated | 56 (100%) | 54 (100%) |
| Completed 3-month comparative regimen period | 55 (98.2%) | 54 (100%) |
| Permanently discontinued the IMP during the 3-month comparative regimen period | 1 (1.8%) | 0 |
| Subject's request for treatment discontinuation | 1 (1.8%) | 0 |
| Reason for treatment discontinuation during the 3-month comparative regimen period | | |
| Adverse event | 0 | 0 |
| Lack of efficacy | 0 | 0 |
| Poor compliance to protocol | 0 | 0 |
| Other reasons | 1 (1.8%) | 0 |
| Status at last study contact of patients who permanently discontinued the treatment during the 3-month comparative regimen period | | |
| Alive | 1 (1.8%) | 0 |
| Dead | 0 | 0 |

Note:
percentages are calculated using the number of patients randomized as denominator.

TABLE 44

Sub-study analysis populations

| | HOE901-U300 Adaptable Dosing Intervals | HOE901-U300 Fixed Dosing Intervals | All |
|---|---|---|---|
| Randomized sub-study population | 56 (100%) | 54 (100%) | 110 (100%) |
| Efficacy sub-study populations | | | |
| Modified Intent-to-Treat (mITT) | 55 (98.2%) | 54 (100%) | 109 (99.1%) |
| Sub-study completers | 55 (98.2%) | 54 (100%) | 109 (99.1%) |
| Safety sub-study population | 56 | 54 | 110 |

Note:
patients are tabulated according to their randomized treatment.

2.1.2 Demographics and Baseline Characteristics

TABLE 45

Demographics and patient characteristics at baseline—Randomized sub-study population

| | H0E901-U300 Adaptable Dosing Intervals (N = 56) | HOE901-U300 Fixed Dosing Intervals (N = 54) | All (N = 110) |
|---|---|---|---|
| Age (years) | | | |
| Number | 56 | 54 | 110 |
| Mean (SD) | 61.0 (7.4) | 58.9 (9.6) | 60.0 (8.6) |
| Median | 61.0 | 61.0 | 61.0 |
| Min:Max | 40:77 | 28:74 | 28:77 |
| Age Group (years) [n (%)] | | | |
| Number | 56 | 54 | 110 |
| <65 | 36 (64.3%) | 39 (72.2%) | 75 (68.2%) |
| [65-75[ | 18 (32.1%) | 15 (27.8%) | 33 (30.0%) |
| ≥75 | 2 (3.6%) | 0 | 2 (1.8%) |
| Gender [n (%)] | | | |
| Number | 56 | 54 | 110 |
| Male | 24 (42.9%) | 25 (46.3%) | 49 (44.5%) |
| Female | 32 (57.1%) | 29 (53.7%) | 61 (55.5%) |
| Race [n (%)] | | | |
| Number | 56 | 54 | 110 |
| Caucasian/White | 51 (91.1%) | 52 (96.3%) | 103 (93.6%) |
| Black | 5 (8.9%) | 1 (1.9%) | 6 (5.5%) |
| Asian/Oriental | 0 | 1 (1.9%) | 1 (0.9%) |
| Other | 0 | 0 | 0 |

TABLE 45-continued

Demographics and patient characteristics at baseline—Randomized sub-study population

| | HOE901-U300 Adaptable Dosing Intervals (N = 56) | HOE901-U300 Fixed Dosing Intervals (N = 54) | All (N = 110) |
|---|---|---|---|
| Ethnicity [n (%)] | | | |
| Number | 56 | 54 | 110 |
| Hispanic | 4 (7.1%) | 4 (7.4%) | 8 (7.3%) |
| Not Hispanic | 52 (92.9%) | 50 (92.6%) | 102 (92.7%) |
| World region [n (%)] | | | |
| Number | 56 | 54 | 110 |
| North America | 20 (35.7%) | 15 (27.8%) | 35 (31.8%) |
| Western Europe | 3 (5.4%) | 3 (5.6%) | 6 (5.5%) |
| Eastern Europe | 29 (51.8%) | 30 (55.6%) | 59 (53.6%) |
| Rest of the world | 4 (7.1%) | 6 (11.1%) | 10 (9.1%) |

Age is assessed at main study baseline.

TABLE 46

Baseline (month 6) efficacy data related to injection time—Randomized sub-study population

| | HOE901-U300 Adaptable Dosing Intervals (N = 56) | HOE901-U300 Fixed Dosing Intervals (N = 54) | All (N = 110) |
|---|---|---|---|
| Average injection time from previous injection (hours) | | | |
| Number | 56 | 53 | 109 |
| Mean (SD) | 24.05 (0.49) | 24.00 (0.10) | 24.02 (0.35) |
| Median | 24.00 | 24.00 | 24.00 |
| Q1:Q3 | 24.00:24.01 | 24.00:24.02 | 24.00:24.01 |
| Min:Max | 23.7:27.6 | 23.7:24.2 | 23.7:27.6 |
| Average injection time from reference injection (hours) | | | |
| Number | 56 | 53 | 109 |
| Mean (SD) | 24.03 (0.60) | 24.20 (0.63) | 24.11 (0.62) |
| Median | 24.00 | 24.00 | 24.00 |
| Q1:Q3 | 23.93:24.25 | 23.95:24.68 | 23.94:24.44 |
| Min:Max | 21.5:26.3 | 22.2:25.6 | 21.5:26.3 |

Average: mean interval value over at least 3 times intervals during the last 7 days preceding month 6.

2.1.3 Measurement of Treatment Compliance

TABLE 47

Compliance—Dosing regimen compliance during the 3-month comparative regimen period—Percentage of injections (time from previous injection) by dosing interval category—Safety sub-study population

| % of injections by patient | HOE901-U300 Adaptable Dosing Intervals (N = 56) | HOE901-U300 Fixed Dosing Intervals (N = 54) |
|---|---|---|
| <21.5 hours or >26.5 hours | | |
| Number | 55 | 52 |
| Mean (SD) | 23.02 (26.62) | 3.85 (10.97) |
| Median | 16.67 | 0.00 |
| Q1:Q3 | 0.00:36.36 | 0.00:0.00 |
| Min:Max | 0.0:100.0 | 0.0:46.2 |

TABLE 47-continued

Compliance—Dosing regimen compliance during the 3-month comparative regimen period—Percentage of injections (time from previous injection) by dosing interval category—Safety sub-study population

| % of injections by patient | HOE901-U300 Adaptable Dosing Intervals (N = 56) | HOE901-U300 Fixed Dosing Intervals (N = 54) |
|---|---|---|
| [23-25] hours | | |
| Number | 55 | 52 |
| Mean (SD) | 63.44 (26.60) | 87.96 (22.01) |
| Median | 66.67 | 100.00 |
| Q1:Q3 | 41.67:83.33 | 83.33:100.00 |
| Min:Max | 0.0:100.0 | 16.7:100.0 |
| [21.5-23[hours or]25-26.5] hours | | |
| Number | 55 | 52 |
| Mean (SD) | 13.54 (15.23) | 8.19 (16.11) |
| Median | 8.33 | 0.00 |

TABLE 47-continued

Compliance—Dosing regimen compliance during the 3-month comparative regimen period—Percentage of injections (time from previous injection) by dosing interval category—Safety sub-study population

| % of injections by patient | HOE901-U300 Adaptable Dosing Intervals (N = 56) | HOE901-U300 Fixed Dosing Intervals (N = 54) |
|---|---|---|
| Q1:Q3 | 0.00:25.00 | 0.00:8.71 |
| Min:Max | 0.0:58.3 | 0.0:66.7 |

Note:
Percentage of injections (time from previous injection) in each dosing interval category is calculated for each patient using all intervals obtained during the last 7 days values before Month 7.5 and Month 9 visits.

Note:
Only patients with at least 3 time intervals during the last 7 days values before Month 7.5 or Month 9 visits are considered for this table.

TABLE 48

Compliance—Number of patients for whom less than 20% of injections are outside the 23 to 25-hour time window from the previous injection time—Safety sub-study population

| | HOE901-U300 Adaptable Dosing Intervals (N = 56) | HOE901-U300 Fixed Dosing Intervals (N = 54) |
|---|---|---|
| Patients for whom less than 20% of injections are outside the 23 to 25-hour time window from the previous injection time | 19/55 (34.5%) | 41/52 (78.8%) |

Note:
Percentage of injections (time from previous injection) is calculated using all intervals obtained during the last 7 days values before Month 7.5 and Month 9 visits.
Note:
Only patients with at least 3 time intervals during the last 7 days values before Month 7.5 or Month 9 visits are considered for this table.

TABLE 49

Compliance—Dosing regimen compliance during the 3-month comparative regimen period—Percentage of injections (time from reference injection) by dosing interval category—Safety sub-study population

| % of injections by patient | HOE901-U300 Adaptable Dosing Intervals (N = 56) | HOE901-U300 Fixed Dosing Intervals (N = 54) |
|---|---|---|
| <21.5 hours or >26.5 hours | | |
| Number | 55 | 52 |
| Mean (SD) | 17.27 (19.25) | 0.82 (3.05) |
| Median | 14.29 | 0.00 |
| Q1:Q3 | 0.00:28.57 | 0.00:0.00 |
| Min:Max | 0.0:64.3 | 0.0:14.3 |
| [23-25] hours | | |
| Number | 55 | 52 |
| Mean (SD) | 64.96 (25.45) | 83.52 (25.22) |
| Median | 71.43 | 100.00 |
| Q1:Q3 | 50.00:85.71 | 75.65:100.00 |
| Min: Max | 0.0:100.0 | 0.0:100.0 |
| [21.5-23[hours or ]25-26.5] hours | | |
| Number | 55 | 52 |
| Mean (SD) | 17.77 (19.40) | 15.65 (24.67) |
| Median | 14.29 | 0.00 |
| Q1:Q3 | 0.00:28.57 | 0.00:21.43 |
| Min: Max | 0.0:78.6 | 0.0:100.0 |

Note:
Percentage of injections (time from reference injection chosen at the start of the main study) in each dosing interval category is calculated for each patient using all intervals obtained during the last 7 days values before Month 7.5 and Month 9 visits.
Note:
Only patients with at least 3 time intervals during the last 7 days values before Month 7.5 or Month 9 visits are considered for this table.

2.2 Efficacy Evaluation 2.2.1 Primary Efficacy Endpoint

TABLE 50

Main efficacy analysis-Mean change in HbA1c (%) from baseline (month 6) to Month 9 endpoint using LOCF procedure-mITT sub-study population

| HbA1c (%) | HOE901-U300 Adaptable Dosing Intervals (N = 55) | HOE901-U300 Fixed Dosing Intervals (N = 54) |
|---|---|---|
| Baseline (month 6) | | |
| Number | 55 | 52 |
| Mean (SD) | 7.21 (0.91) | 7.17 (0.88) |
| Median | 7.10 | 7.00 |
| Min:Max | 5.7:10.6 | 5.7:9.4 |
| Month 9 endpoint (LOCF) | | |
| Number | 55 | 52 |
| Mean (SD) | 7.25 (0.96) | 7.12 (0.96) |
| Median | 7.10 | 6.80 |
| Min:Max | 5.5:9.9 | 5.8:10.7 |
| Change from baseline to Month 9 endpoint (LOCF) | | |
| Number | 55 | 52 |
| Mean (SD) | 0.03 (0.56) | −0.05 (0.72) |
| Median | 0.00 | 0.00 |
| Min:Max | −1.4:1.4 | −2.8:1.8 |
| LS Mean (SE) [a] | 0.22 (0.111) | 0.14 (0.121) |
| 95% CI | (−0.006 to 0.436) | (−0.099 to 0.380) |
| LS Mean difference (SE) vs. HOE901-U300 Fixed | | |
| Dosing intervals [a] | 0.07 (0.123) | |
| 95% CI | (−0.169 to 0.318) | |

LOCF = Last observation carried forward.
[a] Analysis of covariance (ANCOVA) model with treatment regimen and country as fixed effects and baseline HbA1c value as a covariate.

The Mean HbA1c (%) by Visit During the 3-Month Comparative Regimen Period—mITT Sub-Study Population is Described in FIG. 9.

2.2.2 Secondary Endpoints
2.2.2.1 Fasting Plasma Glucose

TABLE 51

Mean change in FPG (mmol/L) from baseline (month 6) to Month 9 endpoint using LOCF procedure-mITT sub-study population

| FPG (mmol/L) | HOE901-U300 Adaptable Dosing Intervals (N = 55) | HOE901-U300 Fixed Dosing Intervals (N = 54) |
|---|---|---|
| Baseline (month 6) | | |
| Number | 54 | 51 |
| Mean (SD) | 7.33 (2.09) | 6.78 (2.58) |
| Median | 7.20 | 6.50 |
| Min:Max | 2.4:11.4 | 2.5:15.3 |
| Month 9 endpoint (LOCF) | | |
| Number | 54 | 51 |
| Mean (SD) | 7.61 (2.38) | 7.07 (3.06) |
| Median | 7.25 | 6.60 |
| Min:Max | 3.7:14.0 | 3.0:20.6 |
| Change from baseline to Month 9 endpoint (LOCF) | | |
| Number | 54 | 51 |
| Mean (SD) | 0.28 (2.46) | 0.29 (2.31) |
| Median | 0.45 | 0.20 |
| Min:Max | −5.0:7.7 | −5.8:9.1 |
| LS Mean (SE) [a] | 1.40 (0.391) | 1.18 (0.419) |
| 95% CI | (0.624 to 2.177) | (0.350 to 2.015) |
| LS Mean difference (SE) vs. HOE901-U300 Fixed | | |
| Dosing Intervals [a] | 0.22 (0.429) | |
| 95% CI | (−0.634 to 1.070) | |

FPG = Fasting Plasma Glucose.
LOCF = Last observation carried forward.
[a] Analysis of covariance (ANCOVA) model with treatment regimen and country as fixed effects and baseline FPG value as a covariate.

2.2.2.2 Basal and Mealtime Insulin Dose

The Average Daily Basal (Glargine) and Mealtime Insulin Dose (U) by Visit During the 3-Month Comparative Regimen Period—mITT Sub-Study Population is Described in FIG. 10.

2.3 Safety Evaluation
2.3.1 Extent of Exposure

TABLE 52

Exposure to investigational product during the 3-month comparative regimen period-Safety sub-study population

| | HOE901-U300 Adaptable Dosing Intervals (N = 56) | HOE901-U300 Fixed Dosing Intervals (N = 54) |
|---|---|---|
| Cumulative exposure to the sub-study 3-month treatment (patient years) | 13.82 | 13.38 |
| Duration of the sub-study 3-month treatment (days) | | |
| Number | 55 | 53 |
| Mean (SD) | 91.8 (4.9) | 92.2 (6.2) |
| Median | 92.0 | 92.0 |
| Min:Max | 77:112 | 83:126 |
| Duration of the sub-study 3-month treatment by category [n(%)] | | |
| Missing duration | 1 (1.8%) | 1 (1.9%) |
| up to 6 weeks | 0 | 0 |
| >6 to 12 weeks | 2 (3.6%) | 3 (5.6%) |
| >12 weeks | 53 (94.6%) | 50 (92.6%) |

TABLE 52-continued

Exposure to investigational product during the 3-month comparative regimen period-Safety sub-study population

|  | HOE901-U300 Adaptable Dosing Intervals (N = 56) | HOE901-U300 Fixed Dosing Intervals (N = 54) |
|---|---|---|
| Cumulative duration of the sub-study 3-month treatment by category [n(%)] | | |
| Missing duration | 1 (1.8%) | 1 (1.9%) |
| ≥1 days | 55 (98.2%) | 53 (98.1%) |
| >6 weeks | 55 (98.2%) | 53 (98.1%) |
| >12 weeks | 53 (94.6%) | 50 (92.6%) |

2.3.2 Hypoglycemia

TABLE 53

Number (%) of patients with at least one hypoglycemia event during the 3-month comparative regimen period-Safety sub-study population

| | All hypoglycemia | | Nocturnal hypoglycemia (00:00-05:59) | |
|---|---|---|---|---|
| Type of hypoglycemia event n(%) | HOE901-U300 Adaptable Dosing Intervals (N = 56) | HOE901-U300 Fixed Dosing Intervals (N = 54) | HOE901-U300 Adaptable Dosing Intervals (N = 56) | HOE901-U300 Fixed Dosing Intervals (N = 54) |
| Any hypoglycemia event | 32 (57.1%) | 36 (66.7%) | 15 (26.8%) | 13 (24.1%) |
| Severe hypoglycemia | 0 | 1 (1.9%) | 0 | 1 (1.9%) |
| Documented symptomatic hypoglycemia | | | | |
| ≤3.9 mmol/L (70 mg/dL) | 18 (32.1%) | 23 (42.6%) | 11 (19.6%) | 9 (16.7%) |
| <3.0 mmol/L (54 mg/dL) | 11 (19.6%) | 12 (22.2%) | 3 (5.4%) | 6 (11.1%) |
| Asymptomatic hypoglycemia | | | | |
| ≤3.9 mmol/L (70 mg/dL) | 22 (39.3%) | 24 (44.4%) | 3 (5.4%) | 6 (11.1%) |
| <3.0 mmol/L (54 mg/dL) | 2 (3.6%) | 6 (11.1%) | 1 (1.8%) | 1 (1.9%) |
| Probable symptomatic hypoglycemia | 1 (1.8%) | 0 | 0 | 0 |
| Relative hypoglycemia | | | | |
| >3.9 mmol/L (70 mg/dL) | 3 (5.4%) | 0 | 1 (1.8%) | 0 |
| Severe and/or confirmed[a] hypoglycemia | | | | |
| ≤3.9 mmol/L (70 mg/dL) | 31 (55.4%) | 36 (66.7%) | 14 (25.0%) | 13 (24.1%) |
| <3.0 mmol/L (54 mg/dL) | 13 (23.2%) | 16 (29.6%) | 4 (7.1%) | 8 (14.8%) | n (%) = number and percentage of patients with at least one hypoglycemia event.
[a]Severe and/or confirmed hypoglycemia = severe and/or confirmed by plasma glucose <= 3.9 mmol/L (70 mg/dL) (resp. <3.0 mmol/L (54 mg/dL)).
Note:
All hypoglycemia events with missing time are counted in the column "All hypoglycemia", but not classified as "nocturnal" or "daytime".)

2.3.3 Treatment-Emergent Adverse Events

TABLE 54

Treatment emergent adverse events during the 3-month comparative regimen period-Safety sub-study population

| n (%) | HOE901-U300 Adaptable Dosing Intervals (N = 56) | HOE901-U300 Fixed Dosing Intervals (N = 54) |
|---|---|---|
| Patients with any TEAE | 15 (26.8%) | 15 (27.8%) |
| Patients with any treatment emergent SAE | 4 (7.1%) | 5 (9.3%) |

TABLE 54-continued

Treatment emergent adverse events during the 3-month comparative regimen period-Safety sub-study population

| n (%) | HOE901-U300 Adaptable Dosing Intervals (N = 56) | HOE901-U300 Fixed Dosing Intervals (N = 54) |
|---|---|---|
| Patients with any TEAE leading to death | 0 | 0 |
| Patients with any TEAE leading to permanent treatment discontinuation | 0 | 0 |

TEAE: Treatment emergent adverse event, SAE: Serious Adverse Event.
n (%) = number and percentage of patients with at least one TEAE.

TABLE 55

Number (%) of patients with TEAE(s) by primary SOC, HLGT, HLT and PT events during the 3-month comparative regimen period-Safety sub-study population

| PRIMARY SYSTEM ORGAN CLASS<br>HLGT: High Level Group Term<br>HLT: High Level Term<br>Preferred Term n(%) | HOE901-U300 Adaptable Dosing Intervals (N = 56) | HOE901-U300 Fixed Dosing Intervals (N = 54) |
|---|---|---|
| Any class | 15 (26.8%) | 15 (27.8%) |
| INFECTIONS AND INFESTATIONS | 7 (12.5%) | 4 (7.4%) |
| HLGT: Bacterial infectious disorders | 2 (3.6%) | 0 |
| HLT: Bacterial infections NEC | 1 (1.8%) | 0 |
| Conjunctivitis bacterial | 1 (1.8%) | 0 |
| HLT: Staphylococcal infections | 1 (1.8%) | 0 |
| Staphylococcal infection | 1 (1.8%) | 0 |
| HLGT: Infections-pathogen unspecified | 6 (10.7%) | 3 (5.6%) |
| HLT: Abdominal and gastrointestinal infections | 0 | 1 (1.9%) |
| Gastroenteritis | 0 | 1 (1.9%) |
| HLT: Bone and joint infections | 1 (1.8%) | 0 |
| Osteomyelitis | 1 (1.8%) | 0 |
| HLT: Infections NEC | 2 (3.6%) | 0 |
| Localised infection | 1 (1.8%) | 0 |
| Postoperative wound infection | 1 (1.8%) | 0 |
| HLT: Lower respiratory tract and lung infections | 1 (1.8%) | 0 |
| Bronchitis | 1 (1.8%) | 0 |
| HLT: Upper respiratory tract infections | 2 (3.6%) | 2 (3.7%) |
| Nasopharyngitis | 2 (3.6%) | 1 (1.9%) |
| Upper respiratory tract infection | 0 | 1 (1.9%) |
| HLGT: Viral infectious disorders | 1 (1.8%) | 1 (1.9%) |
| HLT: Influenza viral infections | 1 (1.8%) | 0 |
| Influenza | 1 (1.8%) | 0 |
| HLT: Viral infections NEC | 0 | 1 (1.9%) |
| Gastroenteritis viral | 0 | 1 (1.9%) |
| NEOPLASMS BENIGN, MALIGNANT AND UNSPECIFIED (INCL CYSTS AND POLYPS) | 0 | 1 (1.9%) |
| HLGT: Reproductive neoplasms female benign | 0 | 1 (1.9%) |
| HLT: Uterine neoplasms benign | 0 | 1 (1.9%) |
| Uterine leiomyoma | 0 | 1 (1.9%) |
| HLGT: Reproductive neoplasms female malignant and unspecified | 0 | 1(1.9%) |
| HLT: Endometrial neoplasms malignant | 0 | 1 (1.9%) |
| Endometrial cancer | 0 | 1(1.9%) |
| METABOLISM AND NUTRITION DISORDERS | 1 (1.8%) | 0 |
| HLGT: Glucose metabolism disorders (incl diabetes mellitus) | 1 (1.8%) | 0 |
| HLT: Hyperglycaemic conditions NEC | 1 (1.8%) | 0 |
| Hyperglycaemia | 1 (1.8%) | 0 |
| NERVOUS SYSTEM DISORDERS | 1 (1.8%) | 1 (1.9%) |
| HLGT: Headaches | 1 (1.8%) | 0 |
| HLT: Headaches NEC | 1 (1.8%) | 0 |
| Headache | 1 (1.8%) | 0 |
| HLGT: Neurological disorders NEC | 1 (1.8%) | 1 (1.9%) |
| HLT: Nervous system disorders NEC | 1 (1.8%) | 0 |
| Nervous system disorder | 1 (1.8%) | 0 |
| HLT: Neurological signs and symptoms NEC | 1 (1.8%) | 1 (1.9%) |
| Dizziness | 1 (1.8%) | 1 (1.9%) |
| EYE DISORDERS | 0 | 1 (1.9%) |
| HLGT: Ocular infections, irritations and inflammations | 0 | 1 (1.9%) |
| HLT: Lid, lash and lacrimal infections, irritations and inflammations | 0 | 1 (1.9%) |
| Eyelid cyst | 0 | 1 (1.9%) |

TABLE 55-continued

Number (%) of patients with TEAE(s) by primary SOC, HLGT, HLT and PT events during the 3-month comparative regimen period-Safety sub-study population

| PRIMARY SYSTEM ORGAN CLASS<br>HLGT: High Level Group Term<br>HLT: High Level Term<br>Preferred Term n(%) | HOE901-U300 Adaptable<br>Dosing Intervals<br>(N = 56) | HOE901-U300 Fixed<br>Dosing Intervals<br>(N = 54) |
|---|---|---|
| CARDIAC DISORDERS | 2 (3.6%) | 0 |
| HLGT: Cardiac disorder signs and symptoms | 1 (1.8%) | 0 |
| HLT: Cardiac signs and symptoms NEC | 1 (1.8%) | 0 |
| Palpitations | 1 (1.8%) | 0 |
| HLGT: Coronary artery disorders | 2 (3.6%) | 0 |
| HLT: Coronary artery disorders NEC | 1 (1.8%) | 0 |
| Coronary artery disease | 1 (1.8%) | 0 |
| HLT: Ischaemic coronary artery disorders | 1 (1.8%) | 0 |
| Angina pectoris | 1 (1.8%) | 0 |
| RESPIRATORY, THORACIC AND MEDIASTINAL DISORDERS | 3 (5.4%) | 2 (3.7%) |
| HLGT: Bronchial disorders (excl neoplasms) | 0 | 1 (1.9%) |
| HLT: Bronchospasm and obstruction | 0 | 1 (1.9%) |
| Asthma | 0 | 1 (1.9%) |
| HLGT: Respiratory disorders NEC | 3 (5.4%) | 0 |
| HLT: Breathing abnormalities | 1 (1.8%) | 0 |
| Sleep apnoea syndrome | 1 (1.8%) | 0 |
| HLT: Coughing and associated symptoms | 2 (3.6%) | 0 |
| Cough | 2 (3.6%) | 0 |
| HLT: Upper respiratory tract signs and symptoms | 1 (1.8%) | 0 |
| Oropharyngeal pain | 1 (1.8%) | 0 |
| HLGT: Upper respiratory tract disorders (excl infections) | 0 | 1 (1.9%) |
| HLT: Nasal congestion and inflammations | 0 | 1 (1.9%) |
| Nasal congestion | 0 | 1 (1.9%) |
| GASTROINTESTINAL DISORDERS | 3 (5.4%) | 3 (5.6%) |
| HLGT: Benign neoplasms gastrointestinal | 1 (1.8%) | 0 |
| HLT: Benign neoplasms gastrointestinal (excl oral cavity) | 1 (1.8%) | 0 |
| Large intestine polyp | 1 (1.8%) | 0 |
| HLGT: Gastrointestinal motility and defaecation conditions | 0 | 3 (5.6%) |
| HLT: Diarrhoea (excl infective) | 0 | 3 (5.6%) |
| Diarrhoea | 0 | 3 (5.6%) |
| HLGT: Gastrointestinal signs and symptoms | 2 (3.6%) | 0 |
| HLT: Nausea and vomiting symptoms | 2 (3.6%) | 0 |
| Nausea | 1 (1.8%) | 0 |
| Vomiting | 1 (1.8%) | 0 |
| HEPATOBILIARY DISORDERS | 0 | 1 (1.9%) |
| HLGT: Bile duct disorders | 0 | 1 (1.9%) |
| HLT: Obstructive bile duct disorders (excl neoplasms) | 0 | 1 (1.9%) |
| Bile duct stone | 0 | 1 (1.9%) |
| MUSCULOSKELETAL AND CONNECTIVE TISSUE DISORDERS | 4 (7.1%) | 3 (5.6%) |
| HLGT: Joint disorders | 2 (3.6%) | 1 (1.9%) |
| HLT: Osteoarthropathies | 2 (3.6%) | 0 |
| Osteoarthritis | 1 (1.8%) | 0 |
| Spinal osteoarthritis | 1 (1.8%) | 0 |
| HLT: Spondyloarthropathies | 0 | 1 (1.9%) |
| Spondylitis | 0 | 1 (1.9%) |
| HLGT: Musculoskeletal and connective tissue deformities (incl intervertebral disc disorders) | 0 | 1 (1.9%) |
| HLT: Intervertebral disc disorders NEC | 0 | 1 (1.9%) |
| Intervertebral disc protrusion | 0 | 1 (1.9%) |
| HLGT: Musculoskeletal and connective tissue disorders NEC | 2 (3.6%) | 0 |
| HLT: Musculoskeletal and connective tissue pain and discomfort | 2 (3.6%) | 0 |
| Musculoskeletal pain | 1 (1.8%) | 0 |
| Pain in extremity | 1 (1.8%) | 0 |
| HLGT: Synovial and bursal disorders | 0 | 1 (1.9%) |
| HLT: Synovial disorders | 0 | 1 (1.9%) |
| Synovial cyst | 0 | 1 (1.9%) |
| REPRODUCTIVE SYSTEM AND BREAST DISORDERS | 0 | 1 (1.9%) |
| HLGT: Menopause and related conditions | 0 | 1 (1.9%) |
| HLT: Menopausal effects on the genitourinary tract | 0 | 1 (1.9%) |
| Postmenopausal haemorrhage | 0 | 1 (1.9%) |
| GENERAL DISORDERS AND ADMINISTRATION SITE CONDITIONS | 1 (1.8%) | 0 |

TABLE 55-continued

Number (%) of patients with TEAE(s) by primary SOC, HLGT, HLT and PT events during the 3-month comparative regimen period-Safety sub-study population

| PRIMARY SYSTEM ORGAN CLASS<br>HLGT: High Level Group Term<br>HLT: High Level Term<br>Preferred Term n(%) | HOE901-U300 Adaptable<br>Dosing Intervals<br>(N = 56) | HOE901-U300 Fixed<br>Dosing Intervals<br>(N = 54) |
|---|---|---|
| HLGT: General system disorders NEC | 1 (1.8%) | 0 |
| HLT: Oedema NEC | 1 (1.8%) | 0 |
| Oedema peripheral | 1 (1.8%) | 0 |
| INVESTIGATIONS | 0 | 1 (1.9%) |
| HLGT: Renal and urinary tract investigations and urinalyses | 0 | 1 (1.9%) |
| HLT: Renal function analyses | 0 | 1 (1.9%) |
| Blood creatinine increased | 0 | 1 (1.9%) |
| INJURY, POISONING AND PROCEDURAL COMPLICATIONS | 3 (5.4%) | 3 (5.6%) |
| HLGT: Bone and joint injuries | 0 | 1 (1.9%) |
| HLT: Upper limb fractures and dislocations | 0 | 1 (1.9%) |
| Humerus fracture | 0 | 1 (1.9%) |
| HLGT: Exposures, chemical injuries and poisoning | 0 | 1 (1.9%) |
| HLT: Poisoning and toxicity | 0 | 1 (1.9%) |
| Toxicity to various agents | 0 | 1 (1.9%) |
| HLGT: Injuries NEC | 1 (1.8%) | 0 |
| HLT: Muscle, tendon and ligament injuries | 1 (1.8%) | 0 |
| Ligament sprain | 1 (1.8%) | 0 |
| HLGT: Procedural related injuries and complications NEC | 2 (3.6%) | 1 (1.9%) |
| HLT: Gastrointestinal and hepatobiliary procedural complications | 0 | 1 (1.9%) |
| Abdominal wound dehiscence | 0 | 1 (1.9%) |
| HLT: Non-site specific procedural complications | 2 (3.6%) | 0 |
| Procedural pain | 2 (3.6%) | 0 |

TEAE: Treatment emergent adverse event, SOC: System organ class, HLGT: High level group term, HLT: High level term, PT: Preferred term.
MedDRA 16.0.
n(%) = number and percentage of patients with at least one TEAE.
Note:
Table sorted by SOC internationally agreed order and HLGT, HLT, PT by alphabetic order.

2.3.4 Serious Treatment-Emergent Adverse Events

TABLE 56

Number (%) of patients with treatment emergent SAE(s) by Primary SOC, HLGT, HLT and PT during the 3-month comparative regimen period-Safety sub-study population

| PRIMARY SYSTEM ORGAN CLASS<br>HLGT: High Level Group Term<br>HLT: High Level Term<br>Preferred Term n(%) | HOE901-U300 Adaptable<br>Dosing Intervals<br>(N = 56) | HOE901-U300 Fixed<br>Dosing Intervals<br>(N = 54) |
|---|---|---|
| Any class | 4 (7.1%) | 5 (9.3%) |
| INFECTIONS AND INFESTATIONS | 2 (3.6%) | 0 |
| HLGT: Infections-pathogen unspecified | 2 (3.6%) | 0 |
| HLT: Bone and joint infections | 1 (1.8%) | 0 |
| Osteomyelitis | 1 (1.8%) | 0 |
| HLT: Infections NEC | 1 (1.8%) | 0 |
| Postoperative wound infection | 1 (1.8%) | 0 |
| NEOPLASMS BENIGN, MALIGNANT AND UNSPECIFIED (INCL CYSTS AND POLYPS) | 0 | 1 (1.9%) |
| HLGT: Reproductive neoplasms female benign | 0 | 1 (1.9%) |
| HLT: Uterine neoplasms benign | 0 | 1 (1.9%) |
| Uterine leiomyoma | 0 | 1 (1.9%) |
| HLGT: Reproductive neoplasms female malignant and unspecified | 0 | 1 (1.9%) |
| HLT: Endometrial neoplasms malignant | 0 | 1 (1.9%) |
| Endometrial cancer | 0 | 1 (1.9%) |
| CARDIAC DISORDERS | 1 (1.8%) | 0 |
| HLGT: Coronary artery disorders | 1 (1.8%) | 0 |

TABLE 56-continued

Number (%) of patients with treatment emergent SAE(s) by Primary SOC, HLGT, HLT and PT during the 3-month comparative regimen period-Safety sub-study population

| PRIMARY SYSTEM ORGAN CLASS<br>HLGT: High Level Group Term<br>HLT: High Level Term<br>Preferred Term n(%) | HOE901-U300 Adaptable<br>Dosing Intervals<br>(N = 56) | HOE901-U300 Fixed<br>Dosing Intervals<br>(N = 54) |
|---|---|---|
| HLT: Coronary artery disorders NEC | 1 (1.8%) | 0 |
| Coronary artery disease | 1 (1.8%) | 0 |
| RESPIRATORY, THORACIC AND MEDIASTINAL DISORDERS | 0 | 1 (1.9%) |
| HLGT: Bronchial disorders (excl neoplasms) | 0 | 1 (1.9%) |
| HLT: Bronchospasm and obstruction | 0 | 1 (1.9%) |
| Asthma | 0 | 1 (1.9%) |
| HEPATOBILIARY DISORDERS | 0 | 1 (1.9%) |
| HLGT: Bile duct disorders | 0 | 1 (1.9%) |
| HLT: Obstructive bile duct disorders (excl neoplasms) | 0 | 1 (1.9%) |
| Bile duct stone | 0 | 1 (1.9%) |
| MUSCULOSKELETAL AND CONNECTIVE TISSUE DISORDERS | 0 | 2 (3.7%) |
| HLGT: Joint disorders | 0 | 1 (1.9%) |
| HLT: Spondyloarthropathies | 0 | 1 (1.9%) |
| Spondylitis | 0 | 1 (1.9%) |
| HLGT: Synovial and bursal disorders | 0 | 1 (1.9%) |
| HLT: Synovial disorders | 0 | 1 (1.9%) |
| Synovial cyst | 0 | 1 (1.9%) |
| REPRODUCTIVE SYSTEM AND BREAST DISORDERS | 0 | 1 (1.9%) |
| HLGT: Menopause and related conditions | 0 | 1 (1.9%) |
| HLT: Menopausal effects on the genitourinary tract | 0 | 1 (1.9%) |
| Postmenopausal haemorrhage | 0 | 1 (1.9%) |
| INJURY, POISONING AND PROCEDURAL COMPLICATIONS | 1 (1.8%) | 2 (3.7%) |
| HLGT: Bone and joint injuries | 0 | 1 (1.9%) |
| HLT: Upper limb fractures and dislocations | 0 | 1 (1.9%) |
| Humerus fracture | 0 | 1 (1.9%) |
| HLGT: Procedural related injuries and complications NEC | 1 (1.8%) | 1 (1.9%) |
| HLT: Gastrointestinal and hepatobillary procedural complications | 0 | 1 (1.9%) |
| Abdominal wound dehiscence | 0 | 1 (1.9%) |
| HLT: Non-site specific procedural complications | 1 (1.8%) | 0 |
| Procedural pain | 1 (1.8%) | 0 |

TEAE: Treatment emergent adverse event, SOC: System organ class, HLGT: High level group term, HLT: High level term, PT: Preferred term.
MedDRA 16.0.
n (%) = number and percentage of patients with at least one treatment emergent SAE.
Note:
Table sorted by SOC internationally agreed order and HLGT, HLT, PT by alphabetic order.

2.3.5 Treatment Emergent Adverse Events Leading to Withdrawal

TABLE 57

Number (%) of patients with TEAE(s) leading to permanent treatment discontinuation by Primary SOC, HLGT, HLT and PT during the 3-month comparative regimen period-Safety sub-study population No data TEAE: Treatment emergent adverse event, SOC: System organ class, HLGT: High level group term, HLT: High level term, PT: Preferred team
MedDRA 16.0.
n (%) = number and percentage of patients with at least one TEAE leading to permanent treatment discontinuation.
Note:
Table sorted by SOC internationally agreed order and HLGT, HLT, PT by alphabetic order.

2.3.6 Other Significant Treatment Emergent Adverse Events

2.3.6.1 Injection Site Reactions

TABLE 58

Number (%) of patients experiencing at least one TEAE by relevant Standardized MedDRA Queries and Preferred Term-Injection site reactions during the 3-month comparative regimen period-Safety sub-study population No data TEAE: Treatment emergent adverse event, PT: Preferred term.
MedDRA 16.0
n (%) = number and percentage of patients with at least one injection site reactions TEAE.
Note:
Table sorted by decreasing frequency of PT in HOE901-U300 adaptable dosing intervals regimen.

2.3.6.2 Hypersensitivity Reactions

TABLE 59

Number (%) of patients experiencing at least one TEAE by relevant Standardized MedDRA Queries and Preferred Term-Hypersensitivity reactions during the 3-month comparative regimen period-Safety sub-study population

| Preferred Term | HOE901-U300 Adaptable Dosing Intervals (N = 56) | HOE901-U300 Fixed Dosing Intervals (N = 54) |
|---|---|---|
| Any hypersensitivity reactions | 0 | 1 (1.9%) |
| Asthma | 0 | 1 (1.9%) |

TEAE: Treatment emergent adverse event, PT: Preferred term.
MedDRA 16.0
n (%) = number and percentage of patients with at least one hypersensitivity reactions TEAE.
Note:
Table sorted by decreasing frequency of PT in HOE901-U300 adaptable dosing intervals regimen.

EXAMPLE 4: 16-WEEK, RANDOMIZED, OPEN-LABEL, CONTROLLED STUDY COMPARING THE EFFICACY AND SAFETY OF A NEW FORMULATION OF INSULIN GLARGINE VERSUS LANTUS IN PATIENTS WITH TYPE 1 DIABETES MELLITUS

Phase of Development:

2

Objectives:

Primary objective: To compare the glucose control during treatment with a new formulation of insulin glargine (HOE901-U300) and Lantus in adult patients with type 1 diabetes mellitus.

Secondary objectives:

To compare HOE901-U300 and Lantus given in the morning or in the evening regarding the continuous glucose monitoring (CGM) data: diurnal glucose exposure; diurnal glucose stability as measured by rate of change in median curve; diurnal glucose variability as measured by interquartile range (IQR); mean and variation in glucose profiles To compare HOE901-U300 and Lantus regarding glycated hemoglobin A1c (HbA1c), self-measured plasma glucose (fasting plasma glucose, prior to injection of study drug, 7-point profiles)

To compare the incidence and frequency of hypoglycemic episodes classified as defined by ADA criteria, both symptomatic, confirmed by plasma glucose £70 mg/dL and CGM-detected To assess the safety and tolerability of HOE901-U300

Methodology:

Multicenter, open-label, randomized, 4-arm parallel-group, comparative Phase 2 study comparing HOE901-U300 and Lantus in patients with type 1 diabetes mellitus. Patients were randomized to receive once daily basal insulin (HOE901-U300 or Lantus) and to the sequence of the injection time during study period A and study period B (morning then evening or evening then morning) with a ratio of 1:1:1:1. No formal sample size estimation was performed for this exploratory study.

Number of Patients:

planned 56, randomized 59, treated 59, Evaluated: efficacy 59, safety 59

Diagnosis and Criteria for Inclusion:

Inclusion criteria: Patients with type 1 diabetes mellitus; signed written informed consent. Key exclusion criteria: Age <18 years and >70 years; HbA1c >9% at screening; less than 1 year on basal plus mealtime insulin; Patients receiving >0.5 U/kg body weight basal insulin and patients not on stable insulin dose (±20% total basal insulin dose) in the last 30 days prior to screening visit; Hospitalization for diabetic ketoacidosis or history of severe hypoglycemia (requiring 3rd party assistance) in the last 6 months prior to randomization.

Study Treatments

Investigational Medicinal Products:

Tested drug: HOE901-U300; Control drug: Lantus

Formulations: HOE901-U300 was supplied as 300 U/mL insulin glargine solution for subcutaneous (SC) injection in 3 mL cartridges. Lantus was supplied as insulin glargine solution for SC injection 100 U/mL in 10 mL vials.

Route of administration: SC injection

Injection of HOE901-U300 was through the commercially available BD Ultra-Fine™ Short Needle Insulin Syringe with half-unit-scale. Injection of Lantus was to be done using commercially available BD insulin syringes:

for doses of 1-30 U insulin glargine: BD Ultra-Fine™ Short Needle Insulin Syringe with half-unit-scale [8 mm (5/16")×31 G];

for doses >30 U insulin glargine: BD Ultra-Fine™ Short Needle Insulin Syringe [8 mm (5/16")×31 G] with whole unit scale.

Dose regimen: Once daily injection in the morning or evening for 8 weeks during Period A then in the evening or morning respectively for another 8 weeks during Period B according to randomization.

Starting dose: Patients on Lantus or on once daily NPH or once daily insulin detemir prior to the baseline visit: the daily dose (U) of HOE901-U300 or Lantus was equal to the daily basal insulin doses on the day prior to the baseline visit. Patients on more than once daily NPH or insulin detemir prior to the baseline visit: 80% of total daily NPH or insulin detemir dose (=total daily dose reduced by 20%) on the day prior to the baseline visit.

Doses during the study: Dosing of insulin glargine given as HOE901-U300 or Lantus was done based on self-measured, fasting, pre breakfast plasma glucose levels (target range 80-130 mg/dL; 4.4-7.2 mmol/L), and taking into account also the presence of hypoglycemia. Minimum dose increments for the basal insulin were to be 1.5 U. Batch number: HOE901—U300: C1011129; Lantus: supplied by local pharmacies.

Non-Investigational Medicinal Products:

Short-acting mealtime (bolus) insulin analogue (glulisine, aspart or lispro).

Patients in both treatment groups were to continue with their mealtime insulin analogue during the study.

Mealtime insulin doses were to be adjusted based on SMPG data, including 2-hour postprandial plasma glucose results and the carbohydrate content of the meal to optimize glycemic control. The target range for 2-hour postprandial plasma glucose was <160 mg/dL (8.3 mmol/L). Bolus insulin doses could be reduced as basal insulin doses were increased.

Duration of Treatment:

Up to 16 weeks (8 weeks during Period A and 8 weeks during Period B)

Duration of Observation:

Up to 4-week screening (including a 2-week CGM training period);

2×8-week comparative efficacy and safety treatment period;

4 week post-treatment safety follow-up period after study completion or permanent discontinuation of study treatment.

In total the maximum study duration was up to 24 weeks per patient

Criteria for Evaluation:

Efficacy

Primary Efficacy Endpoint:

Percent (%) of time in glycemic range of 80-140 mg/dL (4.4-7.8 mmol/L) during week 7 and 8 within treatment period A and during week 15 and 16 in treatment period B based on CGM.

Secondary Efficacy Endpoints:

Percent time above upper limit/below lower limit of glycemic range (% time in hyperglycemia/hypoglycemia).

The following secondary efficacy endpoints are not presented in this KRM: Diurnal glucose exposure; Diurnal glucose stability; Diurnal glucose variability; Mean and variation in glucose profiles; Average time within glycemic range in the last four hours of each dosing interval during 14 days of CGM usage in the last 2 weeks of the 8 weeks treatment period; Hyperglycemic AUC (Area below the CGM profile and above the upper limit of the glycemic range divided by total time period); and hypoglycemic AUC (Area above the CGM profile and below the lower limit of the glycemic range divided by total time period.

Further Secondary Efficacy Endpoints:

insulin dose; Not presented in this KRM: $HbA_{1c}$, fasting plasma glucose (FPG), pre-injection SMPG, 7-point SMPG.

Safety

Hypoglycemia, occurrence of adverse events particularly treatment emergent adverse events (TEAEs) and serious adverse events (SAEs), injection site reactions and hypersensitivity reactions. Following information not presented in KRM: physical examination, other safety information including clinical laboratory data, vital signs and 12-lead ECG.

Statistical Methods:

The primary endpoint was analyzed using a linear mixed model with treatment (HOE901-U300 or Lantus) and period (treatment period A or B) as fixed effects, and patient as random effect. Adjusted mean estimates for each treatment with standard errors, the adjusted estimate of treatment mean difference with standard error and a 95 confidence interval for the treatment mean difference will be provided. The statistical test was two-sided tests at a nominal 5% significance level. The same model was used for secondary efficacy endpoints % time in hyperglycemia/hypoglycemia, diurnal glucose exposure, diurnal glucose stability and diurnal glucose variability. Other efficacy endpoints were descriptive. CGM related parameters were analyzed based on CGM population, non-CGM parameters were based on mITT population.

Safety analyses were descriptive, based on the safety population.

Summary:

Population Characteristics:

A total of 59 patients with type 1 diabetes were randomized to 1 of 4 arms: HOE901-U300 morning injection in Period A followed by evening injection in Period B (n=15), HOE901-U300 evening then morning injection (n=15), Lantus morning then evening injection (n=15), or Lantus evening then morning injection (n=14). A total of 59 patients were exposed to IMP (safety population) and included in the mITT and CGM populations (efficacy populations). One patient (3.3%) in the HOE901-U300 group and 3 patients (10.3%) in the Lantus group discontinued the study treatment prematurely. Demographics and baseline characteristics were balanced between treatment groups. The mean age of the study population was 44.2 years, 2 patients were 65 years or older. All patients were Caucasian. The mean BMI at baseline was 27.3 kg/m². The mean duration of diabetes prior to study start was 22.1 years. The median dose of daily total insulin was 0.565 U/kg body weight. Mean $HbA_{1c}$ at baseline was 7.46%.

Efficacy Results:

Primary Efficacy Endpoint:

During the last 2 weeks of each 8-week treatment period, when the basal insulin dose was to be kept as stable as possible, plasma glucose measured by CGM was observed within glycemic range in 31.75% (LS mean) of time in the HOE901-U300 group and in 30.99% (LS mean) of time in the Lantus group. The LS mean difference was 0.75% [95% CI: −3.614 to 5.124].

Secondary Efficacy Endpoints:

During the last 2 weeks of each 8-week treatment period, percent time above the upper limit of glycemic range of 140 mg/dL (7.8 mmol/L) was comparable between treatment groups (58.24% in the HOE901-U300 group and 57.38% in the Lantus group in LS mean), so was the percent of time below the lower limit of 80 mg/dL (4.4 mmol/L) with 10.01% in the HOE901-U300 group and 11.64% in the Lantus group in LS mean.

Graphical presentation of average glucose based on CGM by hour of the day during the entire treatment period (FIG. 11) suggests smaller excursions in the HOE901-U300 group than in the Lantus group. The profile appears flatter with HOE901-U300 than with Lantus even more during morning injection period (FIG. 12) than during evening injection period (FIG. 13).

Overall, in the HOE901-U300 and in the Lantus treatment groups, basal insulin was similarly increased mostly in the first 6 weeks of the study and remained relatively stable thereafter (at baseline, mean daily basal insulin dose was similar in both treatment groups: HOE901-U300: 24.9 units; Lantus: 25.0 units; at week 16, HOE901-U300: 30.11 units; Lantus: 28.22 units).

Mean mealtime insulin daily dose was higher at baseline in the HOE901-U300 group (29.92 units) than in the Lantus group (23.69 units), but was comparable at week 16 (HOE901-U300: 27.34 units; Lantus: 26.31 units).

Safety Results:

During the on-treatment period, the percentages of patients experiencing hypoglycemia were generally comparable for overall and each category of hypoglycemia events (all hypoglycemia) in the HOE901-U300 group and the Lantus group. Consistently, similarity was observed in the hypoglycemia reporting between the following subgroups:

the morning and evening injection groups within the HOE901-U300 group;

the morning and evening injection groups within the Lantus group;

the HOE901-U300 morning injection groups and the Lantus morning injection groups;

the HOE901-U300 evening injection groups and the Lantus evening injection groups;

The percentages of patients experiencing nocturnal hypoglycemia were consistently lower in the HOE901-U300 group than in the Lantus group regardless of morning or evening injection time. The favorable numerical trends in the HOE901-U300 group have to be interpreted with caution because of the small number of patients.

The percentage of patients with any TEAEs was higher in the HOE901-U300 group (24/30 [80.0%]) than in the Lantus group (19/29 [65.5%]). In the HOE901-U300 group, one patient experienced serious intestinal obstruction (unrelated to IMP) and another patient discontinued treatment due to pregnancy. No death was reported during the study. TEAEs linked to injection site reactions were observed in 2/30 [6.7%] patients of the HOE901-U300 group, and in 1/29 [3.4%] patient of the Lantus group. There is no concern regardingTEAEs linked to hypersensitivity reaction which occurred in 4/40 patients of the HOE901-U300 group and in 1/30 patient of the Lantus group.

Conclusions:

Plasma glucose measured by CGM was observed within glycemic target range (80-140 mg/dL or 4.4-7.8 mmol/L) for a similar percentage of time during the last 2 weeks of each 8-week treatment period in the HOE901-U300 group and in the Lantus group. Notably, this target range was tighter as compared with the ADA recommendation of 70-180 mg/dL (3.9-10.0 mmol/L).

In both treatment groups, the percent time spent above upper limit of glycemic range was higher (57%-58%) than the percent time spent below lower limit of target range (10-11%).

Overall, the percentage of patients with at least one event regardless of the category of hypoglycemia, during study was comparable in both treatment groups (HOE901-U300, Lantus) and for both injection times (morning or evening). The numerical trends in favor of the HOE901-U300 group for nocturnal hypoglycemia have to be interpreted with caution because of the small number of patients.

HOE901-U300 and Lantus, administered either in the morning or in the evening, were well tolerated during the study period, and no specific safety concerns were observed.

EXAMPLE 5: AN INVESTIGATIONAL NEW INSULIN U300: GLUCOSE CONTROL AND HYPOGLYCEMIA IN TYPE 2 DIABETES WITH BASAL INSULIN (EDITION II)

Aims:

An investigational new insulin U300 with an even flatter and more prolonged PK/PD profile than insulin glargine 100 U/mL (U100) is in clinical development. The phase 3 EDITION II study compared the efficacy and safety of U300 versus U100 in people with T2DM using a basal-insulin regimen in combination with OAD.

Methods:

In this multicenter, open-label, 6-month study, participants were randomized (1:1) to U300 or U100 once daily in the evening. Insulin dose was titrated to a target fasting plasma glucose (FPG) of 80-100 mg/dL. The primary endpoint was change in $HbA_{1c}$ from baseline to 6 months and the $1^{st}$ main secondary efficacy endpoint in a hierarchical analysis was the percentage of participants with severe or confirmed (≤70 mg/dL) nocturnal (2400-0559 h) hypoglycemic event from week 9 to month 6.

Results:

811 participants were randomised [mean age 58.2 (SD 9.2) yr, duration of diabetes 12.6 (7.0) yr, BMI 34.8 (6.4) kg/m$^2$, basal insulin dose 0.67 (0.24) U/kg]. Baseline $HbA_{1c}$ was comparable between groups; U300: 8.26 (0.86) % vs U100: 8.22 (0.77) %. U300 was non-inferior to U100 for change in $HbA_{1c}$ [LS mean change −0.57 (SE: 0.09) % and −0.56 (SE: 0.09) %, respectively at 6 months; difference −0.01 (95% CI: −0.14 to +0.12) %]. No relevant differences were seen for FPG, 8-point self-monitored plasma glucose profiles and pre-injection plasma glucose. The percentage of participants with severe or confirmed nocturnal hypoglycemia was significantly lower with U300 vs U100 from week 9 to month 6 [21.6% vs 27.9%; relative risk (RR) 0.77 (95% CI: 0.61 to 0.99); p=0.038]. Over the 6-month treatment period, the incidence of any nocturnal hypoglycemia (% of participants with event) was lower with U300 vs U100 [30.5% vs 41.6%; RR 0.73 (95% CI: 0.60 to 0.89)] as was the incidence of any hypoglycemic event at any time of the day (24 h) [U300 71.5%; U100 79.3%; RR 0.90 (95% CI: 0.84 to 0.97)]. Severe hypoglycemia at any time of day was reported by 1.0% of U300 and 1.5% of U100 participants. No between-treatment differences in serious adverse events were seen.

Conclusion:

In people with T2DM using a basal-insulin regimen with OAD, U300 was well tolerated and as effective as U100 in blood glucose control. U300 was associated with 23% reduction in severe or confirmed nocturnal hypoglycemia from week 9 to month 6 compared with U100 and with a lower incidence of any nocturnal hypoglycemia event and hypoglycemia at any time of the day (24 h) over the entire 6-month study duration.

EXAMPLE 6: 6-MONTH, MULTICENTER, RANDOMIZED, OPEN-LABEL, PARALLEL-GROUP STUDY COMPARING THE EFFICACY AND SAFETY OF A NEW FORMULATION OF INSULIN GLARGINE AND LANTUS BOTH IN COMBINATION WITH ORAL ANTIHYPERGLYCEMIC DRUG(S) IN PATIENTS WITH TYPE 2 DIABETES MELLITUS WITH A 6-MONTH SAFETY EXTENSION PERIOD—ADMINISTRATION SUB-STUDY COMPARING ADAPTABLE DOSING INTERVALS WITH FIXED DOSING INTERVALS

1 Synopsis

Phase of Development:

Substudy to phase 3 main study

Objectives:

Primary Objective:

To compare the efficacy of HOE901-U300 injected once daily every 24 hours and HOE901-U300 injected once daily at intervals of 24±3 hours in terms of change of HbA1c from month 6 of the main study (=baseline of sub-study) to month 9 of the main study (=endpoint of sub-study) in patients with type 2 diabetes mellitus.

Main Secondary Objectives:

To compare the safety of the two injection regimens for HOE901-U300 in terms of occurrence of hypoglycemia.

Methodology:

Patients randomized on HOE901-U300 and having received HOE901-U300 in the 6-month main study period are randomized 1:1 to administer HOE901-U300 once daily either every 24 hours (fixed dosing intervals) or every 24±3 hours (adaptable dosing intervals).

Patients on HOE901-U300 completing the 6-month main study period and meeting the eligibility criteria for the sub-study were eligible for the sub-study. No specific sample size was requested for the primary analysis that is descriptive.

| Number of patients: | Planned: up to 300 (150 pre treatment arm) |
|---|---|
| | Randomized: 89 |
| | Treated: 87 |
| | Evaluated: Efficacy: 86 Safety: 87 |

Diagnosis and Criteria for Inclusion:

Inclusion Criteria:

Completion of the 6-month study period in main study (Visit 10), Randomized and treated with HOE901-U300 during the 6-month treatment period (Baseline—month 6), Signed written informed consent for sub-study obtained.

Key Exclusion Criteria:

Patient not willing to use the adaptable injection intervals of 24±3 hours on at least two days per week; In the investigator's opinion, not able to comply with an adaptable dosing schedule; Health condition which precludes further participation of the patient in the study.

Study Treatments

Investigational Medicinal Product:

Tested drug: HOE901-U300

Formulation:

HOE901-U300 (insulin glargine 300 U/mL solution) is a sterile, non-pyrogenic, clear, colorless solution in a glass cartridge assembled in a pen-injector (prefilled, disposable pen).

Route of Administration:

subcutaneous injection

Tested Regimen:

Adaptable dosing intervals: HOE901-U300 administered once daily every 24±3 hours.

The injection time may have been adapted according to individual needs by up to 3 hours earlier or later than the daily reference injection time in the evening fixed at the start of the main study. The maximum intervals, ie, 3 hours earlier or 3 hours later than the fixed daily reference injection time was to be used on at least 2 days of the week at the patients' choice. The injection time fixed at start of the main study was to be maintained as reference time for the variation.

Control Regimen:

Fixed dosing intervals: HOE901-U300, once daily injection every 24 hours.

Patients continued to inject HOE901-U300 once daily every 24 hours at the injection time fixed at start of the main study.

Dose:

The dose of HOE901-U300 was to be titrated as needed to achieve or maintain fasting plasma glucose in the target range of 80 to 100 mg/dL (4.4 mmol/L to 5.6 mmol/L) without hypoglycemia. Changes in the insulin dose were based on fasting self-monitored capillary plasma glucose (SMPG) measurements.

Non-Investigational Medicinal Products:

Patients in both treatment regimens were to continue their oral antihyperglycemic background therapy during participation in the sub-study. Doses were to be kept stable throughout the study unless there was a specific safety issue related to these treatments. No other concomitant antidiabetic treatments were to be used in this study.

Short term use (ie, 10 days at maximum) of short-acting insulin therapy (eg, due to acute illness or surgery) was not considered as rescue therapy. Rescue medication was considered as Non-investigational Medicinal Product.

Duration of Treatment:

The sub-study consisted of a 3 month comparative efficacy and safety treatment period starting at completion of the 6-month main study period and ending at completion of Month 9 of the main study.

After completion, patients on the adaptable dosing arm may have continued this regimen up to the end of the main study (Month 12). Patients injecting HOE901-U300 every 24 hours continued with their treatment regimen up to the end of the main study.

Duration of Observation:

The analysis period for efficacy and safety is the 3-month study period starting at Month 6 of the main study and ending at Month 9 of the main study. Results presented in the present KRM refer to this period.

Criteria for Evaluation:

Primary Efficacy Endpoint:

change in $HbA_{1c}$ from baseline (Month 6) to endpoint (Month 9).

Secondary Efficacy Endpoints:

change in FPG (central laboratory) and change in daily dose of basal insulin, from baseline (Month 6) to endpoint (Month 9).

Safety:

Hypoglycemia (including nocturnal), occurrence of adverse events particularly treatment-emergent adverse events (TEAEs) and serious adverse events (SAEs), TEAEs leading to withdrawal, injection site reactions and hypersensitivity reactions. Following information not presented in KRM: other safety information including vital signs and overdose.

Statistical Methods:

For this 3-month sub-study, Baseline is defined as Month 6 of the main study; the Endpoint is Month 9 of the main study using last observation carried forward (LOCF) procedure.

The primary efficacy endpoint (change in $HbA_{1c}$ from baseline [Month 6] to endpoint [Month 9]) was analyzed using an analysis of covariance (ANCOVA) model with treatment regimen and country as fixed effects and using the $HbA_{1c}$ baseline value as a covariate. Differences between HOE901-U300 adaptable dosing regimen and HOE901-U300 fixed dosing regimen and two-sided 95% confidence intervals were estimated within the framework of ANCOVA.

All continuous secondary efficacy variables were analyzed using an ANCOVA model with treatment regimen and country as fixed effects and using the corresponding baseline value as a covariate.

Safety analyses were descriptive, based on the safety population.

Summary

Population Characteristics:

A total of 89 patients with type 2 diabetes mellitus were randomized to the sub-study: 45 patients to the HOE901-U300 adaptable dosing interval regimen and 44 patients to the HOE901-U300 fixed dosing interval regimen; 87 patients were exposed to IMP (safety population). The mITT sub-study population (efficacy population) included 86 patients.

A total of 40 (88.9%) patients randomized to HOE901-U300 adaptable dosing intervals and 38 (86.4%) randomized to HOE901-U300 fixed dosing intervals completed the 3-month comparative regimen period. 1 patient (2.2%) randomized to HOE901-U300 adaptable dosing intervals and 2 patients (4.5%) randomized to HOE901-U300 fixed dosing intervals discontinued the sub-study prematurely and also discontinued the extension period of the main study.

Demographics and patient characteristics at baseline (Month 6) were well-balanced between both regimen groups. The mean age of the sub-study population was 57.8 years; 16 of 89 (18.0%) patients were 65 years. 3 patients in the adaptable dosing interval regimen and 2 patients in the fixed dosing interval regimen were on insulin or insulin secretagogue started as rescue therapy during the main study period. No patient in either regimen group started rescue therapy during the 3-month comparative regimen period.

Compliance to Dosing Interval Regimens:

Compliance to dosing interval regimen was assessed taking into account the time interval between 2 consecutive injections and the time interval between an injection and the reference injection time as scheduled at the main study baseline.

During the sub-study, on average 28.04% of the injections per patient in the adaptable dosing interval group were taken at the extreme intervals of <21.5 hours or >26.5 hours between 2 consecutive injections versus 2.41% of injections in patients in the fixed dosing interval group, while 88.77% of the injections per patient in the fixed dosing interval group versus 53.09% of the injections per patient in the adaptable dosing interval group were taken within a 23-25 hour interval between 2 consecutive injections.

Evaluation of the time intervals between the actual injection and the reference injection times showed a higher percentage of injections per patient within the 23-25 hour interval in the fixed dosing interval group (mean 65.07%) compared with the adaptable dosing interval group (56.38%). In the adaptable dosing interval group 21.69% injections per patient were taken at intervals of 21.5-23 hours or at intervals of 25-26.5 hours (25.51% in the fixed dosing interval group). These data suggest that the majority of injections were taken up to 3 hours before or after the reference injection time, which was to be fixed as per protocol in the evening.

Based on the documented injection times during the week preceding the visits at Month 7.5 and at Month 9, a total of 47.5% of patients in the adaptable dosing group had 4 or more of their injection intervals outside the 21.5-26.5 hours interval after previous injection and therefore were considered to be compliant with the adaptable dosing interval regimen versus 2.6% of patients in the fixed dosing interval regimen. In the fixed dosing interval group, in 61.5% of patients all consecutive injection intervals were within 23-25 hours and therefore patients can be considered to be compliant with the fixed dosing interval regimen.

Efficacy:

Primary Efficacy Endpoint (Month 9):

The LS mean change in $HbA_{1c}$ from baseline (Month 6) to endpoint (Month 9) was similar in the groups of adaptable dosing intervals (−0.12% [95% CI: −0.422 to 0.183]) and fixed dosing intervals (−0.25% [95% CI: −0.574 to 0.072]) with the LS mean difference of 0.13% [95% CI: −0.152 to 0.415].

Secondary Efficacy Endpoints (Month 9):

The LS mean change in FPG from baseline (Month 6) to endpoint (Month 9) was similar in the groups of adaptable dosing intervals (−0.46 mmol/L [95% CI: −1.521 to 0.609]) and fixed dosing intervals (−0.25 mmol/L [95% CI: −1.378 to 0.881]) with the LS mean difference of −0.21 [95% CI: −1.200 to 0.784].

In both dosing interval regimens, the average daily basal insulin dose remained stable during the 3-month comparative regimen period Safety:

During the 3-month comparative substudy period, hypoglycemia events were reported in 16/44 (36.4%) of patients in the adaptable dosing interval regimen and 18/43 (41.9%) of patients in the fixed dosing interval regimen Each category of hypoglycemia event was reported by a comparable percentage of patients in both regimens. No event of severe hypoglycemia or severe nocturnal hypoglycemia occurred in either regimen.

The percentages of patients with any TEAE (adaptable dosing intervals 9/44 [20.5%]; fixed dosing intervals 11/43 [25.6%]) or with a serious TEAE (adaptable dosing intervals 2/44 [4.5%]; fixed dosing intervals 0/43) were comparable between the regimens.

No TEAEs leading to treatment discontinuationor to death, or linked to injection site reaction or to hypersensitivity reaction were observed in either dosing interval regimen during the 3-month substudy period.

Conclusions:

The evaluation of the duration of the injection intervals and the % patients with shorter or longer injection intervals than the regular 24-hour period suggests that the majority of patients in both dosing interval regimen groups followed the injection schedule as randomized and used either adaptable dosing intervals (HOE901-U300 once daily every 24 hours±3 hours on at least 2 days a week) or fixed dosing intervals (HOE901-U300 once daily every 24 hours). This allows a comparison of the two dosing interval regimens for efficacy and safety analyses.

The efficacy analyses in terms of HbA1c and FPG change from baseline (Month 6) to endpoint (Month 9) showed comparable results for the two dosing interval regimens.

Overall incidence of hypoglycemia (% of patients with at least one event) during the 3-month substudy period was comparable in both regimens regardless of the category of hypoglycemia.

HOE901-U300 given at either adaptable or fixed dosing intervals was well tolerated during the 3-month comparative substudy period; no specific safety concerns were observed.

Taken together, the substudy results suggest that occasional adaptation of the injection intervals by up to 3 hours earlier or later than the reference time for the once daily injection for HOE901-U300 had no effects on main efficacy (HbA1c) and safety endpoints, particularly hypoglycemia events, as compared with once daily injections at 24-hour intervals.

2 Results
2.1 Study Patients
2.1.1 Study disposition

TABLE 60

| Patient disposition-Randomized sub-study population | | |
|---|---|---|
| | HOE901-U300 Adaptable Dosing Intervals (N = 45) | HOE901-U300 Fixed Dosing Intervals (N = 44) |
| Randomized and treated | 44 (97.8%) | 43 (97.7%) |
| Completed 3-month comparative regimen period | 40 (88.9%) | 38 (86.4%) |
| Rescue intake during the 3-month comparative regimen period [a] | 3 (6.7%) | 2 (4.5%) |

TABLE 60-continued

Patient disposition-Randomized sub-study population

| | HOE901-U300 Adaptable Dosing Intervals (N = 45) | HOE901-U300 Fixed Dosing Intervals (N = 44) |
|---|---|---|
| Permanently discontinued the IMP during the 3-month comparative regimen period | 1 (2.2%) | 2 (4.5%) |
| Subject's request for treatment discontinuation | 1 (2.2%) | 1 (2.3%) |
| Reason for treatment discontinuation during the 3-month comparative regimen period | | |
| Adverse event | 0 | 0 |
| Lack of efficacy | 0 | 0 |
| Poor compliance to protocol | 0 | 1 (2.3%) |
| Other reasons | 1 (2.2%) | 1 (2.3%) |
| Status at last study contact of patients who permanently discontinued the treatment during the 3-month comparative regimen period | | |
| Alive | 1 (2.2%) | 2 (4.5%) |
| Dead | 0 | 0 |

Note:
percentages are calculated using the number of patients randomized as denominator.
[a] Includes patients who started rescue therapy during the main 6-month period and continued during the 3-month comparative regimen period.

TABLE 61

Sub-study analysis populations

| | HOE901-U300 Adaptable Dosing Intervals | HOE901-U300 Fixed Dosing Intervals | All |
|---|---|---|---|
| Randomized sub-study population | 45 (100%) | 44 (100%) | 89 (100%) |
| Efficacy sub-study populations | | | |
| Modified Intent-to-Treat (mITT) | 44 (97.8%) | 42 (95.5%) | 86 (96.6%) |
| Sub-study completers | 40 (88.9%) | 38 (86.4%) | 78 (87.6%) |
| Safety sub-study population | 44 | 43 | 87 |

Note:
patients are tabulated according to their randomized treatment.

2.1.2 Demographics and Baseline Characteristics

TABLE 62

Demographics and patient characteristics at baseline-Randomized sub-study population

| | HOE901-U300 Adaptable Dosing Intervals (N = 45) | HOE901-U300 Fixed Dosing Intervals (N = 44) | All (N = 89) |
|---|---|---|---|
| Age (years) | | | |
| Number | 45 | 44 | 89 |
| Mean (SD) | 58.4 (8.2) | 57.2 (10.0) | 57.8 (9.1) |
| Median | 59.0 | 57.0 | 58.0 |
| Min:Max | 27:72 | 33:84 | 27:84 |
| Age Group (years) [n (%)] | | | |
| Number | 45 | 44 | 89 |
| <65 | 36 (80.0%) | 37 (84.1%) | 73 (82.0%) |
| [65-75[ | 9 (20.0%) | 6 (13.6%) | 15 (16.9%) |
| ≥75 | 0 | 1 (2.3%) | 1 (1.1%) |
| Gender [n (%)] | | | |
| Number | 45 | 44 | 89 |
| Male | 22 (48.9%) | 22 (50.0%) | 44 (49.4%) |
| Female | 23 (51.1%) | 22 (50.0%) | 45 (50.6%) |
| Race [n (%)] | | | |
| Number | 45 | 44 | 89 |
| Caucasian/White | 42 (93.3%) | 40 (90.9%) | 82 (92.1%) |
| Black | 3 (6.7%) | 3 (6.8%) | 6 (6.7%) |
| Asian/Oriental | 0 | 0 | 0 |
| Other | 0 | 1 (2.3%) | 1 (1.1%) |
| Ethnicity [n (%)] | | | |
| Number | 45 | 44 | 89 |
| Hispanic | 5 (11.1%) | 7 (15.9%) | 12 (13.5%) |
| Not Hispanic | 40 (88.9%) | 37 (84.1%) | 77 (86.5%) |
| World region [n (%)] | | | |
| Number | 45 | 44 | 89 |
| North America | 22 (48.9%) | 29 (65.9%) | 51 (57.3%) |
| Western Europe | 3 (6.7%) | 1 (2.3%) | 4 (4.5%) |
| Eastern Europe | 20 (44.4%) | 13 (29.5%) | 33 (37.1%) |
| Rest of the world | 0 | 1 (2.3%) | 1 (1.1%) |

Age is assessed at main study baseline.

TABLE 63

Baseline (Month 6) efficacy data related to dosing interval-Randomized sub-study population

| | HOE901-U300 Adaptable Dosing Intervals (N = 45) | HOE901-U300 Fixed Dosing Intervals (N = 44) | All (N = 89) |
|---|---|---|---|
| Average injection time between 2 consecutive injections (hours) | | | |
| Number | 41 | 40 | 81 |
| Mean (SD) | 23.98 (0.13) | 23.99 (0.12) | 23.99 (0.13) |
| Median | 24.00 | 24.00 | 24.00 |
| Q1:Q3 | 24.00:24.00 | 24.00:24.02 | 24.00:24.01 |
| Min:Max | 23.2:24.1 | 23.3:24.2 | 23.2:24.2 |
| Average injection time from reference injection (hours) | | | |
| Number | 42 | 41 | 83 |
| Mean (SD) | 24.13 (0.58) | 24.20 (1.32) | 24.16 (1.01) |
| Median | 24.00 | 24.00 | 24.00 |
| Q1:Q3 | 24.00:24.50 | 23.98:24.38 | 24.00:24.49 |
| Min:Max | 22.6:25.6 | 20.2:28.7 | 20.2:28.7 |

Average: mean interval value over at least 3 times intervals during the last 7 days preceding month 6.

2.1.3 Compliance to Dosing Interval Regimen

TABLE 64

Compliance-Dosing interval regimen compliance during the 3-month comparative regimen period-Percentage of injections per patient by dosing interval category (time between 2 consecutive injections)-Safety sub-study population

| % of injections by patient | HOE901-U300 Adaptable Dosing Intervals (N = 44) | HOE901-U300 Fixed Dosing Intervals (N = 43) |
|---|---|---|
| <21.5 hours or >26.5 hours | | |
| Number | 40 | 38 |
| Mean (SD) | 28.04 (24.38) | 2.41 (8.86) |
| Median | 28.64 | 0.00 |
| Q1:Q3 | 0.00:52.27 | 0.00:0.00 |
| Min:Max | 0.0:75.0 | 0.0:50.0 |
| [23-25] hours | | |
| Number | 40 | 38 |
| Mean (SD) | 53.09 (27.19) | 88.77 (20.54) |
| Median | 47.73 | 100.00 |
| Q1:Q3 | 33.33:75.00 | 83.33:100.00 |
| Min:Max | 8.3:100.0 | 16.7:100.0 |
| [21.5-23[ hours or ]25-26.5] hours | | |
| Number | 40 | 38 |
| Mean (SD) | 18.86 (20.88) | 8.81 (17.13) |
| Median | 9.09 | 0.00 |
| Q1:Q3 | 0.00:33.33 | 0.00:8.33 |
| Min:Max | 0.0:66.7 | 0.0:80.0 |

Note:
Percentage of injections (time between 2 consecutive injections) in each dosing interval category is calculated for each patient using all injection intervals obtained during the last 7 days values before Month 7.5 and Month 9 visits.
Note:
Only patients with at least 3 time intervals during the last 7 days values before Month 7.5 or Month 9 visits are considered for this table.

TABLE 65

Compliance-Dosing interval regimen compliance during the 3-month comparative regimen period-Number (%) patients by injection interval between 2 consecutive injections-Safety sub-study population

| Number (%) of patients with | HOE901-U300 Adaptable Dosing Intervals (N = 44) | H0E901-U300 Fixed Dosing Intervals (N = 43) |
|---|---|---|
| ≥12 injection intervals in the range of [23-25] hours | 4/40 (10.0%) | 17/39 (43.6%) |
| 100% of injection intervals in the range of [23-25] hours | 6/40 (15.0%) | 24/39 (61.5%) |
| ≥4 injection intervals > 25 hours or <23 hours | 27/40 (67.5%) | 5/39 (12.8%) |
| ≥4 injection intervals > 25 hours | 18/40 (45.0%) | 1/39 (2.6%) |
| ≥4 injection intervals < 23 hours | 13/40 (32.5%) | 1/39 (2.6%) |
| ≥4 injection intervals > 26.5 hours or <21.5 hours | 19/40 (47.5%) | 1/39 (2.6%) |
| ≥4 injection intervals > 26.5 hours | 7/40 (17.5%) | 0/39 |
| ≥4 injection intervals < 21.5 hours | 3/40 (7.5%) | 1/39 (2.6%) |

Note:
Number of injections (time between 2 consecutive injections) is calculated using all injection intervals (maximum 12) obtained during the last 7 days values before Month 7.5 and Month 9 visits.

TABLE 66

Compliance-Dosing interval regimen compliance during the 3-month comparative regimen period-Percentage of injections (time from reference injection) by dosing interval category-Safety sub-study population

| % of injections by patient | HOE901-U300 Adaptable Dosing Intervals (N = 44) | HOE901-U300 Fixed Dosing Intervals (N = 43) |
|---|---|---|
| <21.5 hours or >26.5 hours | | |
| Number | 40 | 39 |
| Mean (SD) | 21.93 (21.45) | 9.42 (26.43) |
| Median | 28.57 | 0.00 |
| Q1:Q3 | 0.00:28.57 | 0.00:0.00 |
| Min:Max | 0.0:100.0 | 0.0:100.0 |
| [23-25] hours | | |
| Number | 40 | 39 |
| Mean (SD) | 56.38 (28.41) | 65.07 (39.62) |
| Median | 64.29 | 85.71 |
| Q1:Q3 | 40.66:71.43 | 28.57:100.00 |
| Min:Max | 0.0:100.0 | 0.0:100.0 |
| [21.5-23[ hours or ]25-26.5] hours | | |
| Number | 40 | 39 |
| Mean (SD) | 21.69 (23.29) | 25.51 (34.30) |
| Median | 14.84 | 7.14 |
| Q1:Q3 | 0.00:35.71 | 0.00:50.00 |
| Min:Max | 0.0:100.0 | 0.0:100.0 |

Note:
Percentage of injections (time from reference injection chosen at the start of the main study) in each dosing interval category is calculated for each patient using all injection intervals obtained during the last 7 days values before Month 7.5 and Month 9 visits.
Note:
Only patients with at least 3 time intervals during the last 7 days values before Month 7.5 or Month 9 visits are considered for this table.

2.2 Efficacy Evaluation 2.2.1 Primary Efficacy Endpoint

TABLE 67

Main efficacy analysis-Mean change in HbA1c (%) from baseline (month 6) to Month 9 endpoint using LOCF procedure-mITT sub-study population

| HbA1c (%) | HOE901-U300 Adaptable Dosing Intervals (N = 44) | HOE901-U300 Fixed Dosing Intervals (N = 42) |
|---|---|---|
| Baseline (month 6) | | |
| Number | 40 | 37 |
| Mean (SD) | 7.41 (0.96) | 7.47 (1.05) |
| Median | 7.35 | 7.30 |
| Min:Max | 5.8:9.1 | 5.9:10.3 |
| Month 9 endpoint (LOCF) | | |
| Number | 40 | 37 |
| Mean (SD) | 7.47 (0.87) | 7.49 (1.11) |
| Median | 7.35 | 7.30 |
| Min:Max | 6.0:9.1 | 5.8:10.0 |
| Change from baseline to Month 9 endpoint (LOCF) | | |
| Number | 40 | 37 |
| Mean (SD) | 0.06 (0.64) | 0.02 (0.63) |
| Median | 0.00 | −0.10 |
| Min:Max | −1.3:1.7 | −1.3:1.5 |
| LS Mean (SE) [a] | −0.12 (0.151) | −0.25 (0.162) |
| 95% CI | (−0.422 to 0.183) | (−0.574 to 0.072) |
| LS Mean difference (SE) vs. HOE901-U300 Fixed | | |
| Dosing Intervals [a] | 0.13 (0.142) | |
| 95% CI | (−0.152 to 0.415) | |

LOCF = Last observation carried forward.
[a] Analysis of covariance (ANCOVA) model with treatment regimen and country as fixed effects and baseline HbA1c value as a covariate.
Note:
For all patients rescued during the 3-month comparative regimen period, the last post-baseline HbA1c measurement before rescue and during sub-study 3-month on-treatment period will be used as the HbA1c endpoint.

FIG. 14 describes the mean HbA1c (%) by visit during the 3-month comparative regimen period—mITT sub-study population.

2.2.2 Secondary Endpoints 2.2.2.1 Fasting Plasma Glucose

TABLE 68

Mean change in FPG (mmol/L) from baseline (month 6) to Month 9 endpoint using LOCF procedure-mITT sub-study population

| FPG (mmol/L) | HOE901-U300 Adaptable Dosing Intervals (N = 44) | HOE901-U309 Fixed Dosing Intervals (N = 42) |
|---|---|---|
| Baseline (month 6) | | |
| Number | 39 | 38 |
| Mean (SD) | 7.08 (1.83) | 7.13 (2.71) |
| Median | 7.00 | 6.45 |
| Min:Max | 3.7:9.9 | 3.3:13.8 |
| Month 9 endpoint (LOCF) | | |
| Number | 39 | 38 |
| Mean (SD) | 7.38 (2.30) | 7.44 (2.16) |
| Median | 7.10 | 7.25 |
| Min:Max | 3.3:11.7 | 4.1:12.5 |

TABLE 68-continued

Mean change in FPG (mmol/L) from baseline (month 6) to Month 9 endpoint using LOCF procedure-mITT sub-study population

| FPG (mmol/L) | HOE901-U300 Adaptable Dosing Intervals (N = 44) | HOE901-U309 Fixed Dosing Intervals (N = 42) |
|---|---|---|
| Change from baseline to Month 9 endpoint (LOCF) | | |
| Number | 39 | 38 |
| Mean (SD) | 0.30 (2.44) | 0.31 (2.62) |
| Median | 0.10 | 0.30 |
| Min:Max | −3.7:5.9 | −6.7:5.5 |
| LS Mean (SE) [a] | −0.46 (0.534) | −0.25 (0.566) |
| 95% CI | (−1.521 to 0.609) | (−1.378 to 0.881) |
| LS Mean difference (SE) vs. HOE901-U300 Fixed | | |
| Dosing Intervals [a] | −0.21 (0.497) | |
| 95% CI | (−1.200 to 0.784) | |

FPG = Fasting Plasma Glucose.
LOCF = Last observation carried forward.
[a] Analysis of covariance (ANCOVA) model with treatment regimen and country as fixed effects and baseline FPG value as a covariate.
Note:
For all patients rescued during the 3-month comparative regimen period, the last post-baseline FPG measurement before rescue and during sub-study 3-month on-treatment period will be used as the FPG endpoint.

2.2.2.2 Basal Insulin Dose

FIG. 15 describes the average daily basal (glargine) insulin dose (U) by visit during the 3-month comparative regimen period—mITT sub-study population.

2.3 Safety Evaluation 2.3.1 Extent of Exposure

TABLE 69

Exposure to investigational product during the 3-month comparative regimen period-Safety sub-study population

| | HOE901-U300 Adaptable Dosing Intervals (N = 44) | HOE901-U300 Fixed Dosing Intervals (N = 43) |
|---|---|---|
| Cumulative exposure to the sub-study 3-month treatment (patient years) | 10.98 | 10.40 |
| Duration of the sub-study 3-month treatment (days) | | |
| Number | 44 | 42 |
| Mean (SD) | 91.2 (4.8) | 90.4 (10.7) |
| Median | 92.0 | 92.0 |
| Min:Max | 76:104 | 42:117 |
| Duration of the sub-study 3-month treatment by category [n (%)] | | |
| Missing duration | 0 | 1 (2.3%) |
| up to 6 weeks | 0 | 1 (2.3%) |
| >6 to 12 weeks | 3 (6.8%) | 3 (7.0%) |
| >12 weeks | 41 (93.2%) | 38 (88.4%) |
| Cumulative duration of the sub-study 3-month treatment by category [n (%)] | | |
| Missing duration | 0 | 1 (2.3%) |
| ≥1 days | 44 (100%) | 42 (97.7%) |
| >6 weeks | 44 (100%) | 41 (95.3%) |
| >12 weeks | 41 (93.2%) | 38 (88.4%) |

2.3.2 Hypoglycemia

TABLE 70

Number (%) of patients with at least one hypoglycemia event during the
3-month comparative regimen period-Safety sub-study population

| Type of hypoglycemia event n (%) | All hypoglycemia | | Nocturnal hypoglycemia (00:00-05:59) | |
|---|---|---|---|---|
| | HOE901-U300 Adaptable Dosing Intervals (N = 44) | HOE901-U300 Fixed Dosing Intervals (N = 43) | HOE901-U300 Adaptable Dosing Intervals (N = 44) | HOE901-U300 Fixed Dosing Intervals (N = 43) |
| Any hypoglycemia event | 16 (36.4%) | 18 (41.9%) | 7 (15.9%) | 10 (23.3%) |
| Severe hypoglycemia | 0 | 0 | 0 | 0 |
| Documented symptomatic hypoglycemia | | | | |
| ≤3.9 mmol/L (70 mg/dL) | 10 (22.7%) | 14 (32.6%) | 5 (11.4%) | 7 (16.3%) |
| <3.0 mmol/L (54 mg/dL) | 4 (9.1%) | 5 (11.6%) | 4 (9.1%) | 2 (4.7%) |
| Asymptomatic hypoglycemia | | | | |
| ≤3.9 mmol/L (70 mg/dL) | 11 (25.0%) | 9 (20.9%) | 3 (6.8%) | 4 (9.3%) |
| <3.0 mmol/L (54 mg/dL) | 1 (2.3%) | 0 | 0 | 0 |
| Probable symptomatic hypoglycemia | 1 (2.3%) | 2 (4.7%) | 0 | 0 |
| Relative hypoglycemia | | | | |
| >3.9 mmol/L (70 mg/dL) | 0 | 2 (4.7%) | 0 | 0 |
| Severe and/or confirmed[a] hypoglycemia | | | | |
| ≤3.9 mmol/L (70 mg/dL) | 16 (36.4%) | 18 (41.9%) | 7 (15.9%) | 10 (23.3%) |
| <3.0 mmol/L (54 mg/dL) | 4 (9.1%) | 5 (11.6%) | 4 (9.1%) | 2 (4.7%) | n (%) = number and percentage of patients with at least one hypoglycemia event.
[a]Severe and/or confirmed hypoglycemia = severe and/or confirmed by plasma glucose ≤3.9 mmol/L (70 mg/dL) (resp. <3.0 mmol/L (54 mg/dL)).
Note:
All hypoglycemia events with missing time are counted in the column "All hypoglycemia", but not classified as "nocturnal" or "daytime".

2.3.3 Treatment-Emergent Adverse Events

TABLE 71

Treatment emergent adverse events during the 3-month
comparative regimen period-Safety sub-study population

| n (%) | HOE901-U300 Adaptable Dosing Intervals (N = 44) | HOE901-U300 Fixed Dosing Intervals (N = 43) |
|---|---|---|
| Patients with any TEAE | 9 (20.5%) | 11 (25.6%) |
| Patients with any treatment emergent SAE | 2 (4.5%) | 0 |
| Patients with any TEAE leading to death | 0 | 0 |
| Patients with any TEAE leading to permanent treatment discontinuation | 0 | 0 |

TEAE: Treatment emergent adverse event,
SAE: Serious Adverse Event.
n (%) = number and percentage of patients with at least one TEAE.

TABLE 72

Number (%) of patients with TEAE(s) by primary SOC, HLGT, HLT and PT
events during the 3-month comparative regimen period-Safety sub-study population

| PRIMARY SYSTEM ORGAN CLASS HLGT: High Level Group Term HLT: High Level Term Preferred Term n (%) | HOE901-U300 Adaptable Dosing Intervals (N = 44) | HOE901-U300 Fixed Dosing Intervals (N = 43) |
|---|---|---|
| Any class | 9 (20.5%) | 11 (25.6%) |
| INFECTIONS AND INFESTATIONS | 3 (6.8%) | 4 (9.3%) |
| HLGT: Infections-pathogen unspecified | 2 (4.5%) | 4 (9.3%) |
| HLT: Female reproductive tract infections | 0 | 1 (2.3%) |
| Vaginal infection | 0 | 1 (2.3%) |
| Vulvovaginitis | 0 | 1 (2.3%) |
| HLT: Lower respiratory tract and lung infections | 0 | 2 (4.7%) |
| Bronchitis | 0 | 2 (4.7%) |

TABLE 72-continued

Number (%) of patients with TEAE(s) by primary SOC, HLGT, HLT and PT events during the 3-month comparative regimen period-Safety sub-study population

| PRIMARY SYSTEM ORGAN CLASS<br>HLGT: High Level Group Term<br>HLT: High Level Term<br>Preferred Term n (%) | HOE901-U300<br>Adaptable Dosing<br>Intervals<br>(N = 44) | HOE901-U300<br>Fixed Dosing<br>Intervals<br>(N = 43) |
|---|---|---|
| HLT: Upper respiratory tract infections | 1 (2.3%) | 1 (2.3%) |
| Nasopharyngitis | 1 (2.3%) | 1 (2.3%) |
| HLT: Urinary tract infections | 1 (2.3%) | 0 |
| Urinary tract infection | 1 (2.3%) | 0 |
| HLGT: Viral infectious disorders | 1 (2.3%) | 0 |
| HLT: Influenza viral infections | 1 (2.3%) | 0 |
| Influenza | 1 (2.3%) | 0 |
| METABOLISM AND NUTRITION DISORDERS | 0 | 1 (2.3%) |
| HLGT: Electrolyte and fluid balance conditions | 0 | 1 (2.3%) |
| HLT: Total fluid volume decreased | 0 | 1 (2.3%) |
| Dehydration | 0 | 1 (2.3%) |
| NERVOUS SYSTEM DISORDERS | 0 | 3 (7.0%) |
| HLGT: Headaches | 0 | 2 (4.7%) |
| HLT: Headaches NEC | 0 | 2 (4.7%) |
| Headache | 0 | 2 (4.7%) |
| Sinus headache | 0 | 1 (2.3%) |
| HLGT: Structural brain disorders | 0 | 1 (2.3%) |
| HLT: Structural brain disorders NEC | 0 | 1 (2.3%) |
| Cerebral atrophy | 0 | 1 (2.3%) |
| EAR AND LABYRINTH DISORDERS | 0 | 2 (4.7%) |
| HLGT: Inner ear and VIIIth cranial nerve disorders | 0 | 2 (4.7%) |
| HLT: Inner ear signs and symptoms | 0 | 2 (4.7%) |
| Vertigo | 0 | 2 (4.7%) |
| CARDIAC DISORDERS | 0 | 1 (2.3%) |
| HLGT: Cardiac neoplasms | 0 | 1 (2.3%) |
| HLT: Cardiac neoplasms NEC | 0 | 1 (2.3%) |
| Pericardial cyst | 0 | 1 (2.3%) |
| HLGT: Coronary artery disorders | 0 | 1 (2.3%) |
| HLT: Coronary artery disorders NEC | 0 | 1 (2.3%) |
| Coronary artery disease | 0 | 1 (2.3%) |
| HLGT: Heart failures | 0 | 1 (2.3%) |
| HLT: Heart failures NEC | 0 | 1 (2.3%) |
| Cardiac failure congestive | 0 | 1 (2.3%) |
| HLGT: Myocardial disorders | 0 | 1 (2.3%) |
| HLT: Cardiomyopathies | 0 | 1 (2.3%) |
| Congestive cardiomyopathy | 0 | 1 (2.3%) |
| VASCULAR DISORDERS | 0 | 2 (4.7%) |
| HLGT: Arteriosclerosis, stenosis, vascular insufficiency and necrosis | 0 | 1 (2.3%) |
| HLT: Non-site specific necrosis and vascular insufficiency NEC | 0 | 1 (2.3%) |
| Venous stenosis | 0 | 1 (2.3%) |
| HLGT: Vascular hypertensive disorders | 0 | 1 (2.3%) |
| HLT: Vascular hypertensive disorders NEC | 0 | 1 (2.3%) |
| Hypertension | 0 | 1 (2.3%) |
| RESPIRATORY, THORACIC AND MEDIASTINAL DISORDERS | 0 | 3 (7.0%) |
| HLGT: Respiratory disorders NEC | 0 | 1 (2.3%) |
| HLT: Breathing abnormalities | 0 | 1 (2.3%) |
| Dyspnoea | 0 | 1 (2.3%) |
| HLGT: Upper respiratory tract disorders (excl infections) | 0 | 2 (4.7%) |
| HLT: Nasal congestion and inflammations | 0 | 1 (2.3%) |
| Nasal congestion | 0 | 1 (2.3%) |
| HLT: Paranasal sinus disorders (excl infections and neoplasms) | 0 | 1 (2.3%) |
| Sinus congestion | 0 | 1 (2.3%) |
| GASTROINTESTINAL DISORDERS | 0 | 1 (2.3%) |
| HLGT: Gastrointestinal signs and symptoms | 0 | 1 (2.3%) |
| HLT: Nausea and vomiting symptoms | 0 | 1 (2.3%) |
| Nausea | 0 | 1 (2.3%) |
| SKIN AND SUBCUTANEOUS TISSUE DISORDERS | 1 (2.3%) | 1 (2.3%) |
| HLGT: Epidermal and dermal conditions | 0 | 1 (2.3%) |
| HLT: Papulosquamous conditions | 0 | 1 (2.3%) |
| Lichen sclerosus | 0 | 1 (2.3%) |
| HLGT: Skin and subcutaneous tissue disorders NEC | 1 (2.3%) | 0 |
| HLT: Skin and subcutaneous tissue ulcerations | 1 (2.3%) | 0 |
| Skin ulcer | 1 (2.3%) | 0 |
| MUSCULOSKELETAL AND CONNECTIVE TISSUE DISORDERS | 3 (6.8%) | 1 (2.3%) |
| HLGT: Joint disorders | 1 (2.3%) | 0 |
| HLT: Osteoarthropathies | 1 (2.3%) | 0 |

TABLE 72-continued

Number (%) of patients with TEAE(s) by primary SOC, HLGT, HLT and PT events during the 3-month comparative regimen period-Safety sub-study population

| PRIMARY SYSTEM ORGAN CLASS<br>HLGT: High Level Group Term<br>HLT: High Level Term<br>Preferred Term n (%) | HOE901-U300<br>Adaptable Dosing<br>Intervals<br>(N = 44) | HOE901-U300<br>Fixed Dosing<br>Intervals<br>(N = 43) |
|---|---|---|
| Spinal osteoarthritis | 1 (2.3%) | 0 |
| HLGT: Musculoskeletal and connective tissue disorders NEC | 1 (2.3%) | 0 |
| HLT: Musculoskeletal and connective tissue pain and discomfort | 1 (2.3%) | 0 |
| Pain in extremity | 1 (2.3%) | 0 |
| HLGT: Tendon, ligament and cartilage disorders | 1 (2.3%) | 1 (2.3%) |
| HLT: Cartilage disorders | 1 (2.3%) | 1 (2.3%) |
| Osteochondrosis | 1 (2.3%) | 1 (2.3%) |
| RENAL AND URINARY DISORDERS | 1 (2.3%) | 0 |
| HLGT: Urolithiases | 1 (2.3%) | 0 |
| HLT: Renal lithiasis | 1 (2.3%) | 0 |
| Nephrolithiasis | 1 (2.3%) | 0 |
| REPRODUCTIVE SYSTEM AND BREAST DISORDERS | 1 (2.3%) | 0 |
| HLGT: Vulvovaginal disorders (excl infections and inflammations) | 1 (2.3%) | 0 |
| HLT: Vulvovaginal disorders NEC | 1 (2.3%) | 0 |
| Vaginal haemorrhage | 1 (2.3%) | 0 |
| GENERAL DISORDERS AND ADMINISTRATION SITE CONDITIONS | 2 (4.5%) | 1 (2.3%) |
| HLGT: General system disorders NEC | 2 (4.5%) | 1 (2.3%) |
| HLT: Asthenic conditions | 0 | 1 (2.3%) |
| Fatigue | 0 | 1 (2.3%) |
| HLT: Oedema NEC | 1 (2.3%) | 0 |
| Oedema peripheral | 1 (2.3%) | 0 |
| HLT: Pain and discomfort NEC | 2 (4.5%) | 0 |
| Chest pain | 1 (2.3%) | 0 |
| Non-cardiac chest pain | 1 (2.3%) | 0 |
| INVESTIGATIONS | 0 | 2 (4.7%) |
| HLGT: Cardiac and vascular investigations (excl enzyme tests) | 0 | 1 (2.3%) |
| HLT: Vascular tests NEC (incl blood pressure) | 0 | 1 (2.3%) |
| Blood pressure increased | 0 | 1 (2.3%) |
| HLGT: Physical examination and organ system status topics | 0 | 1 (2.3%) |
| HLT: Physical examination procedures and organ system status | 0 | 1 (2.3%) |
| Weight increased | 0 | 1 (2.3%) |
| INJURY, POISONING AND PROCEDURAL COMPLICATIONS | 1 (2.3%) | 0 |
| HLGT: Medication errors | 1 (2.3%) | 0 |
| HLT: Overdoses | 1 (2.3%) | 0 |
| Accidental overdose | 1 (2.3%) | 0 |
| SURGICAL AND MEDICAL PROCEDURES | 0 | 1 (2.3%) |
| HLGT: Head and neck therapeutic procedures | 0 | 1 (2.3%) |
| HLT: Paranasal therapeutic procedures | 0 | 1 (2.3%) |
| Sinus operation | 0 | 1 (2.3%) |

TEAE: Treatment emergent adverse event,
SOC: System organ class,
HLGT: High level group term,
HLT: High level term,
PT: Preferred term.
MedDRA 16.0.
n (%) = number and percentage of patients with at least one TEAE.
Note:
Table sorted by SOC internationally agreed order and HLGT, HLT, PT by alphabetic order.

2.3.4 Serious Treatment-Emergent Adverse Events

TABLE 73

Number (%) of patients with treatment emergent SAE(s) by Primary SOC, HLGT, HLT and PT during the 3-month comparative regimen period-Safety sub-study population

| PRIMARY SYSTEM ORGAN CLASS<br>HLGT: High Level Group Term<br>HLT: High Level Term<br>Preferred Term n (%) | HOE901-U300<br>Adaptable Dosing<br>Intervals<br>(N = 44) | HOE901-U300<br>Fixed Dosing<br>Intervals<br>(N = 43) |
|---|---|---|
| Any class | 2 (4.5%) | 0 |
| MUSCULOSKELETAL AND CONNECTIVE TISSUE DISORDERS | 1 (2.3%) | 0 |
| HLGT: Joint disorders | 1 (2.3%) | 0 |
| HLT: Osteoarthropathies | 1 (2.3%) | 0 |
| Spinal osteoarthritis | 1 (2.3%) | 0 |
| GENERAL DISORDERS AND ADMINISTRATION SITE CONDITIONS | 1 (2.3%) | 0 |
| HLGT: General system disorders NEC | 1 (2.3%) | 0 |
| HLT: Pain and discomfort NEC | 1 (2.3%) | 0 |
| Chest pain | 1 (2.3%) | 0 |

TEAE: Treatment emergent adverse event,
SOC: System organ class,
HLGT: High level group term,
HLT: High level term,
PT: Preferred term.
MedDRA 16.0.
n (%) = number and percentage of patients with at least one treatment emergent SAE.
Note:
Table sorted by SOC internationally agreed order and HLGT, HLT, PT by alphabetic order.

2.3.5 Treatment Emergent Adverse Events Leading to Withdrawal

TABLE 74

Number (%) of patients with TEAE(s) leading to permanent treatment discontinuation by Primary SOC, HLGT, HLT and PT during the 3-month comparative regimen period-Safety sub-study population No data TEAE: Treatment emergent adverse event,
SOC: System organ class,
HLGT: High level group term,
HLT: High level term,
PT: Preferred term.
MedDRA 16.0.
n (%) = number and percentage of patients with at least one TEAE leading to permanent treatment discontinuation.
Note:
Table sorted by SOC internationally agreed order and HLGT, HLT, PT by alphabetic order.

2.3.6 Other Significant Treatment Emergent Adverse Events

2.3.6.1 Injection Site Reactions

TABLE 75

Number (%) of patients experiencing at least one TEAE by relevant Standardized MedDRA Queries and Preferred Term-Injection site reactions during the 3-month comparative regimen period-Safety sub-study population No data TEAE: Treatment emergent adverse event,
PT: Preferred term.
MedDRA 16.0
n (%) = number and percentage of patients with at least one injection site reactions TEAE.
Note:
Table sorted by decreasing frequency of PT in HOE901-U300 adaptable dosing intervals regimen.

2.3.6.2 Hypersensitivity Reactions

TABLE 76

Number (%) of patients experiencing at least one TEAE by relevant Standardized MedDRA Queries and Preferred Term-Hypersensitivity reactions during the 3-month comparative regimen period-Safety sub-study population No data TEAE: Treatment emergent adverse event, PT: Preferred term.
MedDRA 16.0
n (%) = number and percentage of patients with at least one hypersensitivity reactions TEAE.
Note:
Table sorted by decreasing frequency of PT in HOE901-U300 adaptable dosing intervals regimen.

The invention claimed is:

1. A method of treating Type II Diabetes Mellitus in a patient who has an increased risk of hypoglycemia comprising administering to the patient an aqueous pharmaceutical formulation comprising 300 U/mL of insulin glargine [equimolar to 300 IU human insulin], wherein the treatment reduces the risk of nocturnal hypoglycemia and wherein the patient who has an increased risk of hypoglycemia is a diabetes type II patient having experienced at least one hypoglycemic event, wherein the time interval between administrations is in the range of 20 hours to 23.5 hours or in the range of 24.5 hours to 28 hours on at least two days per week for the duration of treatment.

2. The method of claim 1, wherein the nocturnal hypoglycemia is selected from symptomatic hypoglycemia, severe symptomatic hypoglycemia, documented symptomatic hypoglycemia, probable symptomatic hypoglycemia, relative symptomatic hypoglycemia, and asymptomatic hypoglycemia.

3. The method of claim 1, wherein the patient to be treated has a HbA1c value of at least 8% at the onset of treatment.

4. The method of claim 1, wherein the patient to be treated has a BMI of at least 30 kg/m$^2$ at the onset of treatment.

5. The method of claim 1, wherein the patient to be treated received a basal insulin directly prior to the treatment.

6. The method of claim 1, wherein the patient to be treated received a mealtime short-acting insulin directly prior to the treatment.

7. The method of claim 1, wherein the formulation is administered once daily in the evening at a predetermined time.

8. The method of claim 1, wherein the patient additionally receives a mealtime short-acting insulin.

9. The method of claim 1, wherein the aqueous pharmaceutical formulation comprises one or more excipients selected from the group consisting of zinc, m-cresol, glycerol, polysorbate 20, and sodium.

10. The method of claim 9, wherein the aqueous pharmaceutical formulation comprises 90 μg/mL zinc, 2.7 mg/mL m-cresol, and 20 mg/ml glycerol 85%.

11. The method of claim 9, wherein the aqueous pharmaceutical formulation comprising 90 μg/mL zinc, 2.7 mg/mL m-cresol, 20 μg/mL polysorbate 20 and 20 mg/mL glycerol 85%.

12. The method of claim 1, wherein the pH of the aqueous pharmaceutical formulation is between 3.4 and 4.6.

13. The method of claim 12, wherein the pH of the aqueous pharmaceutical formulation is 4.

14. The method of claim 1, wherein the Diabetes Mellitus Type II is not adequately controlled with at least one oral antihyperglycemic alone.

15. The method of claim 14, wherein the at least one oral antihyperglycemic is metformin.

16. The method of claim 15, wherein a treatment with at least 1.5 g/day of metformin does not adequately control the Diabetes Mellitus.

17. The method of claim 16, wherein the aqueous pharmaceutical formulation is administered in combination with at least one oral antihyperglycemic agent.

18. The method of claim 17, wherein the at least one antihyperglycemic agent is metformin.

19. The method of claim 1, wherein the aqueous pharmaceutical formulation is administered on at least three days per week.

20. The method of claim 1, wherein the aqueous pharmaceutical formulation is administered on at least four days per week.

* * * * *